(12) United States Patent
Briner et al.

(10) Patent No.: US 8,680,091 B2
(45) Date of Patent: *Mar. 25, 2014

(54) 6-ARYLALKYLAMINO-2,3,4,5-TETRAHYDRO-1H-BENZO[D]AZEPINES AS 5-HT$_{2C}$ RECEPTOR AGONISTS

(75) Inventors: Karen Briner, Indianapolis, IN (US); Manuel Javier Cases-Thomas, Reading (GB); Marta Adeva Bartolome, Madrid (ES); Christopher Stanley Galka, Carmel, IN (US); Alicia Marcos Llorente, Madrid (ES); Maria Angeles Martinez-Grau, Madrid (ES); Michael Philip Mazanetz, Abingdon (GB); John Cunningham O'Toole, Indianapolis, IN (US); Richard Edmund Rathmell, Hampshire (GB); Matthew Robert Reinhard, Indianapolis, IN (US); Selma Sapmaz, Basingstoke (GB); Andrew Caerwyn Williams, Hampshire (GB)

(73) Assignee: Eli Lilly and Company, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/156,575

(22) Filed: Jun. 9, 2011

(65) Prior Publication Data
US 2011/0269745 A1   Nov. 3, 2011

Related U.S. Application Data

(63) Continuation of application No. 11/996,751, filed as application No. PCT/US2006/034335 on Sep. 1, 2006, now abandoned.

(60) Provisional application No. 60/731,081, filed on Oct. 28, 2005.

(30) Foreign Application Priority Data

Sep. 1, 2005   (EP) ..................................... 05380191

(51) Int. Cl.
| | | |
|---|---|---|
| *A61K 31/55* | (2006.01) | |
| *C07D 223/16* | (2006.01) | |
| *C07D 401/12* | (2006.01) | |
| *C07D 403/12* | (2006.01) | |
| *C07D 409/12* | (2006.01) | |
| *C07D 417/12* | (2006.01) | |

(52) U.S. Cl.
USPC ..................................... 514/217.01; 540/594

(58) Field of Classification Search
USPC ..................................... 514/217.01; 540/594
See application file for complete search history.

(56) References Cited

U.S. PATENT DOCUMENTS

| 4,265,890 A | 5/1981 | Holden et al. |
| 4,985,352 A | 6/1991 | Julius et al. |
| 5,639,748 A | 6/1997 | DeMarinis et al. |
| 5,698,766 A | 12/1997 | Julius et al. |

FOREIGN PATENT DOCUMENTS

| EP | 0285287 A2 | 10/1988 |
| EP | 1213017 A2 | 6/2002 |
| WO | 93/03015 A1 | 2/1993 |
| WO | 93/04686 A1 | 3/1993 |
| WO | 93/04866 A1 | 3/1993 |
| WO | 02/74746 A1 | 3/2002 |
| WO | 03/006466 A1 | 1/2003 |
| WO | 03/045940 A2 | 6/2003 |
| WO | 03/086306 A2 | 10/2003 |
| WO | 2005/003096 A1 | 1/2005 |
| WO | 2005/019179 A2 | 3/2005 |
| WO | 2005/019180 A1 | 3/2005 |
| WO | 2005/042490 A2 | 5/2005 |
| WO | 2005/042491 A1 | 5/2005 |
| WO | 2005/082859 A1 | 9/2005 |
| WO | 2006/069363 A2 | 6/2006 |
| WO | 2006/071740 A2 | 7/2006 |

OTHER PUBLICATIONS

Vikers et al., Psycholpharmacology, 167: 274-280 (2003).
Tecott et al., Nature, 374: 542-546 (1995).
Martin et al., Pharmacol. Biochem. Behav., 71: 615 (2002).
Chou-Green et al., Physiology & Behavior, 78: 641-649 (2003).
Leysen et al., Trends in Drug Research II, 29: 49-61 (1998).
Frank et al., Neuropsychopharmacology 27: 869-873 (2002).
Upton et al., Eur. J. Pharmacol., 359:33 (1998).
Fitzgerald, Ennis, Annual Reports in Medicinal Chemistry, 37: 21-30 (2002).
Nelson et al., Naunyn-Schmiedeberg's Arch. Pharm., 359: 1-6 (1999).
V. Setola et al., Mol. Pharmacology, 63: 1223-1229 (2003).
Frishman, Kotob, Journal of Clinical Pharmacology, 39: 7-16 (1999).

(Continued)

*Primary Examiner* — Brenda Coleman
(74) *Attorney, Agent, or Firm* — R. Craig Tucker

(57) ABSTRACT

The present invention provides 6-substituted 2,3,4,5-tetrahydro-1H-benzo[d]azepines of Formula (I) as selective 5-HT2c receptor agonists for the treatment of 5-HT2c associated disorders including obesity, obsessive/compulsive disorder, depression, and anxiety, where, R6 is —NR10R11, where R10 is substituted phenylalkyl or substituted pyridylalkyl and other substituents are as defined in the specification.

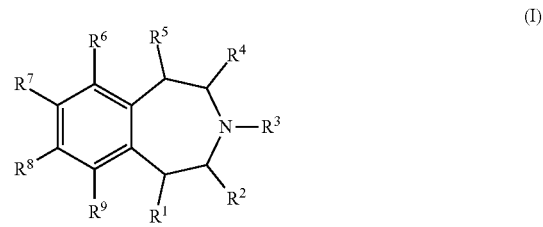

(I)

24 Claims, No Drawings

(56) References Cited

OTHER PUBLICATIONS

Seeman, Van Tol, Trends in Pharmacological Sciences, 15: 264-270 (1994).
Data Base Registry: XP002419374, 2005.
Database Registry: XP002419375, 2005.
Database Registry: XP002419376, 2005.
Database Registry: XP002419377, 2005.
Alain Dhainaut, et al. New Triazine Derivatives as Potent Modulators of Multidrug Resistance, J. Med. Chem, 1992, 2481-2496, vol. 35.
Kitaw Negash, et al. Further Definition of the D1 Dopamine Receptor Pharmacophore: Synthesis of trans-6,6a,7,8,9,13b-Hexahydro-5H-benzo[d]naphth[2,1-b]azepines as Rigid Analogues of Beta-Phenyldopamine, J. Med Chem, 1997, 2140-2147, vol. 40.
Istvan Gacsalyi, et al. Receptor Binding Profile and Anxiolytic-Type Activity of Deramciclane (EGIS-3886) in Animal Models, Drug Development Research, 1997, 333-348, vol. 40.
Brian M Smith, et al. Discovery and SAR of new benzazepines as potent and selective 5-irr2c receptor agonists for the treatment of obesity, Bioorg. Med. Chem. Lett. vol. 15 (5), 1467-1470 (2005).

6-ARYLALKYLAMINO-2,3,4,5-TETRAHYDRO-1H-BENZO[D]AZEPINES AS 5-HT$_{2C}$ RECEPTOR AGONISTS

This application is a Continuation of U.S. application Ser. No. 11/996,751 filed Jan. 25, 2008, which is a U.S. national stage application of International Application PCT/US2006/034335, filed Sep. 1, 2006, which claims priority of U.S. provisional application Ser. No. 60/731,081, filed Oct. 28, 2005, and to EP application 05380191.6, filed Sep. 1, 2005.

The neurotransmitter serotonin (5-hydroxytryptamine, 5-HT) has a rich pharmacology arising from a heterogeneous population of at least seven receptor classes. The serotonin 5-HT$_2$ class is further subdivided into at least three subtypes, designated 5-HT$_{2A}$, 5-HT$_{2B}$, and 5-HT$_{2C}$. The 5-HT$_{2C}$ receptor has been isolated and characterized (Julius, et al., U.S. Pat. No. 4,985,352), and transgenic mice lacking the 5-HT$_{2C}$ receptor have been reported to exhibit seizures and an eating disorder resulting in increased consumption of food (Julius et al., U.S. Pat. No. 5,698,766). The 5-HT$_{2C}$ receptor has also been linked to various other neurological disorders including obesity (Vickers et al., Psychopharmacology, 167: 274-280 (2003)), hyperphagia (Tecott et al., Nature, 374: 542-546 (1995)), obsessive compulsive disorder (Martin et al., Pharmacol. Biochem. Behav., 71: 615 (2002); Chou-Green et al., Physiology & Behavior, 78: 641-649 (2003)), depression (Leysen, Kelder, Trends in Drug Research II, 29: 49-61 (1998)), anxiety (Curr. Opin. Invest. Drugs 2(4), p. 317 (1993)), substance abuse, sleep disorder (Frank et al., Neuropsychopharmacology 27: 869-873 (2002)), hot flashes (EP 1213017 A2), epilepsy (Upton et al., Eur. J. Pharmacol., 359: 33 (1998); Fitzgerald, Ennis, Annual Reports in Medicinal Chemistry, 37: 21-30 (2002)), and hypogonadism (Curr. Opin. Invest. Drugs 2(4), p. 317 (1993)).

Certain substituted 2,3,4,5-tetrahydro-1H-benzo[d]azepine compounds have been disclosed as useful therapeutics as for example:

U.S. Pat. No. 4,265,890 describes certain substituted 2,3,4,5-tetrahydro-1H-benzo[d]azepine compounds as dopaminergic receptor antagonists for use as antipsychotics and antiemetics, inter alia.

EP 0 285 287 describes certain substituted 2,3,4,5-tetrahydro-1H-benzo[d]azepine compounds for use as agents to treat gastrointestinal motility disorders, inter alia.

WO 93/03015 and WO 93/04686 describe certain substituted 2,3,4,5-tetrahydro-1H-benzo[d]azepine compounds as alpha-adrenergic receptor antagonists for use as agents to treat hypertension and cardiovascular diseases in which changes in vascular resistance are desirable, inter alia.

WO 02/074746 A1 describes certain substituted 2,3,4,5-tetrahydro-1H-benzo[d]azepine compounds as 5-HT$_{2C}$ agonists for the treatment of hypogonadism, obesity, hyperphagia, anxiety, depression, sleep disorder, inter alia.

WO 03/006466 A1 describes certain substituted tricyclic hexahydroazepinoindole and indoline compounds as 5-HT ligands and consequently their usefulness for treating diseases wherein modulation of 5-HT activity is desired.

WO 05/019180 describes 6-(2,2,2-trifluoroethylamino)-7-chloro-2,3,4,5-tetrahydro-1H-benzo[d]azepine as a potent and selective 5-HT$_{2C}$ agonist for the treatment of obesity, anxiety, depression, and obsessive-compulsive disorder.

High affinity 5-HT$_{2C}$ receptor agonists would provide useful therapeutics for the treatment of the above mentioned 5-HT$_{2C}$ receptor-associated disorders including obesity, hyperphagia, obsessive/compulsive disorder, depression, anxiety, substance abuse, sleep disorder, hot flashes, and hypogonadism. High affinity 5-HT$_{2C}$ receptor agonists that are also selective for the 5-HT$_{2C}$ receptor, would provide such therapeutic benefit without the undesirable adverse events associated with current therapies. Achieving selectivity for the 5-HT$_{2C}$ receptor, particularly as against the 5-HT$_{2A}$ and 5-HT$_{2B}$ receptors, has proven difficult in designing 5-HT$_{2C}$ agonists. 5-HT$_{2A}$ receptor agonists have been associated with problematic hallucinogenic adverse events. (Nelson et al., Naunyn-Schmiedeberg's Arch. Pharm., 359: 1-6 (1999)). 5-HT$_{2B}$ receptor agonists have been associated with cardiovascular related adverse events, such as valvulopathy. (V. Setola et al., Mol. Pharmacology, 63: 1223-1229 (2003), and ref. cited therein).

Previous references to substituted 2,3,4,5-tetrahydro-1H-benzo[d]azepine compounds as potential therapeutics have predominantly recited their uses as alpha adrenergic and/or dopaminergic modulators. Adrenergic modulators are often associated with the treatment of cardiovascular diseases (Frishman, Kotob, Journal of Clinical Pharmacology, 39: 7-16 (1999)). Dopaminergic receptors are primary targets in the treatment of schizophrenia and Parkinson's disease (Seeman, Van Tol, Trends in Pharmacological Sciences, 15: 264-270 (1994)). It will be appreciated by those skilled in the art that selectivity as against these and other physiologically important receptors will generally also be preferred characteristics for therapeutics for the specific treatment of 5-HT$_{2C}$ associated disorders as described above.

The present invention provides selective 5-HT$_{2C}$ agonist compounds of Formula I:

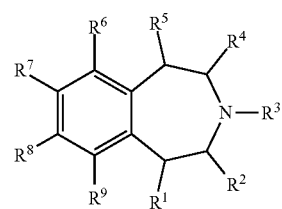

where:
$R^1$ is hydrogen, fluoro, or $(C_1-C_3)$alkyl;
$R^2$, $R^3$, and $R^4$ are each independently hydrogen, methyl, or ethyl;
$R^5$ is hydrogen, fluoro, methyl, or ethyl;
$R^6$ is —NR$^{10}$R$^{11}$;
$R^7$ is hydrogen, halo, cyano, $(C_1-C_6)$alkyl optionally substituted with 1 to 6 fluoro substituents, $(C_2-C_6)$alkenyl optionally substituted with 1 to 6 fluoro substituents, $(C_3-C_7)$cycloalkyl optionally substituted with 1 to 4 fluoro substituents, $(C_1-C_6)$alkoxy optionally substituted with 1 to 6 fluoro substituents, $(C_1-C_6)$alkylthio optionally substituted with 1 to 6 fluoro substituents, Ph$^1$-$(C_0-C_3)$alkyl optionally substituted with 1 to 6 fluoro substituents, Ph$^1$-$(C_0-C_3)$alkyl-O— optionally substituted with 1 to 6 fluoro substituents, or Ph$^1$-$(C_0-C_3)$alkyl-S— optionally substituted with 1 to 6 fluoro substituents;
$R^8$ is hydrogen, halo, cyano, —SCF$_3$, or hydroxy;
$R^9$ is hydrogen, halo, cyano, —CF$_3$, —SCF$_3$, hydroxy, or $(C_1-C_3)$alkoxy optionally substituted with 1 to 6 fluoro substituents;
$R^{10}$ is Ph$^2$—$(C_1-C_3)$-n-alkyl or Ar$^1$—$(C_1-C_3)$-n-alkyl, wherein the n-alkyl moiety is optionally substituted with $(C_1-C_3)$alkyl, dimethyl, gem-ethano or 1 to 2 fluoro substituents;
$R^{11}$ is hydrogen, $(C_1-C_3)$alkyl optionally substituted with 1 to 6 fluoro substituents, or allyl;

Ph$^1$ is phenyl optionally substituted with 1 to 5 independently selected halo substituents, or with 1 to 3 substituents independently selected from the group consisting of halo, cyano, —SCF$_3$, (C$_1$-C$_6$)alkyl optionally further substituted with 1 to 6 fluoro substituents, and (C$_1$-C$_6$)alkoxy optionally further substituted with 1 to 6 fluoro substituents;

Ph$^2$ is phenyl substituted with R$^{12}$ and optionally further substituted with 1 or 2 substituents independently selected from the group consisting of halo, cyano, —SCF$_3$, methyl, —CF$_3$, methoxy, —OCF$_3$, nitro, and hydroxy;

Ar$^1$ is 5-R$^{13}$-pyridin-2-yl or 6-R$^{13}$-pyridin-3-yl optionally further substituted with one or two substituents independently selected from the group consisting of halo, cyano, methyl, —CF$_3$, hydroxy, and methoxy;

R$^{12}$ is a substituent selected from the group consisting of:
a) Het$^1$-(C$_0$-C$_3$)alkyl optionally substituted on the alkyl moiety with 1 to 6 fluoro substituents;
b) Het$^2$-(C$_0$-C$_3$)alkyl optionally substituted on the alkyl moiety with 1 to 6 fluoro substituents;
c) Het$^3$-(C$_0$-C$_3$)alkyl optionally substituted on the alkyl moiety with 1 to 6 fluoro substituents;
d) Ar$^2$-(C$_0$-C$_3$)alkyl optionally substituted on the alkyl moiety with 1 to 6 fluoro substituents;
e) (C$_1$-C$_6$)alkyl-C(R$^{14}$)=C(R$^{14}$)— optionally substituted on the alkyl moiety with 1 to 6 fluoro substituents;
f) (R$^{14}$)$_2$C=C[(C$_1$-C$_6$)alkyl]- optionally substituted on the alkyl moiety with 1 to 6 fluoro substituents;
g) (C$_3$-C$_7$)cycloalkyl-(C$_0$-C$_3$)alkyl-C(R$^{14}$)=C(R$^{15}$)— optionally substituted on the cycloalkyl moiety with 1 to 4 substituents selected from the group consisting of methyl and fluoro, and independently optionally substituted on the alkyl moiety with 1 to 4 fluoro substituents;
h) (R$^{15}$)CH=C[(C$_3$-C$_7$)cycloalkyl-(C$_0$-C$_3$)alkyl]- optionally substituted on the cycloalkyl moiety with 1 to 4 substituents selected from the group consisting of methyl and fluoro, and independently optionally substituted on the alkyl moiety with 1 to 4 fluoro substituents;
i) (C$_1$-C$_6$)alkyl-C≡C— optionally substituted on the alkyl moiety with 1 to 6 fluoro substituents;
j) (C$_3$-C$_7$)cycloalkyl-(C$_0$-C$_3$)alkyl-C≡C— optionally substituted on the cycloalkyl moiety with 1 to 4 substituents selected from the group consisting of methyl and fluoro, and independently optionally substituted on the alkyl moiety with 1 to 4 fluoro substituents;
k) (C$_3$-C$_7$)cycloalkyl-(C$_0$-C$_3$)alkyl-C(O)—(C$_1$-C$_5$)alkyl optionally substituted on the cycloalkyl moiety with 1 to 4 substituents selected from the group consisting of methyl and fluoro, and independently optionally substituted on either or both alkyl moieties independently with 1 to 4 fluoro substituents;
l) Ph$^1$-(C$_0$-C$_3$)alkyl-C(O)—(C$_1$-C$_5$)alkyl optionally substituted on either or both alkyl moieties independently with 1 to 4 fluoro substituents;
m) pyridyl-(C$_0$-C$_3$)alkyl-C(O)—(C$_1$-C$_5$)alkyl, optionally substituted on the pyridyl moiety with 1 to 3 substituents independently selected from the group consisting of halo, (C$_1$-C$_3$)alkyl, (C$_1$-C$_3$)alkoxy, —CF$_3$, —O—CF$_3$, nitro, cyano, and trifluoromethylthio, and independently optionally substituted on either or both alkyl moieties independently with 1 to 4 fluoro substituents;
n) (C$_1$-C$_6$)alkyl-O—(C$_1$-C$_3$)alkyl-C(O)— optionally substituted on the (C$_1$-C$_6$)alkyl moiety with 1 to 6 fluoro substituents and independently optionally substituted on the (C$_1$-C$_3$)alkyl moiety with 1 to 4 fluoro substituents;
o) (C$_3$-C$_7$)cycloalkyl-(C$_0$-C$_3$)alkyl-O—(C$_1$-C$_3$)alkyl-C(O)— optionally substituted on the cycloalkyl moiety with 1 to 4 substituents consisting of methyl and fluoro, and independently optionally substituted on either or both alkyl moieties independently with 1 to 4 fluoro substituents;
p) Ph$^1$-(C$_0$-C$_3$)alkyl-O—(C$_1$-C$_3$)alkyl-C(O)— optionally substituted on either or both alkyl moieties independently with 1 to 4 fluoro substituents;
q) (C$_1$-C$_6$)alkyl-S—(C$_1$-C$_3$)alkyl-C(O)— optionally substituted on the (C$_1$-C$_6$)alkyl moiety with 1 to 6 fluoro substituents and independently optionally substituted on the (C$_1$-C$_3$)alkyl moiety with 1 to 4 fluoro substituents;
r) (C$_3$-C$_7$)cycloalkyl-(C$_0$-C$_3$)alkyl-S—(C$_1$-C$_3$)alkyl-C(O)— optionally substituted on the cycloalkyl moiety with 1 to 4 substituents selected from the group consisting of methyl and fluoro, and independently optionally substituted on either or both alkyl moieties independently with 1 to 4 fluoro substituents;
s) Ph$^1$-(C$_0$-C$_3$)alkyl-S—(C$_1$-C$_3$)alkyl-C(O)— optionally substituted on either or both alkyl moieties independently with 1 to 4 fluoro substituents;
t) (C$_1$-C$_6$)alkyl-NR$^{16}$—(C$_1$-C$_3$)alkyl-C(O)— optionally substituted on the (C$_1$-C$_6$)alkyl moiety with 1 to 6 fluoro substituents and independently optionally substituted on the (C$_1$-C$_3$)alkyl moiety with 1 to 4 fluoro substituents;
u) (C$_3$-C$_7$)cycloalkyl-(C$_0$-C$_3$)alkyl-NR$^{16}$—(C$_1$-C$_3$)alkyl-C(O)— optionally substituted on the cycloalkyl moiety with 1 to 4 substituents selected from the group consisting of methyl and fluoro, and independently optionally substituted on either or both alkyl moieties independently with 1 to 4 fluoro substituents;
v) Ph$^1$-(C$_0$-C$_3$)alkyl-NR$^{16}$—(C$_1$-C$_3$)alkyl-C(O)— optionally substituted on either or both alkyl moieties independently with 1 to 4 fluoro substituents;
w) (C$_1$-C$_6$)alkyl-O—(C$_1$-C$_3$)alkyl-SO$_2$— optionally substituted on the (C$_1$-C$_6$)alkyl moiety with 1 to 6 fluoro substituents and independently optionally substituted on the (C$_1$-C$_3$)alkyl moiety with 1 to 4 fluoro substituents;
x) (C$_3$-C$_7$)cycloalkyl-(C$_0$-C$_3$)alkyl-O—(C$_1$-C$_3$)alkyl-SO$_2$— optionally substituted on the cycloalkyl moiety with 1 to 4 substituents selected from the group consisting of methyl and fluoro, and independently optionally substituted on either or both alkyl moieties independently with 1 to 4 fluoro substituents;
y) Ph$^1$-(C$_0$-C$_3$)alkyl-O—(C$_1$-C$_3$)alkyl-SO$_2$— optionally substituted on either or both alkyl moieties independently with 1 to 4 fluoro substituents;
z) (C$_1$-C$_6$)alkyl-S—(C$_1$-C$_3$)alkyl-SO$_2$— optionally substituted on the (C$_1$-C$_6$)alkyl moiety with 1 to 6 fluoro substituents and independently optionally substituted on the (C$_1$-C$_3$)alkyl moiety with 1 to 4 fluoro substituents;
aa) (C$_3$-C$_7$)cycloalkyl-(C$_0$-C$_3$)alkyl-S—(C$_1$-C$_3$)alkyl-SO$_2$— optionally substituted on the cycloalkyl moiety with 1 to 4 substituents selected from the group consisting of methyl and fluoro, and independently optionally substituted on either or both alkyl moieties independently with 1 to 4 fluoro substituents;
ab) Ph$^1$-(C$_0$-C$_3$)alkyl-S—(C$_1$-C$_3$)alkyl-SO$_2$— optionally substituted on either or both alkyl moieties independently with 1 to 4 fluoro substituents;
ac) (C$_1$-C$_6$)alkyl-NR$^{16}$—(C$_1$-C$_3$)alkyl-SO$_2$— optionally substituted on the (C$_1$-C$_6$)alkyl moiety with 1 to 6 fluoro substituents and independently optionally substituted on the (C$_1$-C$_3$)alkyl moiety with 1 to 4 fluoro substituents;
ad) (C$_3$-C$_7$)cycloalkyl-(C$_0$-C$_3$)alkyl-NR$^{16}$—(C$_1$-C$_3$)alkyl-SO$_2$— optionally substituted on the cycloalkyl moiety with 1 to 4 substituents selected from the group consisting of methyl and fluoro, and independently optionally substituted on either or both alkyl moieties independently with 1 to 4 fluoro substituents;

ae) $Ph^1$-$(C_0$-$C_3)$alkyl-$NR^{16}$—$(C_1$-$C_3)$alkyl-$SO_2$— optionally substituted on either or both alkyl moieties independently with 1 to 4 fluoro substituents;

af) $R^{17}R^{18}$—N—C(O)—$(C_1$-$C_5)$alkyl optionally substituted on the alkyl moiety with 1 to 6 fluoro substituents;

ag) $R^{17}R^{18}$—N—C(S)—$(C_1$-$C_5)$alkyl optionally substituted on the alkyl moiety with 1 to 6 fluoro substituents;

ah) $(C_3$-$C_7)$cycloalkyl-$(C_0$-$C_3)$alkyl-S— optionally substituted on the cycloalkyl moiety with 1 to 4 substituents selected from the group consisting of methyl and fluoro, and independently optionally substituted on the alkyl moiety with 1 to 4 fluoro substituents;

ai) $(C_3$-$C_7)$cycloalkyl-$(C_0$-$C_3)$alkyl-S—$(C_1$-$C_5)$alkyl optionally substituted on the cycloalkyl moiety with 1 to 4 substituents selected from the group consisting of methyl and fluoro, and independently optionally substituted on either or both alkyl moieties independently with 1 to 4 fluoro substituents;

aj) $Ph^1$-$(C_0$-$C_3)$alkyl-S—$(C_1$-$C_5)$alkyl optionally substituted on the $(C_1$-$C_5)$alkyl moiety with 1 to 6 fluoro substituents and independently optionally substituted on the —$(C_0$-$C_3)$alkyl moiety with 1 to 4 fluoro substituents;

ak) $Ar^3$—$(C_0$-$C_3)$alkyl-S—$(C_1$-$C_5)$alkyl optionally substituted on the $(C_1$-$C_5)$alkyl moiety with 1 to 6 fluoro substituents and independently optionally substituted on the —$(C_0$-$C_3)$alkyl moiety with 1 to 4 fluoro substituents;

al) $Ar^3$—$(C_0$-$C_3)$alkyl-O—$(C_1$-$C_5)$alkyl optionally substituted on the $(C_1$-$C_5)$alkyl moiety with 1 to 6 fluoro substituents and independently optionally substituted on the —$(C_0$-$C_3)$alkyl moiety with 1 to 4 fluoro substituents;

am) $Het^1$-$(C_0$-$C_3)$alkyl-S—$(C_0$-$C_5)$alkyl wherein $Het^1$ is linked through any carbon atom of $Het^1$ and wherein the $(C_0$-$C_5)$alkyl moiety is optionally substituted with 1 to 6 fluoro substituents and independently optionally substituted on the —$(C_0$-$C_3)$alkyl moiety with 1 to 4 fluoro substituents;

an) $Het^1$-$(C_0$-$C_3)$alkyl-O—$(C_0$-$C_5)$alkyl wherein $Het^1$ is linked through any carbon atom of $Het^1$ and wherein the $(C_0$-$C_5)$alkyl moiety is optionally substituted with 1 to 6 fluoro substituents and independently optionally substituted on the —$(C_0$-$C_3)$alkyl moiety with 1 to 4 fluoro substituents;

ao) $Het^2$-$(C_0$-$C_3)$alkyl-S—$(C_0$-$C_5)$alkyl optionally substituted on the $(C_0$-$C_5)$alkyl moiety with 1 to 6 fluoro substituents and independently optionally substituted on the —$(C_0$-$C_3)$alkyl moiety with 1 to 4 fluoro substituents;

ap) $R^{16}R^{19}$—N—C(O)—S—$(C_0$-$C_5)$alkyl optionally substituted on the alkyl moiety with 1 to 6 fluoro substituents;

aq) $R^{16}R^{19}$—N—C(O)—O—$(C_0$-$C_5)$alkyl optionally substituted on the alkyl moiety with 1 to 6 fluoro substituents;

ar) $R^{16}R^{19}$—N—C(O)—$NR^{16}$—$(C_0$-$C_5)$alkyl optionally substituted on the alkyl moiety with 1 to 6 fluoro substituents;

as) $(C_1$-$C_6)$alkyl-C(O)—$(C_1$-$C_3)$alkyl-S— optionally substituted on the $(C_1$-$C_6)$alkyl moiety with 1 to 6 fluoro substituents and independently optionally substituted on the $(C_1$-$C_3)$alkyl moiety with 1 to 4 fluoro substituents;

at) $(C_1$-$C_6)$alkyl-$SO_2$—$(C_1$-$C_3)$alkyl-S— optionally substituted on the $(C_1$-$C_6)$alkyl moiety with 1 to 6 fluoro substituents and independently optionally substituted on the $(C_1$-$C_3)$alkyl moiety with 1 to 4 fluoro substituents;

au) $(C_3$-$C_7)$cycloalkyl-$(C_0$-$C_3)$alkyl-C(O)—$(C_1$-$C_3)$alkyl-O— optionally substituted on the cycloalkyl moiety with 1 to 4 substituents selected from the group consisting of methyl and fluoro, and independently optionally substituted on either or both alkyl moieties independently with 1 to 4 fluoro substituents;

av) $(C_3$-$C_7)$cycloalkyl-$(C_0$-$C_3)$alkyl-$SO_2$—$(C_1$-$C_3)$alkyl-O— optionally substituted on the cycloalkyl moiety with 1 to 4 substituents selected from the group consisting of methyl and fluoro, and independently optionally substituted on either or both alkyl moieties independently with 1 to 4 fluoro substituents;

aw) $(C_3$-$C_7)$cycloalkyl-$(C_0$-$C_3)$alkyl-C(O)—$(C_1$-$C_3)$alkyl-S— optionally substituted on the cycloalkyl moiety with 1 to 4 substituents selected from the group consisting of methyl and fluoro, and independently optionally substituted on either or both alkyl moieties independently with 1 to 4 fluoro substituents;

ax) $(C_3$-$C_7)$cycloalkyl-$(C_0$-$C_3)$alkyl-$SO_2$—$(C_1$-$C_3)$alkyl-S— optionally substituted on the cycloalkyl moiety with 1 to 4 substituents selected from the group consisting of methyl and fluoro, and independently optionally substituted on either or both alkyl moieties independently with 1 to 4 fluoro substituents;

ay) $Ph^1$-$(C_0$-$C_3)$alkyl-$SO_2$—$(C_1$-$C_3)$alkyl-O— optionally substituted on either or both alkyl moieties independently with 1 to 4 fluoro substituents;

az) $Ph^1$-$(C_0$-$C_3)$alkyl-C(O)—$(C_1$-$C_3)$alkyl-S— optionally substituted on either or both alkyl moieties independently with 1 to 4 fluoro substituents;

ba) $Ph^1$-$(C_0$-$C_3)$alkyl-$SO_2$—$(C_1$-$C_3)$alkyl-S— optionally substituted on either or both alkyl moieties independently with 1 to 4 fluoro substituents;

bb) $R^{17}R^{18}N$—C(O)—$(C_1$-$C_3)$alkyl-S— optionally substituted on the alkyl moiety with 1 to 4 fluoro substituents;

bc) $R^{17}R^{18}N$—C(S)—$(C_1$-$C_3)$alkyl-S— optionally substituted on the alkyl moiety with 1 to 4 fluoro substituents;

bd) $R^{17}R^{18}N$—C(S)—$(C_1$-$C_3)$alkyl-O— optionally substituted on the alkyl moiety with 1 to 4 fluoro substituents;

be) $(C_3$-$C_7)$cycloalkyl-$(C_0$-$C_3)$alkyl-$SO_2$—$(C_1$-$C_5)$alkyl optionally substituted on the cycloalkyl moiety with 1 to 4 substituents selected from the group consisting of methyl and fluoro, and independently optionally substituted on the $(C_0$-$C_3)$alkyl moiety with 1 to 4 fluoro substituents and further optionally substituted on the $(C_1$-$C_5)$alkyl moiety with 1 to 6 fluoro substituents;

bf) $Ph^1$-$(C_0$-$C_3)$alkyl-$SO_2$—$(C_1$-$C_5)$alkyl optionally substituted on the $(C_0$-$C_3)$alkyl moiety with 1 to 4 fluoro substituents and independently optionally substituted on the $(C_1$-$C_5)$alkyl moiety with 1 to 6 fluoro substituents;

bg) $Ar^3$—$(C_0$-$C_3)$alkyl—$SO_2$—$(C_1$-$C_5)$alkyl optionally substituted on the $(C_0$-$C_3)$alkyl moiety with 1 to 4 fluoro substituents and independently optionally substituted on the $(C_1$-$C_5)$alkyl moiety with 1 to 6 fluoro substituents;

bh) $Het^2$-$(C_0$-$C_3)$alkyl-$SO_2$—$(C_0$-$C_5)$alkyl optionally substituted on the $(C_0$-$C_3)$alkyl moiety with 1 to 4 fluoro substituents and independently optionally substituted on the $(C_1$-$C_5)$alkyl moiety with 1 to 6 fluoro substituents;

bi) $R^{17}R^{18}N$—$(C_1$-$C_3)$alkyl optionally substituted on the alkyl moiety with 1 to 4 fluoro substituents;

bj) $(C_1$-$C_6)$alkyl-C(O)—N($R^{16}$)—$(C_0$-$C_5)$alkyl optionally substituted on either or both alkyl moieties independently with 1 to 6 fluoro substituents;

bk) (C$_3$-C$_7$)cycloalkyl-C(O)—N(R$^{16}$)—(C$_0$-C$_5$)alkyl optionally substituted on the cycloalkyl moiety with 1 to 4 substituents selected from the group consisting of methyl and fluoro, and independently optionally substituted on the alkyl moiety with 1 to 6 fluoro substituents;

bl) Ph$^1$-(C$_0$-C$_3$)alkyl-C(O)—N(R$^{16}$)—(C$_0$-C$_5$)alkyl optionally substituted on the (C$_0$-C$_3$)alkyl moiety with 1 to 4 fluoro substituents and independently optionally substituted on the (C$_0$-C$_5$)alkyl moiety with 1 to 6 fluoro substituents;

bm) Ar$^3$—(C$_0$-C$_3$)alkyl-C(O)—N(R$^{16}$)—(C$_0$-C$_5$)alkyl optionally substituted on the (C$_0$-C$_3$)alkyl moiety with 1 to 4 fluoro substituents and independently optionally substituted on the (C$_0$-C$_5$)alkyl moiety with 1 to 6 fluoro substituents;

bn) (C$_1$-C$_6$)alkyl-C(S)—N(R$^{16}$)—(C$_0$-C$_5$)alkyl optionally substituted on either or both alkyl moieties independently with 1 to 6 fluoro substituents;

bo) (C$_3$-C$_7$)cycloalkyl-C(S)—N(R$^{16}$)—(C$_0$-C$_5$)alkyl optionally substituted on the cycloalkyl moiety with 1 to 4 substituents selected from the group consisting of methyl and fluoro, and independently optionally substituted on the alkyl moiety with 1 to 6 fluoro substituents;

bp) Ph$^1$-(C$_0$-C$_3$)alkyl-C(S)—N(R$^{16}$)—(C$_0$-C$_5$)alkyl optionally substituted on the (C$_0$-C$_3$)alkyl moiety with 1 to 4 fluoro substituents and independently optionally substituted on the (C$_0$-C$_5$)alkyl moiety with 1 to 6 fluoro substituents;

bq) Ar$^3$—(C$_0$-C$_3$)alkyl-C(S)—N(R$^{16}$)—(C$_0$-C$_5$)alkyl optionally substituted on the (C$_0$-C$_3$)alkyl moiety with 1 to 4 fluoro substituents and independently optionally substituted on the (C$_0$-C$_5$)alkyl moiety with 1 to 6 fluoro substituents;

br) (C$_1$-C$_6$)alkyl-O—N=C(CH$_3$)— optionally substituted on the (C$_1$-C$_6$)alkyl moiety with 1 to 6 fluoro substituents;

bs) (C$_0$-C$_3$)alkyl-O—N=C[(C$_1$-C$_6$)alkyl]- optionally substituted on the (C$_0$-C$_3$)alkyl moiety with 1 to 4 fluoro substituents and independently optionally substituted on the (C$_1$-C$_6$)alkyl moiety with 1 to 6 fluoro substituents;

bt) HO—N=C[(C$_0$-C$_1$)alkyl-(C$_3$-C$_7$)cycloalkyl]- optionally substituted on the cycloalkyl moiety with 1 to 4 substituents selected from the group consisting of methyl and fluoro, and independently optionally substituted on either or both alkyl moieties independently with 1 to 2 fluoro substituents;

bu) CH$_3$—O—N=C[(C$_0$-C$_1$)alkyl-(C$_3$-C$_7$)cycloalkyl]- optionally substituted on the cycloalkyl moiety with 1 to 4 substituents selected from the group consisting of methyl and fluoro, and independently optionally substituted on either or both alkyl moieties independently with 1 to 2 fluoro substituents;

R$^{13}$ is a substituent selected from the group consisting of:
a) Het$^2$-(C$_0$-C$_3$)alkyl optionally substituted on the alkyl moiety with 1 to 6 fluoro substituents;

b) Het$^3$-(C$_0$-C$_3$)alkyl optionally substituted on the alkyl moiety with 1 to 6 fluoro substituents;

c) Ar$^2$—(C$_0$-C$_3$)alkyl optionally substituted on the alkyl moiety with 1 to 6 fluoro substituents;

d) (C$_1$-C$_6$)alkyl-C(R$^{14}$)=C(R$^{14}$)— optionally substituted on the alkyl moiety with 1 to 6 fluoro substituents;

e) (R$^{14}$)$_2$C=C[(C$_1$-C$_6$)alkyl]- optionally substituted on the alkyl moiety with 1 to 6 fluoro substituents;

f) (C$_3$-C$_7$)cycloalkyl-(C$_0$-C$_3$)alkyl-C(R$^{14}$)=C(R$^{15}$)— optionally substituted on the cycloalkyl moiety with 1 to 4 substituents selected from the group consisting of methyl and fluoro, and independently optionally substituted on the alkyl moiety with 1 to 4 fluoro substituents;

g) (R$^{15}$)CH=C[(C$_3$-C$_7$)cycloalkyl-(C$_0$-C$_3$)alkyl]- optionally substituted on the cycloalkyl moiety with 1 to 4 substituents selected from the group consisting of methyl and fluoro, and independently optionally substituted on the alkyl moiety with 1 to 4 fluoro substituents;

h) (C$_1$-C$_6$)alkyl-C≡C— optionally substituted on the alkyl moiety with 1 to 6 fluoro substituents;

i) (C$_3$-C$_7$)cycloalkyl-(C$_0$-C$_1$)alkyl-C≡C— optionally substituted on the cycloalkyl moiety with 1 to 4 substituents selected from the group consisting of methyl and fluoro, and independently optionally substituted on the alkyl moiety with 1 to 2 fluoro substituents;

j) (C$_1$-C$_6$)alkyl-O—(C$_1$-C$_5$)alkyl optionally substituted on either or both alkyl moieties independently with 1 to 6 fluoro substituents;

k) (C$_3$-C$_7$)cycloalkyl-(C$_0$-C$_3$)alkyl-O—(C$_0$-C$_5$)alkyl optionally substituted on the cycloalkyl moiety with 1 to 4 substituents selected from the group consisting of methyl and fluoro, and independently optionally substituted on the (C$_0$-C$_3$)alkyl moiety with 1 to 4 fluoro substituents and further optionally substituted on the (C$_0$-C$_5$)alkyl moiety with 1 to 6 fluoro substituents;

l) Ph$^1$-(C$_0$-C$_3$)alkyl-O—(C$_0$-C$_5$)alkyl optionally substituted on the (C$_0$-C$_3$)alkyl moiety with 1 to 4 fluoro substituents and independently optionally substituted on the (C$_0$-C$_5$)alkyl moiety with 1 to 6 fluoro substituents;

m) Ar$^3$—(C$_0$-C$_3$)alkyl-O—(C$_0$-C$_5$)alkyl optionally substituted on the (C$_0$-C$_3$)alkyl moiety with 1 to 4 fluoro substituents and independently optionally substituted on the (C$_0$-C$_5$)alkyl moiety with 1 to 6 fluoro substituents;

n) Het$^2$-(C$_0$-C$_3$)alkyl-O—(C$_0$-C$_5$)alkyl optionally substituted on the (C$_0$-C$_3$)alkyl moiety with 1 to 4 fluoro substituents and independently optionally substituted on the (C$_0$-C$_5$)alkyl moiety with 1 to 6 fluoro substituents;

o) (C$_3$-C$_7$)cycloalkyl-(C$_0$-C$_3$)alkyl-C(O)—(C$_1$-C$_5$)alkyl optionally substituted on the cycloalkyl moiety with 1 to 4 substituents selected from the group consisting of methyl and fluoro, and independently optionally substituted on the (C$_0$-C$_3$)alkyl moiety with 1 to 4 fluoro substituents and further optionally substituted on the (C$_1$-C$_5$)alkyl moiety with 1 to 6 fluoro substituents;

p) Ph$^1$-(C$_0$-C$_3$)alkyl-C(O)—(C$_1$-C$_5$)alkyl optionally substituted on the (C$_0$-C$_3$)alkyl moiety with 1 to 4 fluoro substituents and independently optionally substituted on the (C$_1$-C$_5$)alkyl moiety with 1 to 6 fluoro substituents;

q) pyridyl-(C$_0$-C$_3$)alkyl-C(O)—(C$_1$-C$_5$)alkyl optionally be substituted on the pyridyl moiety with 1 to 3 substituents independently selected from the group consisting of halo, (C$_1$-C$_3$)alkyl, (C$_1$-C$_3$)alkoxy, —CF$_3$, —O—CF$_3$, nitro, cyano, and trifluoromethylthio, and independently optionally substituted on the (C$_0$-C$_3$)alkyl moiety with 1 to 4 fluoro substituents, and independently optionally substituted on the (C$_1$-C$_5$)alkyl moiety with 1 to 6 fluoro substituents;

r) (C$_1$-C$_6$)alkyl-C(O)—(C$_1$-C$_3$)alkyl-O— optionally substituted on the (C$_1$-C$_6$)alkyl moiety with 1 to 6 fluoro substituents and independently optionally substituted on the (C$_1$-C$_3$)alkyl moiety with 1 to 4 fluoro substituents;

s) (C$_3$-C$_7$)cycloalkyl-(C$_0$-C$_3$)alkyl-C(O)—(C$_1$-C$_3$)alkyl-O— optionally substituted on the cycloalkyl moiety with 1 to 4 substituents selected from the group consisting of methyl and fluoro, and independently optionally substituted on either or both of the alkyl moieties independently with 1 to 4 fluoro substituents;

t) $Ph^1$-$(C_0$-$C_3)$alkyl-C(O)—$(C_1$-$C_3)$alkyl-O— optionally substituted on either or both of the alkyl moieties independently with 1 to 4 fluoro substituents;

u) pyridyl-$(C_0$-$C_3)$alkyl-C(O)—$(C_1$-$C_3)$alkyl-O— optionally be substituted on the pyridyl moiety with 1 to 3 substituents independently selected from the group consisting of halo, $(C_1$-$C_3)$alkyl, $(C_1$-$C_3)$alkoxy, —$CF_3$, —O—$CF_3$, nitro, cyano, and trifluoromethylthio, and independently optionally substituted on either or both of the alkyl moieties independently with 1 to 4 fluoro substituents;

v) $R^{17}R^{18}$N—C(O)—$(C_1$-$C_3)$alkyl-O— optionally substituted on the alkyl moiety with 1 to 4 fluoro substituents;

w) $R^{17}R^{18}$N—C(S)—$(C_1$-$C_3)$alkyl-O— optionally substituted on the alkyl moiety with 1 to 4 fluoro substituents;

x) $(C_3$-$C_7)$cycloalkyl-$(C_0$-$C_3)$alkyl-S— substituted on the cycloalkyl moiety with 1 to 4 substituents selected from the group consisting of methyl and fluoro, and independently optionally substituted on either or both of the alkyl moieties independently with 1 to 4 fluoro substituents;

y) $(C_1$-$C_6)$alkyl-S—$(C_1$-$C_5)$alkyl optionally substituted on either or both alkyl moieties independently with 1 to 6 fluoro substituents;

z) $(C_3$-$C_7)$cycloalkyl-$(C_0$-$C_3)$alkyl-S—$(C_1$-$C_5)$alkyl optionally substituted on the cycloalkyl moiety with 1 to 4 substituents selected from the group consisting of methyl and fluoro, and independently optionally substituted on the $(C_0$-$C_3)$alkyl moiety with 1 to 4 fluoro substituents, and independently optionally substituted on the $(C_1$-$C_5)$alkyl moiety with 1 to 6 fluoro substituents;

aa) $Ph^1$-$(C_0$-$C_3)$alkyl-S—$(C_1$-$C_5)$alkyl optionally substituted on the $(C_0$-$C_3)$alkyl moiety with 1 to 4 fluoro substituents and independently optionally substituted on the $(C_1$-$C_5)$alkyl moiety with 1 to 6 fluoro substituents;

ab) $Ar^3$—$(C_0$-$C_3)$alkyl-S—$(C_1$-$C_5)$alkyl optionally substituted on the $(C_0$-$C_3)$alkyl moiety with 1 to 4 fluoro substituents and independently optionally substituted on the $(C_1$-$C_5)$alkyl moiety with 1 to 6 fluoro substituents;

ac) $(C_1$-$C_6)$alkyl-C(O)—$(C_1$-$C_3)$alkyl-S— optionally substituted on the $(C_1$-$C_6)$alkyl moiety with 1 to 6 fluoro substituents and independently optionally substituted on the $(C_1$-$C_3)$alkyl moiety with 1 to 4 fluoro substituents;

ad) $(C_3$-$C_7)$cycloalkyl-$(C_0$-$C_3)$alkyl-C(O)—$(C_1$-$C_3)$alkyl-S— optionally substituted on the cycloalkyl moiety with 1 to 4 substituents selected from the group consisting of methyl and fluoro, and independently optionally substituted on either or both of the alkyl moieties independently with 1 to 4 fluoro substituents;

ae) $Ph^1$-$(C_0$-$C_3)$alkyl-C(O)—$(C_1$-$C_3)$alkyl-S— optionally substituted on either or both of the alkyl moieties independently with 1 to 4 fluoro substituents;

af) pyridyl-$(C_0$-$C_3)$alkyl-C(O)—$(C_1$-$C_3)$alkyl-S— optionally be substituted on the pyridyl moiety with 1 to 3 substituents independently selected from the group consisting of halo, $(C_1$-$C_3)$alkyl, $(C_1$-$C_3)$alkoxy, —$CF_3$, —O—$CF_3$, nitro, cyano, and trifluoromethylthio, and independently optionally substituted on either or both of the alkyl moieties independently with 1 to 4 fluoro substituents;

ag) $R^{17}R^{18}$N—C(O)—$(C_1$-$C_3)$alkyl-S— optionally substituted on the alkyl moiety with 1 to 4 fluoro substituents;

ah) $R^{17}R^{18}$N—C(S)—$(C_1$-$C_3)$alkyl-S— optionally substituted on the alkyl moiety with 1 to 4 fluoro substituents;

ai) $(C_1$-$C_6)$alkyl-$SO_2$—$(C_0$-$C_5)$alkyl optionally substituted on either or both of the alkyl moieties independently with 1 to 6 fluoro substituents;

aj) $(C_3$-$C_7)$cycloalkyl-$(C_0$-$C_3)$alkyl-$SO_2$—$(C_0$-$C_5)$alkyl optionally substituted on the cycloalkyl moiety with 1 to 4 substituents selected from the group consisting of methyl and fluoro, and independently optionally substituted on the $(C_0$-$C_3)$alkyl moiety with 1 to 4 fluoro substituents, and independently optionally substituted on the $(C_0$-$C_5)$alkyl moiety with 1 to 6 fluoro substituents;

ak) $Ph^1$-$(C_0$-$C_3)$alkyl-$SO_2$—$(C_0$-$C_5)$alkyl optionally substituted on the $(C_0$-$C_3)$alkyl moiety with 1 to 4 fluoro substituents and independently optionally substituted on the $(C_0$-$C_5)$alkyl moiety with 1 to 6 fluoro substituents;

al) $Ar^3$—$(C_0$-$C_3)$alkyl-$SO_2$—$(C_0$-$C_5)$alkyl optionally substituted on the $(C_0$-$C_3)$alkyl moiety with 1 to 4 fluoro substituents and independently optionally substituted on the $(C_0$-$C_5)$alkyl moiety with 1 to 6 fluoro substituents;

am) $Het^2$-$(C_0$-$C_3)$alkyl-$SO_2$—$(C_0$-$C_5)$alkyl optionally substituted on the $(C_0$-$C_3)$alkyl moiety with 1 to 4 fluoro substituents and independently optionally substituted on the $(C_0$-$C_5)$alkyl moiety with 1 to 6 fluoro substituents;

an) $R^{17}R^{18}$—N—C(O)—$(C_1$-$C_5)$alkyl optionally substituted on the $(C_1$-$C_5)$alkyl moiety with 1 to 6 fluoro substituents;

ao) $R^{17}R^{18}$—N—C(S)—$(C_1$-$C_5)$alkyl optionally substituted on the $(C_1$-$C_5)$alkyl moiety with 1 to 6 fluoro substituents;

ap) $R^{17}R^{18}$N—$(C_1$-$C_3)$alkyl optionally substituted on the $(C_1$-$C_3)$alkyl moiety with 1 to 4 fluoro substituents;

aq) $(C_1$-$C_6)$alkyl-C(O)—N($R^{16}$)—$(C_0$-$C_5)$alkyl optionally substituted on either or both of the alkyl moieties independently with 1 to 6 fluoro substituents;

ar) $(C_3$-$C_7)$cycloalkyl-C(O)—N($R^{16}$)—$(C_0$-$C_5)$alkyl optionally substituted on the cycloalkyl moiety with 1 to 4 substituents selected from the group consisting of methyl and fluoro, and independently optionally substituted on the $(C_0$-$C_5)$alkyl moiety with 1 to 6 fluoro substituents;

as) $Ph^1$-$(C_0$-$C_3)$alkyl-C(O)—N($R^{16}$)—$(C_0$-$C_5)$alkyl optionally substituted on the $(C_0$-$C_3)$alkyl moiety with 1 to 4 fluoro substituents and independently optionally substituted on the $(C_0$-$C_5)$alkyl moiety with 1 to 6 fluoro substituents;

at) $Ar^3$—$(C_0$-$C_3)$alkyl-C(O)—N($R^{16}$)—$(C_0$-$C_5)$alkyl optionally substituted on the $(C_0$-$C_3)$alkyl moiety with 1 to 4 fluoro substituents and independently optionally substituted on the $(C_0$-$C_5)$alkyl moiety with 1 to 6 fluoro substituents;

au) $(C_1$-$C_6)$alkyl-C(S)—N($R^{16}$)—$(C_0$-$C_5)$alkyl optionally substituted on either or both of the alkyl moieties independently with 1 to 6 fluoro substituents;

av) $(C_3$-$C_7)$cycloalkyl-C(S)—N($R^{16}$)—$(C_0$-$C_5)$alkyl optionally substituted on the cycloalkyl moiety with 1 to 4 substituents selected from the group consisting of methyl and fluoro, and independently optionally substituted on the $(C_0$-$C_5)$alkyl moiety with 1 to 6 fluoro substituents;

aw) $Ph^1$-$(C_0$-$C_3)$alkyl-C(S)—N($R^{16}$)—$(C_0$-$C_5)$alkyl optionally substituted on the $(C_0$-$C_3)$alkyl moiety with 1 to 4 fluoro substituents and independently optionally substituted on the $(C_0$-$C_5)$alkyl moiety with 1 to 6 fluoro substituents;

ax) $Ar^3$—$(C_0$-$C_3)$alkyl-C(S)—N($R^{16}$)—$(C_0$-$C_5)$alkyl optionally substituted on the $(C_0$-$C_3)$alkyl moiety with 1 to 4 fluoro substituents and independently optionally substituted on the $(C_0-C_5)$alkyl moiety with 1 to 6 fluoro substituents;

$R^{14}$ is hydrogen or $(C_1-C_2)$alkyl optionally substituted with 1 to 5 fluoro substituents;

$R^{15}$ is hydrogen or methyl optionally substituted with 1 to 3 fluoro substituents;

$R^{16}$ is hydrogen or $(C_1-C_3)$alkyl optionally substituted with 1 to 5 fluoro substituents;

$R^{17}$ is $(C_1-C_6)$alkyl optionally substituted with 1 to 6 fluoro substituents, $Ph^1$-$(C_1-C_3)$alkyl optionally substituted on the alkyl moiety with 1 to 4 fluoro substituents, or $(C_3-C_7)$cycloalkyl-$(C_0-C_3)$alkyl optionally substituted on the cycloalkyl moiety with 1 to 4 substituents independently selected from methyl and fluoro and independently optionally substituted on the alkyl moiety with 1 to 4 fluoro substituents;

$R^{18}$ is hydrogen or $(C_1-C_3)$alkyl, or $R^{17}$ and $R^{18}$ taken together with the nitrogen atom to which they are attached, form $Het^1$, imidazolidin-2-onyl, imidazolidin-2,4-dionyl, or tetrahydropyrimidin-2-onyl optionally substituted with 1 or 2 methyl substituents;

$R^{19}$ is $(C_1-C_3)$alkyl optionally substituted with 1 to 5 fluoro substituents;

$Ar^2$ is an aromatic heterocycle substituent selected from the group consisting of pyrrolyl, pyrazolyl, imidazolyl, pyrimidinyl, oxazolyl, isoxazolyl, 1,2,3-oxadiazolyl, 1,2,4-oxadiazolyl, 1,3,4-oxadiazolyl, 1,2,5-oxadiazolyl, thiophenyl, thiazolyl, isothiazolyl, and 1,2,3-thiadiazolyl, 1,2,4-thiadiazolyl, 1,3,4-thiadiazolyl, 1,2,5-thiadiazolyl, 1,2,3-triazolyl, 1,2,4-triazolyl, wherein the heterocycle is substituted with a substituent selected from the group consisting of $H_2N$—, $R^{15}R^{17}N$—, $R^{17}NH$—$C(O)$—, $R^{17}C(O)NH$—, $R^{17}O$—$C(O)NH$—, $(C_1-C_6)$alkyl-$C(O)$—, $(C_3-C_7)$cycloalkyl-$(C_0-C_3)$alkyl-$C(O)$—, $(C_3-C_7)$cycloalkyl-$(C_0-C_3)$alkyl, N-linked $Het^1$, and N-linked $Het^1$-$C(O)$—, and which is optionally further substituted with a substituent selected from the group consisting of methyl, cyano, halo, and trifluoromethyl;

$Ar^3$ is an aromatic heterocycle substituent selected from the group consisting of pyrrolyl, furanyl, thiophenyl, thiazolyl, isothiazolyl, oxazolyl, isoxazolyl, and pyridyl, any of which may optionally be substituted with 1 to 3 substituents independently selected from the group consisting of halo, $(C_1-C_3)$alkyl, $(C_1-C_3)$alkoxy, —$CF_3$, —O—$CF_3$, nitro, cyano, and trifluoromethylthio;

$Het^1$ is a saturated, nitrogen-containing heterocycle substituent selected from the group consisting of pyrrolidinyl, piperidinyl, homopiperidinyl, morpholinyl, thiomorpholinyl, homomorpholinyl, and homothiomorpholinyl, any of which may optionally be substituted with $(C_1-C_5)$alkyl or with 2 methyl substituents;

$Het^2$ is a saturated, oxygen-containing heterocycle substituent selected from the group consisting of tetrahydrofuranyl and tetrahydropyranyl, any of which may optionally be substituted with $(C_1-C_6)$alkyl or with 2 methyl substituents;

$Het^3$ is a nitrogen containing heterocycle selected from the group consisting of pyrrolidin-2-onyl, piperidin-2-onyl, oxazolidin-2-onyl, pyrrolin-2-onyl, and dihydropyridin-2-onyl;

or a pharmaceutically acceptable salt or solvate thereof.

This invention also provides pharmaceutical compositions which comprise a compound of Formula I, or a pharmaceutically acceptable salt or solvate thereof, in association with a pharmaceutically acceptable carrier, diluent, or excipient.

In another aspect of the present invention, there is provided a method for increasing activation of the 5-$HT_{2C}$ receptor in mammals comprising administering to a mammal in need of such activation an effective amount of a compound of Formula I, or a pharmaceutically acceptable salt or solvate thereof.

The present invention also provides a method for treating obesity in mammals comprising administering to a mammal in need of such treatment an effective amount of a compound of Formula I, or a pharmaceutically acceptable salt or solvate thereof.

The present invention also provides a method for treating obsessive/compulsive disorder in mammals comprising administering to a mammal in need of such treatment an effective amount of a compound of Formula I, or a pharmaceutically acceptable salt or solvate thereof.

Furthermore, the present invention provides a method for treating depression in mammals comprising administering to a mammal in need of such treatment an effective amount of a compound of Formula I, or a pharmaceutically acceptable salt or solvate thereof.

Furthermore, the present invention provides a method for treating anxiety in mammals comprising administering to a mammal in need of such treatment an effective amount of a compound of Formula I, or a pharmaceutically acceptable salt or solvate thereof.

In preferred embodiments of the above methods of treatment utilizing a compound of Formula I, or a pharmaceutically acceptable salt or solvate thereof, the mammal is a human.

In another aspect of the present invention, there is provided a compound of Formula I, or a pharmaceutically acceptable salt or solvate thereof, for use in selectively increasing activation of the 5-$HT_{2C}$ receptor and/or for use in treating a variety of disorders associated with decreased activation of 5-$HT_{2C}$ receptors. Preferred embodiments of this aspect of the invention include a compound of Formula I, or a pharmaceutically acceptable salt or solvate thereof, for use in the treatment of obesity, hyperphagia, obsessive/compulsive disorder, depression, anxiety, substance abuse, sleep disorder, hot flashes, and/or hypogonadism. Particularly preferred embodiments of this aspect of the invention include the treatment of obesity, obsessive/compulsive disorder, depression, and/or anxiety.

In another aspect of the present invention, there is provided the use of one or more compounds of Formula I, or a pharmaceutically acceptable salt or solvate thereof, in the manufacture of a medicament for the activation of 5-$HT_{2C}$ receptors in a mammal. In preferred embodiments of this aspect of the invention, there is provided the use of one or more compounds of Formula I, or a pharmaceutically acceptable salt or solvate thereof, in the manufacture of a medicament for the treatment of obesity, hyperphagia, obsessive/compulsive disorder, depression, anxiety, substance abuse, sleep disorder, hot flashes, and/or hypogonadism. Particularly preferred embodiments of this aspect of the invention include the use of one or more compounds of Formula I, or a pharmaceutically acceptable salt or solvate thereof, in the manufacture of medicaments for the treatment of obesity, obsessive/compulsive disorder, depression, and/or anxiety.

Additionally, the present invention provides a pharmaceutical formulation adapted for the treatment of obesity, or for the treatment of obsessive/compulsive disorder, or for the treatment of depression, or for the treatment of anxiety, each of which comprise a compound of Formula I, or a pharmaceutically acceptable salt or solvate thereof, in association with a pharmaceutically acceptable carrier, diluent or excipient.

In those instances where the disorders which can be treated by 5-HT$_{2C}$ agonists are known by established and accepted classifications, their classifications can be found in various sources. For example, at present, the fourth edition of the Diagnostic and Statistical Manual of Mental Disorders (DSM-IV™) (1994, American Psychiatric Association, Washington, D.C.), provides a diagnostic tool for identifying many of the disorders described herein. Also, the International Classification of Diseases, Tenth Revision (ICD-10), provides classifications for many of the disorders described herein. The skilled artisan will recognize that there are alternative nomenclatures, nosologies, and classification systems for disorders described herein, including those as described in the DSM-IV and ICD-10, and that terminology and classification systems evolve with medical scientific progress.

The general chemical terms used throughout have their usual meanings. For example, the term "alkyl" refers to a branched or unbranched saturated hydrocarbon group. The term "n-alkyl" refers to an unbranched alkyl group. By way of illustration, but without limitation, the term "$(C_1-C_2)$alkyl" refers to methyl and ethyl. The term "$(C_1-C_3)$ n-alkyl" refers to methyl, ethyl, and propyl. The term "$(C_1-C_3)$alkyl" refers to methyl, ethyl, propyl, and isopropyl. The term "$(C_1-C_5)$alkyl" refers to all branched and unbranched alkyl groups having from one to five carbon atoms. The term "$(C_1-C_6)$alkyl" refers to all branched and unbranched alkyl groups having from one to six carbon atoms. The term "$(C_3-C_6)$alkyl" refers to all branched and unbranched alkyl groups having from three to six carbon atoms. The term "$(C_2-C_6)$alkyl" refers to all branched and unbranched alkyl groups having from two to six carbon atoms.

$(C_x-C_y)$alkyl may also be used in conjunction with other substituents to indicate a branched or unbranched saturated hydrocarbon linker for the substituent, where x and y indicate the range of carbon atoms permitted in the linker moiety. By way of illustration, but without limitation, —$(C_0-C_1)$alkyl refers to a single bond or a methylene linker moiety; —$(C_0-C_2)$alkyl refers to a single bond, methylene, methyl-methylene, or ethylene linker moiety; —$(C_0-C_3)$alkyl further includes trimethylene, alpha- or beta-methyl ethylene, or ethyl methylene; —$(C_0-C_5)$alkyl refers to a bond or a saturated, branched or unbranched hydrocarbon linker having from 1 to 5 carbon atoms. —$(C_1-C_2)$alkyl, —$(C_1-C_3)$alkyl, —$(C_1-C_5)$alkyl, and —$(C_1-C_6)$alkyl refer to branched or unbranched alkylene linkers having from 1 to 2, 3, 5, or 6 carbon atoms, respectively.

The term "alkenyl" refers to a branched or unbranched hydrocarbon group having one or more carbon-carbon double bonds. By way of illustration, but without limitation, the term "$(C_2-C_6)$alkenyl" refers to a branched or unbranched hydrocarbon group having from 2 to 6 carbon atoms and 1 or more carbon-carbon double bonds. Allyl means a propyl-2-en-1-yl moiety (CH$_2$=CH—CH$_2$—).

The term "$(C_3-C_7)$cycloalkyl" refers to cyclopropyl, cyclobutyl, cyclopentyl, cyclohexyl and cycloheptyl. Cycloalkylalkyl refers to a cycloalkyl moiety linked through a branched or unbranched alkylene linker, as for example, but without limitation, —CH$_2$—, —CH$_2$CH$_2$—, —CH(CH$_3$)—, —CH$_2$CH$_2$CH$_2$—, —CH$_2$CH(CH$_3$)—, —CH(CH$_3$)CH$_2$—, —CH(CH$_2$CH$_3$)—, and the like. $(C_3-C_7)$cycloalkyl($C_0$-$C_{1,2 \text{ or } 3}$)alkyl, refers to a cycloalkyl moiety linked through a single bond (i.e. $C_0$-alkyl) or an alkylene linker having 1, 2, or 3 carbon atoms, respectively. Each alkyl, cycloalkyl, and cycloalkylalkyl group may be optionally substituted as provided for herein.

The terms "alkoxy", "phenyloxy", "sulfonyloxy", and "carbonyloxy" refer to an alkyl group, phenyl group, sulfonyl group, or carbonyl group, respectively, that is bonded through an oxygen atom.

The terms "alkylthio", "trifluoromethylthio", "cycloalkylthio" ("cyclohexylthio"), "phenylthio", and "furanylthio" refer to an alkyl group, trifluoromethyl group, cycloalkyl (cyclohexyl) group, phenyl group, or furanyl group, respectively, that is bonded through a sulfur atom.

The terms "alkylcarbonyl", "alkoxycarbonyl", "phenylcarbonyl", and "phenyloxycarbonyl", refer to an alkyl, alkoxy, phenyl, or phenyloxy group bonded through a carbonyl moiety.

The terms "alkylsulfonyl" (t-butylsulfonyl), "$(C_3-C_7)$cycloalkylsulfonyl", "phenylsulfonyl", "Ph$^1$-$(C_0-C_3)$alkylsulfonyl", and "Ar$^2$—$(C_0-C_3)$alkylsulfonyl", refer to an alkyl (t-butyl), $(C_3-C_7)$cycloalkyl, phenyl, Ph$^1$-$(C_0-C_3)$alkyl, or Ar$^2$—$(C_0-C_3)$alkyl group bonded through a sulfonyl moiety (—SO$_2$—).

The term "N-linked" means that the referenced moiety is linked through its nitrogen atom, by way of illustration, but without limitation, N-linked Het$^1$ means the Het$^1$ moiety is linked through a nitrogen atom in the ring of the Het$^1$ moiety.

The term "halo" refers to fluoro, chloro, bromo, or iodo. Preferred halo groups are fluoro, chloro, and bromo. More preferred halo groups are fluoro and chloro.

The terms "gem-", "geminal", or "geminate" refer to two identical substituents bonded to a common carbon atom, as for example, but without limitation, gem-methyl, meaning two methyl groups bound to a common carbon atom, as for instance in a 3,3-dimethyltetrahydrobenzofuranyl group. For the purposes of this application, gem-ethano means an ethylene substituent wherein both carbons are bound to the same carbon atom of the substituted group to form a cyclopropyl moiety, as for example, but without limitation, the ethano substituent on the 2-phenyl-(1,1-ethano)ethylamino group below:

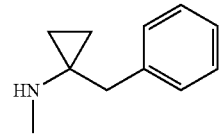

The term "amino protecting group" as used in this specification refers to a substituent commonly employed to block or protect the amino functionality while reacting other functional groups on the compound. Examples of such amino protecting groups include the formyl group, the trityl group, the acetyl group, the trichloroacetyl group, the trifluoroacetyl group, the chloroacetyl, bromoacetyl, and iodoacetyl groups, carbamoyl-type blocking groups such as benzyloxycarbonyl, 9-fluorenylmethoxycarbonyl ("FMOC"), t-butoxycarbonyl (t-BOC), and like amino protecting groups. The species of amino protecting group employed is not critical so long as the derivatized amino group is stable to the conditions of subsequent reactions on other positions of the molecule and can be removed at the appropriate point without disrupting the remainder of the molecule. The selection and use (addition and subsequent removal) of amino protecting groups is well known within the ordinary skill of the art. Further examples of groups referred to by the above terms are described by T. W.

Greene and P. G. M. Wuts, "Protective Groups in Organic Synthesis", 3$^{rd}$ edition, John Wiley and Sons, New York, N.Y., 1999, chapter 7, hereafter referred to as "Greene".

The term "pharmaceutical" or "pharmaceutically acceptable" when used herein as an adjective, means substantially non-toxic and substantially non-deleterious to the recipient.

By "pharmaceutical composition" it is further meant that the carrier, solvent, excipients and/or salt must be compatible with the active ingredient of the composition (e.g. a compound of Formula I). It is understood by those of ordinary skill in this art that the terms "pharmaceutical formulation" and "pharmaceutical composition" are generally interchangeable, and they are so used for the purposes of this application.

The term "effective amount" means an amount of a compound of Formula I which is capable of activating 5-HT$_{2C}$ receptors and/or eliciting a given pharmacological effect.

The term "suitable solvent" refers to any solvent, or mixture of solvents, inert to the ongoing reaction that sufficiently solubilizes the reactants to afford a medium within which to effect the desired reaction.

It is understood that compounds of the present invention may exist as stereoisomers. As such, all enantiomers, diastereomers, and mixtures thereof, are included within the scope of the present invention. Where specific stereochemistries are identified in this application, the Cahn-Prelog-Ingold designations of (R)—and (S)—and the cis and trans designation of relative stereochemistry are used to refer to specific isomers and relative stereochemistry. Known optical rotations are designated by (+) and (−) for dextrorotatary and levorotatary, respectively. Where a chiral compound is resolved into its isomers, but absolute configurations or optical rotations are not determined, the isomers are arbitrarily designated as isomer 1, isomer 2, etc. While all enantiomers, diastereomers, and mixtures thereof, are contemplated within the present invention, preferred embodiments are single enantiomers and single diastereomers.

It is generally understood by those skilled in this art, that compounds intended for use in pharmaceutical compositions are routinely, though not necessarily, converted to a salt form in efforts to optimize such characteristics as the handling properties, stability, pharmacokinetic, and/or bioavailability, etc. Methods for converting a compound to a given salt form are well known in the art (see for example, Berge, S. M, Bighley, L. D., and Monkhouse, D. C., *J. Pharm. Sci.*, 66:1, (1977)). In that the compounds of the present invention are amines and therefore basic in nature, they readily react with a wide variety of pharmaceutically acceptable organic and inorganic acids to form pharmaceutically acceptable acid addition salts therewith. Such salts are also embodiments of this invention.

Typical inorganic acids used to form such salts include hydrochloric, hydrobromic, hydroiodic, nitric, sulfuric, phosphoric, hypophosphoric, metaphosphoric, pyrophosphoric acid, and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include chloride, bromide, iodide, nitrate, acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, isobutyrate, phenylbutyrate, α-hydroxybutyrate, butyne-1,4-dicarboxylate, hexyne-1,4-dicarboxylate, caprate, caprylate, cinnamate, citrate, formate, fumarate, glycolate, heptanoate, hippurate, lactate, malate, maleate, hydroxymaleate, malonate, mandelate, nicotinate, isonicotinate, oxalate, phthalate, terephthalate, propiolate, propionate, phenylpropionate, salicylate, sebacate, succinate, suberate, benzenesulfonate, p-bromobenzenesulfonate, chlorobenzenesulfonate, ethylsulfonate, 2-hydroxyethylsulfonate, methylsulfonate (mesylate), naphthalene-1-sulfonate, naphthalene-2-sulfonate, naphthalene-1,5-sulfonate, p-toluenesulfonate, xylenesulfonate, tartrate, and the like.

It is well known that such compounds can form salts in various molar ratios with the acid to provide, for example, the hemi-acid, mono-acid, di-acid salt, etc. Where in the salt formation procedure, the acid is added in a specific stoichiometric ratio, unless otherwise analyzed to confirm, the salt is presumed, but not known, to form in that molar ratio. Terms such as "(acid)$_x$," are understood to mean that the molar ratio of the salt formed is not known and can not be presumed, as for example, but without limitation, (HCl)$_x$ and (methanesulfonic acid)$_x$.

Abbreviations used herein are defined as follows:
"ADPP" means 1,1'-(azodicarbonyl)dipiperidine.
"AIBN" means 2,2'-azobisisobutyronitrile.
"BINAP" means (±)-2,2'-bis(diphenylphosphino)-1,1'-binaphthalene.
"Boc" or "t-Boc" means tert-butoxycarbonyl.
"Brine" means a saturated aqueous sodium chloride solution.
"t-Bu" means tert-butyl.
"CV" means calorific value of oxygen.
"DCE" means 1,2-dichloroethane.
"DCM" means dichloromethane (i.e. methylene chloride, CH$_2$Cl$_2$).
"DIBAL-H" means diisobutylaluminum hydride.
"DMAP" means 4-dimethylaminopyridine.
"DMF" means N,N-dimethylformamide.
"DMSO" means dimethylsulfoxide.
"DOI" means (±)-1-(2,5-dimethoxy-4-[$^{125}$I]-iodophenyl)-2-aminopropane.
"DPPF" means 1,1'-bis(diphenylphosphino)ferrocene.
"EDC" means 1-[3-(dimethylamino)propyl]-3-ethylcarbodiimide hydrochloride.
"EDTA" means ethylenediaminetetraacetic acid.
"ee" means enantiomeric excess.
"EE" means energy expenditure.
"EtOAc" means ethyl acetate.
"EtOH" means ethanol.
"GC-MS" means gas chromatography-mass spectrometry.
"GDP" means guanosine diphosphate.
"GTP" means guanosine triphosphate.
"GTPγ[$^{35}$S]" means guanosine triphosphate having the terminal phosphate substituted with $^{35}$S in place of an oxygen.
"HOBt" means 1-hydroxybenzotriazole hydrate.
"HPLC" means high-pressure liquid chromatography.
"ISPA" means immunoadsorption scintillation proximity assay.
"MeOH" means methanol.
"MS (APCI+)" means mass spectroscopy using atmospheric pressure chemical ionization.
"MS (ES+)" means mass spectroscopy using electrospray ionization.
"NBS" means N-bromosuccinimide.
"NMP" means 1-methyl-2-pyrrolidinone.
"Pd/C" means palladium on activated carbon.
"psi" means pounds per square inch.
"RQ" means respiratory quotient.
"SCX chromatography" means chromatography on a SCX column or cartridge.

"SCX column" or "SCX cartridge", as used herein, refers to a Varian Bond Elute® silica based strong cation exchange resin column or disposable cartridge or equivalent.

"SFC" means supercritical fluid chromatography.

"Tf" in a chemical structure means the trifluoromethanesulfonyl moiety (—SO$_2$CF$_3$).

"Ts" in a chemical structure means the 4-methylbenzenesulfonyl moiety.

"TFA" means trifluoroacetic acid.

"THF" means tetrahydrofuran.

While all of the compounds of the present invention are useful as 5-HT$_{2C}$ agonists, certain classes are preferred, as for example, compounds having any of the following enumerated selections of substituents: Compounds wherein 1) $R^7$ is halo;
2) $R^7$ is chloro;
3) $R^7$ is fluoro;
4) $R^7$ is (C$_1$-C$_6$)alkyl optionally substituted with 1 to 6 fluoro substituents;
5) $R^7$ is (C$_1$-C$_3$)alkyl optionally substituted with 1 to 6 fluoro substituents;
6) $R^7$ is —CF$_3$;
7) $R^7$ is (C$_3$-C$_6$)alkenyl optionally substituted with 1 to 6 fluoro substituents;
8) $R^7$ is (C$_3$-C$_6$)alkenyl;
9) $R^7$ is cyano;
10) $R^{1-5}$ are each hydrogen;
11) $R^5$ is methyl or ethyl;
12) $R^5$ is methyl;
13) $R^3$ is methyl;
14) $R^8$ is hydrogen;
15) $R^9$ is hydrogen;
16) $R^9$ is (C$_1$-C$_3$)alkoxy;
17) $R^9$ is methoxy;
18) $R^9$ is halo;
19) $R^9$ is chloro;
20) $R^9$ is cyano;
21) $R^9$ is —CF$_3$;
22) $R^{11}$ is hydrogen;
23) $R^{11}$ is methyl;
24) $R^{10}$ is Ph$^2$-methyl-;
25) $R^{10}$ is Ph$^2$-CH(CH$_3$)— (i.e. C$_1$-n-alkyl substituted with methyl);
26) $R^{10}$ is Ph$^2$-CH(CH$_2$CH$_3$)— (i.e. C$_1$-n-alkyl substituted with ethyl);
27) $R^{10}$ is

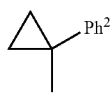

(i.e. C$_1$-n-alkyl substituted with gem-ethano);

28) $R^{10}$ is Ar$^1$-methyl-;
29) $R^{10}$ is Ar$^1$—CH(CH$_3$)— (i.e. C$_1$-n-alkyl substituted with methyl);
30) $R^{10}$ is Ar$^2$—CH(CH$_2$CH$_3$)— (i.e. C$_1$-n-alkyl substituted with ethyl);
31) $R^{10}$ is

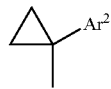

(i.e. C$_1$-n-alkyl substituted with gem-ethano);

32) Ph$^2$ is substituted in the para position;
33) Ph$^2$ is substituted in the para position and further substituted in the meta-position with halo, hydroxy, or cyano;
34) Ph$^2$ is substituted in the para position and further substituted in the meta-position with fluoro or chloro;
35) Ph$^2$ is monosubstituted;
36) Ph$^2$ is monosubstituted in the para position;
37) Ph$^2$ is substituted with Het$^1$-(C$_0$-C$_3$)alkyl optionally substituted on the alkyl moiety with 1 to 6 fluoro substituents;
38) Ph$^2$ is substituted with Het$^2$-(C$_0$-C$_3$)alkyl optionally substituted on the alkyl moiety with 1 to 6 fluoro substituents;
39) Ph$^2$ is substituted with Het$^3$-(C$_0$-C$_3$)alkyl optionally substituted on the alkyl moiety with 1 to 6 fluoro substituents;
40) Ph$^2$ is substituted with Ar$^2$—(C$_0$-C$_3$)alkyl optionally substituted on the alkyl moiety with 1 to 6 fluoro substituents;
41) Ph$^2$ is substituted with (C$_1$-C$_6$)alkyl-C(R$^{14}$)=C(R$^{14}$)— optionally substituted on the alkyl moiety with 1 to 6 fluoro substituents;
42) Ph$^2$ is substituted with (R$^{14}$)$_2$C=C[(C$_1$-C$_6$)alkyl]- optionally substituted on the alkyl moiety with 1 to 6 fluoro substituents;
43) Ph$^2$ is substituted with (C$_3$-C$_7$)cycloalkyl-(C$_0$-C$_3$)alkyl-C(R$^{14}$)=C(R$^{15}$)— optionally substituted on the cycloalkyl moiety with 1 to 4 substituents selected from the group consisting of methyl and fluoro, and further optionally substituted on the alkyl moiety with 1 to 4 fluoro substituents;
44) Ph$^2$ is substituted with (R$^{15}$)CH=C[(C$_3$-C$_7$)cycloalkyl-(C$_0$-C$_3$)alkyl]- optionally substituted on the cycloalkyl moiety with 1 to 4 substituents selected from the group consisting of methyl and fluoro, and further optionally substituted on the alkyl moiety with 1 to 4 fluoro substituents;
45) Ph$^2$ is substituted with (C$_1$-C$_6$)alkyl-C≡C— optionally substituted on the alkyl moiety with 1 to 6 fluoro substituents;
46) Ph$^2$ is substituted with (C$_3$-C$_7$)cycloalkyl-(C$_0$-C$_3$)alkyl-C≡C— optionally substituted on the cycloalkyl moiety with 1 to 4 substituents selected from the group consisting of methyl and fluoro, and further optionally substituted on the alkyl moiety with 1 to 4 fluoro substituents;
47) Ph$^2$ is substituted with (C$_3$-C$_7$)cycloalkyl-(C$_0$-C$_3$)alkyl-C(O)—(C$_1$-C$_5$)alkyl optionally substituted on the cycloalkyl moiety with 1 to 4 substituents selected from the group consisting of methyl and fluoro, and further optionally substituted on either or both alkyl moieties independently with 1 to 4 fluoro substituents;
48) Ph$^2$ is substituted with Ph$^1$-(C$_0$-C$_3$)alkyl-C(O)—(C$_1$-C$_5$)alkyl optionally substituted on either or both alkyl moieties independently with 1 to 4 fluoro substituents;
49) Ph$^2$ is substituted with pyridyl-(C$_0$-C$_3$)alkyl-C(O)—(C$_1$-C$_5$)alkyl, optionally substituted on the pyridyl moiety with 1 to 3 substituents independently selected from the group consisting of halo, (C$_1$-C$_3$)alkyl, (C$_1$-C$_3$)

alkoxy, —$CF_3$, —O—$CF_3$, nitro, cyano, and trifluoromethylthio, and optionally substituted on either or both alkyl moieties independently with 1 to 4 fluoro substituents;

50) $Ph^2$ is substituted with $(C_1-C_6)$alkyl-O—$(C_1-C_3)$alkyl-C(O)— optionally substituted on the $(C_1-C_6)$alkyl moiety with 1 to 6 fluoro substituents and further optionally substituted on the $(C_1-C_3)$alkyl moiety with 1 to 4 fluoro substituents;

51) $Ph^2$ is substituted with $(C_3-C_7)$cycloalkyl-$(C_0-C_3)$alkyl-O—$(C_1-C_3)$alkyl-C(O)— optionally substituted on the cycloalkyl moiety with 1 to 4 substituents selected from the group consisting of methyl and fluoro, and further optionally substituted on either or both alkyl moieties independently with 1 to 4 fluoro substituents;

52) $Ph^2$ is substituted with $Ph^1$-$(C_0-C_3)$alkyl-O—$(C_1-C_3)$alkyl-C(O)— optionally substituted on either or both alkyl moieties independently with 1 to 4 fluoro substituents;

53) $Ph^2$ is substituted with $(C_1-C_6)$alkyl-S—$(C_1-C_3)$alkyl-C(O)— optionally substituted on the $(C_1-C_6)$alkyl moiety with 1 to 6 fluoro substituents and further optionally substituted on the $(C_1-C_3)$alkyl moiety with 1 to 4 fluoro substituents;

54) $Ph^2$ is substituted with $(C_3-C_7)$cycloalkyl-$(C_0-C_3)$alkyl-S—$(C_1-C_3)$alkyl-C(O)— optionally substituted on the cycloalkyl moiety with 1 to 4 substituents selected from the group consisting of methyl and fluoro, and further optionally substituted on either or both alkyl moieties independently with 1 to 4 fluoro substituents;

55) $Ph^2$ is substituted with $Ph^1$-$(C_0-C_3)$alkyl-S—$(C_1-C_3)$alkyl-C(O)— optionally substituted on either or both alkyl moieties with 1 to 4 fluoro substituents;

56) $Ph^2$ is substituted with $(C_1-C_6)$alkyl-$NR^{16}$—$(C_1-C_3)$alkyl-C(O)— optionally substituted on the $(C_1-C_6)$alkyl moiety with 1 to 6 fluoro substituents and further optionally substituted on the $(C_1-C_3)$alkyl moiety with 1 to 4 fluoro substituents;

57) $Ph^2$ is substituted with $(C_3-C_7)$cycloalkyl-$(C_0-C_3)$alkyl-$NR^{16}$—$(C_1-C_3)$alkyl-C(O)— optionally substituted on the cycloalkyl moiety with 1 to 4 substituents selected from the group consisting of methyl and fluoro, and further optionally substituted on either or both alkyl moieties independently with 1 to 4 fluoro substituents;

58) $Ph^2$ is substituted with $Ph^1$-$(C_0-C_3)$alkyl-$NR^{16}$—$(C_1-C_3)$alkyl-C(O)-optionally substituted on either or both alkyl moieties independently with 1 to 4 fluoro substituents;

59) $Ph^2$ is substituted with $(C_1-C_6)$alkyl-O—$(C_1-C_3)$alkyl-$SO_2$— optionally substituted on the $(C_1-C_6)$alkyl moiety with 1 to 6 fluoro substituents and further optionally substituted on the $(C_1-C_3)$alkyl moiety with 1 to 4 fluoro substituents;

60) $Ph^2$ is substituted with $(C_3-C_7)$cycloalkyl-$(C_0-C_3)$alkyl-O—$(C_1-C_3)$alkyl-$SO_2$— optionally substituted on the cycloalkyl moiety with 1 to 4 substituents selected from the group consisting of methyl and fluoro, and further optionally substituted on either or both alkyl moieties independently with 1 to 4 fluoro substituents;

61) $Ph^2$ is substituted with $Ph^1$-$(C_0-C_3)$alkyl-O—$(C_1-C_3)$alkyl-$SO_2$— optionally substituted on either or both alkyl moieties independently with 1 to 4 fluoro substituents;

62) $Ph^2$ is substituted with $(C_1-C_6)$alkyl-S—$(C_1-C_3)$alkyl-$SO_2$— optionally substituted on the $(C_1-C_6)$alkyl moiety with 1 to 6 fluoro substituents and further optionally substituted on the $(C_1-C_3)$alkyl moiety with 1 to 4 fluoro substituents;

63) $Ph^2$ is substituted with $(C_3-C_7)$cycloalkyl-$(C_0-C_3)$alkyl-S—$(C_1-C_3)$alkyl-$SO_2$—optionally substituted on the cycloalkyl moiety with 1 to 4 substituents selected from the group consisting of methyl and fluoro, and further optionally substituted on either or both alkyl moieties independently with 1 to 4 fluoro substituents;

64) $Ph^2$ is substituted with $Ph^1$-$(C_0-C_3)$alkyl-S—$(C_1-C_3)$alkyl-$SO_2$— optionally substituted on either or both alkyl moieties independently with 1 to 4 fluoro substituents;

65) $Ph^2$ is substituted with $(C_1-C_6)$alkyl-$NR^{16}$—$(C_1-C_3)$alkyl-$SO_2$— optionally substituted on the $(C_1-C_6)$alkyl moiety with 1 to 6 fluoro substituents and further optionally substituted on the $(C_1-C_3)$alkyl moiety with 1 to 4 fluoro substituents;

66) $Ph^2$ is substituted with $(C_3-C_7)$cycloalkyl-$(C_0-C_3)$alkyl-$NR^{16}$—$(C_1-C_3)$alkyl-$SO_2$— optionally substituted on the cycloalkyl moiety with 1 to 4 substituents selected from the group consisting of methyl and fluoro, and further optionally substituted on either or both alkyl moieties independently with 1 to 4 fluoro substituents;

67) $Ph^2$ is substituted with $Ph^1$-$(C_0-C_3)$alkyl-$NR^{16}$—$(C_1-C_3)$alkyl-$SO_2$— optionally substituted on either or both alkyl moieties independently with 1 to 4 fluoro substituents;

68) $Ph^2$ is substituted with $R^{17}R^{18}$—N—C(O)—$(C_1-C_5)$alkyl optionally substituted on the alkyl moiety with 1 to 6 fluoro substituents;

69) $Ph^2$ is substituted with $(C_3-C_7)$cycloalkyl-$(C_0-C_3)$alkyl-S— optionally substituted on the cycloalkyl moiety with 1 to 4 substituents selected from the group consisting of methyl and fluoro, and further optionally substituted on the alkyl moiety with 1 to 4 fluoro substituents;

70) $Ph^2$ is substituted with $(C_3-C_7)$cycloalkyl-$(C_0-C_3)$alkyl-S—$(C_1-C_5)$alkyl optionally substituted on the cycloalkyl moiety with 1 to 4 substituents selected from the group consisting of methyl and fluoro, and further optionally substituted on either or both alkyl moieties independently with 1 to 4 fluoro substituents;

71) $Ph^2$ is substituted with $Ph^1$-$(C_0-C_3)$alkyl-S—$(C_1-C_5)$alkyl optionally substituted on the $(C_1-C_5)$alkyl moiety with 1 to 6 fluoro substituents;

72) $Ph^2$ is substituted with $Ar^3$—$(C_0-C_3)$alkyl-S—$(C_1-C_5)$alkyl optionally substituted on the $(C_1-C_5)$alkyl moiety with 1 to 6 fluoro substituents;

73) $Ph^2$ is substituted with $Ar^3$—$(C_0-C_3)$alkyl-O—$(C_1-C_5)$alkyl optionally substituted on the $(C_1-C_5)$alkyl moiety with 1 to 6 fluoro substituents;

74) $Ph^2$ is substituted with $Het^1$-$(C_0-C_3)$alkyl-S—$(C_0-C_5)$alkyl wherein $Het^1$ is linked through any carbon atom of $Het^1$ and wherein the $(C_0-C_5)$alkyl moiety is optionally substituted with 1 to 6 fluoro substituents;

75) $Ph^2$ is substituted with $Het^1$-$(C_0-C_3)$alkyl-O—$(C_0-C_5)$alkyl wherein $Het^1$ is linked through any carbon atom of $Het^1$ and wherein the $(C_0-C_5)$alkyl moiety is optionally substituted with 1 to 6 fluoro substituents;

76) $Ph^2$ is substituted with $Het^2$-$(C_0-C_3)$alkyl-S—$(C_0-C_5)$alkyl optionally substituted on the $(C_0-C_5)$alkyl moiety with 1 to 6 fluoro substituents;

77) $Ph^2$ is substituted with $R^{16}R^{19}$—N—C(O)—S—$(C_0-C_5)$alkyl optionally substituted on the alkyl moiety with 1 to 6 fluoro substituents;

78) $Ph^2$ is substituted with $R^{16}R^{19}$—N—C(O)—O—($C_0$-$C_5$)alkyl optionally substituted on the alkyl moiety with 1 to 6 fluoro substituents;
79) $Ph^2$ is substituted with $R^{16}R^{19}$—N—C(O)—$NR^{16}$—($C_0$-$C_5$)alkyl optionally substituted on the alkyl moiety with 1 to 6 fluoro substituents;
80) $Ph^2$ is substituted with ($C_1$-$C_6$)alkyl-C(O)—($C_1$-$C_3$)alkyl-S— optionally substituted on the ($C_1$-$C_6$)alkyl moiety with 1 to 6 fluoro substituents and further optionally substituted on the ($C_1$-$C_3$)alkyl moiety with 1 to 4 fluoro substituents;
81) $Ph^2$ is substituted with ($C_1$-$C_6$)alkyl-$SO_2$—($C_1$-$C_3$)alkyl-S— optionally substituted on the ($C_1$-$C_6$)alkyl moiety with 1 to 6 fluoro substituents and further optionally substituted on the ($C_1$-$C_3$)alkyl moiety with 1 to 4 fluoro substituents;
82) $Ph^2$ is substituted with ($C_3$-$C_7$)cycloalkyl-($C_0$-$C_3$)alkyl-C(O)—($C_1$-$C_3$)alkyl-O— optionally substituted on the cycloalkyl moiety with 1 to 4 substituents selected from the group consisting of methyl and fluoro, and further optionally substituted on either or both alkyl moieties independently with 1 to 4 fluoro substituents;
83) $Ph^2$ is substituted with ($C_3$-$C_7$)cycloalkyl-($C_0$-$C_3$)alkyl-$SO_2$—($C_1$-$C_3$)alkyl-O— optionally substituted on the cycloalkyl moiety with 1 to 4 substituents selected from the group consisting of methyl and fluoro, and further optionally substituted on either or both alkyl moieties independently with 1 to 4 fluoro substituents;
84) $Ph^2$ is substituted with ($C_3$-$C_7$)cycloalkyl-($C_0$-$C_3$)alkyl-C(O)—($C_1$-$C_3$)alkyl-S— optionally substituted on the cycloalkyl moiety with 1 to 4 substituents selected from the group consisting of methyl and fluoro, and further optionally substituted on either or both alkyl moieties independently with 1 to 4 fluoro substituents;
85) $Ph^2$ is substituted with ($C_3$-$C_7$)cycloalkyl-($C_0$-$C_3$)alkyl-$SO_2$—($C_1$-$C_3$)alkyl-S— optionally substituted on the cycloalkyl moiety with 1 to 4 substituents selected from the group consisting of methyl and fluoro, and further optionally substituted on either or both alkyl moieties independently with 1 to 4 fluoro substituents;
86) $Ph^2$ is substituted with $Ph^1$-($C_0$-$C_3$)alkyl-$SO_2$—($C_1$-$C_3$)alkyl-O— optionally substituted on either or both alkyl moieties independently with 1 to 4 fluoro substituents;
87) $Ph^2$ is substituted with $Ph^1$-($C_0$-$C_3$)alkyl-C(O)—($C_1$-$C_3$)alkyl-S— optionally substituted on either or both alkyl moieties independently with 1 to 4 fluoro substituents;
88) $Ph^2$ is substituted with $Ph^1$-($C_0$-$C_3$)alkyl-$SO_2$—($C_1$-$C_3$)alkyl-S— optionally substituted on either or both alkyl moieties independently with 1 to 4 fluoro substituents;
89) $Ph^2$ is substituted with $R^{17}R^{18}$N—C(O)—($C_1$-$C_3$)alkyl-S— optionally substituted on the alkyl moiety with 1 to 4 fluoro substituents;
90) $Ph^2$ is substituted with ($C_3$-$C_7$)cycloalkyl-($C_0$-$C_3$)alkyl-$SO_2$—($C_1$-$C_5$)alkyl optionally substituted on the cycloalkyl moiety with 1 to 4 substituents selected from the group consisting of methyl and fluoro, and further optionally substituted on the ($C_0$-$C_3$)alkyl moiety with 1 to 4 fluoro substituents and further optionally substituted on the ($C_1$-$C_5$)alkyl moiety with 1 to 6 fluoro substituents;
91) $Ph^2$ is substituted with $Ph^1$-($C_0$-$C_3$)alkyl-$SO_2$—($C_1$-$C_5$)alkyl optionally substituted on the ($C_0$-$C_3$)alkyl moiety with 1 to 4 fluoro substituents and further optionally substituted on the ($C_1$-$C_5$)alkyl moiety with 1 to 6 fluoro substituents;
92) $Ph^2$ is substituted with $Ar^3$—($C_0$-$C_3$)alkyl-$SO_2$—($C_1$-$C_5$)alkyl optionally substituted on the ($C_0$-$C_3$)alkyl moiety with 1 to 4 fluoro substituents and further optionally substituted on the ($C_1$-$C_5$)alkyl moiety with 1 to 6 fluoro substituents;
93) $Ph^2$ is substituted with $Het^2$-($C_0$-$C_3$)alkyl-$SO_2$—($C_0$-$C_5$)alkyl optionally substituted on the ($C_0$-$C_3$)alkyl moiety with 1 to 4 fluoro substituents and further optionally substituted on the ($C_1$-$C_5$)alkyl moiety with 1 to 6 fluoro substituents;
94) $Ph^2$ is substituted with $R^{17}R^{18}$N—($C_1$-$C_3$)alkyl optionally substituted on the alkyl moiety with 1 to 4 fluoro substituents;
95) $Ph^2$ is substituted with ($C_1$-$C_6$)alkyl-C(O)—N($R^{16}$)—($C_0$-$C_5$)alkyl optionally substituted on either or both alkyl moieties independently with 1 to 6 fluoro substituents;
96) $Ph^2$ is substituted with ($C_3$-$C_7$)cycloalkyl-C(O)—N($R^{16}$)—($C_0$-$C_5$)alkyl optionally substituted on the cycloalkyl moiety with 1 to 4 substituents selected from the group consisting of methyl and fluoro, and further optionally substituted on the alkyl moiety with 1 to 6 fluoro substituents;
97) $Ph^2$ is substituted with $Ph^1$-($C_0$-$C_3$)alkyl-C(O)—N($R^{16}$)—($C_0$-$C_5$)alkyl optionally substituted on the ($C_0$-$C_3$)alkyl moiety with 1 to 4 fluoro substituents and further optionally substituted on the ($C_0$-$C_5$)alkyl moiety with 1 to 6 fluoro substituents;
98) $Ph^2$ is substituted with $Ar^3$—($C_0$-$C_3$)alkyl-C(O)—N($R^{16}$)—($C_0$-$C_5$)alkyl optionally substituted on the ($C_0$-$C_3$)alkyl moiety with 1 to 4 fluoro substituents and further optionally substituted on the ($C_0$-$C_5$)alkyl moiety with 1 to 6 fluoro substituents;
99) $Ph^2$ is substituted with ($C_1$-$C_6$)alkyl-O—N=C($CH_3$)— optionally substituted on the ($C_1$-$C_6$)alkyl moiety with 1 to 6 fluoro substituents;
100) $Ph^2$ is substituted with ($C_0$-$C_3$)alkyl-O—N=C[($C_1$-$C_6$)alkyl]- optionally substituted on the ($C_0$-$C_3$)alkyl moiety with 1 to 4 fluoro substituents and further optionally substituted on the ($C_1$-$C_6$)alkyl moiety with 1 to 6 fluoro substituents;
101) $Ph^2$ is substituted with HO—N=C[($C_0$-$C_1$)alkyl-($C_3$-$C_7$)cycloalkyl]- optionally substituted on the cycloalkyl moiety with 1 to 4 substituents selected from the group consisting of methyl and fluoro, and further optionally substituted on either or both alkyl moieties independently with 1 to 2 fluoro substituents;
102) $Ph^2$ is substituted with $CH_3$—O—N=C[($C_0$-$C_1$)alkyl-($C_3$-$C_7$)cycloalkyl]-optionally substituted on the cycloalkyl moiety with 1 to 4 substituents selected from the group consisting of methyl and fluoro, and further optionally substituted on either or both alkyl moieties independently with 1 to 2 fluoro substituents;
103) $Ar^1$ is 5-$R^{13}$-pyridin-2-yl;
104) $Ar^1$ is 5-$R^{13}$-pyridin-2-yl and $R^{13}$ is $Ar^3$—($C_0$-$C_3$)alkyl-$SO_2$—($C_0$-$C_5$)alkyl optionally substituted on the ($C_0$-$C_3$)alkyl moiety with 1 to 4 fluoro substituents and further optionally substituted on the ($C_0$-$C_5$)alkyl moiety with 1 to 6 fluoro substituents;
105) $Ar^1$ is 5-$R^{13}$-pyridin-2-yl and $R^{13}$ is $Ar^3$—($C_0$-$C_3$)alkyl-$SO_2$—($C_0$-$C_5$)alkyl;
106) $Ar^1$ is 6-$R^{13}$-pyridin-3-yl;

107) $Ar^1$ is substituted with $Het^2$-$(C_0$-$C_3)$alkyl optionally substituted on the alkyl moiety with 1 to 4 fluoro substituents;

108) $Ar^1$ is substituted with $Het^3$-$(C_0$-$C_3)$alkyl optionally substituted on the alkyl moiety with 1 to 4 fluoro substituents;

109) $Ar^1$ is substituted with $Ar^2$—$(C_0$-$C_3)$alkyl optionally substituted on the alkyl moiety with 1 to 4 fluoro substituents;

110) $Ar^1$ is substituted with $(C_1$-$C_6)$alkyl-$C(R^{14})$=$C(R^{14})$— optionally substituted on the alkyl moiety with 1 to 6 fluoro substituents;

111) $Ar^1$ is substituted with $(R^{14})_2C$=$C[(C_1$-$C_6)$alkyl]- optionally substituted on the alkyl moiety with 1 to 6 fluoro substituents;

112) $Ar^1$ is substituted with $(C_3$-$C_7)$cycloalkyl-$(C_0$-$C_3)$alkyl-$C(R^{14})$=$C(R^{15})$— optionally substituted on the cycloalkyl moiety with 1 to 4 substituents selected from the group consisting of methyl and fluoro, and further optionally substituted on the alkyl moiety with 1 to 4 fluoro substituents;

113) $Ar^1$ is substituted with $(R^{15})CH$=$C[(C_3$-$C_7)$cycloalkyl-$(C_0$-$C_3)$alkyl]- optionally substituted on the cycloalkyl moiety with 1 to 4 substituents selected from the group consisting of methyl and fluoro, and further optionally substituted on the alkyl moiety with 1 to 4 fluoro substituents;

114) $Ar^1$ is substituted with $(C_1$-$C_6)$alkyl-C≡C— optionally substituted on the alkyl moiety with 1 to 6 fluoro substituents;

115) $Ar^1$ is substituted with $(C_3$-$C_7)$cycloalkyl-$(C_0$-$C_1)$alkyl-C≡C— optionally substituted on the cycloalkyl moiety with 1 to 4 substituents selected from the group consisting of methyl and fluoro, and further optionally substituted on the alkyl moiety with 1 to 2 fluoro substituents;

116) $Ar^1$ is substituted with $(C_1$-$C_6)$alkyl-O—$(C_1$-$C_5)$alkyl optionally substituted on either or both alkyl moieties independently with 1 to 6 fluoro substituents;

117) $Ar^1$ is substituted with $(C_3$-$C_7)$cycloalkyl-$(C_0$-$C_3)$alkyl-O—$(C_0$-$C_5)$alkyl optionally substituted on the cycloalkyl moiety with 1 to 4 substituents selected from the group consisting of methyl and fluoro, and further optionally substituted on the $(C_0$-$C_3)$alkyl moiety with 1 to 4 fluoro substituents and further optionally substituted on the $(C_0$-$C_5)$alkyl moiety with 1 to 6 fluoro substituents;

118) $Ar^1$ is substituted with $Ph^1$-$(C_0$-$C_3)$alkyl-O—$(C_0$-$C_5)$alkyl optionally substituted on the $(C_0$-$C_3)$alkyl moiety with 1 to 4 fluoro substituents and further optionally substituted on the $(C_0$-$C_5)$alkyl moiety with 1 to 6 fluoro substituents;

119) $Ar^1$ is substituted with $Ar^3$—$(C_0$-$C_3)$alkyl-O—$(C_0$-$C_5)$alkyl optionally substituted on the $(C_0$-$C_3)$alkyl moiety with 1 to 4 fluoro substituents and further optionally substituted on the $(C_0$-$C_5)$alkyl moiety with 1 to 6 fluoro substituents;

120) $Ar^1$ is substituted with $Het^2$-$(C_0$-$C_3)$alkyl-O—$(C_0$-$C_5)$alkyl optionally substituted on the $(C_0$-$C_3)$alkyl moiety with 1 to 4 fluoro substituents and further optionally substituted on the $(C_0$-$C_5)$alkyl moiety with 1 to 6 fluoro substituents;

121) $Ar^1$ is substituted with $(C_3$-$C_7)$cycloalkyl-$(C_0$-$C_3)$alkyl-$C(O)$—$(C_1$-$C_5)$alkyl optionally substituted on the cycloalkyl moiety with 1 to 4 substituents selected from the group consisting of methyl and fluoro, and further optionally substituted on the $(C_0$-$C_3)$alkyl moiety with 1 to 4 fluoro substituents and further optionally substituted on the $(C_1$-$C_5)$alkyl moiety with 1 to 6 fluoro substituents;

122) $Ar^1$ is substituted with $Ph^1$-$(C_0$-$C_3)$alkyl-$C(O)$—$(C_1$-$C_5)$alkyl optionally substituted on the $(C_0$-$C_3)$alkyl moiety with 1 to 4 fluoro substituents and further optionally substituted on the $(C_1$-$C_5)$alkyl moiety with 1 to 6 fluoro substituents;

123) $Ar^1$ is substituted with pyridyl-$(C_0$-$C_3)$alkyl-$C(O)$—$(C_1$-$C_5)$alkyl optionally be substituted on the pyridyl moiety with 1 to 3 substituents independently selected from the group consisting of halo, $(C_1$-$C_3)$alkyl, $(C_1$-$C_3)$alkoxy, —$CF_3$, —O—$CF_3$, nitro, cyano, and trifluoromethylthio, and optionally substituted on the $(C_0$-$C_3)$alkyl moiety with 1 to 4 fluoro substituents and further optionally substituted on the $(C_1$-$C_5)$alkyl moiety with 1 to 6 fluoro substituents;

124) $Ar^1$ is substituted with $(C_1$-$C_6)$alkyl-$C(O)$—$(C_1$-$C_3)$alkyl-O— optionally substituted on the $(C_1$-$C_6)$alkyl moiety with 1 to 6 fluoro substituents and further optionally substituted on the $(C_1$-$C_3)$alkyl moiety with 1 to 4 fluoro substituents;

125) $Ar^1$ is substituted with $(C_3$-$C_7)$cycloalkyl-$(C_0$-$C_3)$alkyl-$C(O)$—$(C_1$-$C_3)$alkyl-O— optionally substituted on the cycloalkyl moiety with 1 to 4 substituents selected from the group consisting of methyl and fluoro, and further optionally substituted on either or both of the alkyl moieties independently with 1 to 4 fluoro substituents;

126) $Ar^1$ is substituted with $Ph^1$-$(C_0$-$C_3)$alkyl-$C(O)$—$(C_1$-$C_3)$alkyl-O— optionally substituted on either or both of the alkyl moieties independently with 1 to 4 fluoro substituents;

127) $Ar^1$ is substituted with pyridyl-$(C_0$-$C_3)$alkyl-$C(O)$—$(C_1$-$C_3)$alkyl-O-optionally be substituted on the pyridyl moiety with 1 to 3 substituents independently selected from the group consisting of halo, $(C_1$-$C_3)$alkyl, $(C_1$-$C_3)$alkoxy, —$CF_3$, —O—$CF_3$, nitro, cyano, and trifluoromethylthio, and optionally substituted on either or both of the alkyl moieties independently with 1 to 4 fluoro substituents;

128) $Ar^1$ is substituted with $R^{17}R^{18}N$—$C(O)$—$(C_1$-$C_3)$alkyl-O— optionally substituted on the alkyl moiety with 1 to 4 fluoro substituents;

129) $Ar^1$ is substituted with $(C_3$-$C_7)$cycloalkyl-$(C_0$-$C_3)$alkyl-S— substituted on cycloalkyl moiety with 2 to 4 methyl substituents and further optionally substituted on the alkyl moiety with 1 to 4 fluoro substituents;

130) $Ar^1$ is substituted with $(C_1$-$C_6)$alkyl-S—$(C_1$-$C_5)$alkyl optionally substituted on either or both alkyl moieties independently with 1 to 6 fluoro substituents;

131) $Ar^1$ is substituted with $(C_3$-$C_7)$cycloalkyl-$(C_0$-$C_3)$alkyl-S—$(C_1$-$C_5)$alkyl optionally substituted on the cycloalkyl moiety with 1 to 4 substituents selected from the group consisting of methyl and fluoro, and further optionally substituted on the $(C_0$-$C_3)$alkyl moiety with 1 to 4 fluoro substituents, and further optionally substituted on the $(C_1$-$C_5)$alkyl moiety with 1 to 6 fluoro substituents;

132) $Ar^1$ is substituted with $Ph^1$-$(C_0$-$C_3)$alkyl-S—$(C_1$-$C_5)$alkyl optionally substituted on the $(C_0$-$C_3)$alkyl moiety with 1 to 4 fluoro substituents and further optionally substituted on the $(C_1$-$C_5)$alkyl moiety with 1 to 6 fluoro substituents;

133) $Ar^1$ is substituted with $Ar^3$—$(C_0$-$C_3)$alkyl-S—$(C_1$-$C_5)$alkyl optionally substituted on the $(C_0$-$C_3)$alkyl moi- 134) $Ar^1$ is substituted with $(C_1-C_6)$alkyl-C(O)—$(C_1-C_3)$alkyl-S— optionally substituted on the $(C_1-C_6)$alkyl moiety with 1 to 6 fluoro substituents and further optionally substituted on the $(C_1-C_3)$alkyl moiety with 1 to 4 fluoro substituents;

135) $Ar^1$ is substituted with $(C_3-C_7)$cycloalkyl-$(C_0-C_3)$alkyl-C(O)—$(C_1-C_3)$alkyl-S— optionally substituted on the cycloalkyl moiety with 1 to 4 substituents selected from the group consisting of methyl and fluoro, and further optionally substituted on either or both of the alkyl moieties independently with 1 to 4 fluoro substituents;

136) $Ar^1$ is substituted with $Ph^1$-$(C_0-C_3)$alkyl-C(O)—$(C_1-C_3)$alkyl-S— optionally substituted on either or both of the alkyl moieties independently with 1 to 4 fluoro substituents;

137) $Ar^1$ is substituted with pyridyl-$(C_0-C_3)$alkyl-C(O)—$(C_1-C_3)$alkyl-S— optionally be substituted on the pyridyl moiety with 1 to 3 substituents independently selected from the group consisting of halo, $(C_1-C_3)$alkyl, $(C_1-C_3)$alkoxy, —$CF_3$, —O—$CF_3$, nitro, cyano, and trifluoromethylthio, and optionally substituted on either or both of the alkyl moieties independently with 1 to 4 fluoro substituents;

138) $Ar^1$ is substituted with $R^{17}R^{18}N$—C(O)—$(C_1-C_3)$alkyl-S— optionally substituted on the alkyl moiety with 1 to 4 fluoro substituents;

139) $Ar^1$ is substituted with $(C_1-C_6)$alkyl-$SO_2$—$(C_0-C_5)$alkyl optionally substituted on either or both of the alkyl moieties independently with 1 to 6 fluoro substituents;

140) $Ar^1$ is substituted with $(C_3-C_7)$cycloalkyl-$(C_0-C_3)$alkyl-$SO_2$—$(C_0-C_5)$alkyl optionally substituted on the cycloalkyl moiety with 1 to 4 substituents selected from the group consisting of methyl and fluoro, and further optionally substituted on the $(C_0-C_3)$alkyl moiety with 1 to 4 fluoro substituents and further optionally substituted on the $(C_0-C_5)$alkyl moiety with 1 to 6 fluoro substituents;

141) $Ar^1$ is substituted with $Ph^1$-$(C_0-C_3)$alkyl-$SO_2$—$(C_0-C_5)$alkyl optionally substituted on the $(C_0-C_3)$alkyl moiety with 1 to 4 fluoro substituents and further optionally substituted on the $(C_0-C_5)$alkyl moiety with 1 to 6 fluoro substituents;

142) $Ar^1$ is substituted with $Ar^3$—$(C_0-C_3)$alkyl-$SO_2$—$(C_0-C_5)$alkyl optionally substituted on the $(C_0-C_3)$alkyl moiety with 1 to 4 fluoro substituents and further optionally substituted on the $(C_0-C_5)$alkyl moiety with 1 to 6 fluoro substituents;

143) $Ar^1$ is substituted with $Het^2$-$(C_0-C_3)$alkyl-$SO_2$—$(C_0-C_5)$alkyl optionally substituted on the $(C_0-C_3)$alkyl moiety with 1 to 4 fluoro substituents and further optionally substituted on the $(C_0-C_5)$alkyl moiety with 1 to 6 fluoro substituents;

144) $Ar^1$ is substituted with $R^{17}R^{18}$—N—C(O)—$(C_1-C_5)$alkyl optionally substituted on the $(C_1-C_5)$alkyl moiety with 1 to 6 fluoro substituents;

145) $Ar^1$ is substituted with $R^{17}R^{18}N$—$(C_1-C_3)$alkyl optionally substituted on the $(C_1-C_3)$alkyl moiety with 1 to 4 fluoro substituents;

146) $Ar^1$ is substituted with $(C_1-C_6)$alkyl-C(O)—N($R^{16}$)—$(C_0-C_5)$alkyl optionally substituted on either or both of the alkyl moieties independently with 1 to 6 fluoro substituents;

147) $Ar^1$ is substituted with $(C_3-C_7)$cycloalkyl-C(O)—N($R^{16}$)—$(C_0-C_5)$alkyl optionally substituted on the cycloalkyl moiety with 1 to 4 substituents selected from the group consisting of methyl and fluoro, and further optionally substituted on the $(C_0-C_5)$alkyl moiety with 1 to 6 fluoro substituents;

148) $Ar^1$ is substituted with $Ph^1$-$(C_0-C_3)$alkyl-C(O)—N($R^{16}$)—$(C_0-C_5)$alkyl optionally substituted on the $(C_0-C_3)$alkyl moiety with 1 to 4 fluoro substituents and further optionally substituted on the $(C_0-C_5)$alkyl moiety with 1 to 6 fluoro substituents;

149) $Ar^1$ is substituted with $Ar^3$—$(C_0-C_3)$alkyl-C(O)—N($R^{16}$)—$(C_0-C_5)$alkyl optionally substituted on the $(C_0-C_3)$alkyl moiety with 1 to 4 fluoro substituents and further optionally substituted on the $(C_0-C_5)$alkyl moiety with 1 to 6 fluoro substituents;

150) $Ar^2$ is substituted with $R^{15}R^{17}N$—, wherein $R^{15}$ is hydrogen and $R^{17}$ is $(C_1-C_6)$alkyl or $(C_3-C_7)$cycloalkyl-$(C_0-C_3)$alkyl;

151) $Ar^2$ is thiazolyl, isothiazolyl, oxazolyl, isoxazolyl, or pyrazolyl;

152) $Het^1$ is pyrrolidinyl, piperidinyl, homopiperidinyl, or morpholinyl optionally be substituted with $(C_1-C_6)$alkyl or with 2 methyl substituents;

153) $Het^1$ is pyrrolidinyl, piperidinyl, homopiperidinyl, or morpholinyl;

154) $Het^1$ is pyrrolidinyl, piperidinyl, homopiperidinyl optionally be substituted with $(C_1-C_6)$alkyl or with 2 methyl substituents;

155) $Het^1$ is pyrrolidinyl, piperidinyl, homopiperidinyl;

It will be understood that the above classes are preferred selections for each substituent and may be combined with preferred selections for other substituents to form additional preferred classes. Exemplary combinations include, but are not limited to:

156) Any one of preferred embodiments 1) through 9) (the preferred selections for $R^7$), combined with any one of preferred embodiments 24) through 155) (the preferred selections for $R^{10}$ and substituents thereon);

157) Any one of preferred embodiments 24) through 155) (the preferred selections for $R^{10}$ and substituents thereon), wherein $R^7$ is halogen;

158) Any one of preferred embodiments 24) through 155) (the preferred selections for $R^{10}$ and substituents thereon), wherein $R^7$ is chloro;

159) Any one of preferred embodiments 32) through 36) (the preferred positions for substituents on $Ph^2$), combined with any one of preferred embodiments 37) through 102) (the preferred selections for substituents on $Ph^2$);

160) Any one of preferred embodiments 103) through 149) (the preferred selections for mono-substitutions on $Ar^1$), wherein $Ar^1$ is further substituted with a substituent selected from the group consisting of halo, cyano, methyl, —$CF_3$, and methoxy;

161) A preferred combination according to any one of 156) through 160), wherein $R^{1-5}$, $R^8$, and $R^9$ are each hydrogen;

162) A preferred combination according to any one of 156) through 161), wherein $R^{11}$ is hydrogen;

Generally, a methylene linker from the 6-position nitrogen atom to the phenyl or pyridyl moiety is preferred over longer or larger linkers, as in compounds wherein $R^{10}$ is $Ph^2$-methyl- or $R^{10}$ is $Ar^1$-methyl-.

Also generally, for 6-benzylamino compounds, (i.e. compounds wherein $R^{10}$ is $Ph^2$) substitution at the para-position of the phenyl moiety is particularly preferred.

One favored group of compounds of the present invention is that represented by formula (Ia), and pharmaceutically acceptable salts thereof:

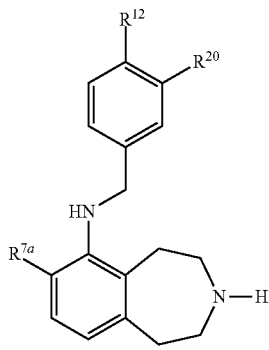

wherein
$R^{7a}$ is halogen, and especially chloro;
$R^{12}$ is as defined in relation to formula (I); and
$R^{20}$ is halo, hydroxy, or cyano;
or a pharmaceutically acceptable salt or solvate thereof.

Preferred compounds according to formula (Ia) are those wherein $R^{20}$ is fluoro or chloro.

Another favored group of compounds of the present invention is that represented by formula (Ib), and pharmaceutically acceptable salts thereof:

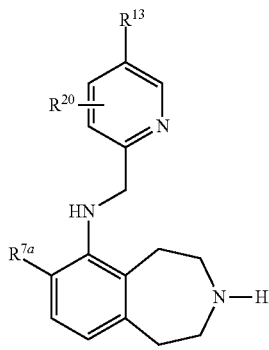

wherein
$R^{7a}$ is halogen, and especially chloro;
$R^{13}$ is as defined in relation to formula (I); and
$R^{20}$ is halo, hydroxy, or cyano;
or a pharmaceutically acceptable salt or solvate thereof.

Preferred compounds according to formula (Ib) are those wherein $R^{20}$ is fluoro or chloro.

Yet another favored group of compounds of the present invention is that represented by formula (Ic), and pharmaceutically acceptable salts thereof:

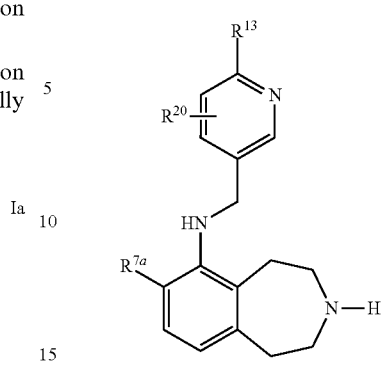

wherein
$R^{7a}$ is halogen, and especially chloro;
$R^{13}$ is as defined in relation to formula (I); and
$R^{20}$ is halo, hydroxy, or cyano;
or a pharmaceutically acceptable salt or solvate thereof.

Preferred compounds according to formula (Ic) are those wherein $R^{20}$ is fluoro or chloro.

Generally, compounds according to formula (Ib) are preferred over compounds of formula (Ic).

Specific preferred compounds of the present invention are those described in the Examples herein, including the free bases and the pharmaceutically acceptable salts and solvates thereof.

It will be appreciated that the preferred definitions of the various substituents recited herein may be taken alone or in combination and, unless otherwise stated, apply to the generic formula (I) for compounds of the present invention, as well as to the preferred classes of compounds represented by formulae (Ia), (Ib), and/or (Ic).

The compounds of the invention can be prepared according to the following synthetic schemes by methods well known and appreciated in the art. Suitable reaction conditions for the steps of these schemes are well known in the art and appropriate substitutions of solvents and co-reagents are within the skill of the art. Likewise, it will be appreciated by those skilled in the art that synthetic intermediates may by isolated and/or purified by various well known techniques as needed or desired, and that frequently, it will be possible to use various intermediates directly in subsequent synthetic steps with little or no purification. Furthermore, the skilled artisan will appreciate that in some circumstances, the order in which moieties are introduced is not critical. The particular order of steps required to produce the compounds of Formula I is dependent upon the particular compound being synthesized, the starting compound, and the relative liability of the substituted moieties as is well appreciated by those of ordinary skill in the art. All substituents, unless otherwise indicated, are as previously defined, and all reagents are well known and appreciated in the art.

The compounds of Formula I may be prepared by a variety of procedures, some of which are described below. All substituents, unless otherwise indicated, are as previously defined, and all reagents are well known and appreciated in the art. The products of each step can be recovered by conventional methods including extraction, evaporation, precipitation, chromatography, filtration, trituration, crystallization, and the like.

In Scheme I, appropriately substituted 6-trifluoromethanesulfonyloxy-2,3,4,5-tetrahydro-1H-benzo[d]azepines (a) can be converted to the compounds (c), under Buchwald's coupling conditions, by treatment with an appropriate amine (b) in the presence of an effective palladium catalyst/ligand system, and a base in a suitable solvent, typically toluene or 1,4-dioxane under an inert atmosphere. While a variety of catalysts and ligands can be used, typical catalysts include tris(dibenzylideneacetone)-dipalladium(0), palladium(II) acetate or a mixture of both, and typical ligands include (±)-2,2'-bis(diphenylphosphino)-1,1'-binaphthalene (BINAP). Introduction of a second substituent $R^{11}$, if needed, may be performed to provide compounds (d). Pg is a suitable protecting group for a secondary amine such as, but not limited to, trifluoroacetyl, tert-butoxycarbonyl, or benzyl. Compounds of Formula (Ia) where $R^3$ is H, may be obtained from compounds (d) by removing the protecting group Pg under conditions well known to the skilled artisan. Compounds of Formula (Ia) where $R^3$ is methyl or ethyl, may be either obtained from intermediates (c) where Pg is methyl or ethyl, respectively; or, alternately, compounds of Formula (Ia) where $R^3$ is H, may be converted to the N-methyl or N-ethyl derivatives (Ia) where $R^3$ is methyl or ethyl via alkylation conditions well known in the art. An appropriate compound of Formula (Ia) is one in which variables $R^1$, $R^2$, $R^3$, $R^4$, $R^5$, $R^7$, $R^8$, $R^9$, $R^{10}$ and $R^{11}$ are as previously defined for Formula I.

sodium borohydride in a suitable solvent, typically methanol or ethanol. Nitriles (e) and (g) are either commercially available or may be prepared by methods well known to the skilled artisan.

Scheme II

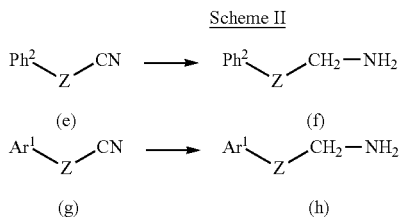

Z: bond or alkyl linker

As illustrated in Scheme III, nitriles (e) and (g) can be also reduced in the presence of a suitable protecting group for an amine such as, but not limited to, di-tert-butyl-dicarbonate. Reduction of nitriles (e) and (g) can be performed by hydrogen, at atmospheric pressure or 60 psi, using Degussa-type Pd/C as catalyst in a suitable solvent, such as methanol, ethanol, THF/iso-propanol, ethyl acetate and the like in the Scheme I

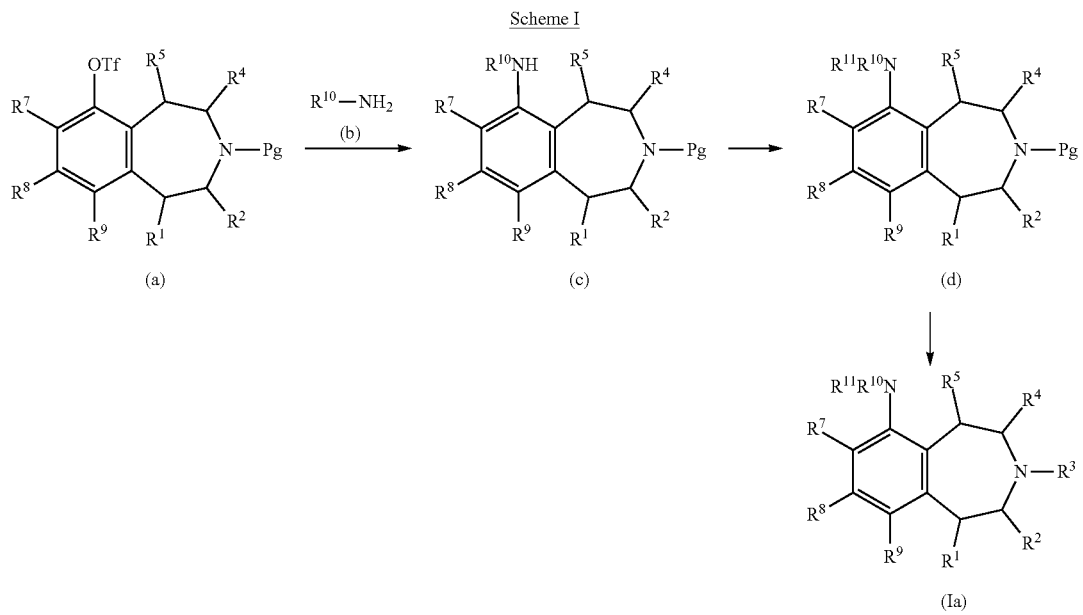

Amines (b) are either commercially available or may be prepared by a variety of methods. For example, as illustrated in Scheme II, amines of formula (f) and (h) can be prepared from nitriles (e) and (g) in the presence of hydrogen, at atmospheric pressure or 60 psi, using Degussa-type Pd/C as catalyst in a suitable solvent, such as methanol/hydrochloric acid, ethanol/hydrochloric acid, methanol/water/acetic acid, ethanol/water/acetic acid, THF/iso-propanol and the like. Alternately, hydrogenation can be performed at atmospheric pressure or 60 psi using Raney Nickel® as catalyst in a suitable solvent, typically methanol or ethanol in the presence of ammonia. Alternately, nitriles (e) and (g) can be reduced using lithium aluminum hydride or borane (THF or dimethylsulfide complex) in a suitable solvent, typically THF. Nitriles (e) and (g) can be also reduced using cobalt(II) chloride hexahydrate or nickel(II) chloride hexahydrate and presence of di-tert-butyl-dicarbonate. Alternately, other suitable reducing agents could be cobalt(II) chloride hexahydrate or nickel(II) chloride hexahydrate and sodium borohydride in a suitable solvent, typically methanol or ethanol in the presence of di-tert-butyl-dicarbonate. Deprotection of the nitrogen gives the desired amines (f) and (h). Nitriles (e) and (g) are either commercially available or may be prepared by methods well known to the skilled artisan.

Scheme III

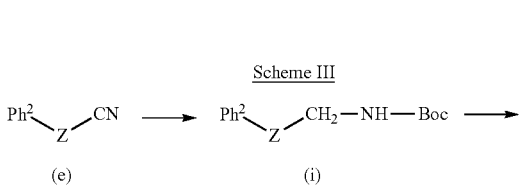

-continued

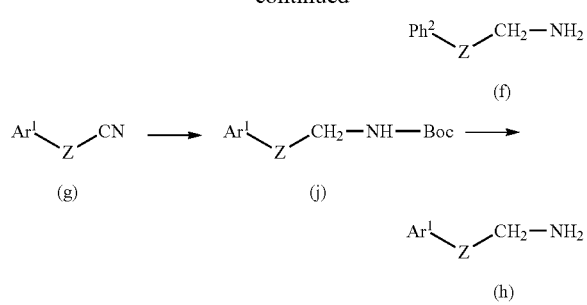

Z: bond or alkyl linker

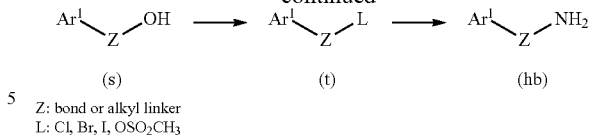

Z: bond or alkyl linker
L: Cl, Br, I, OSO$_2$CH$_3$

Amines (fa) and (ha) can also be prepared as illustrated in Scheme IV. Bromination of compounds (k) and (n) using NBS and AIBN in a suitable solvent, typically carbon tetrachloride, chloroform or dichloromethane provides bromides (l) and (o), respectively. Reaction of compounds (l) and (o) with di-tert-butyl-iminodicarboxylate in the presence of a base such as sodium hydride, potassium carbonate, cesium carbonate or potassium tert-butoxide, in a suitable solvent, typically DMF or THF, afford compounds (m) and (p). Deprotection gives the desired amines (f) and (h). Compounds (k) and (n) are either commercially available or may be prepared by methods well known to the skilled artisan.

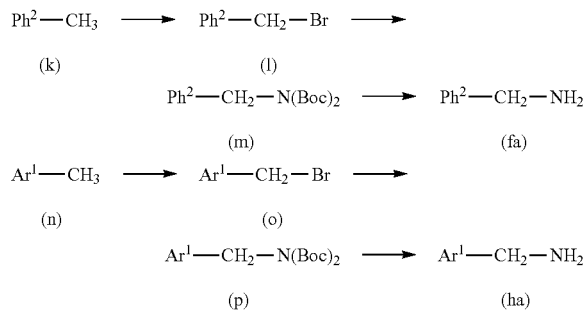

Amines (fb) and (hb) may be prepared from the corresponding alcohols (q) and (s), respectively, via reaction sequences well known to the skilled in the art, as illustrated in Scheme V. The alcohols are converted to intermediates (r) and (s) with a suitable leaving group, such as but not limited to chloride, bromide, or mesylate, which may be displaced by a nucleophile such as azide (N$_3^-$), using a reagent such as sodium azide, di-tert-butyl-iminodicarboxylate in the presence of a suitable base or ammonia. The intermediates obtained from displacement with azide (N$_3^-$) or di-tert-butyl-iminodicarboxylate may be converted to the amines (fb) and (hb) via well known standard procedures.

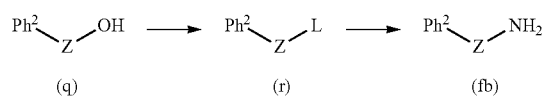

Amines (fc) and (hc) may also be prepared as illustrated in Scheme VI via reductive amination procedures. The corresponding aldehydes (u), R=H, or ketones (u), R=alkyl, are converted to the amines by reaction with a amine reagent, such as but not limited to a ammonium salt, in the presence of a reducing agent, such as sodium triacetoxy borohydride, or sodium cyano borohydride.

Scheme VI

R': Ar$^1$, Ph$^2$
R: H, alkyl
Z: bond or alkyl linker

Amines (fd), (fe), (hd), (he) may also be prepared as illustrated in Scheme VII. The corresponding nitriles (va) or esters (wa) may be dialkylated in the alpha-positions according to methods well known in the art. For example, reaction of compounds (va) with ethylene dibromide or ethylene dichloride in the presence of an appropriate base and in a suitable solvent, such as but not limited to K[NSi(CH$_3$)$_2$] in THF, can afford the gem-ethano compounds (vb). Reduction of the nitrile under conditions some of which have been described above may yield amines (fe) and (he). Alternately, hydrolysis of the nitrile to the primary amide under conditions well described in the literature and rearrangement of the primary amide in the presence of NaOCl or NaOBr (Hofman rearrangement of primary amides) may lead to the amines (fd) and (hd). Alternately, esters (wb) can be hydrolyzed to the corresponding carboxylic acids, which then can be converted to the amines (fd) and (hd), via a Curtius-type rearrangement in the presence of sodium azide and sulfuric acid. Gem-ethano esters (wb) may also be obtained from the corresponding unsaturated esters (we), for example by reaction with CHBr$_3$ in the presence of base, such as for example NaOH under phase transfer catalysis conditions, followed by debromination for example with Mg in methanol, or by reaction with diazomethane under suitable conditions.

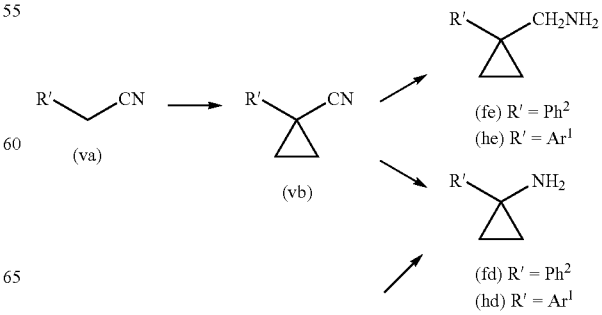

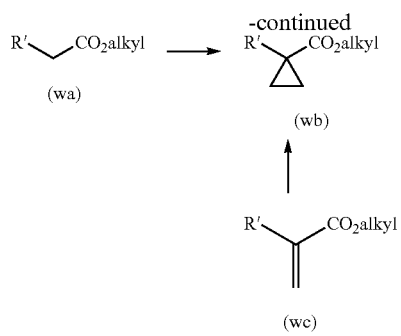

R': Ar¹, Ph²

Amines (ff) and (hf) can be prepared, as illustrated in Scheme VIII, by transformation of appropriately substituted intermediates (xa), (xc), (xd), (xe) into the appropriately substituted heteroaromatic compounds (xb) according to procedures known in the art. Transformations of the nitrile by following the procedures previously described give the desired amines (ff) and (hf). Compounds (xa), (xc), (xd), and (xe) are either commercially available or may be prepared by methods well known to the skilled artisan.

Scheme VIII

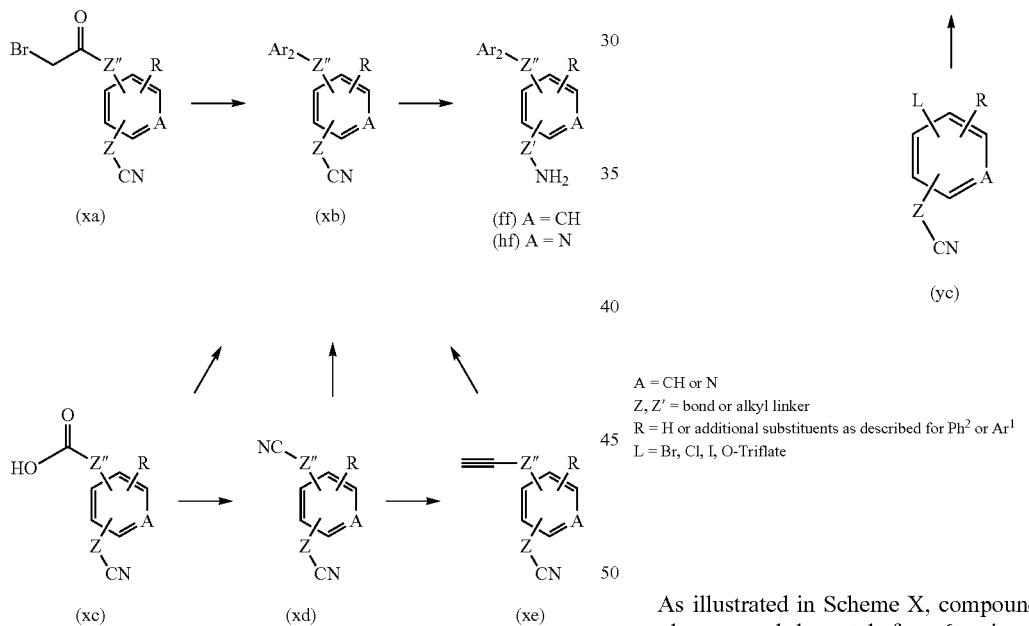

A = CH or N
Z, Z', Z" = bond or alkyl linker
R = H or additional substituents as described for Ph² or Ar¹

Amines (fg) and (hg) can be also prepared, as illustrated in Scheme IX, by the couling of boronic acids (ya) with an appropriately substituted heteroaromatic bromide, chloride, iodide or triflate in the presence of a suitable palladium catalyst/ligand system, and a base in a suitable solvent, typically toluene, DMF or 1,4-dioxane under an inert atmosphere. Transformations of the nitriles (yb) by following the procedures previously described gives the desired amines (fg) and (hg). Boronic acids (ya) are either commercially available or may be prepared by methods well known to the skilled artisan. Alternately, intermediates (yb) can be obtained by reaction of compounds (yc) with an appropriately activated heteroaryl derivative, under appropriate transition metal catalysis, especially in the presence of a suitable palladium reagent, as described in the literature and well known to the skilled artisan [see for example, Li and Gribble, Palladium in Heterocyclic Chemistry, Pergamon, Amsterdam (2000)].

Scheme IX

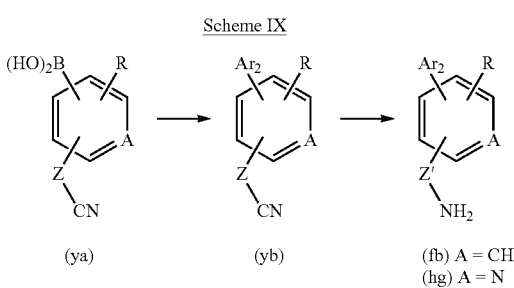

A = CH or N
Z, Z' = bond or alkyl linker
R = H or additional substituents as described for Ph² or Ar¹
L = Br, Cl, I, O-Triflate As illustrated in Scheme X, compounds of Formula (Ia) can be prepared alternately from 6-amino-2,3,4,5-tetrahydro-1H-benzo[d]azepines (za) by reaction with an appropriate bromide (zb), and an appropriate base, such as sodium hydride, potassium carbonate or cesium carbonate, in a suitable solvent, typically DMF, toluene, acetonitrile and the like. Introduction of a second substituent $R^{11}$, if needed, may be performed to provide compounds (d). Pg is a suitable protecting group for a secondary amine such as, but not limited to, trifluoroacetyl or tert-butoxycarbonyl. Compounds of formula (d) are deprotected to give compounds of Formula (Ia). An appropriate compound of Formula (Ia) is one in which variables $R^1$, $R^2$, $R^3$, $R^4$, $R^5$, $R^7$, $R^8$, $R^9$, $R^{10}$ and $R^{11}$ are as previously defined for Formula I. Bromides (zb) are either commercially available or may be prepared by methods well known to the skilled artisan.

Scheme X

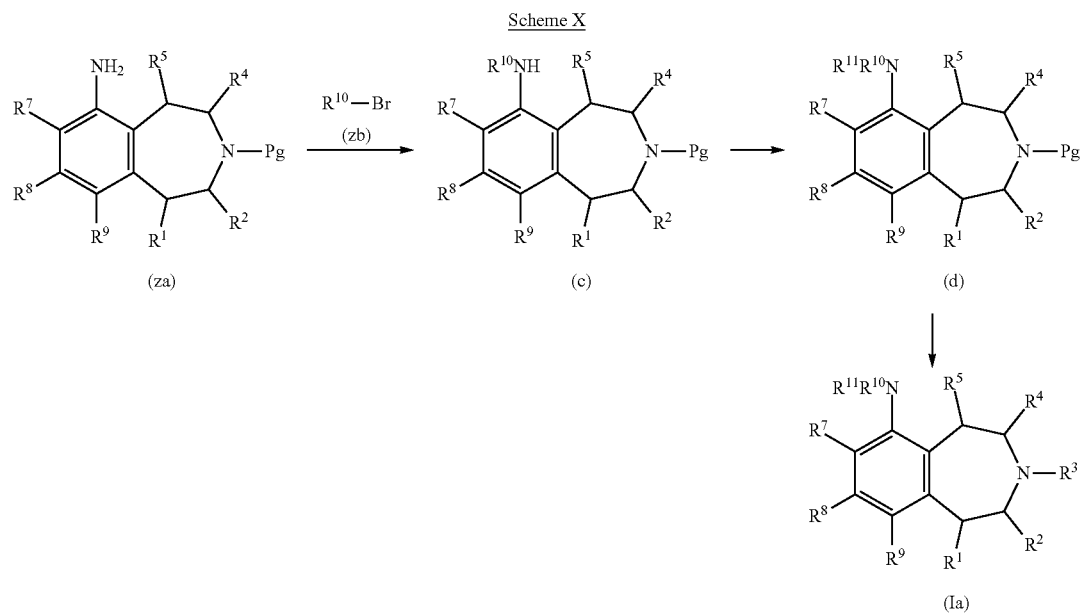

The appropriately substituted 6-trifluoromethanesulfonyloxy-2,3,4,5-tetrahydro-1H-benzo[d]azepines (a) may be prepared as described in Scheme XI starting from 1-naphthol. 1-Naphthol can be converted to 5-hydroxy-1,4-dihydronaphthalene (aa) by Birch reduction using ammonia and lithium metal at low temperature. Methylation of the 6-hydroxy group affords the compound (ab). Ozonolysis of compound (ab) and subsequent reduction with sodium borohydride provide the diol (ac). After converting the two hydroxyl groups into two good leaving groups, for example methanesulfonates, cyclize the compound (ad) to the 6-methoxy-2,3,4,5-tetrahydro-1H-benzo[d]azepines (ae) with aqueous ammonia under pressure. Protect the ring nitrogen by treatment with a variety of alkyl halides, acid chlorides or anhydrides such as trifluoroacetic anhydride to give compounds (af). Subsequently convert the methyl ether (at) to the phenol (ag) with BBr₃ in dichloromethane or other methods well known in the literature [see for example, Greene and Wuts, Protective Groups in Organic Synthesis, 3$^{rd}$ Ed., John Wiley and sons, Chapter III, New York (1999)]. Functionalization of the aromatic ring to introduce substituents R$^7$, R$^8$ and R$^9$ are well known in the art and very depending on the substitution desired. Subsequent trifluoromethanesulfonylation of the appropriately substituted 6-hydroxy-2,3,4,5-tetrahydro-1H-benzo[d]azepines (ah) affords the desired 6-trifluoromethanesulfonyloxy-2,3,4,5-tetrahydro-1H-benzo[d]azepines (a).

Scheme XI

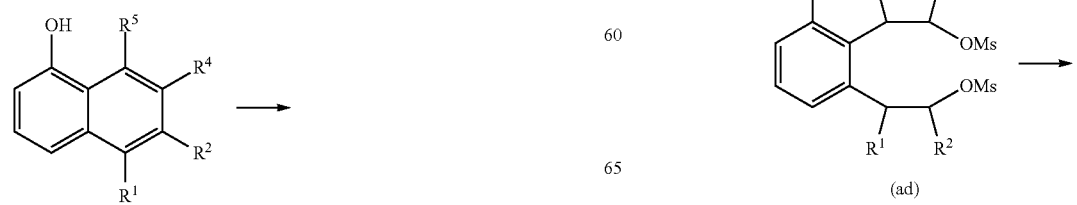

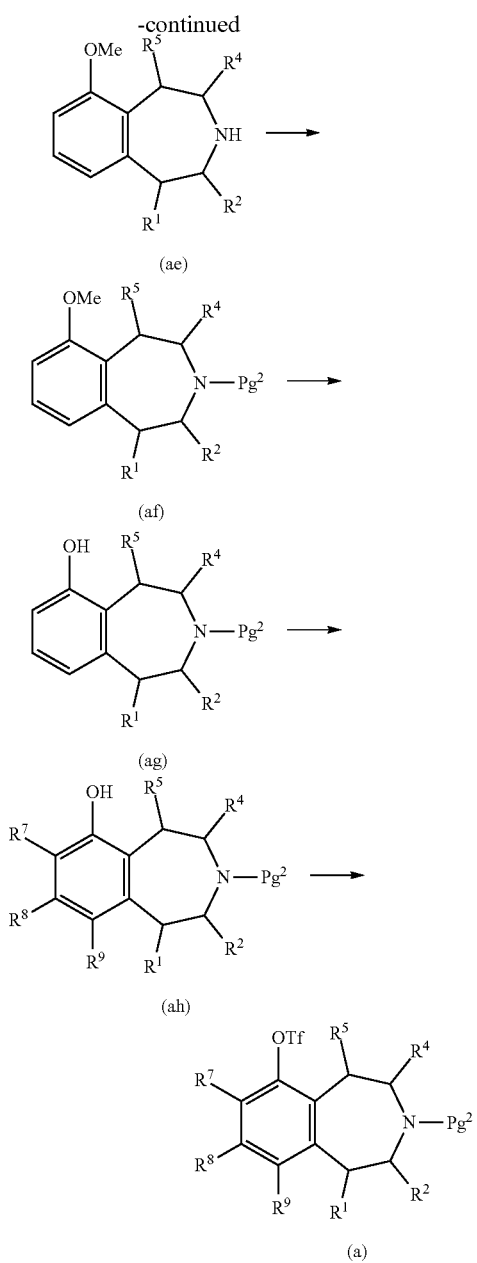

(ae)

(af)

(ag)

(ah)

(a)

The skilled artisan will also appreciate that not all of the substituents in the compounds of Formula I will tolerate certain reaction conditions employed to synthesize the compounds. These moieties may be introduced at a convenient point in the synthesis, or may be protected and then deprotected as necessary or desired, as is well known in the art. The skilled artisan will appreciate that the protecting groups may be removed at any convenient point in the synthesis of the compounds of the present invention. Methods for introducing and removing protecting groups used in this invention are well known in the art; see, for example, Greene and Wuts, Protective Groups in Organic Synthesis, 3$^{rd}$ Ed., John Wiley and sons, New York (1999).

The following Preparations and Examples are illustrative of methods useful for the synthesis of the compounds of the present invention. Exemplified compounds are also particularly preferred compounds of the present invention.

GENERAL PROCEDURE 1-1

Dissolve 7-chloro-3-(2,2,2-trifluoroacetyl)-6-trifluoromethanesulfonyloxy-2,3,4,5-tetrahydro-1H-benzo[d] azepine (1 equiv.), palladium(II) acetate (0.1-0.2 equiv.), BINAP (0.2-0.4 equiv.; BINAP/catalyst ratio 2:1) and cesium carbonate (1.4-3.0 equiv.) in toluene or dioxane (0.05-0.5 M solution). Add the amine (1.2-3.0 equiv.), degas the mixture with vacuum/nitrogen purge and heat at 90-100° C. for 16 h. Cool the mixture to room temperature, dilute with EtOAc, filter through Celite® washing with EtOAc and evaporate the solvent to obtain the crude mixture. Alternatively partition the reaction mixture between brine or saturated aqueous NaHCO$_3$ and EtOAc, ether or DCM, dry the organic phase over Na$_2$SO$_4$, and concentrate to obtain the crude mixture. Purify the crude mixture by chromatography on silica gel eluting with hexane/EtOAc mixtures and further SCX chromatography if needed.

GENERAL PROCEDURE 1-2

Dissolve 7-chloro-3-(2,2,2-trifluoroacetyl)-6-trifluoromethanesulfonyloxy-2,3,4,5-tetrahydro-1H-benzo[d] azepine (1 equiv.), tris(dibenzylideneacetone)-dipalladium (0) (0.1-0.3 equiv.), BINAP (0.2-0.6 equiv.; BINAP/catalyst ratio 2:1) and cesium carbonate (1.4-3.0 equiv.) in toluene or dioxane (0.05-0.5 M solution). Degas under vacuum and fill three times with nitrogen. Add the appropriately substituted amine (1.2-3.0 equiv.) and heat the mixture to 90-100° C. for 16 h under a nitrogen atmosphere. Cool the reaction flask to room temperature, dilute the mixture with EtOAc, filter through Celite® and concentrate in vacuo. Purify by chromatography on silica gel eluting with hexane/EtOAc mixtures and further SCX chromatography if needed.

GENERAL PROCEDURE 1-3

Add 7-chloro-3-(2,2,2-trifluoroacetyl)-6-trifluoromethanesulfonyloxy-2,3,4,5-tetrahydro-1H-benzo[d] azepine (1 equiv.), the appropriate amine (1.2-3.0 equiv.), palladium(II) acetate (0.1 equiv.), tris(dibenzylideneacetone) dipalladium(0) (0.2 equiv.), BINAP (0.6 equiv.; BINAP/catalysts ratio 2:1), cesium carbonate (1.4-3.0 equiv.) and toluene or dioxane (0.05-0.5 M solution) to a flask, degas and fill three times with nitrogen. Heat the mixture at 90-100° C. for 16 h. Dilute the mixture with EtOAc, wash with saturated aqueous NaHCO$_3$ and brine, dry over Na$_2$SO$_4$, filter and concentrate in vacuo to give the crude mixture. Alternatively remove the volatiles from the reaction mixture to give directly the crude mixture, or filter the reaction mixture through Celite® and concentrate in vacuo. Purify by chromatography on silica gel eluting with hexane/EtOAc mixtures and further SCX chromatography if needed.

GENERAL PROCEDURE 2-1

Dissolve the appropriately substituted 7-chloro-3-(2,2,2-trifluoroacetyl)-2,3,4,5-tetrahydro-1H-benzo[d]azepine (1.0 equiv.) in methanol. Add a 0.5 M aqueous solution of potassium carbonate (4.0 equiv.) and stir at room temperature for 6 h. Concentrate in vacuo and partition the residue between water and DCM. Extract the aqueous phase twice with DCM. Dry the combined organic extracts over Na$_2$SO$_4$, filter and concentrate in vacuo. Purify, if necessary, by chromatography on silica gel eluting with 1-20% 2M ammonia/methanol in DCM, or by SCX chromatography eluting with methanol followed by 1.0-7.0 M ammonia in methanol.

GENERAL PROCEDURE 2-2

Dissolve the appropriately substituted 7-chloro-3-(2,2,2-trifluoroacetyl)-2,3,4,5-tetrahydro-1H-benzo[d]azepine in ammonia/methanol solution (1.0-7.0 M). Stir for 1-16 h at room temperature unless otherwise specified. Remove the volatiles in vacuo. Purify, if necessary, by chromatography on silica gel eluting with 1-20% 2M ammonia/methanol in DCM, or by SCX chromatography eluting with methanol followed by 1.0-7.0 M ammonia in methanol.

GENERAL PROCEDURE 2-3

Dissolve the appropriately substituted 7-chloro-3-(2,2,2-trifluoroacetyl)-2,3,4,5-tetrahydro-1H-benzo[d]azepine (1.0 equiv.) in methanol or ethanol (0.1-2M solution) and add from 10-50% by volume of 1.0-5.0 N aqueous sodium hydroxide or lithium hydroxide. Stir the reaction mixture at room temperature for 0.25-16 h and concentrate in vacuo. Partition the residue between EtOAc or DCM and water. Separate and dry the organic phase over Na$_2$SO$_4$, filter, and concentrate in vacuo. Purify, if necessary, by chromatography on silica gel eluting with 1-20% 2M ammonia/methanol in DCM, or by SCX chromatography eluting with methanol followed by 1.0-7.0 M ammonia in methanol, or by reverse phase HPLC.

GENERAL PROCEDURE 3-1

Dissolve the purified free base (1 equiv.) in acetone or methanol and add a solution of succinic acid (1 equiv.) in acetone or methanol. Stir for 1 h at room temperature. Concentrate to an oil, add a minimal volume of DCM and diethyl ether, tert-butylmethyl ether, hexane or pentane to precipitate out the salt. Alternatively, to precipitate out the salt, allow the reaction mixture to stand 1-16 h at room temperature, 4° C. or −10° C. and add ether or hexane. Filter and wash the solid with ether or hexane to obtain the succinate salt. Alternatively, evaporate the solvent in vacuo, wash the solid with ether and filter or decant the solvent to obtain the succinate as a solid. Dry the solid in vacuo or under a stream of nitrogen.

GENERAL PROCEDURE 3-2

Dissolve the purified free base (1 equiv.) in methanol and add a solution of (L)-tartaric acid in methanol. If a solid precipitate out, filter and wash the solid with diethyl ether, tert-butylmethyl ether, hexane or pentane. If no solid formation is observed, remove all the volatiles in vacuo to form a foam. Dry in vacuo or under a stream of nitrogen to obtain the (L)-tartaric acid salt.

Preparation 1

7-Chloro-3-(2,2,2-trifluoroacetyl)-6-trifluoromethanesulfonyloxy-2,3,4,5-tetrahydro-1H-benzo[d]azepine

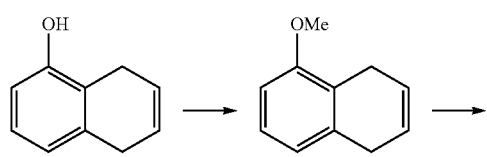

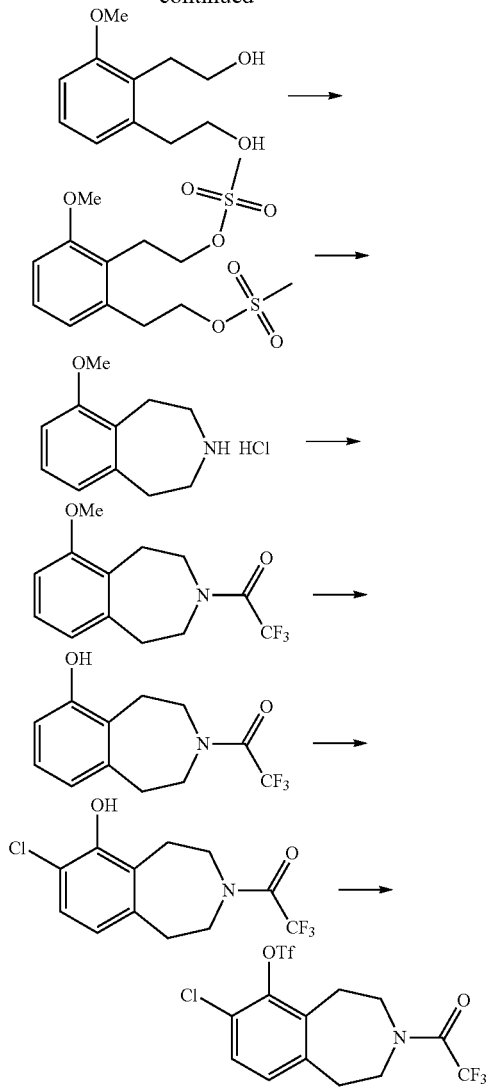

5-Methoxy-1,4-dihydronaphthalene

Add powdered potassium carbonate (193.1 g, 1.397 mol) to a solution of 5-hydroxy-1,4-dihydronaphthalene [68.08 g, 90% potency based on $^1$H-NMR, 0.4657 mol, from Societa Italiana Medicinala Scandicci, s.r.l., Reggello (Firenze), Italy] in ethanol (700 mL). Cool the solution to 0° C. with ice/water and add dimethyl sulfate (88.1 g, 66.1 mL, 0.699 mol) dropwise, maintaining the temperature between 5° C. and 10° C. Then heat the reaction mixture to 40° C. until the TLC (10:1 hexane/EtOAc) shows the absence of starting material (about 2 h). Filter off the solids by vacuum filtration and remove the solvent in vacuo. Dilute the residual brown oil with diethyl ether (500 mL), wash with 10% aqueous NH$_4$OH (500 mL), water (500 mL), brine (500 mL), dry the organic layer over Na$_2$SO$_4$, filter and concentrate in vacuo to give the crude product as a brown oil (73 g). Purify the crude mixture by short path distillation under vacuum (bp 120-130° C./5 Torr) to give the desired intermediate as a clear oil (69.0 g, 92.5% potency corrected) (contains some 1,2,3,4-tetrahydro-5-methoxynaphthalene as an impurity). $^1$H NMR (300 MHz, CDCl$_3$), δ 7.15 (t, 1H, J=7.9), 6.72 (dd, 2H, J=15.7, 7.9), 5.93-5.88 (m, 2H), 3.83 (s, 3H), 3.42-3.39 (m, 2H), 3.30-3.28 (m, 2H); $R_f$=0.58 eluting with 10:1 hexane/EtOAc.

2,3-Bis-(2-hydroxyethyl)-1-methoxybenzene

Charge a four-neck 5 L flask equipped with an over-head mechanical stirrer, reflux condenser, thermocouple, and gas dispersion apparatus with 5-methoxy-1,4-dihydronaphthalene (264.54 g, 89.5% potency based on $^1$H-NMR, 1.478 mol) in DCM (1.3 L) and 2B-3 ethanol (1 L). Add sudan III (10 mg) to give a faint red color. Cool the solution to −65° C. or lower, then pass $O_3$ through the solution until the solution turns a light yellow color and the TLC (10:1 hexane/EtOAc, $KMnO_4$ stain) shows the absence of the starting material (about 30 h). Transfer the solution via cannula into a slurry of $NaBH_4$ (97.8 g, 2.59 mol) in 2B-3 ethanol (500 mL) cooled in ice/water. It is important that the temperature be maintained at or above 0° C., as for example between 0° C. and 10° C., throughout the transfer to ensure the ozonide is completely reduced to the diol. After the transfer is complete, warm the solution to ambient temperature and stir for about 30 min. Cool the slurry to 0° C. with ice/water then slowly add acetone (540 mL, 7.4 mol) to remove excess $NaBH_4$. After all the solids dissolve, remove the solvent in vacuo. Dissolve the yellow solid in DCM (1 L) and water (1 L), separate the layers and extract the aqueous layer with DCM (750 mL). Wash the combined organic layers with brine (1.5 L), add toluene (750 mL) and remove the solvent in vacuo. Dissolve the solid in DCM (500 mL) with heating, then add toluene (750 mL) and concentrate the solution in vacuo to give the desired intermediate as a light yellow solid (283.7 g, 89% potency corrected, mp 82-83° C.) (contains 1,2,3,4-tetrahydro-5-methoxynaphthalene as an impurity (8.6%)). Further purify the product by vacuum drying overnight at 75° C., 5 Torr, to remove all but trace amount of the 1,2,3,4-tetrahydro-5-methoxynaphthalene impurity. $^1$H NMR (300 MHz, $CDCl_3$), δ 7.16 (dd, 1H, J=8.2, 7.6), 6.83 (s, 1H, J=7.0), 6.76 (s, 1H, J=8.2), 3.85-3.77 (m, 7H), 3.01-2.91 (m, 4H), 2.35 (s, 2H); $^{13}$C NMR (300 MHz, DMSO-$d_6$), δ 157.5, 138.9, 126.5, 125.2, 122.0, 108.4, 62.1, 60.5, 55.3, 36.1, 29.6; IR (KBr): 3006, 2960, 2886, 2829, 1583, 1461, 1440, 1264, 1091, 1041 cm$^{-1}$; MS (ES+) m/z 178 (M+H)$^+$; Anal. Calc'd for $C_{11}H_{16}O_3$: C, 67.32; H, 8.22; N, 0. Found: C, 67.26, H, 8.10; N, 0.21; $R_f$=0.23 eluting with 95:5 DCM/methanol.

2,3-Bis-(2-methanesulfonyloxyethyl)-1-methoxybenzene

To a slurry of 2,3-bis-(2-hydroxyethyl)-1-methoxybenzene (50.6 g, 0.258 mol, 1 equiv.) and triethylamine (78.3 g, 0.774 mol, 3 equiv.) in DCM (500 mL) at 0° C., add dropwise a solution of methanesulfonyl chloride (65.0 g, 0.567 mol, 2.2 equiv.) in DCM (100 mL) over 45 min. The addition is exothermic and the methanesulfonyl chloride is added at a rate to keep the temperature below 10° C. After the addition is complete, warm the reaction to ambient temperature. Wash the solution with water (2×500 mL), and then brine (750 mL). Dry the organic layer over $Na_2SO_4$, filter and concentrate in vacuo to obtain the desired intermediate as a dark yellow oil (87.4 g, 96.2%), which is used in the next reaction without further purification. An analytical sample is obtained by flash column chromatography eluting with 100% diethyl ether. $^1$H NMR (300 MHz, $CDCl_3$), δ 7.20 (t, 1H, J=7.9), 6.82 (s, 1H, J=7.2), 6.80 (s, 1H, J=8.2), 4.41-4.34 (m, 4H), 3.83 (s, 3H), 3.16-3.09 (m, 4H), 2.91 (s, 3H), 2.87 (s, 3H); $^{13}$C NMR (300 MHz, $CDCl_3$), δ 158.07, 136.55, 128.26, 123.34, 122.39, 109.24, 69.88, 69.08, 55.55, 37.35, 37.14, 32.57, 26.47; $^{13}$C NMR (300 MHz, DMSO-$d_6$), δ 157.58, 136.79, 127.81, 122.91, 122.00, 109.33, 70.19, 68.88, 55.55, 36.49, 36.47, 31.56, 25.72; IR (KBr): 1586.8, 1469.4, 1358.51, 1267.3, 1173.9, 1105.4, 972.4, 954.6, 914.3 cm$^{-1}$; MS (ES+) m/z 257 (M+H)$^+$; Anal. Calc'd. for $C_{13}H_{20}O_7S_2$: C, 44.31; H, 5.72; N, 0. Found: C, 44.22, H, 5.68; N, 0.13; $R_f$=0.72 eluting with 95:5 DCM/methanol.

6-Methoxy-2,3,4,5-tetrahydro-1H-benzo[d]azepine

Dissolve 2,3-bis-(2-methanesulfonyloxyethyl)-1-methoxybenzene (474.4 g, 1.346 mol) in acetonitrile (7 L) and split the mixture into two equal lots. In two separate runs, add concentrated aqueous $NH_4OH$ (3.5 L) and charge the solution to a pressure vessel (Parr apparatus). Heat the solution in a closed reactor to 100° C. over 20 min (internal pressure reaches about 100 psi), and maintain at 100° C. until the reaction is complete (about 1 h, HPLC monitored). Cool the reaction mixture to ambient temperature. Combine the two lots and remove the solvent in vacuo. Dissolve the residue in MTBE (3.5 L) and water (3.5 L). Adjust the pH to 6.5 using 2M aqueous NaOH or 1M aqueous HCl as appropriate (typically the pH is about pH=5.1 and the adjustment requires about 50 mL 2M aqueous NaOH). Discard the organic layer, adjust the aqueous layer to pH=13 using 50% NaOH (about 150 mL). Extract with MTBE (2×3.5 L), wash the combined organic layers with brine (3.5 L), dry over $Na_2SO_4$, filter and concentrate in vacuo to give the title compound as a crude yellow oil that solidifies upon standing (179.3 g). Use the material for the next step without further purification. Prepare an analytical sample by purification by two Kugelrohr distillations to give a clear oil that solidifies upon standing, mp 44.3-45.0° C. $^{13}$C NMR (300 MHz, DMSO-$d_6$), δ 156.1, 144.4, 130.3, 126.2, 121.5, 108.9, 55.5, 48.2, 47.9, 39.9, 29.1; MS (ES+) m/z 163 (M+H)$^+$; Anal. Calc'd for $C_{11}H_{15}NO$: C, 74.54; H, 8.53; N, 7.90. Found: C, 74.28, H, 8.62; N, 7.86.

6-Methoxy-2,3,4,5-tetrahydro-1H-benzo[d]azepine Hydrochloride

Dissolve crude 6-methoxy-2,3,4,5-tetrahydro-1H-benzo[d]azepine (35.1 g, 0.198 mol) in 2B-3 ethanol (250 mL), heat the solution to reflux and add 2M HCl in ethanol (108.9 mL, 0.218 mol, 1.1 equiv.). Slowly add heptane (700 mL) over 10 min, then remove the heating mantle and cool the solution to ambient temperature, and finally continue the cooling with an ice/water mixture. Collect the resulting solid by vacuum filtration and wash with cold ethanol:heptane (1:2) (3×100 mL), air-dry for 15 min under vacuum, then further dry the product in a vacuum oven at 60° C. for 1 h to give the desired intermediate as a white granular solid (35.53 g, 63%): mp 246.6-246.9° C.; $^1$H NMR (300 MHz, DMSO-$d_6$), δ 9.82 (broad s, 1H), 7.12 (dd, 1H, J=7.6, 7.9), 6.88 (d, 1H J=8.2), 6.78 (d, 1H, J=7.3), 3.75 (s, 3H), 3.20-3.00 (m, 8H); $^{13}$C NMR (300 MHz, DMSO-$d_6$), δ 156.2, 141.3, 127.4, 127.2, 121.6, 109.7, 55.7, 44.9, 44.7, 31.6, 21.7; MS (ES+) m/z 178 (M+H)$^+$; Anal. Calc'd for $C_{11}H_{15}ClNO$: C, 62.12; H, 7.11; N, 6.59. Found: C, 61.95, H, 7.64; N, 6.58.

6-Methoxy-3-(2,2,2-trifluoroacetyl)-2,3,4,5-tetrahydro-1H-benzo[d]azepine

To a slurry of 6-methoxy-2,3,4,5-tetrahydro-1H-benzo[d]azepine hydrochloride (35.3 g, 0.165 mol, 1 equiv.) and triethylamine (69.1 mL, 0.496 mol, 3 equiv.) in DCM (300 mL) cooled at 0° C. with ice/water, add dropwise a solution of trifluoroacetic anhydride (25.7 mL, 0.182 mol, 1.1 equiv.) in DCM (40 mL) over 30 min, but at a rate that maintains the temperature below 10° C. After the addition is complete, warm the reaction mixture to ambient temperature and stir until the reaction is complete (verify by TLC using 9:1 $CH_2Cl_2$:methanol, about 2 h.). Wash the solution with water (2×350 mL), and then brine (350 mL), dry the organic layer over $Na_2SO_4$, filter and concentrate in vacuo to give desired intermediate as a yellow oil that solidifies upon standing (44.9 g, 96%). Use the material without further purification in the next step. Prepare an analytical sample by chromatography on silica gel eluting with 40% diethyl ether in hexane, mp 74-76° C. $^1$H NMR (300 MHz, $CDCl_3$), δ 7.16-7.11 (m, 1H), 6.81-6.74 (m, 2H), 3.81 (s, 3H), 3.79-3.64 (m, 4H), 3.11-3.07 (m, 2H), 2.99-2.95 (m, 2H); $^1$H NMR (300 MHz, DMSO-$d_6$), δ 7.13 (dd, 1H, J=1.5, 7.0), 7.08 (d, 1H, J=1.5), 6.88-6.74 (m, 1H), 3.75 (s, 3H), 3.67-3.61 (m, 4H), 3.04-2.92 (m, 4H); $^{13}$C NMR (300 MHz, DMSO-$d_6$), δ 156.43. 156.38, 155.06, 155.00, 154.60, 154.54, 154.14, 154.08, 141.31, 141.04, 127.44, 127.18, 127.05, 127.01, 122.27, 121.94, 121.90, 118.46, 114.64, 110.80, 109.52, 109.41, 55.63, 55.61, 47.11, 47.07, 46.67, 46.63, 45.61, 45.16, 35.90, 34.65, 26.18, 24.91; Anal. Calc'd for $C_{13}H_{14}F_3NO_2$: C, 57.14; H, 5.16; N, 5.13. Found: C, 57.17, H, 5.27; N, 5.08.

6-Hydroxy-3-(2,2,2-trifluoroacetyl)-2,3,4,5-tetrahydro-1H-benzo[d]azepine

To a 1M solution of $BBr_3$ (1.1 L, 1.6 equiv.), cooled at 0° C. with an ice-water bath, add 6-methoxy-3-(2,2,2-trifluoroacetyl)-2,3,4,5-tetrahydro-1H-benzo[d]azepine (187 g, 0.684 mol) in DCM (200 mL) over 1 h., while maintaining the temperature between 0° C. and 10° C. Warm the reaction mixture to ambient temperature and stir until HPLC indicates completion of the reaction (about 2 h.). Cool the solution to 0° C. and transfer it via cannula into an ice/water solution (1.2 L), thereby precipitating the product as a white solid. Add EtOAc (2 L) to dissolve most of the precipitate, separate the layers and concentrate the organic layer in vacuo. Extract the aqueous layer three times with EtOAc (2×2 L, 1×1 L). Wash the combined organic layers with water (2 L), and then brine (2 L), dry over $Na_2SO_4$, filter and concentrate in vacuo to give the desired intermediate as a light yellow solid (166.3 g, 94%). Use the product for the next step without further purification. Prepare an analytical sample by chromatography on silica gel eluting with 40% diethyl ether in hexane: mp 183.0-185.2° C. $^1$H NMR (300 MHz, DMSO-$d_6$), δ 9.39 (s, 1H), 6.94-6.88 (m, 1H), 6.72-6.68 (m, 1H), 6.61-6.57 (m, 1H), 3.67-3.32 (m, 4H), 2.99-2.86 (m, 4H); $^{13}$C NMR (300 MHz, DMSO-$d_6$), 154.50, 141.47, 141.18, 126.77, 126.64, 125.77, 125.33, 120.38, 120.32, 118.49, 114.67, 113.64, 113.47, 47.31, 47.27, 47.00, 46.96, 45.83, 45.49, 36.17, 34.93, 26.46, 25.18, 20.66, 14.00; MS (ES+) m/z 260 (M+H)$^+$; Anal. Calc'd. for $C_{12}H_{12}F_3NO_2$: C, 55.60; H, 4.67; N, 5.40. Found: C, 55.51, H, 4.71; N, 5.29.

7-Chloro-6-hydroxy-3-(2,2,2-trifluoroacetyl)-2,3,4,5-tetrahydro-1H-benzo[d]azepine Heat a mixture of 6-hydroxy-3-(2,2,2-trifluoroacetyl)-2,3,4,5-tetrahydro-1H-benzo[d]azepine (120 g, 0.4629 mol) and toluene (14.4 L) to 70° C. for 45 min until most of the starting material is dissolved. Add diisobutylamine (1.197 g, 1.62 mL, 9.26 mmol) followed by addition of sulfuryl chloride (62.48 g, 37.19 mL, 0.463 mol) in toluene (360 mL) over 20 min. Stir the reaction mixture for 50 min and then add additional sulfuryl chloride (4.536 g, 2.70 mL, 0.0336 mol) neat and stir the reaction mixture for 15 min at 70° C. Cool the reaction mixture to 24° C. over 30 min and then add 1N hydrochloric acid (2 L). Separate, wash the organic layer with saturated aqueous $NaHCO_3$ (2 L), brine (2 L) and then dry over Na2SO4. Filter and remove the solvent with a rotary evaporator at 70° C. until about 672.5 g remains using the minimum effective vacuum in order to maintain a vapor phase sufficient to prevent drying above the solvent line and self-seeding, thus preventing crystallization under these conditions. Using toluene heated to 70° C., transfer the light-yellow solution to a preheated (70° C.) 3-neck flask equipped with a mechanical stirrer. Lower the temperature to 58° C. over 1 h. If available, seed the solution with crystals of 7-chloro-6-hydroxy-3-(2,2,2-trifluoroacetyl)-2,3,4,5-tetrahydro-1H-benzo[d]azepine from a prior synthesis to enhance crystallization. After 30 min, reduce the temperature further to 55° C. and observe the initiation of the crystallization process. Hold the temperature at 55° C. for 2 h followed by 4 h at 45° C., then turn off the heat allowing the mixture to slowly reach 24° C. (ambient temperature). After stirring for 8 h with the heat off, cool the mixture to 0° C. for 2 h followed by 2 h at –10° C. Collect the resulting dense, white, granular crystals by vacuum filtration at –10° C. Rinse the crystals twice with cold (–10° C.) toluene and vacuum dry at 50° C., 5 Torr, for 12 h., to obtain the desired intermediate as a white solid (120.7 g, 99.5% purity, 88.8%): mp 133-134° C. MS (ES+) m/z 294 (M+H)$^+$. Anal. Calc'd for $C_{12}H_{11}ClF_3NO_2$: C, 49.08; H, 3.78; N, 4.77; Cl, 12.07. Found: C, 49.01; H, 3.63; N, 4.72; Cl, 12.32.

7-Chloro-3-(2,2,2-trifluoroacetyl)-6-trifluoromethanesulfonyloxy-2,3,4,5-tetrahydro-1H-benzo[d]azepine Cool a solution of 7-chloro-6-hydroxy-3-(2,2,2-trifluoroacetyl)-2,3,4,5-tetrahydro-1H-benzo[d]azepine (60 g, 0.204 mol), triethylamine (62.6 mL, 0.448 mol, 2.2 equiv.), and DCM (590 mL) in an ice bath and add dropwise trifluoromethanesulfonic anhydride (43.5 mL, 0.258 mol, 1.26 equiv.) over 70 min. Remove the ice bath and stir the reaction mixture for 2 h. Wash the reaction mixture sequentially with water (500 mL), 1N aqueous HCl (500 mL), water (500 mL), and brine (500 mL). Dry the organic layer over $Na_2SO_4$ and concentrate in vacuo to give the crude product as a brown solid (90 g). Dissolve the solid in warm toluene (200 mL). Further purify by plug filtration chromatography over silica gel (500 g) eluting sequentially with hexane (1 L), hexane/EtOAc (9:1, 1 L), hexane/EtOAc (4:1, 1 L), and hexane/EtOAc (7:3, 9 L). Pool the eluents and evaporate the solvent to obtain the product as a yellow tan solid (86.3 g). Dissolve the solid in warm EtOAc (86 mL) and then add hexane (700 mL). If available, seed the solution with crystals of 7-chloro-3-(2,2,2-trifluoroacetyl)-6-trifluoromethanelsulfonyloxy-2,3,4,5-tetrahydro-1H-benzo[d]azepine from a prior synthesis to enhance crystallization. Allow the mixture to stand at ambient temperature for 30 min. Cool the mixture at about –10° C. for 2 h., filter, rinse the crystals with cold (–10° C.) hexane/EtOAc, and air-dry on the filter under vacuum to obtain the title compound as a first crop of crystals (73.54 g). Concentrate the mother liquor to obtain a solid (12.7 g).

Recrystallize the solid in a mixture of EtOAc/hexane (15 mL:121 mL) to obtain additional title compound (7.65 g, total yield: 81.19 g, 93%).

Preparation 2

6-(4-Acetyl-benzylamino)-7-chloro-3-(2,2,2-trifluoroacetyl)-2,3,4,5-tetrahydro-1H-benzo[d]azepine

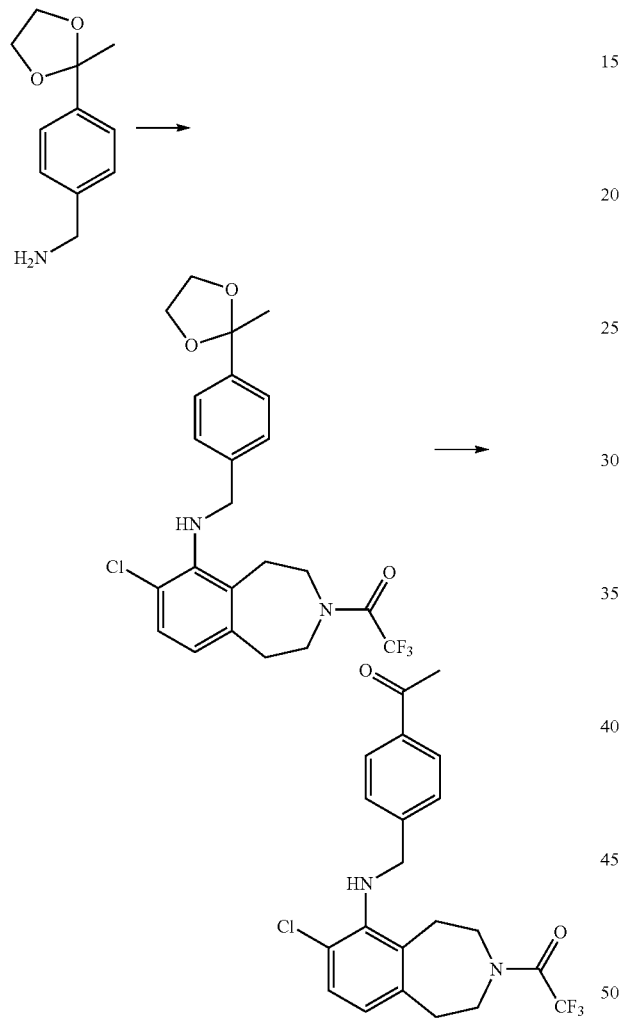

7-Chloro-6-[4-(2-methyl-[1,3]-dioxolan-2-yl)-benzylamino]-3-(2,2,2-trifluoroacetyl)-2,3,4,5-tetrahydro-1H-benzo[d]azepine Use a method similar to the General Procedure 1-3 to couple 7-chloro-3-(2,2,2-trifluoroacetyl)-6-trifluoromethanesulfonyloxy-2,3,4,5-tetrahydro-1H-benzo[d]azepine (200 mg, 0.47 mmol) with 4-(2-methyl-[1,3]dioxolan-2-yl)-benzylamine (prepared by following the procedure described in *J. Med. Chem.* 1978, 21, 507) (182 mg, 0.94 mmol). Purify by chromatography on silica gel eluting with hexane/EtOAc (1:0, 19:1 and 9:1) to obtain the desired intermediate as an oil (150 mg, 68%). GC-MS m/z: 468 (M+).

6-(4-Acetyl-benzylamino)-7-chloro-3-(2,2,2-trifluoroacetyl)-2,3,4,5-tetrahydro-1H-benzo[d]azepine Dissolve 7-chloro-6-[4-(2-methyl-[1,3]dioxolan-2-yl)-benzylamino]-3-(2,2,2-trifluoroacetyl)-2,3,4,5-tetrahydro-1H-benzo[d]azepine (150 mg, 0.32 mmol) in methanol (5 mL) and add 1N aqueous HCl (1 mL). Stir the solution at room temperature for 2 h. Remove the solvent, dissolve the residue in DCM and wash with saturated aqueous NaHCO$_3$. Dry the organic phase over Na$_2$SO$_4$, filter and concentrate in vacuo. Purify by chromatography on silica gel eluting with hexane/EtOAc (1:0, 9:1, 17:3 and 4:1) to obtain the title compound as an oil (107 mg, 79%). GC-MS m/z: 424 (M+).

Preparation 3

7-Chloro-6-[4-(3-methyl-butyryl)-benzylamino]-3-(2,2,2-trifluoroacetyl)-2,3,4,5-tetrahydro-1H-benzo[d]azepine

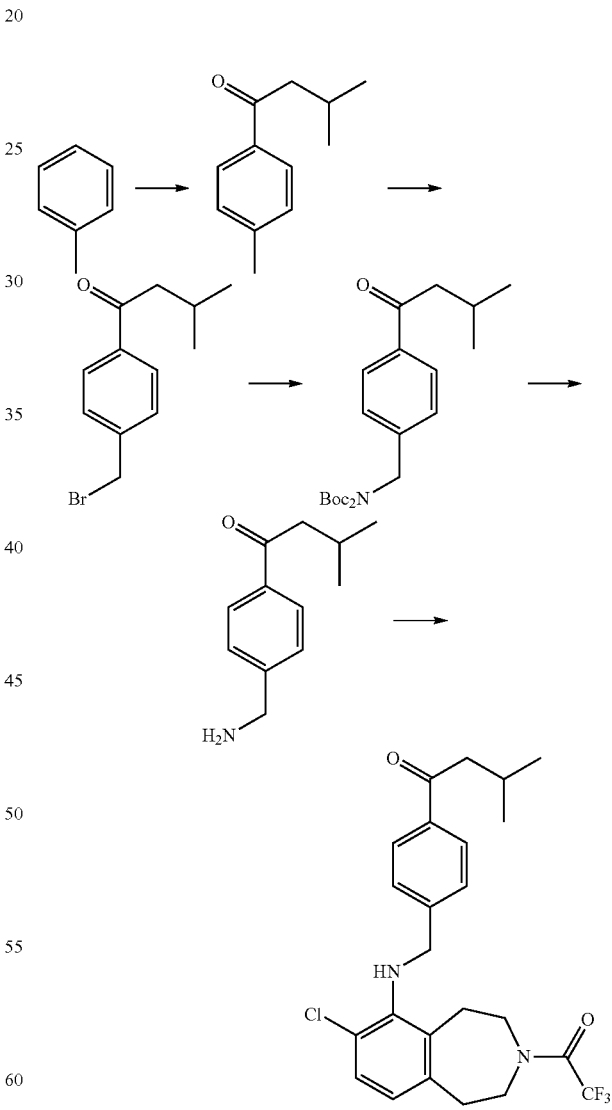

3-Methyl-1-p-tolyl-butan-1-one

Portionwise add aluminum trichloride (3.35 g, 25 mmol) to a solution of isovaleryl chloride (2 mL, 16.4 mmol) in anhydrous toluene (50 mL) at 0° C. Warm to room temperature and stir 12 h. Cool to 0° C. and slowly add cold water (500 mL). Extract with EtOAc, wash the organic phase with brine, dry over Na$_2$SO$_4$ and concentrate in vacuo to obtain the desired intermediate (2.8 g, 97%) as an orange oil suitable for use without additional purification. MS (APCI+) m/z: 176 (M$^+$).

1-(4-Bromomethyl-phenyl)-3-methyl-butan-1-one

Add NBS (1.6 g, 9.2 mmol) to a solution of 3-methyl-1-p-tolyl-butan-1-one (1.5 g, 8.4 mmol) and AIBN (1.4 g, 8.4 mmol) in carbon tetrachloride (30 mL) and heat to reflux for 18 h. Cool the reaction mixture to room temperature and pour into water (500 mL). Extract with EtOAc (3×100 mL), wash the combined organic extracts with brine (300 mL), dry over Na$_2$SO$_4$ and concentrate in vacuo to obtain 2.9 g of a brown oil, consisting of the desired intermediate with a small amount of unreacted 3-methyl-1-p-tolyl-butan-1-one and 1-(4,4-dibromomethyl-phenyl)-3-methyl-butan-1-one. Use this mixture in the next step without additional purification. MS (APCI+) m/z: 255 (M$^+$).

N-Di-(tert-butoxycarbonyl)-4-(3-methyl-butyryl)-benzylamine

Add di-tert-butyl-iminodicarboxylate (5.2 g, 24 mmol) to a slurry of sodium hydride (60% dispersion in mineral oil, 0.7 g, 17.6 mmol) in anhydrous DMF (75 mL) and stir at room temperature under nitrogen for 5 min. Add a solution of 1-(4-bromomethyl-phenyl)-3-methyl-butan-1-one in DMF (20 mL) and stir under nitrogen for 2 h. Quench with slow addition of water (50 mL) and partition between EtOAc/water (1:1, 500 mL). Separate and dry the organic phase over Na$_2$SO$_4$ and concentrate in vacuo to obtain the desired intermediate (5.4 g, 85%) as a brown oily solid suitable for use without additional purification.

4-(3-Methyl-butyryl)-benzylamine

Dissolve N-di-(tert-butoxycarbonyl)-4-(3-methyl-butyryl)-benzylamine (0.5 g, 1.28 mmol) in EtOAc (10 mL). Add 4N hydrogen chloride in dioxane (15 mL) and stir at room temperature for 20 h. Concentrate in vacuo, suspend the resulting tan solid in diethyl ether (30 mL), add hexane (150 mL) and filter the resulting tan precipitate. Wash with hexane (20 mL), suspend in DCM (50 mL), add saturated aqueous NaHCO$_3$ (100 mL) and stir until both layers are clear (15 min). Separate layers and extract the aqueous phase with DCM (2×30 mL). Wash the combined organic extracts with brine, dry over Na$_2$SO$_4$, and concentrate in vacuo to obtain the desired intermediate as a light yellow syrup (160 mg, 65%). MS (ES+) m/z: 192 (M+H)$^+$.

7-Chloro-6-[4-(3-methyl-butyryl)-benzylamino]-3-(2,2,2-trifluoroacetyl)-2,3,4,5-tetrahydro-1H-benzo[d]azepine Use a method similar to the General Procedure 1-3, using 7-chloro-3-(2,2,2-trifluoroacetyl)-6-trifluoromethanesulfonyloxy-2,3,4,5-tetrahydro-1H-benzo[d]azepine (175 mg, 0.42 mmol) and 4-(3-methyl-butyryl)-benzylamine (160 mg, 0.8 mmol) to obtain the title compound as a yellow syrup (85 mg, 45%). MS (ES+) m/z: 467 (M+H)$^+$.

Preparation 4

4-(2-Methylamino-thiazol-4-yl)-benzylamine

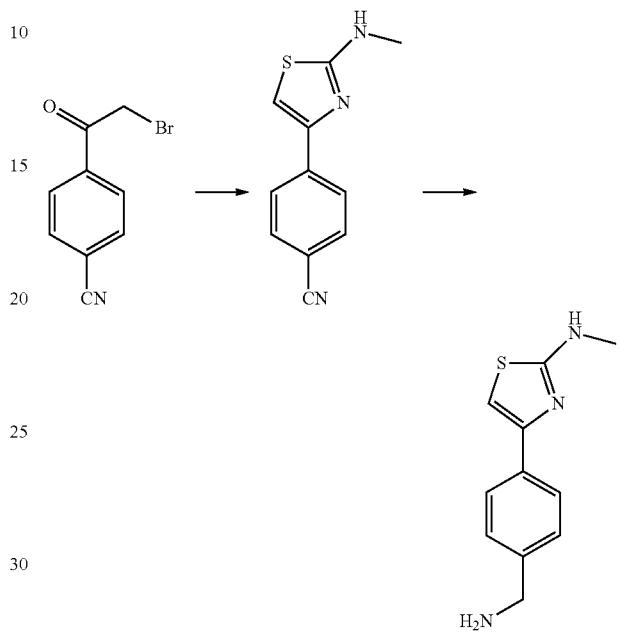

4-(2-Methylamino-thiazol-4-yl)-benzonitrile

Slurry 4-cyanophenacyl bromide (1.12 g, 5 mmol) in absolute ethanol (25 mL). Heat to 40° C. to dissolve, then add N-methyl-thiourea (0.45 g, 5 mmol) and sodium bicarbonate (0.42 g, 5 mmol), and heat to reflux for 5 h. Cool to room temperature, filter the resulting off-white solid and wash with hexane (10 mL). Partition aqueous/ethanolic filtrate between water/EtOAc (4:1) and extract aqueous phase with EtOAc (2×25 mL). Dry the combined organic extracts over Na$_2$SO$_4$, concentrate in vacuo and combine with filtered solid from crude reaction mixture to obtain the desired intermediate (1.1 g, 99%) as an off-white solid suitable for use without additional purification. MS (ES+) m/z: 216 (M+H)$^+$.

4-(2-Methylamino-thiazol-4-yl)-benzylamine

Add 1M lithium aluminum hydride in THF (5.6 mL, 5.6 mmol) under nitrogen to a solution of 4-(2-methylamino-thiazol-4-yl)-benzonitrile (0.4 g, 1.86 mmol) in anhydrous THF (5 mL). After gas evolution stops, heat the reaction mixture to reflux for 30 min. Cool to room temperature, quench by slow addition of water (0.5 mL), 5N aqueous NaOH (5 mL) and additional water (1.5 mL). Add EtOAc (50 mL), stir vigorously for 20 min and filter through Celite®. Separate and dry the organic phase over Na$_2$SO$_4$. Concentrate in vacuo to obtain the title compound (0.4 g, 98%) as a white solid suitable for use without additional purification. MS (ES+) m/z: 220 (M+H)$^+$.

Preparations 5-10

The compounds of Preparations 5-10 may be prepared essentially as described in Preparation 4 by using 4-cyanophenacyl bromide and the appropriately substituted thiourea. iso-Butylthiourea was prepared by following the procedure described in *Tetrahedron Letters,* 1988, 29, 1755-1758. Overall yields and MS (ES+) data are shown in the Table below.

| Prep. | R | R' | Compound | Yield (%) | MS (ES+) m/z |
|---|---|---|---|---|---|
| 5 | Ethyl | H | 4-(2-Ethylamino-thiazol-4-yl)-benzylamine | 85 | 234 (M + H)+ |
| 6 | iso-Propyl | H | 4-(2-iso-Propylamino-thiazol-4-yl)-benzylamine | 65 | 248 (M + H)+ |
| 7 | n-Propyl | H | 4-(2-n-Propylamino-thiazol-4-yl)-benzylamine | 61 | 248 (M + H)+ |
| 8 | —(CH$_2$)$_5$— | | 4-(2-Piperidin-1-yl-thiazol-4-yl)-benzylamine | 43 | 274 (M + H)+ |
| 9 | Cyclopropyl-methyl | H | 4-(2-Cyclopropyl-methylamino-thiazol-4-yl)-benzylamine | 53 | 260 (M + H)+ |
| 10 | iso-Butyl | H | 4-(2-iso-Butylamino-thiazol-4-yl)-benzylamine | 64 | 262 (M + H)+ |

Preparation 11

4-(2-Methylamino-oxazol-4-yl)-benzylamine Hydrochloride

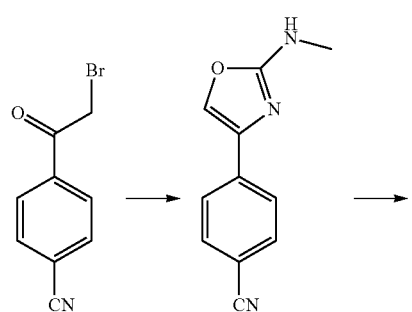

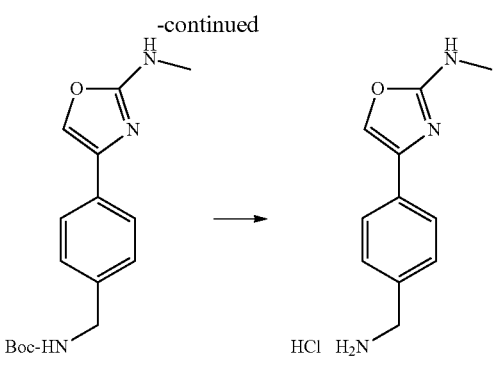

4-(2-Methylamino-oxazol-4-yl)-benzonitrile

Dissolve 4-cyanophenacyl bromide (10 g, 44.6 mmol) and methylurea (6.5 g, 89.3 mmol) in DMF (125 mL). Stir the reaction at 90° C. for 16 h under a nitrogen atmosphere. Cool to room temperature, dilute with hexane/EtOAc (1:1, 250 mL) and wash with 10% aqueous NaCl (4×75 mL). Collect the organic phase, concentrate in vacuo and purify the crude mixture by chromatography on silica gel (330 g) eluting with DCM/methanol (1:0 to 24:1 gradient) to obtain the desired intermediate (2.3 g, 26%). MS (ES+) m/z: 200.2 (M+H)+.

N-(tert-Butoxycarbonyl)-4-(2-methylamino-oxazol-4-yl)-benzylamine

Dissolve 4-(2-methylamino-oxazol-4-yl)-benzonitrile (1.6 g, 7.9 mmol) in methanol (200 mL). Add di-tert-butyl-dicarbonate (2.2 g, 10.3 mmol) and nickel(II) chloride hexahydrate (188 mg, 0.8 mmol). Cool the solution to 0° C. under a nitrogen atmosphere. Add sodium borohydride (1.5 g, 39.7 mmol) portionwise over 5 min at 0° C. under a nitrogen atmosphere. Stir the resulting black mixture for 1 h at room temperature. Concentrate the mixture in vacuo, dilute the residue with EtOAc (150 mL) and wash with saturated aqueous NaHCO$_3$ (30 mL). Collect the organic phase, concentrate in vacuo and purify by chromatography on silica gel (40 g) eluting with hexane/EtOAc (20:1 to 3:2 gradient) to obtain the desired intermediate (1.6 g, 67%). MS (ES+) m/z: 204.1 (M-Boc+H)+.

4-(2-Methylamino-oxazol-4-yl)-benzylamine Hydrochloride

Add 4N hydrogen chloride in dioxane (10.5 mL) to a solution of N-(tert-butoxycarbonyl)-4-(2-methylamino-oxazol-4-yl)-benzylamine (624 mg, 1.6 mmol) in DCM (250 mL). Stir the solution at room temperature for 16 h in a sealed flask. Concentrate the mixture in vacuo to a solid. Slurry the solid in excess of diethyl ether and filter. Collect the white solid to obtain the title compound (1.48 g, 95%). MS (ES+) m/z: 204.1 (M+H)+.

Preparation 12

4-(Cyclopentylthiomethyl)-benzylamine

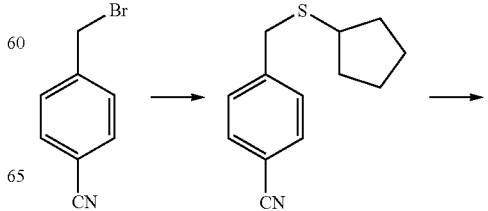

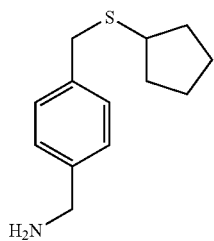

4-(Cyclopentylthiomethyl)-benzonitrile

Add sodium bis(trimethylsilyl)amide (20 mL, 40 mmol, 2M solution in THF) to a solution of cyclopentanethiol (4.3 mL, 40 mmol) in anhydrous THF (100 mL) and stir at room temperature under nitrogen for 1 h. Add 4-bromomethyl-benzonitrile (7.85 g, 40 mmol) and stir the mixture for 24 h at room temperature. Reduce solvent in vacuo and wash with saturated aqueous $NaHCO_3$. Extract with DCM (50 mL), wash organic phase with brine (50 mL) and dry over $MgSO_4$ to obtain a light yellow oil suitable for use without additional purification. GC-MS m/z: 217 (M+).

4-(Cyclopentylthiomethyl)-benzylamine

Add borane-THF complex (13.6 mL, 13.6 mmol, 1M solution in THF) dropwise to a solution of 4-(cyclopentylthiomethyl)-benzonitrile (1.5 g, 6.8 mmol) in anhydrous THF (8 mL) at room temperature and heat the mixture at reflux overnight. Cool to room temperature, add methanol cautiously and stir vigorously until gas evolution stops. Concentrate in vacuo and purify the crude mixture by SCX chromatography to obtain the title compound (0.86 g, 59%). MS (ES+) m/z: 205 $(M-NH_3+H)^+$.

Preparation 13

The compound of Preparation 13 may be prepared essentially as described in Preparation 12 using 4-bromomethyl-benzonitrile and the appropriate thiol. Overall yield and MS (ES+) data are shown in the Table below.

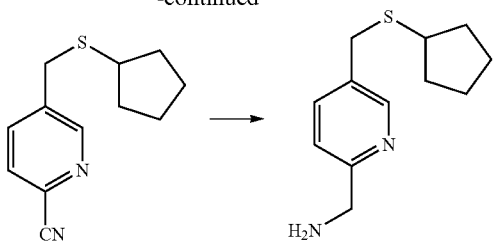

2-Chloro-5-cyclopentylthiomethyl-pyridine

Slurry 2-chloro-5-chloromethyl-pyridine (8.1 g, 45 mmol) and potassium hydroxide (10.3 g, 225 mmol) in methanol at 0° C. under nitrogen atmosphere. Add cyclopentyl mercaptan (4.8 mL, 45 mmol), warm the mixture to room temperature and stir for 16 h. Concentrate in vacuo and partition the residue between water (50 mL) and DCM (200 mL). Collect the organic phase, concentrate in vacuo and purify the crude mixture by chromatography on silica gel (330 g) eluting with hexane/EtOAc (49:1 to 4:1 gradient) to obtain the desired intermediate as an oil (8.4 g, 82%). MS (APCI+) m/z: 227 (M)+.

5-Cyclopentylthiomethyl-pyridine-2-carbonitrile

Set up reaction in 3 separate flasks. To flask number 1 slurry 2-chloro-5-cyclopentylthiomethyl-pyridine (1 g, 4.4 mmol) and copper(I) cyanide (0.78 g, 8.7 mmol) in DMF (5 mL). To flask number 2 slurry 2-chloro-5-cyclopentylthiolmethyl-pyridine (1 g, 4.4 mmol) and copper(I) cyanide (0.78 g, 8.7 mmol) in DMF (5 mL). To flask number 3 slurry 2-chloro-5-cyclopentyl-thiomethyl-pyridine (2 g, 8.8 mmol) and copper(I) cyanide (1.6 g, 17.6 mmol) in DMF (10 mL). Stir each reaction in a sealed flask at 170° C. for 16 h. Follow the

| Prep. | Structure | Compound | Yield (%) | MS (ES+) m/z |
|---|---|---|---|---|
| 13 | 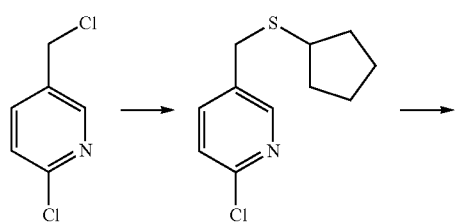 | 4-(Cyclohexylthiomethyl)-benzylamine | 56 | 219 $(M-NH_3 + H)^+$ |

Preparation 14 reactions by GC/MS. Cool all reaction flasks to room temperature. Combine the flask contents and pour into a solution of $NH_4OH$ (120 mL) and hexane/EtOAc (1:1, 100 mL). Collect the organic phase and extract the aqueous phase twice with hexane/EtOAc (1:1, 100 mL). Concentrate in vacuo the combined organic extracts. Purify by chromatography on silica gel (90 g) eluting with hexane/EtOAc (49:1 to 4:1 gradient) to obtain the desired intermediate (2 g, 40%) that contains approximately 10% starting material. Use the material in the next step without additional purification. MS (APCI+) m/z: 218 (M)+.

2-Aminomethyl-5-cyclopentylthiomethyl-pyridine

Add borane-dimethylsulfide complex (6.9 mL, 13.7 mmol, 2M solution in THF) to a solution of 5-cyclopentylthiomethyl-pyridine-2-carbonitrile (1 g, 4 mmol) in THF (12 mL) at room temperature under a nitrogen atmosphere. Stir the solution at room temperature for 16 h. Concentrate the solution in vacuo, dissolve the residue in chloroform (50 mL), add ethylenediamine (0.72 g, 12 mmol) and stir at 50° C. for 1 h. Wash the mixture with water (10 mL), dry the organic phase over $Na_2SO_4$ and concentrate in vacuo. Purify the residue by SCX chromatography followed by chromatography on silica gel (10 g) eluting with DCM/2M ammonia in methanol (1:0 to 9:1 gradient) to obtain the title compound (0.24 g, 27%). MS (ES+) m/z: 223.1 $(M+H)^+$.

Preparation 15

The compound of Preparation 15 may be prepared essentially as described in Preparation 14 using 2-chloro-5-chloromethyl-pyridine and cyclohexyl mercaptan. Overall yield and MS (ES+) data are shown in the Table below.

mmol) in carbon tetrachloride (150 mL) at reflux under a nitrogen atmosphere. Add AIBN (3×0.25 g, 3×1.5 mmol) to the reaction in 0.25 g portions every hour for 3 h. Stir the resulting mixture for one additional hour at reflux. Cool the mixture to room temperature and wash with saturated aqueous $NaHCO_3$ (30 mL). Collect the organic phase, concentrate in vacuo and purify the residue by chromatography on silica gel (330 g) eluting with DCM to obtain the desired intermediate (1.8 g, 44%). MS (ES+) m/z: 199 $(M+2)^+$.

5-iso-Propylthiomethyl-pyridine-2-carbonitrile

Add 2-propanethiol (0.53 mL, 5.6 mmol) to a slurry of 5-bromomethyl-pyridine-2-carbonitrile (1.1 g, 5.6 mmol) and cesium carbonate (1.8 g, 5.6 mmol) in DMF (10 mL) at room temperature under a nitrogen atmosphere. Stir the mixture for 16 h at room temperature. Dilute the mixture with hexane/EtOAc (1:1, 100 mL) and wash with 5% aqueous NaCl (3×30 mL). Collect the organic phase, concentrate in vacuo and purify the residue by chromatography on silica gel (40 g)

| Prep. | Structure | Compound | Yield (%) | MS (ES+) m/z |
|---|---|---|---|---|
| 15 | 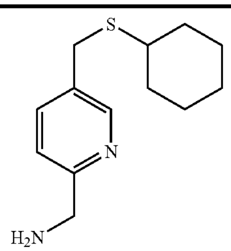 | 2-Aminomethyl-5-cyclohexylthiomethyl-pyridine | 8 | 237.1 $(M + H)^+$ |

Preparation 16

2-Aminomethyl-5-iso-propylthiomethyl-pyridine

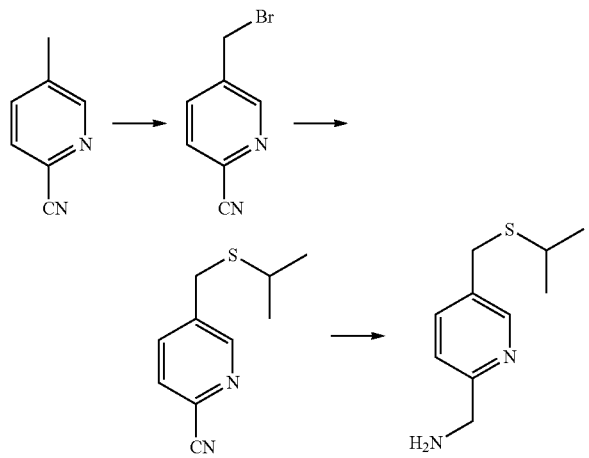

5-Bromomethyl-pyridine-2-carbonitrile

Add AIBN (0.25 g, 1.5 mmol) to a slurry of 5-methyl-pyridine-2-carbonitrile (2.5 g, 21.1 mmol) and NBS (3.7 g, 21.1 eluting with hexane/EtOAc (20:1 to 7:3 gradient) to obtain the desired intermediate (0.83 g, 77%). MS (ES+) m/z: 193.2 $(M+H)^+$.

2-Aminomethyl-5-iso-propylthiomethyl-pyridine

Add borane-dimethylsulfide complex (6.5 mL, 12.9 mmol, 2M solution in THF) to a solution of 5-iso-propylthiomethyl-pyridine-2-carbonitrile (0.83 g, 4.3 mmol) in THF (12 mL) at room temperature under a nitrogen atmosphere. Stir the solution at room temperature for 16 h. Add 5N aqueous HCl (2 mL) and stir for 2 h. Concentrate in vacuo to obtain the hydrochloride salt. Elute the compound through a SCX column to obtain the free base. Dissolve the resulting residue in DCM (30 mL) and wash with saturated aqueous $NaHCO_3$ (5 mL). Collect the organic phase, dry over $Na_2SO_4$ and concentrate in vacuo to obtain the title compound (0.3 g, 36%). MS (ES+) m/z: 197.3 $(M+H)^+$.

Preparation 17

The compound of Preparation 17 may be prepared essentially as described in Preparation 16 using 5-bromomethyl-pyridine-2-carbonitrile and 2-methyl-propanethiol. Overall yield and MS (ES+) data are shown in the Table below.

| Prep. | Structure | Compound | Yield (%) | MS (ES+) m/z |
|---|---|---|---|---|
| 17 | 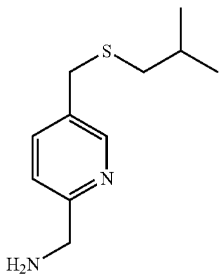 | 2-Aminomethyl-5-(2-methyl-propyl)thiomethyl-pyridine | 4 | 211.2 (M + H)+ |

Preparation 18

3-Aminomethyl-6-[(2,2-dimethylpropyl)thiomethyl]-pyridine

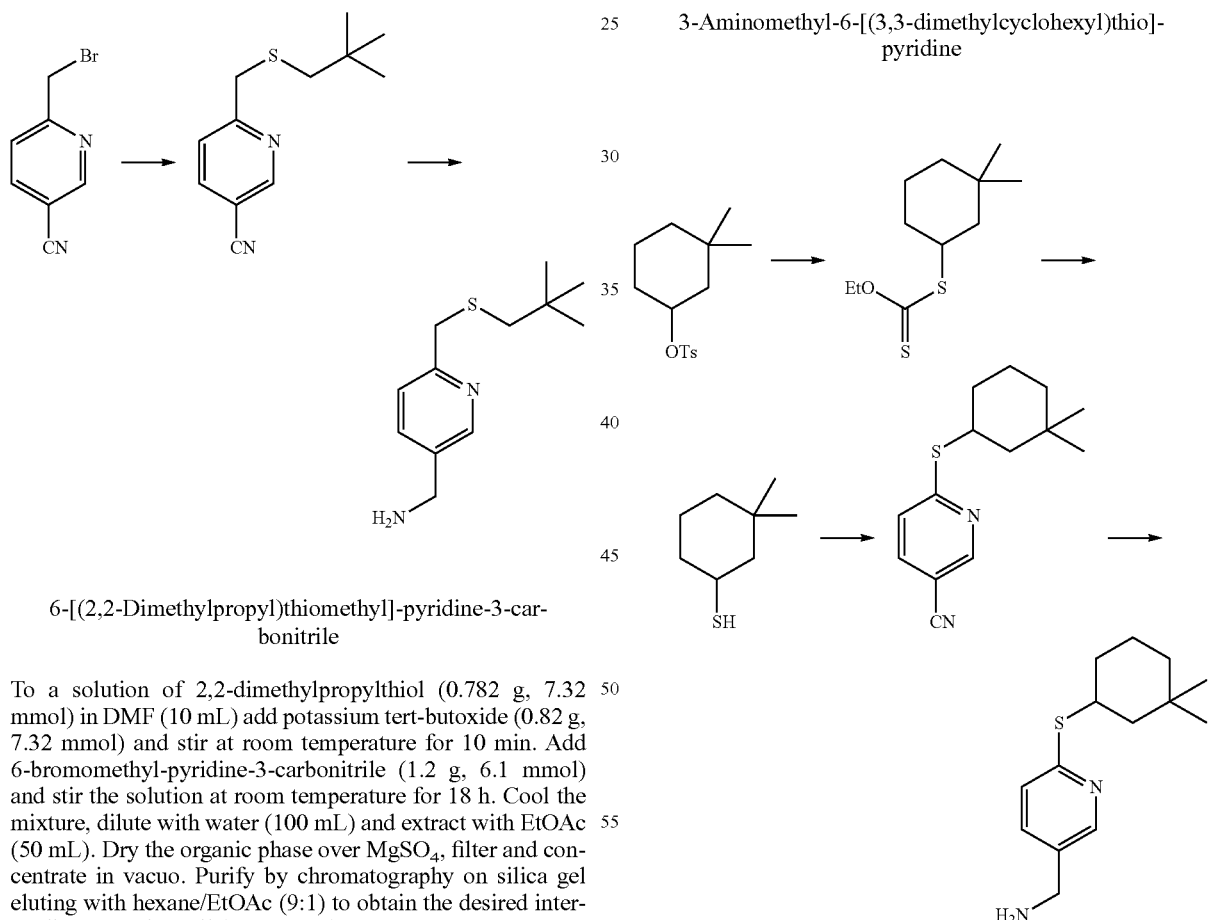

6-[(2,2-Dimethylpropyl)thiomethyl]-pyridine-3-carbonitrile

To a solution of 2,2-dimethylpropylthiol (0.782 g, 7.32 mmol) in DMF (10 mL) add potassium tert-butoxide (0.82 g, 7.32 mmol) and stir at room temperature for 10 min. Add 6-bromomethyl-pyridine-3-carbonitrile (1.2 g, 6.1 mmol) and stir the solution at room temperature for 18 h. Cool the mixture, dilute with water (100 mL) and extract with EtOAc (50 mL). Dry the organic phase over MgSO₄, filter and concentrate in vacuo. Purify by chromatography on silica gel eluting with hexane/EtOAc (9:1) to obtain the desired intermediate as a clear oil (0.5 g, 37%).

3-Aminomethyl-6-[(2,2-dimethylpropyl)thiomethyl]-pyridine

To a slurry of Raney Nickel (0.5 g, 50% in water) in ethanol (100 mL) add a solution of 6-[(2,2-dimethylpropyl)thiomethyl]-pyridine-3-carbonitrile (1 g) in ethanol (10 mL) followed by aqueous ammonia (0.88 M, 5 mL) and hydrogenate the mixture in a Parr shaker at 60 psi for 3 h. Filter the mixture through Celite® washing the filter cake with ethanol (50 mL). Remove the solvent in vacuo to obtain the title compound as a colourless oil (1.07 g, 100%).

Preparation 19

3-Aminomethyl-6-[(3,3-dimethylcyclohexyl)thio]-pyridine

S-(3,3-dimethylcyclohexyl)-O-ethyl dithiocarbonate

To a solution of 3,3-dimethylcyclohexyl 4-methylbenzenesulfonate (10 g, 35.4 mmol) [prepared by following the procedure described in *J. Org. Chem.* 1996, 61, 4716] in DMF (100 mL) add potassium ethyl xanthate (11.3 g, 70.8 mmol)

and heat at 50° C. for 48 h. Cool the mixture and dilute with diethyl ether (500 mL), wash with water (3×500 mL) and brine (2×500 mL). Dry the organic phase over MgSO₄, filter and concentrate in vacuo. Purify by chromatography on silica gel eluting with hexane/diethyl ether (20:1) to obtain the desired intermediate as a clear oil (4 g, 49%).

3,3-Dimethylcyclohexanethiol

To a solution of S-(3,3-dimethylcyclohexyl)-O-ethyl dithiocarbonate (4 g, 17.2 mmol) in DCM (100 mL) add ethylenediamine (6 mL) and stir at room temperature for 18 h. Treat the solution with 2N aqueous HCl(3×100 mL). Dry the organic phase over MgSO₄, filter and concentrate in vacuo, while keeping the water-bath temperature below 25° C., to obtain the desired intermediate as a colourless oil (2 g, 80%).

6-[(3,3-Dimethylcyclohexyl)thio]-pyridine-3-carbonitrile

Add potassium tert-butoxide (777 mg, 6.94 mmol) to a solution of 3,3-dimethylcyclohexanethiol (1 g, 6.94 mmol) in DMF (10 mL) and stir at room temperature for 10 min. Add 6-chloro-nicotinonitrile (547 mg, 3.96 mmol) and warm the solution to 60° C. for 18 h. Cool the mixture, dilute with water (100 mL) and extract with EtOAc (50 mL). Dry the organic phase over MgSO₄, filter and concentrate in vacuo. Purify by chromatography on silica gel eluting with hexane/EtOAc (9:1) to obtain the desired intermediate as a clear oil that solidifies on standing to a white solid (0.37 g, 38%).

3-Aminomethyl-6-[(3,3-dimethylcyclohexyl)thio]-pyridine

To a slurry of Raney Nickel (0.2 g, 50% in water) in ethanol (35 mL) add a solution of 6-[(3,3-dimethylcyclohexyl)thio]-pyridine-3-carbonitrile (0.37 g, 1.5 mmol) in ethanol (5 mL) followed by aqueous ammonia (0.88 M, 2 mL) and hydrogenate the mixture in a Parr shaker at 60 psi for 3 h. Filter the mixture through Celite® washing the filter cake with ethanol. Remove the solvent in vacuo to obtain the title compound as an oil (0.2 g, 53%).

Preparation 20

4-[(3,3-Dimethylcyclohexyl)thio]-benzylamine

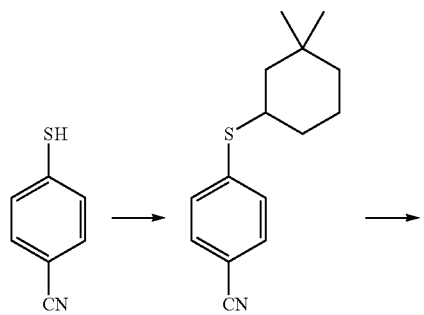

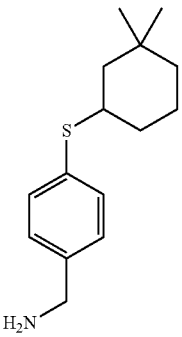

4-[(3,3-Dimethylcyclohexyl)thio]-benzonitrile

To a solution of 4-cyanothiophenol (1 g, 7.4 mmol) in DMF (15 mL) add 3,3-dimethylcyclohexyl tosylate (2.06 g, 7.4 mmol) and potassium carbonate (3.06 g, 22.2 mmol), and warm to 60° C. for 18 h. Dilute the mixture with EtOAc (50 mL) and wash sequentially with water (3×50 mL), saturated aqueous NaHCO₃ (50 mL) and brine (50 mL). Dry the organic phase over MgSO₄, filter and concentrate in vacuo. Purify by chromatography on silica gel eluting with hexane/EtOAc (9:1) to obtain the desired intermediate as a clear oil that solidifies on standing (0.35 g, 20%).

4-[(3,3-Dimethylcyclohexyl)thio]-benzylamine

To a slurry of Raney Nickel (0.2 g, 50% in water) in ethanol (35 mL) add a solution of 4-[(3,3-dimethylcyclohexyl)-thio]-benzonitrile (0.35 g, 1.43 mmol) in ethanol (5 mL) followed by aqueous ammonia (0.88 M, 2 mL) and hydrogenate the mixture in a Parr shaker at 60 psi for 3 h. Filter the mixture through Celite® washing the filter cake with ethanol. Remove the solvent in vacuo to obtain the title compound as a pale yellow oil (0.24 g, 67%).

Preparation 21

4-[(3,3-Dimethylcyclohexyl)thiomethyl]-benzylamine

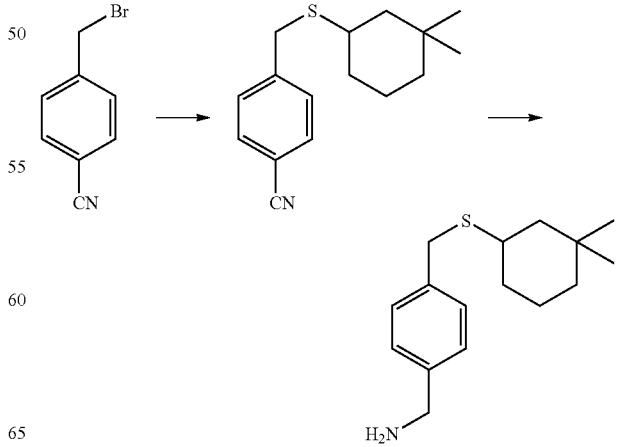

4-[(3,3-Dimethylcyclohexyl)thiomethyl]-benzonitrile

To a solution of 3,3-dimethylcyclohexanethiol (0.6 g, 4.16 mmol) in acetonitrile (50 mL) add potassium carbonate (1.72 g, 12.48 mmol) and stir at room temperature for 10 min. Add 4-cyanobenzyl bromide (816 mg, 4.16 mmol) and stir the suspension for 18 h. Dilute with water (50 mL) and extract with EtOAc (50 mL). Dry the organic phase over $MgSO_4$, filter and concentrate in vacuo. Purify by chromatography on silica gel eluting with hexane/EtOAc (10:1) to obtain the desired intermediate as a clear oil (0.4 g, 37%).

4-[(3,3-Dimethylcyclohexyl)thiomethyl]-benzylamine

To a slurry of Raney Nickel (0.25 g, 50% in water) in ethanol (40 mL) add a solution of 4-[(3,3-dimethylcyclohexyl)thiomethyl]-benzonitrile (0.4 g, 1.54 mmol) in ethanol (5 mL) followed by aqueous ammonia (0.88 M, 2.5 mL) and hydrogenate the mixture in a Parr shaker at 60 psi for 3 h. Filter the mixture through Celite® washing the filter cake with ethanol. Remove the solvent in vacuo to obtain the title compound as an oil (0.4 g, 100%).

Preparation 22

3-Aminomethyl-6-(tert-butylthio)methyl-pyridine

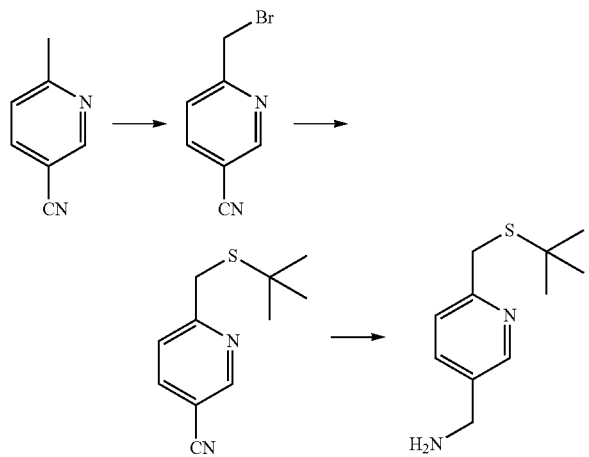

6-Bromomethyl-pyridine-3-carbonitrile

Dissolve 6-methyl-nicotinonitrile (2 g, 17 mmol) and NBS (3.01 g, 17 mmol) in anhydrous DCE (56 mL) under nitrogen. Add AIBN (277 mg, 1.7 mmol) and heat the mixture at 80° C. for 1.5-2 h. Add another batch of AIBN (277 mg, 1.7 mmol) and heat the mixture at 80° C. for a further 1-2 h. Then add a third batch of AIBN (277 mg, 1.7 mmol) and heat the mixture at 80° C. for a further 1-2 h. Cool the reaction to room temperature and concentrate in vacuo. Dissolve the residue in DCM, add silica gel and concentrate in vacuo. Purify by chromatography on silica gel (120 g, pre-packed cartridge) eluting with cyclohexane/EtOAc (98:2 to 7:3 gradient over 55 min, 40 mL/min) to isolate the desired intermediate (2 g, 60%) as a white solid that turns red on standing at room temperature. MS (ES+) m/z: 199 (M+2)$^+$.

6-(tert-Butylthio)methyl-pyridine-3-carbonitrile

Dissolve 6-bromomethyl-pyridine-3-carbonitrile (6.2 g, 31.4 mmol) in anhydrous DMF (60 mL) under nitrogen. Add tert-butylthiol (5.32 mL, 47.2 mmol) followed by cesium carbonate (15.3 g, 47.2 mmol) and stir the resulting suspension overnight. Dissolve the reaction mixture in DCM (200 mL) and add water (200 mL). Extract the aqueous phase with DCM (2×200 mL) and dry the combined organic extracts over $MgSO_4$. Filter, add silica gel and concentrate the mixture in vacuo. Purify the residue by chromatography on silica gel (40 g) eluting with cyclohexane/EtOAc (98:2 to 65:35 gradient) to obtain the desired material as a yellow solid (4.92 g, 76%). MS (ES+) m/z: 207 (M+H)$^+$.

3-Aminomethyl-6-(tert-butylthio)methyl-pyridine

Dissolve 6-(tert-butylthio)methyl-pyridine-3-carbonitrile (4.9 g, 23.8 mmol) in anhydrous THF (20 mL) under nitrogen and cool the mixture at 0° C. Add borane-THF complex (71.3 mL, 71.3 mmol, 1M solution in THF). Stir the reaction mixture at room temperature overnight. Pour slowly the reaction mixture into ice-cold 2N aqueous HCl (200 mL) and stir the resulting solution for 4 h. Concentrate in vacuo, take up the resulting solid with a minimum amount of methanol and filter through SCX-2 column eluting with methanol followed by 3N ammonia in methanol to obtain the title compound as a yellow oil (3.8 g, 77%). MS (ES+) m/z: 211 (M+H)$^+$.

The compounds of Preparations 23-24 may be prepared essentially as described in Preparation 22 using 6-bromomethyl-pyridine-3-carbonitrile and the appropriate thiol. Overall yields and MS (ES+) data are shown in the Table below.

| Prep. | Structure | Compound | Yield (%) | MS (ES+) m/z |
|---|---|---|---|---|
| 23 | 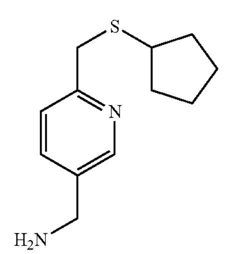 [SMILES: NCc1ccc(CSC2CCCC2)nc1] | 3-Aminomethyl-6-(cyclopentylthio)methyl-pyridine | 46 | 223 (M + H)$^+$ |
| 24 | 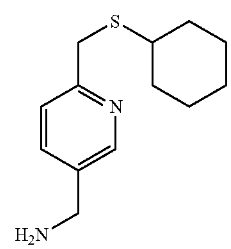 [SMILES: NCc1ccc(CSC2CCCCC2)nc1] | 3-Aminomethyl-6-(cyclohexylthio)methyl-pyridine | 52 | 237 (M + H)$^+$ |

Preparation 25

3-Aminomethyl-6-cyclohexyloxy-pyridine

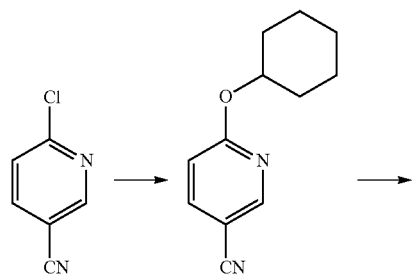

6-Cyclohexyloxy-pyridine-3-carbonitrile

Add sodium bis(trimethylsilyl)amide (3.9 mL, 7.93 mmol, 2M solution in THF) to a solution of cyclohexanol (824 μL, 7.93 mmol) in THF (10 mL). Stir for 30 min at room temperature and then add a solution of 6-chloro-nicotinonitrile (1 g, 7.2 mmol) in anhydrous THF (5 mL). Stir at room temperature overnight and then quench the reaction by addition of saturated aqueous $NaHCO_3$ (100 mL) and extract the aqueous phase with DCM (3×100 mL). Wash the combined organic extracts with brine (100 mL), dry over $MgSO_4$ and concentrate in vacuo to obtain the desired intermediate as a yellow solid (1.04 g, 71%).

3-Aminomethyl-6-cyclohexyloxy-pyridine

Dissolve 6-cyclohexyloxy-pyridine-3-carbonitrile (1 g, 5 mmol) in anhydrous THF (7 mL) under nitrogen and cool the mixture at 0° C. Add borane-THF complex (15 mL, 15 mmol, 1M solution in THF) and stir the reaction mixture at room temperature overnight. Pour slowly the reaction mixture into an ice-cold 5N aqueous HCl (50 mL) and stir the resulting solution for 4 h. Concentrate in vacuo, take up the resulting solid with a minimum amount of methanol and filter through a SCX-2 column eluting with methanol followed by 3N ammonia in methanol to obtain the title compound as a yellow oil (621 mg, 62%). MS (ES+) m/z: 207 (M+H)$^+$.

Preparation 26

The compound of Preparation 26 may be prepared essentially as described in Preparation 25 using 6-chloro-nicotinonitrile and 4,4-dimethyl-cyclohexanol. Overall yield and MS (ES+) data are shown in the Table below.

| Prep. | Structure | Compound | Yield (%) | MS (ES+) m/z | e.e. (%) |
|---|---|---|---|---|---|
| 26 | 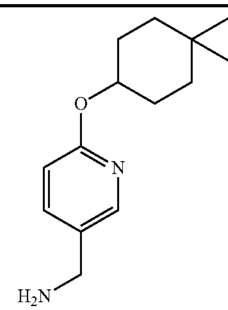 | 3-Aminomethyl-6-(4,4-dimethyl-cyclohexyloxy)-pyridine | 40 | 235 (M + H)$^+$ | — |

Preparations 27 and 28

3-Aminomethyl-6-(3,3-dimethyl-cyclohexyloxy)-pyridine Isomer 1 and 3-Aminomethyl-6-(3,3-dimethyl-cyclohexyloxy)-pyridine Isomer 2

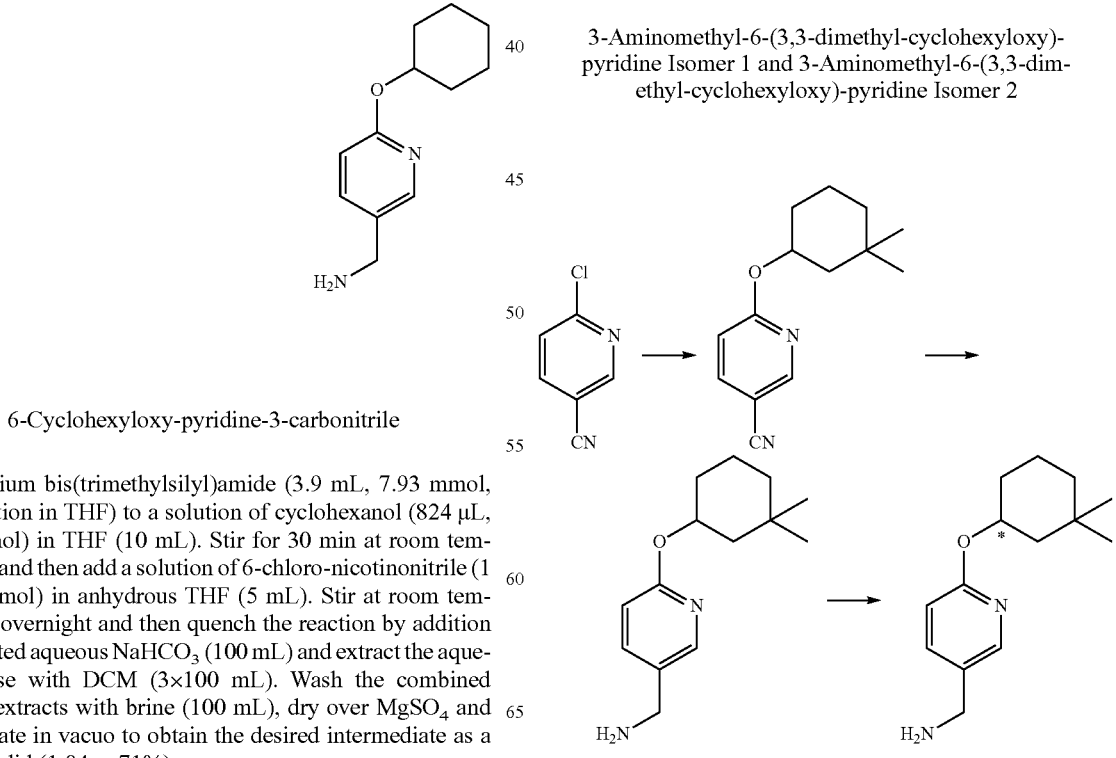

6-(3,3-Dimethyl-cyclohexyloxy)-pyridine-3-carbonitrile

Dissolve 3,3-dimethylcyclohexanol (6 g, 47 mmoles) in anhydrous THF (70 mL) under nitrogen atmosphere and cool at −78° C. Add sodium bis(trimethylsilyl)amide (23.4 mL, 47 mmol, 2M solution in THF) to this solution and stir at −78° C. for 30 min before raising to room temperature. Cool down again to −78° C. and add a solution of 2-chloro-5-cyanopyridine (7.1 g, 51.7 mmoles) in anhydrous THF (20 mL) and stir overnight while warming to room temperature. Add saturated aqueous NaHCO$_3$ (100 mL) and extract the aqueous layer with DCM (3×100 mL). Wash the combined organic extracts with brine (200 mL). Dry over MgSO$_4$, filter and concentrate in vacuo. Purify the crude mixture by chromatography on silica gel eluting with cyclohexane/EtOAc (1:0 to 9:1 gradient) to afford the desired intermediate as a solid (9.14 g, 84%). MS (ES+) m/z: 231.1 (M+H)$^+$.

(±)-3-Aminomethyl-6-(3,3-dimethyl-cyclohexyloxy)-pyridine

Dissolve 6-(3,3-dimethyl-cyclohexyloxy)-pyridine-3-carbonitrile (9.14 g, 39.7 mmoles) in THF (20 mL) at 0° C. under nitrogen and add borane-THF complex (119 mL, 119 mmol, 1M solution in THF). Stir the resulting solution overnight while warming to room temperature. Slowly add the reaction mixture to a mixture of 5N aqueous HCl (100 mL) and THF (50 mL) at 0° C. and stir for 2 h. Concentrate in vacuo and take-up the residue in a minimum amount of methanol for filtration through a SCX-2 column (10 g) eluting with methanol followed by 3N ammonia in methanol to obtain the desired intermediate as an oil (5.85 g, 63%). MS (ES+) m/z: 207 (M+H)$^+$.

3-Aminomethyl-6-(3,3-dimethyl-cyclohexyloxy)-pyridine Isomer 1 and 3-Aminomethyl-6-(3,3-dimethyl-cyclohexyloxy)-pyridine Isomer 2

Separate enantiomers of (±)-3-aminomethyl-6-(3,3-dimethyl-cyclohexyloxy)-pyridine by chiral Supercritical Fluid Chromatography (Instrument: Berger SFC Multigram; Column: 2×AD-H columns in series, 21.2×250 mm each; flow rate: 40 mL/min; mobile phase: 12% methanol with 0.2% dimethylethylamine/88% CO$_2$). 3-Aminomethyl-6-(3,3-dimethyl-cyclohexyloxy)-pyridine Isomer 1 [MS (ES+) m/z: 235 (M+H)$^+$, ee=99%; 3-Aminomethyl-6-(3,3-dimethyl-cyclohexyloxy)-pyridine Isomer 2 [MS (ES+) m/z: 235 (M+H)$^+$, ee=96%.

Preparation 29

3-Aminomethyl-6-(iso-propoxy)methyl-pyridine

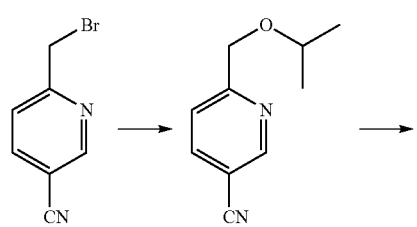

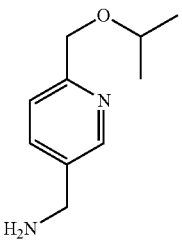

6-(iso-Propoxy)methyl-pyridine-3-carbonitrile

Add iso-propanol (2.2 g, 25 mmol) and tetrabutylammonium sulfate (28 mg, 0.08 mmol) to a solution of potassium hydroxide (7.1 g, 127 mmol) in water (7 mL) and stir at room temperature for 15 min. Add 6-bromomethyl-pyridine-3-carbonitrile (1 g, 5.08 mmol) and stir the mixture for 24 h at room temperature. Add water (15 mL) and extract with DCM (15 mL). Filter through an IST® phase separator frit to separate the organic phase and concentrate in vacuo. Purify by chromatography on silica gel eluting with hexane/EtOAc (1:0 to 1:1 gradient) to obtain the desired intermediate as a crystalline solid (0.4 g, 45%). MS (ES+) m/z: 177 (M+H)$^+$.

3-Aminomethyl-6-(iso-propoxy)methyl-pyridine

Add a solution of borane-THF complex (4.5 mL, 4.54 mmol, 1M solution in THF) to neat 6-(iso-propoxy)methyl-pyridine-3-carbonitrile (0.4 g, 2.27 mmol) and stir the mixture for 16 h at reflux. Cool to room temperature and stir for 48 h. Add 2N aqueous HCl (10 mL) until gas evolution stops and then concentrate in vacuo. Dissolve the crude mixture in methanol and filter through a SCX-2 column eluting with methanol followed by 3N ammonia in methanol to obtain the title compound (190 mg, 46%).

Preparations 30-32

The compounds of Preparations 30-32 may be prepared essentially as described in Preparation 29 using and 6-bromomethyl-pyridine-3-carbonitrile and the appropriate alcohol. Overall yields and MS (ES+) data are shown in the Table below.

| Prep. | Structure | Compound | Yield (%) | MS (ES+) m/z |
|---|---|---|---|---|
| 30 | 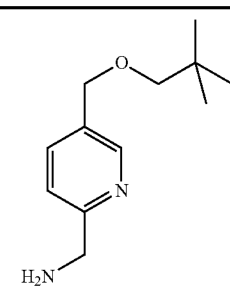 | 3-Aminomethyl-6-[(2,2-dimethylpropoxy)methyl]-pyridine | 20 | 209 (M + H)$^+$ |

| Prep. | Structure | Compound | Yield (%) | MS (ES+) m/z |
|---|---|---|---|---|
| 31 | 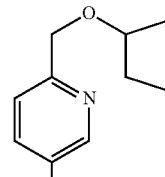 | 3-Amino-methyl-6-(cyclo-pentyloxy)methyl-pyridine | 14 | 207 (M + H)+ |
| 32 | 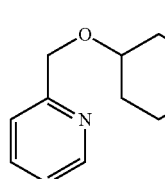 | 3-Amino-methyl-6-(cyclo-hexyloxy)methyl-pyridine | 12 | 221 (M + H)+ |

Preparation 33

2-Aminomethyl-5-cyclohexyloxy-pyridine

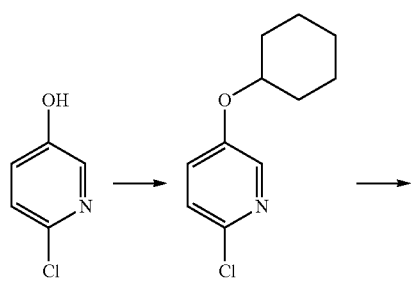

6-Chloro-3-cyclohexyloxy-pyridine

Under a nitrogen atmosphere add 6-chloro-pyridin-3-ol (2.5 g, 19.3 mmol), cyclohexanol (1.93 g, 19.3 mmol), tri-n-butylphosphine (5.07 g, 25.1 mmol), and ADDP (6.32 g, 25.1 mmol) to benzene (100 mL) and THF (10 mL) at 0° C. Stir the mixture at 0° C. for 1 h and at room temperature for 12 h. Dilute with EtOAc and water. Separate the layers and extract the aqueous layer with EtOAc. Wash the organic phase with water (30 mL) and brine (20 mL). Dry the organic phase over Na2SO4, filter, and concentrate in vacuo. Purify the crude mixture by chromatography on silica gel (400 g) eluting with hexane/EtOAc (1:0 to 98:2 gradient) to obtain the desired intermediate as clear oil (1.8 g, 58%). MS (APCI+) m/z: 212 (M+H)+.

5-Cyclohexyloxy-pyridine-2-carbonitrile

Under a nitrogen atmosphere, add 6-chloro-3-cyclohexyloxy-pyridine (1.5 g, 7.1 mmol) and copper(I) cyanide (1.89 g, 21 mmol) to NMP (15 mL). Heat the mixture at 180° C. overnight. Cool the mixture to room temperature and add copper(I) cyanide (0.63 g, 7.1 mmol). Heat the mixture at 180° C. for 6 h. Cool the mixture to room temperature, dilute with 5N aqueous NH4OH and extract with DCM. Separate the layers and extract the aqueous phase with additional DCM. Wash the combined organic extracts with water and brine. Dry the organic phase over Na2SO4, filter, and concentrate in vacuo. Purify the residue by chromatography on silica gel (500 g) eluting with hexane/EtOAc (20:1) to obtain the desired intermediate (820 mg, 57%). MS (ES+) m/z: 203 (M+H)+.

2-Aminomethyl-5-cyclohexyloxy-pyridine

Under a nitrogen atmosphere, add borane-dimethylsulfide complex (20.3 mL, 40.6 mmol, 2M solution in THF) to a solution of 5-cyclohexyloxy-pyridine-2-carbonitrile (0.82 g, 4.06 mmol) in THF (800 mL) at 0° C. Warm the mixture to room temperature and stir overnight. Cool the mixture in an ice-bath, add methanol (15 mL) and concentrated HCl (2 mL). Stir for 2 h, and concentrate in vacuo. Dissolve the residue in saturated aqueous K2CO3. Extract with DCM and wash the organic phase with water and brine. Dry the organic phase over Na2SO4, filter, and concentrate in vacuo to obtain the title compound (0.3 g, 36%). MS (ES+) m/z: 207 (M+H)+.

Preparation 34

2-Aminomethyl-5-cycloheptyloxy-pyridine

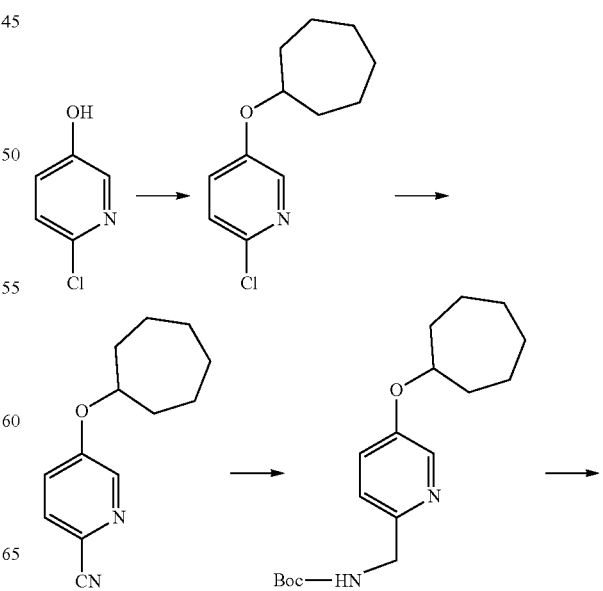

6-Chloro-3-cycloheptyloxy-pyridine

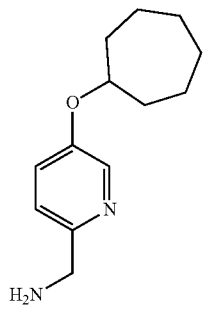

Add 6-chloro-pyridin-3-ol (2 g, 15.4 mmol), cycloheptanol (1.93 g, 17 mmol), tri-n-butylphosphine (4.67 mL, 19.3 mmol), and ADDP (4.87 g, 19.3 mmol) to THF (60 mL) at 0° C. under a nitrogen atmosphere. Stir the mixture at 0° C. for 1 h and at room temperature for 12 h. Dilute with EtOAc (50 mL), add water (50 mL) and separate the layers. Extract the aqueous layer with EtOAc (4×30 mL). Wash the combined organic extracts with water (30 mL) and brine (20 mL). Dry the organic phase over $Na_2SO_4$, filter, and concentrate in vacuo. Purify the crude mixture by chromatography on silica gel (120 g, pre-packed cartridge) eluting with hexane/EtOAc (1:0 to 1:1 gradient over 1.25 h, 80 mL/min) to obtain the desired intermediate as a colorless oil (2.36 g, 68%). MS (APCI+) m/z: 226 (M H)$^+$.

5-Cycloheptyloxy-pyridine-2-carbonitrile

Add 6-chloro-3-cycloheptyloxy-pyridine (2.35 g, 10.4 mmol) and copper(I) cyanide (1.16 g, 13.1 mmol) to NMP (25 mL). Heat the mixture to 190° C. and stir overnight. Cool the mixture to room temperature, add water (50 mL) and diethyl ether (30 mL). Extract the aqueous phase with diethyl ether (3×25 mL). Wash the combined organic extracts with brine (20 mL), dry over $Na_2SO_4$, filter, and concentrate in vacuo. Purify the crude mixture by chromatography on silica gel (45 g, pre-packed cartridge) eluting with hexane/EtOAc (1:0 to 1:1 gradient over 60 min, 80 mL/min) to obtain the desired intermediate as a colorless oil (1.21 g, 54%). MS (APCI+) m/z: 217 (M+H)$^+$.

2-(tert-Butoxycarbonylamino-methyl)-5-cycloheptyloxy-pyridine

Add 5-cycloheptyloxy-pyridine-2-carbonitrile (1.6 g, 7.33 mmol), di-tert-butyl-dicarbonate (3.17 g, 14.7 mmol) and 10% Pd/C (100 mg) to ethanol (25 mL). Bubble hydrogen (via balloon) through the vigorously stirred solution for 8 h and under static pressure overnight. Filter the mixture through cellulose powder (20 □m) and rinse with ethanol. Concentrate in vacuo and purify by chromatography on silica gel (45 g, pre-packed cartridge) eluting with hexane/EtOAc (1:0 to 4:1 over 30 min, 80 mL/min) to obtain the desired intermediate as a colorless oil (1.91 g, 81%). MS (APCI+) m/z: 321 (M+H)$^+$.

2-Aminomethyl-5-cycloheptyloxy-pyridine

Dissolve 2-(tert-butoxycarbonylamino-methyl)-5-cycloheptyloxy-pyridine (1.9 g, 5.95 mmol) in methanol (25 mL) and cool to 0° C. Bubble hydrogen chloride through the vigorously stirred solution for 30 min. Evaporate in vacuo and partition the residue between 3N aqueous NaOH (10 mL) and DCM (20 mL). Separate the two layers and extract the aqueous layer with DCM (2×20 mL). Wash the combined organic extracts with brine (20 mL), dry over $Na_2SO_4$, filter, and concentrate in vacuo to obtain the title compound as a colorless oil (941 mg, 72%). MS (APCI+) m/z: 221 (M+H)$^+$.

Preparation 35

2-Aminomethyl-5-(3,3-dimethylcyclohexyloxy)-pyridine

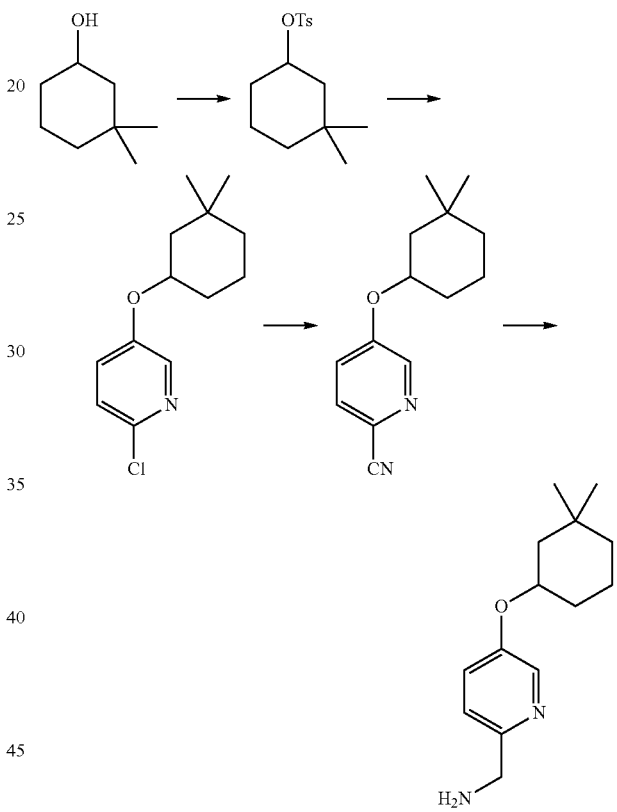

3,3-Dimethylcyclohexyl 4-methylbenzenesulfonate

Under a nitrogen atmosphere, add 3,3-dimethylcyclohexanol (1 g, 9.75 mmol), DMAP (238 mg, 1.95 mmol), triethylamine (2.70 mL, 19.5 mmol), and p-toluenesulfonyl chloride (2.045 g, 10.72 mmol) to DCM (25 mL) at 0° C. Stir the mixture for 1 h at 0° C. and warm to room temperature overnight. Add saturated aqueous $NaHCO_3$ (20 mL) and separate the layers. Extract the aqueous layer with DCM (3×20 mL). Wash the combined organic extracts with water and brine. Dry the organic phase over $Na_2SO_4$, filter, and concentrate in vacuo. Purify the crude mixture by chromatography on silica gel (45 g, pre-packed cartridge) eluting with hexane/EtOAc (1:0 to 1:1 gradient over 60 min, 80 mL/min) to obtain the desired intermediate as a clear oil (1.93 g, 70%). MS (APCI+) m/z: 283 (M+H)$^+$.

6-Chloro-3-(3,3-dimethylcyclohexyloxy)-pyridine

Under a nitrogen atmosphere, add 3,3-dimethylcyclohexyl 4-methylbenzenesulfonate (1.2 g, 4.25 mmol), 6-chloro-pyridin-3-ol (0.5 g, 3.86 mmol) and potassium hydroxide (238 mg, 4.25 mmol) to DMF (10 mL). Heat the mixture to 60° C. and stir overnight. Add water (20 mL) and diethyl ether (20 mL) and separate the layers. Extract the aqueous layer with diethyl ether (3×20 mL). Wash the combined organic extracts with brine (20 mL), dry over $Na_2SO_4$, filter, and concentrate in vacuo. Purify by chromatography on silica gel (80 g, pre-packed cartridge) eluting with hexane/EtOAc (1:0 to 1:1 over 60 min, 80 mL/min) to obtain the desired intermediate as a white solid (728 mg, 79%). MS (APCI+) m/z: 240 $(M+H)^+$.

5-(3,3-Dimethylcyclohexyloxy)-pyridine-2-carbonitrile

Add 6-chloro-3-(3,3-dimethylcyclohexyloxy)-pyridine (1.1 g, 4.59 mmol) and copper(I) cyanide (1.23 g, 13.8 mmol) to NMP (20 mL). Heat the mixture to 190° C. and stir overnight. Cool the mixture to room temperature, add water (30 mL) and diethyl ether (30 mL). Extract the aqueous phase with diethyl ether (3×20 mL). Wash the combined organic extracts with brine (20 mL), dry over $Na_2SO_4$, filter, and concentrate in vacuo. Purify the crude mixture by chromatography on silica gel (80 g, pre-packed cartridge) eluting with hexane/EtOAc (1:0 to 1:1 gradient over 60 min, 80 mL/min) to obtain the desired intermediate as a colorless oil (412 mg, 39%). MS (APCI+) m/z: 231 $(M+H)^+$.

2-Aminomethyl-5-(3,3-dimethylcyclohexyloxy)-pyridine

Under a nitrogen atmosphere, add lithium aluminum hydride (264 mg, 6.95 mmol) to THF (15 mL) at 0° C. Add a solution of 5-(3,3-dimethylcyclohexyloxy)-pyridine-2-carbonitrile (0.4 g, 1.74 mmol) in THF (5 mL), stir at 0° C. for 1 h and warm to room temperature overnight. Cool the mixture at 0° C. and carefully add water (0.3 mL). Add diethyl ether (25 mL), 3N aqueous NaOH (0.3 mL) and water (0.9 mL), and stir for 1 h at room temperature. Filter the solid residue and concentrate the filtrate in vacuo to obtain the title compound as a colorless oil (360 mg, 88%). MS (APCI+) m/z: 235 $(M+H)^+$.

Preparation 36

(Z)-4-(2-Cyclohexylvinyl)-benzylamine

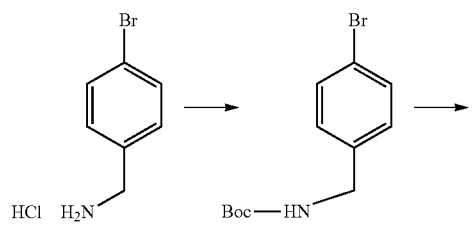

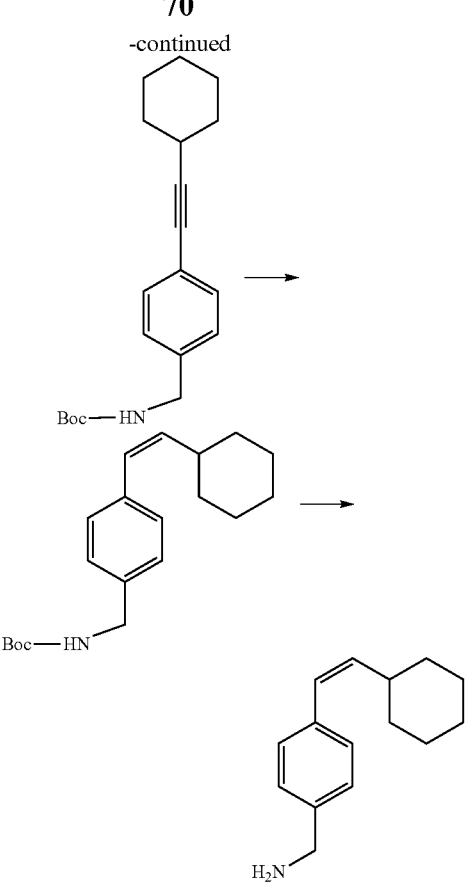

N-(tert-Butoxycarbonyl)-4-bromo-benzylamine

Slurry 4-bromo-benzylamine hydrochloride (25 g, 112.6 mmol) in DCM (400 mL). Add triethylamine (31.4 mL, 225.2 mmol) and di-tert-butyl-dicarbonate (24.55 g, 112.6 mmol) and stir the solution at room temperature for 16 h under a nitrogen atmosphere. Wash the mixture with water, dry the organic phase over $Na_2SO_4$ and concentrate in vacuo to obtain a solid. Wash the solid with hexane, filter and dry to obtain the desired intermediate as a white solid (31.735 g, 99%) suitable for use without further purification. MS (ES+) m/z: 230 $[M-(t-Bu)+H]^+$.

N-(tert-Butoxycarbonyl)-4-cyclohexylethynyl-benzylamine

Add cyclohexylacetylene (1.1 mL, 8.4 mmol) to a slurry of N-(tert-butoxycarbonyl)-4-bromo-benzylamine (2 g, 6.9 mmol), dichlorobis(triphenylphosphine)palladium (147 mg, 0.2 mmol), copper(I) iodide (67 mg, 0.4 mmol) and triethylamine (1.4 mL, 9.7 mmol) in DMF (7 mL). Stir the reaction in a sealed flask at 110° C. for 16 h. Cool to room temperature, dilute with water (10 mL) and hexane/EtOAc (1:1, 100 mL). Filter the bi-phasic mixture through Celite®, collect the organic phase and wash with 5% aqueous NaCl (3×30 mL). Concentrate the organic phase in vacuo and purify by chromatography on silica gel (120 g) eluting with hexane/EtOAc (20:1 to 3:2 gradient) to obtain the desired intermediate (0.75 g, 34%). MS (ES+) m/z: 258 $[M-(t-Bu)+H]^+$.

(Z)—N-tert-Butoxycarbonyl)-4-(2-cyclohexylvinyl)benzylamine

Dissolve N-(tert-butoxycarbonyl)-4-cyclohexylethynyl-benzylamine (0.5 g, 1.6 mmol) in EtOAc (20 mL). Transfer the solution to a pressure vessel and hydrogenate at 30 psi for 3 h in the presence of 5% palladium on calcium carbonate (poisoned with 3.5% lead, 0.25 g). Filter the catalyst through Celite®, wash the filter cake with excess of EtOAc followed by excess of DCM and concentrate the filtrate in vacuo to an oil (HPLC shows starting material still present). Dissolve the oil in EtOAc (20 mL) again. Transfer the solution to a pressure vessel and hydrogenate contents at 30 psi for 2 h in the presence of 5% palladium on calcium carbonate (poisoned with 3.5% lead, 0.25 g). Filter the catalyst through Celite®, wash the filter cake with excess of EtOAc followed by excess of DCM and concentrate the filtrate in vacuo to an oil (HPLC shows all starting material consumed). Use this material in the next step without additional purification (0.49 g). MS (ES+) m/z: 260.2 [M-(t-Bu)+H]$^+$.

(Z)-4-(2-Cyclohexylvinyl)-benzylamine

Add trifluoroacetic acid (1 mL) to a solution of (Z)—N-(tert-butoxycarbonyl)-4-(2-cyclohexylvinyl)-benzylamine (0.49 g, 1.5 mmol) in DCM (10 mL). Stir the mixture at room temperature for 2 h, concentrate in vacuo and purify the residue by SCX chromatography to obtain the title compound (0.3 g, 87%, estimate 10% of alkane present). Use this material in the next step without additional purification. MS (ES+) m/z: 199.3 (M-NH$_3$+H)$^+$.

Preparation 37

(E)-3-Aminomethyl-6-(2-cyclohexylvinyl)-pyridine

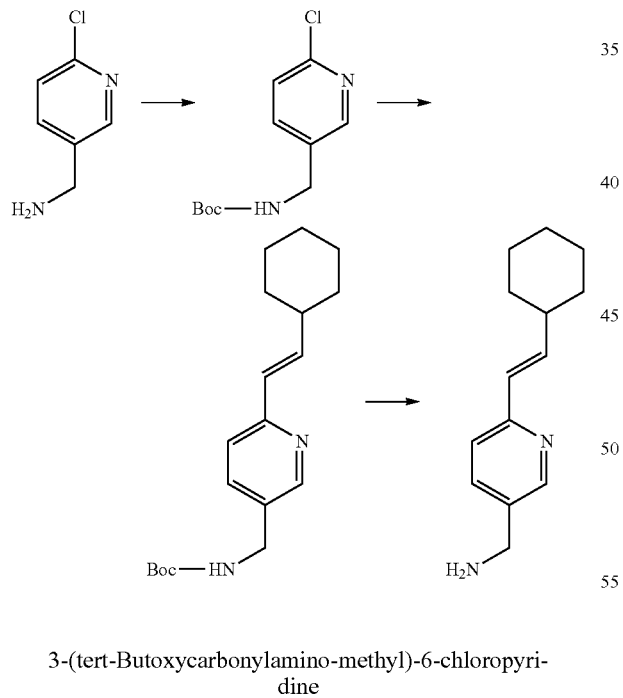

3-(tert-Butoxycarbonylamino-methyl)-6-chloropyridine

Dissolve 3-aminomethyl-6-chloropyridine (1.65 g, 11.57 mmol) in DCM (58 mL) and add triethylamine (2.42 mL, 17.26 mmol) followed by di-tert-butyl-dicarbonate (3.03 g, 13.88 mmol). Stir the resulting solution at room temperature overnight. Add DCM and saturated aqueous NaHCO$_3$. Separate the aqueous phase and extract twice with DCM. Dry the combined organic extracts over MgSO$_4$, filter and concentrate in vacuo. Purify by chromatography on silica gel (120 g, pre-packed cartridge) eluting stepwise with hexane/EtOAc (1:0 over 5 min, 19:1 over 5 min, 9:1 over 5 min and 85:15 over 5 min; 50 mL/min) to obtain the desired intermediate (2.41 g, 86%). MS (APCI+) m/z: 187 [M-(t-Bu)+H]$^+$.

(E)-3-(tert-Butoxycarbonylamino-methyl)-6-(2-cyclohexylvinyl)-pyridine

Combine 3-(tert-butoxycarbonylamino-methyl)-6-chloropyridine (1.42 g, 5.85 mmol), 2-cyclohexylvinyl boronic acid (1.35 g, 8.78 mmol), [1,1'-bis(diphenylphosphino)-ferrocene]dichloropalladium(II) complex with DCM (239 mg, 0.293 mmol), and 2M aqueous Na$_2$CO$_3$ (9.65 mL, 19.2 mmol) in 1,4-dioxane (60 mL). Purge the resulting solution with nitrogen for 5 min and heat at 90° C. overnight. Cool the reaction mixture to room temperature and partition the mixture between EtOAc and water. Separate the aqueous phase and extract twice with EtOAc. Dry the combined organic extracts over MgSO$_4$, filter and concentrate in vacuo. Purify by chromatography on silica gel (120 g, pre-packed cartridge) eluting stepwise with hexane/EtOAc (1:0 over 5 min, 49:1 over 5 min, 19:1 over 5 min, 9:1 over 5 min and 85:15 over 5 min; 50 mL/min) to obtain the desired intermediate (1.3 g, 70%). MS (APCI+) m/z: 317 (M+H)$^+$.

(E)-3-Aminomethyl-6-(2-cyclohexylvinyl)-pyridine

Dissolve (E)-3-(tert-butoxycarbonylamino-methyl)-6-(2-cyclohexylvinyl)-pyridine (1.3 g, 4.11 mmol) in EtOAc (60 mL) and bubble hydrogen chloride through the solution for 20 min. Stir the mixture overnight at room temperature. Concentrate the mixture in vacuo and dissolve the resulting solid in water. Adjust the pH to 9-11 with 20% aqueous K$_2$CO$_3$ and extract with DCM. Dry the combined organic extracts over MgSO$_4$, filter and concentrate in vacuo to obtain the title compound (0.78 g, 88%). MS (APCI+) m/z: 217 (M+H)$^+$.

Preparation 38

(E)-2-Aminomethyl-5-(2-cyclohexylvinyl)-pyridine (E)-5-(2-Cyclohexylvinyl)-pyridine-2-carbonitrile Combine a mixture of 5-bromo-2-cyano-pyridine (2 g, 10.93 mmol), 2-cyclohexylvinyl boronic acid (2.52 g, 16.39 mmol), [1,1'-bis(diphenylphosphino)ferrocene]dichloropalladium (II) complex with DCM (446 mg, 0.546 mmol) and 2M aqueous Na$_2$CO$_3$ (18.2 mL, 36.07 mmol) in 1,4-dioxane (110 mL). Purge with nitrogen and heat at 90° C. overnight. Cool the reaction to room temperature and partition between EtOAc and water. Separate the aqueous phase and extract with EtOAc. Dry the combined organic extracts over MgSO₄, filter and concentrate in vacuo. Purify by chromatography on silica gel (120 g, pre-packed cartridge) eluting stepwise with hexane/EtOAc (1:0 over 5 min, 49:1 over 5 min and 19:1 over 5 min; 50 mL/min) to obtain the desired intermediate (1.76 g, 76%). MS (APCI+) m/z: 213 (M+H)⁺.

(E)-2-Aminomethyl-5-(2-cyclohexylvinyl)-pyridine

Cool a stirred solution of (E)-5-(2-cyclohexylvinyl)-pyridine-2-carbonitrile (1.76 g, 8.3 mmol) in THF (55 mL) to 0° C. under nitrogen. Carefully add lithium aluminum hydride (1.26 g, 33.2 mmol) and warm to room temperature overnight. Quench the reaction mixture with sequential addition of water (1.26 mL), 15% aqueous NaOH (1.26 mL) and water (3×1.26 mL), and stir for 3 h. Filter the mixture through Celite®, wash with EtOAc, and concentrate in vacuo. Purify the crude mixture by chromatography on silica gel (120 g, pre-packed cartridge) eluting stepwise with DCM/(chloroform:methanol:concentrated NH₄OH 80:18:2) (1:0 over 5 min, 49:1 over 5 min, 19:1 over 5 min, 93:7 over 5 min and 9:1 over 5 min; 50 mL/min) to obtain the title compound (608 mg, 34%). MS (APCI+) m/z: 217 (M+H)⁺.

Preparation 39

(Z)-3-Aminomethyl-6-(2-cyclohexylvinyl)-pyridine

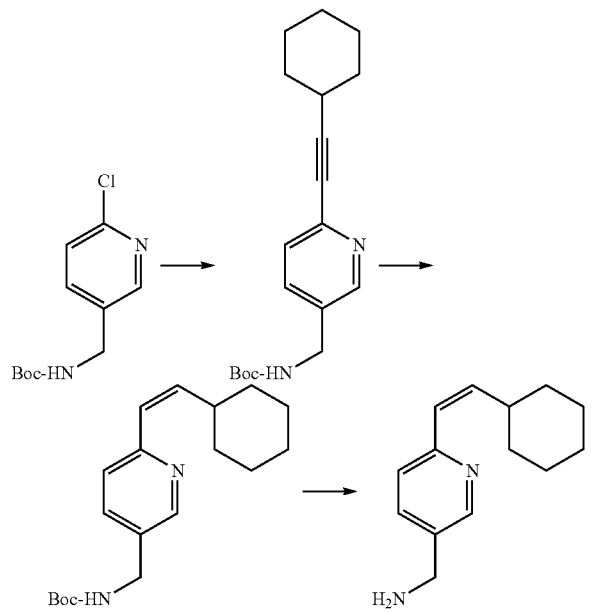

3-(tert-Butoxycarbonylamino-methyl)-6-cyclohexyl-ethynyl-pyridine

Under a nitrogen atmosphere, add 3-(tert-butoxycarbonylamino-methyl)-6-chloropyridine (1 g, 4.12 mmol), cyclohexylacetylene (0.446 g, 4.12 mmol), dichlorobis(triphenylphosphine)-palladium (578 mg, 0.824 mmol), copper(I) iodide (157 mg, 0.824 mmol) and triethylamine (8.6 mL, 6.18 mmol) to THF (20 mL). Heat the mixture to reflux overnight. Cool the mixture to room temperature, and dilute with saturated aqueous NaHCO₃ (50 mL) and EtOAc (50 mL). Separate the layers and extract the aqueous layer with EtOAc (4×30 mL). Wash the combined organic extracts with brine (20 mL), dry over Na₂SO₄, filter and concentrate in vacuo. Purify the crude mixture by chromatography on silica gel (120 g, pre-packed cartridge) eluting with hexane/EtOAc (1:0 to 6:1 gradient over 1.25 h, 80 mL/min) to obtain the desired intermediate as a colorless oil (0.71 g, 55%). MS (APCI+) m/z: 215 (M-Boc+H)⁺.

(Z)-3-(tert-Butoxycarbonylamino-methyl)-6-(2-cyclohexylvinyl)-pyridine

Add 3-(tert-butoxycarbonylamino-methyl)-6-cyclohexylethynyl-pyridine (0.7 g, 2.21 mmol) and Lindlar's Catalyst (0.1 g) to EtOAc (20 mL). Bubble hydrogen (via balloon) through the mixture for 2 h and stir under static atmosphere of hydrogen overnight. Filter the catalyst through Celite® and concentrate the filtrate in vacuo. Purify the crude mixture by chromatography on silica gel (80 g, pre-packed cartridge) eluting with hexane/EtOAc (1:0 to 9:1 gradient over 1.25 h, 80 mL/min) to obtain the desired intermediate as a colorless oil (0.21 g, 30%) and starting material (0.42 g, 60%). Repeat the reaction on the recovered starting material to obtain the desired intermediate (242 mg, 57%; 452 mg total, 64% overall). MS (APCI+) m/z: 217 (M-Boc+H)⁺.

(Z)-3-Aminomethyl-6-(2-cyclohexylvinyl)-pyridine

Add (Z)-3-(tert-butoxycarbonylamino-methyl)-6-(2-cyclohexylvinyl)-pyridine (0.42 g, 1.33 mmol) to methanol (20 mL) and cool to 0° C. Bubble hydrogen chloride into the solution until saturated, and allow the mixture to warm to room temperature. Concentrate the mixture in vacuo and partition the residue between 3N aqueous NaOH (30 mL) and DCM (30 mL). Separate the layers and extract the aqueous phase with DCM (3×30 mL). Wash the combined organic extracts with brine (30 mL), dry over Na₂SO₄, filter, and concentrate in vacuo to obtain the title compound as a colorless oil (0.89 g, 80%). MS (APCI+) m/z: 217 (M+H)⁺.

Preparation 40

(Z)-2-Aminomethyl-5-(2-cyclohexylvinyl)-pyridine

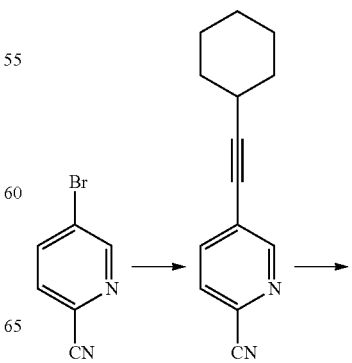

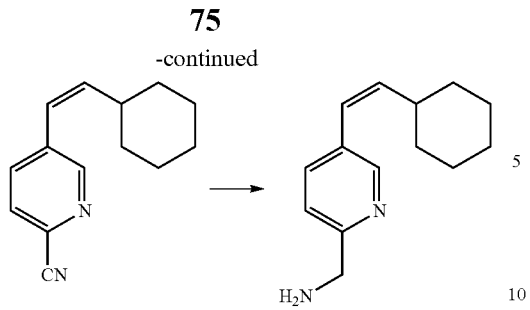

5-Cyclohexylethynyl-pyridine-2-carbonitrile

Under a nitrogen atmosphere, add 5-bromo-2-cyano-pyridine (1.5 g, 8.2 mmol), cyclohexylacetylene (0.887 g, 8.2 mmol), dichlorobis(triphenylphosphine)palladium (575 mg, 0.82 mmol), copper(I) iodide (234 mg, 1.23 mmol) and triethylamine (11.4 mL, 82 mmol) to THF (50 mL). Heat the mixture to reflux and stir for 4 h. Cool the mixture to room temperature and dilute with saturated aqueous NaHCO$_3$ (50 mL) and EtOAc (50 mL). Separate the layers and extract the aqueous layer with EtOAc (4×30 mL). Wash the combined organic extracts with brine (20 mL), dry over Na$_2$SO$_4$, filter and concentrate in vacuo. Purify the crude mixture by chromatography on silica gel (120 g, pre-packed cartridge) eluting with hexane/EtOAc (1:0 to 9:1 gradient over 1.25 h, 80 mL/min) to obtain the desired intermediate as a colorless oil (1.28 g, 74%). MS (APCI+) m/z: 211 (M H)$^+$.

(Z)-5-(2-Cyclohexylvinyl)-pyridine-2-carbonitrile

Add 5-cyclohexylethynyl-pyridine-2-carbonitrile (1.4 g, 4.16 mmol) and Lindlar's Catalyst (0.5 g) to EtOAc (20 mL). Bubble hydrogen (via balloon) through the mixture for 2 h and stir under static atmosphere of hydrogen overnight. Filter the catalyst through Celite® and concentrate the filtrate in vacuo. Purify by chromatography on silica gel (80 g, pre-packed cartridge) eluting with hexane/EtOAc (1:0 to 9:1 gradient over 1.25 h, 80 mL/min) to obtain the desired intermediate as a colorless oil (0.89 g, 80%). MS (APCI+) m/z: 213 (M+H)$^+$.

(Z)-2-Aminomethyl-5-(2-cyclohexylvinyl)-pyridine

Under a nitrogen atmosphere, add lithium aluminum hydride (965 mg, 25.4 mmol) to THF (20 mL) at 0° C. Add a solution of (Z)-5-(2-cyclohexylvinyl)-pyridine-2-carbonitrile (1.8 g, 1.74 mmol) in THF (5 mL) and stir at 0° C. for 1 h and to room temperature overnight. Cool the mixture to 0° C. and carefully add water (0.95 mL). Add diethyl ether (125 mL), 3N aqueous NaOH (0.95 mL), and water (2.85 mL) and stir for 1 h at room temperature. Filter the solid residue and concentrate in vacuo to obtain the title compound as a colorless oil (0.49 g, 30%). MS (APCI+) m/z: 217 (M+H)$^+$.

Preparation 41

4-(2-Cyclohexyl-2-oxo-ethyl)-benzylamine

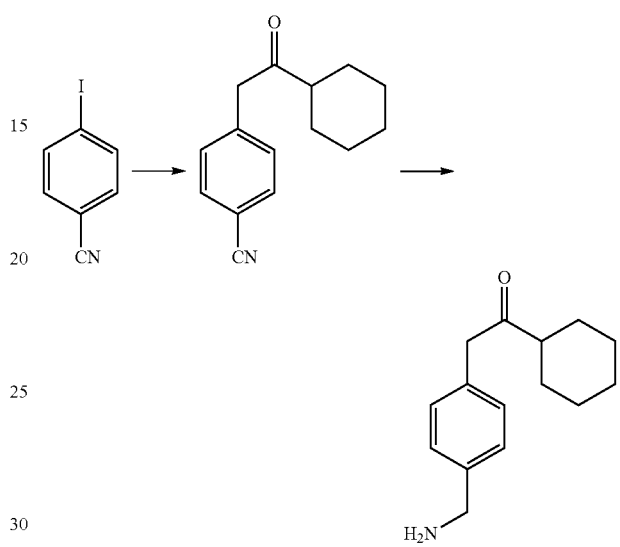

4-(2-Cyclohexyl-2-oxo-ethyl)-benzonitrile

Add 4-iodobenzonitrile (1.0 g, 4.37 mmol) and 1-cyclohexyl-ethanone (717 mg, 5.68 mmol) to a suspension of tris(dibenzylideneacetone)dipalladium(0) (60 mg, 0.065 mmol), BINAP (98 mg, 0.157 mmol) and sodium tert-butoxide (546 mg, 5.68 mmol) in anhydrous THF (26 mL). Heat the mixture at 70° C. under nitrogen atmosphere. After 6 h, add tris(dibenzylideneacetone)dipalladium(0) (60 mg, 0.065 mmol), BINAP (98 mg, 0.157 mmol), sodium tert-butoxide (294 mg, 3.06 mmol) and 1-cyclohexyl-ethanone (386 mg, 3.06 mmol) and allow to stir the mixture at 70° C. under nitrogen overnight. Add water and extract twice with EtOAc. Dry the combined organic extracts over MgSO$_4$, filter and concentrate in vacuo. Purify by chromatography on silica gel eluting with hexane/EtOAc (92:8) to obtain the desired intermediate as a yellow oil (902 mg, 91%).

4-(2-Cyclohexyl-2-oxo-ethyl)-benzylamine

Bubble nitrogen for 10 min into a solution of 4-(2-cyclohexyl-2-oxo-ethyl)-benzonitrile (478 mg, 2.10 mmol) in methanol (80 mL) with concentrated HCl (5 drops). Add 10% Pd/C (Degussa type E101, 96 mg) and submit the mixture to hydrogenation at atmospheric pressure overnight. Filter the catalyst through Celite® and concentrate in vacuo to obtain the hydrochloride salt of the title compound. Wash with diethyl ether/hexane (1:1) and filter the white solid. Add saturated aqueous NaHCO$_3$ and extract twice with EtOAc. Dry the combined organic extracts over MgSO$_4$, filter and concentrate in vacuo to obtain the title compound as a yellow oil (145 mg, 30%). MS (ES+) m/z: 232 (M+H)+.

Preparation 42

4-(Morpholin-4-ylmethyl)-benzylamine

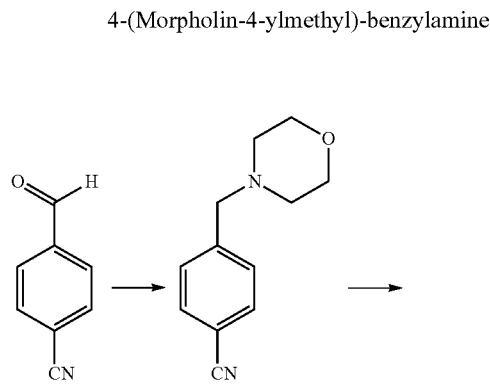

4-(Morpholin-4-ylmethyl)-benzonitrile

Dissolve 4-cyanobenzaldehyde (5 g, 38.1 mmol), morpholine (4.15 g, 47.7 mmol) and acetic acid (2.2 mL, 38.1 mmol) in DCE (100 mL). Add sodium cyanoborohydride (3.59 g, 57.2 mmol), and stir the mixture overnight. Add water (100 mL), separate the layers and extract the aqueous layer with DCM (3×50 mL). Wash the combined organic extracts with brine, dry over Na$_2$SO$_4$, filter and concentrate in vacuo. Purify by chromatography on silica gel (80 g, pre-packed cartridge) eluting with hexane/EtOAc (1:0 to 1:2 over 1.25 h, 80 mL/min) to obtain the desired intermediate as a colorless oil (6.1 g, 79%). MS (APCI+) m/z: 203 (M+H)+.

4-(Morpholin-4-ylmethyl)-benzylamine

Under a nitrogen atmosphere, add lithium aluminum hydride (1.13 g, 29.7 mmol) to THF (50 mL) at 0° C. followed by a solution of 4-(morpholin-4-ylmethyl)-benzonitrile (2 g, 9.89 mmol) in THF (10 mL). Stir at 0° C. for 1 h and at room temperature overnight. Cool the mixture to 0° C., and carefully add water (1.15 mL). Add diethyl ether (125 mL), 3N aqueous NaOH (1.15 mL), water (3.45 mL), and stir for 1 h at room temperature. Filter the solid residue and concentrate the filtrate in vacuo to obtain the title compound as a colorless oil (1.87 g, 94%). MS (APCI+) m/z: 207 (M+H)+.

Preparation 43

4-(Pyrrolidin-1-ylmethyl)-benzylamine

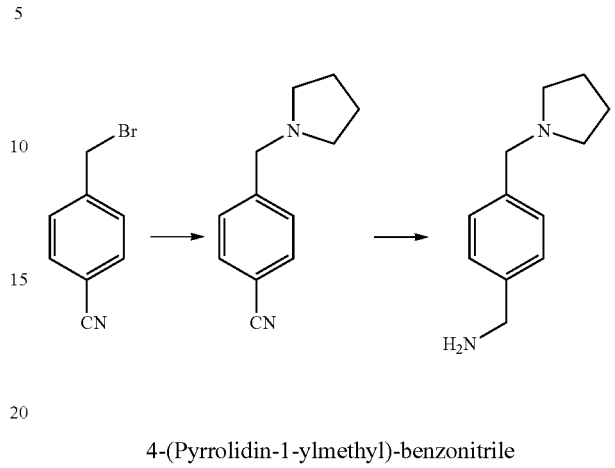

4-(Pyrrolidin-1-ylmethyl)-benzonitrile

Add pyrrolidine (0.89 mL, 10.74 mmol) to a stirred solution of 4-bromomethyl-benzonitrile (1 g, 5.1 mmol) and triethylamine (1.5 mL, 10.74 mmol) in anhydrous THF (26 mL). Stir reaction overnight at room temperature. Partition the reaction mixture between EtOAc and water. Extract the aqueous phase twice with EtOAc. Dry the combined organic extracts over MgSO$_4$, filter, and concentrate in vacuo to obtain the desired intermediate (918 mg, 97%) suitable for use without further purification. MS (APCI+) m/z: 187 (M+H)+.

4-(Pyrrolidin-1-ylmethyl)-benzylamine

Dissolve 4-(pyrrolidin-1-ylmethyl)-benzonitrile (918 mg, 4.93 mmol) in methanol (32 mL). Add cobalt(II) chloride hexahydrate (2.7 g, 9.87 mmol) and stir for 20 min. Cool the mixture to 0° C., and carefully add sodium borohydride (1.86 g, 49.3 mmol) in small batches. Stir the mixture for 1.5 h at room temperature. Quench the mixture with water and partition between water and chloroform. Extract the aqueous phase three times with chloroform/iso-propanol (3:1). Dry the combined organic extracts over MgSO$_4$, filter, and concentrate in vacuo. Purify by chromatography on silica gel (80 g) eluting with a gradient of DCM/(chloroform:methanol: concentrated NH$_4$OH 80:18:2) (1:0 over 5 min, 19:1 over 5 min, 9:1 over 5 min, 85:15; 50 mL/min) to give the title compound (421 mg, 45%). MS (ES+) m/z: 191 (M+H)+, Preparation 44

4-(Piperidin-1-ylmethyl)-benzylamine

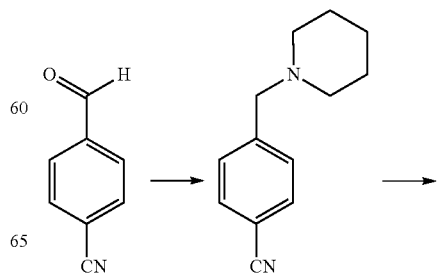

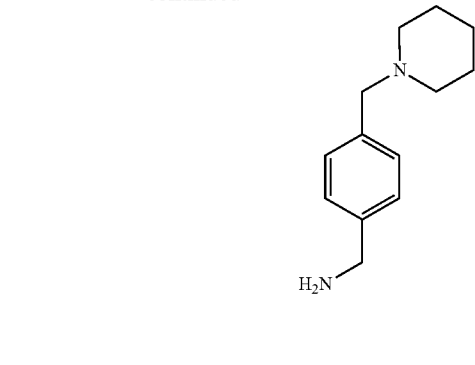

4-(Piperidin-1-ylmethyl)-benzonitrile

Under a nitrogen atmosphere, add sodium cyanoborohydride (5.77 g, 91.6 mmol) to a solution of 4-cyanobenzaldehyde (3 g, 22.9 mmol), piperidine (5.84 g, 68.7 mmol) and acetic acid (2.75 g, 45.8 mmol) in methanol (30 mL) at 0° C. with stirring. Warm the mixture to room temperature and stir overnight. Add water (100 mL), saturated aqueous $K_2CO_3$ (50 mL), and extract with DCM. Wash the combined organic extracts with water and brine. Dry the organic phase over $Na_2SO_4$, filter, and concentrate in vacuo. Purify by chromatography on silica gel (400 g) eluting with hexane/EtOAc (1:0 to 4:1 gradient) to obtain the desired intermediate as a clear oil (2.48 g, 54%). MS (APCI+) m/z: 201 (M+H)⁺.

4-(Piperidin-1-ylmethyl)-benzylamine

Add 4-(piperidin-1-ylmethyl)-benzonitrile (890 mg, 4.45 mmol), 2M hydrogen chloride in ether (8.9 mL, 17.8 mmol) and 10% Pd/C (90 mg) to methanol (100 mL) in a pressure vessel. Flush the vessel three times with hydrogen and charge to 50 psi with hydrogen. Stir at room temperature for 2 h. Filter the catalyst through Celite® and concentrate the filtrate in vacuo. Purify by chromatography on silica gel (100 g) eluting with a gradient of DCM to 4:1 DCM/(chloroform:methanol:concentrated $NH_4OH$ 80:18:2) to obtain the title compound as a colorless oil (0.82 g, 90%). MS (ES+) m/z: 205 (M+H)⁺.

Preparation 45

The compound of Preparation 45 may be prepared essentially as described in Preparation 44 by using 4-cyanobenzaldehyde and (±)-1-methyl-2,2,2-trifluoro-ethylamine. MS (ES+) data is shown in the Table below.

| Prep. | Structure | Compound | MS (ES+) m/z |
|---|---|---|---|
| 45 | 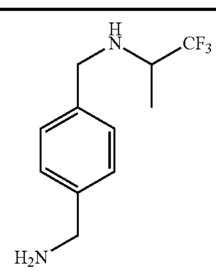 | (±)-4-[(1-Methyl-2,2,2-trifluoro-ethylamino)-methyl]-benzylamine | 233 (M + H)⁺ |

Preparation 46

(R)-1-Methyl-2,2,2-trifluoro-ethylamine Hydrochloride

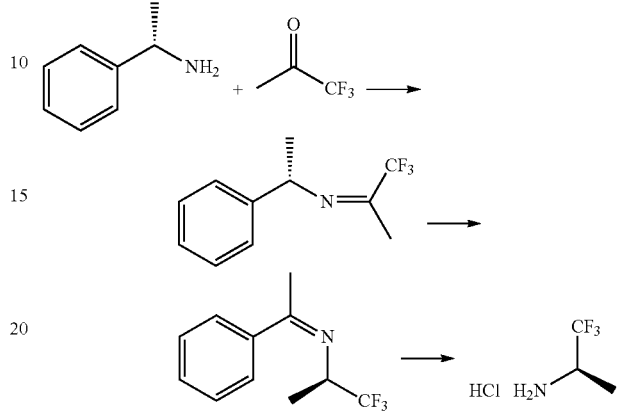

(S)-(1-Phenylethyl)-(2',2',2'-trifluoro-1-methylethylidene)-amine

Use a 22 liter 3-neck round-bottom flask equipped with a dry ice condenser and inlet tube in one side neck, mechanical stirrer in center neck and a Dean-Stark trap with dry ice condenser at top in other side neck. Chill a solution of cold 1,1,1-trifluoroacetone (2100 g, 18.74 mol) and cold toluene (1000 mL) in a wet ice-acetone bath at all times. To a cold mixture of (S)-(−)-α-methylbenzylamine (550 g, 4.54 mol) and p-toluenesulfonic acid monohydrate (8.63 g, 0.0454 mol) in toluene (1000 mL) at 0° C. add a cooled solution of 1,1,1-trifluoroacetone (753 g, 6.72 mol) in cold toluene via teflon tubing under positive pressure of nitrogen (with the Teflon tubing below the surface of the reaction mixture and stopcock to prevent back-up). Remove the dry ice condenser in side neck and replace it with inlet with tubing. However, keep the Dean-Stark trap and dry ice condenser on the other side neck. Heat the reaction mixture slowly to 111° C. Remove water distillate and turn off heat. Slowly add the organic distillate to the reaction mixture at a rate to keep trifluoroacetone distillation under control. Heat the reaction slowly to 111° C. Turn off heat and remove water and organic distillate. Add a cooled solution of 1,1,1-trifluoroacetone (789 g, 7.04 mol) in toluene to the hot reaction mixture at a rate to keep trifluoroacetone distillation under control. Heat the reaction mixture slowly to 111° C. Turn off heat and remove the distillate. Cool the reaction mixture and concentrate in vacuo at 60° C. Add hexane (4 L) in portions to aid in removal of toluene to obtain the desired intermediate as a pale yellow oil of the crude product (1410 g).

(R)-(1'-Phenylethylidene)-(2,2,2-trifluoro-1-methylethyl)-amine

To crude (S)-(1-phenylethyl)-(2',2',2'-trifluoro-1-methylethylidene)-amine (1410 g, 4.54 mol theory) and washings with 20 g of toluene at room temperature, add DBU (1050 g, 6.897 mol) in portions to keep temperature below 60° C. Heat the reaction at 60° C. overnight (14 h) under nitrogen until the starting material rearranges to the desired intermediate (2460 g of solution). MS (ES+) m/z: 216.2 (M+H)+.

(R)-1-Methyl-2,2,2-trifluoro-ethylamine Hydrochloride

Dilute the first half (1230 g) of the above reaction mixture with heptane (1500 mL) and DCM (1500 mL). Add 5N aqueous HCl (1250 mL) to the solution mixture and stir for 30 min until only acetophenone is present in the organic phase. Wash the bottom aqueous phase with 1:1 heptane/DCM (2×500 mL) and then cool the aqueous phase in an ice bath. Add ice-cold DCM (1500 mL) and then cold 5N aqueous NaOH (1250 mL) dropwise to the biphasic mixture and stir for 15 min. Separate the bottom organic phase. Extract the aqueous phase with DCM (2×500 mL) and distill the combined organic phase carefully (40-60° C. pot temperature) while cooling the receiving flask in a dry ice/acetone bath. Collect the distillate. Add cold 5N aqueous HCl (500 mL) dropwise and stir for 30 min. Concentrate the mixture in vacuo, using toluene for azeotropic removal of water, to afford the title compound as a white solid. Repeat the procedure with the second half of the previous reaction mixture to obtain the title compound as a white solid (451 g total, 66%). MS (ES+) m/z: 114.1 (M+H)+. $[\alpha]_D = -1.4°$ (c=0.5, MeOH).

Preparation 47

(R)-4-[(1-Methyl-2,2,2-trifluoro-ethylamino)-methyl]-benzylamine

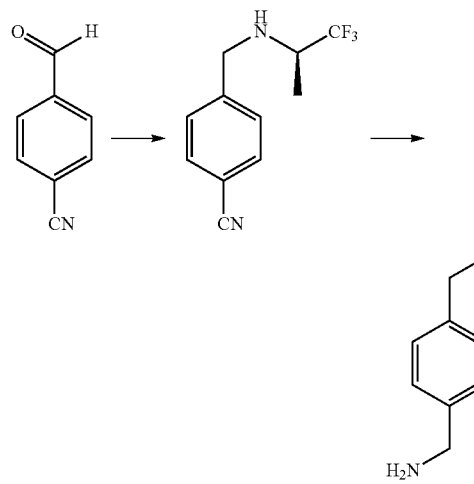

(R)-4-[(1-Methyl-2,2,2-trifluoro-ethylamino)-methyl]-benzonitrile

Add sodium cyanoborohydride (3.36 g, 53.5 mmol) to a solution of 4-cyanobenzaldehyde (1.75 g, 13.35 mmol) and (R)-1-methyl-2,2,2-trifluoro-ethylamine hydrochloride (2 g, 13.37 mmol) in methanol (17 mL) containing acetic acid (1.53 mL, 26.75 mmol). Stir the mixture at room temperature overnight. Partition the mixture between 1N aqueous NaOH/DCM (1:1, 500 mL) and extract the aqueous layer twice with DCM. Dry the combined organic extracts over MgSO4, concentrate in vacuo and purify by chromatography on silica gel (120 g) eluting with hexane/EtOAc (19:1, 9:1, 85:15 and 4:1) to obtain the desired intermediate (0.83 g, 27%). MS (ES+) m/z: 229 (M+H)+.

(R)-4-[(1-Methyl-2,2,2-trifluoro-ethylamino)-methyl]-benzylamine

Add cobalt(II) chloride hexahydrate (1.45 g, 6.09 mmol) to a solution of (R)-4-[(1-methyl-2,2,2-trifluoro-ethylamino)-methyl]-benzonitrile (695 mg, 3.045 mmol) in methanol (20 mL). Add sodium borohydride (1.15 g, 30.45 mmol) in small batches and stir at room temperature for 3 h. Quench with water, add chloroform and filter the mixture through Celite®. Separate layers and extract the aqueous phase twice with chloroform. Dry the combined organic extracts over MgSO4, filter and concentrate in vacuo. Purify by chromatography on silica gel (40 g) eluting with a gradient of DCM to 19:1 and 9:1 DCM/(chloroform:methanol:concentrated NH4OH 80:18:2) to obtain the title compound as an oil (0.4 g, 57%). MS (ES+) m/z: 233 (M+H)+.

Preparation 48

The compound of Preparation 48 may be prepared essentially as described in Preparation 47 by using 4-cyanobenzaldehyde and homopiperidine. Overall yield and MS (ES+) data are shown in the Table below.

| Prep. | Structure | Compound | Yield (%) | MS (ES+) m/z |
|---|---|---|---|---|
| 48 | 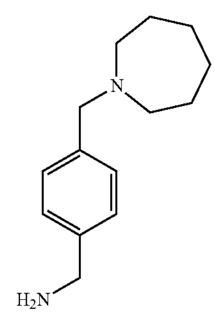 [SMILES: NCc1ccc(CN2CCCCCC2)cc1] | 4-(Azepan-1-ylmethyl)-benzylamine | 18 | 219 (M+H)+ |

Preparation 49

4-[(2,2,2-Trifluoroethylamino)-methyl]-benzylamine

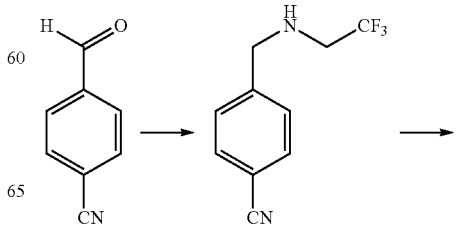

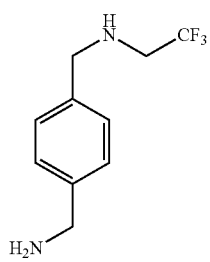

4-[(2,2,2-Trifluoroethylamino)-methyl]-benzonitrile

Add sodium cyanoborohydride (957 mg, 15.24 mmol) to a stirred solution of 4-cyanobenzaldehyde (500 mg, 3.81 mmol), 2,2,2-trifluoroethylamine (0.3 mL, 3.81 mmol) and acetic acid (0.44 mL, 7.62 mmol) in methanol (5 mL). Stir the mixture overnight at room temperature. Partition the mixture between 1N aqueous NaOH and DCM. Extract the aqueous phase twice with DCM. Dry the combined organic extracts over $MgSO_4$, filter and concentrate in vacuo to obtain the desired intermediate (749 mg, 92%) suitable for use without further purification. MS (ES+) m/z: 215 $(M+H)^+$.

4-[(2,2,2-Trifluoroethylamino)-methyl]-benzylamine

Dissolve 4-[(2,2,2-trifluoroethylamino)-methyl]-benzonitrile (633 mg, 2.955 mmol) in methanol (22 mL). Add cobalt (II) chloride hexahydrate (1.41 g, 5.91 mmol) and stir for 20 min. Carefully add sodium borohydride (1.12 g, 29.55 mmol) in small batches and stir the mixture overnight. Quench the mixture with water and filter through celite, washing filter-cake with chloroform:methanol:concentrated $NH_4OH$ (80:18:2). Concentrate the filtrate in vacuo, and partition the residue between water and chloroform. Extract the aqueous phase three times with chloroform iso-propanol (3:1). Dry the combined organic extracts over $MgSO_4$, filter and concentrate in vacuo. Purify by chromatography on silica gel (40 g, pre-packed cartridge) eluting with DCM/(chloroform:methanol:concentrated $NH_4OH$ 80:18:2) (1:0 over 5 min, 19:1 over 5 min, 9:1 over 5 min, 85:15 over 5 min, 4:1; 50 mL/min) to obtain the title compound (316 mg, 49%). MS (ES+) m/z: 219 $(M+H)^+$.

Preparation 50

4-[N-(tert-Butoxycarbonyl)-N-(cyclohexyl)-aminomethyl]-benzylamine

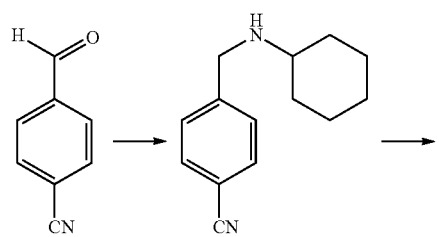

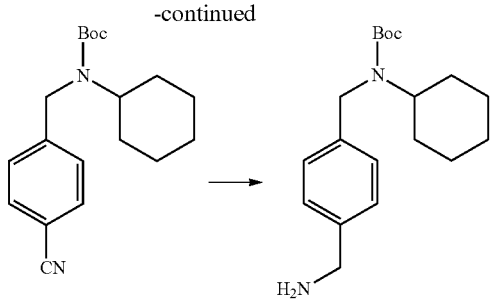

4-(Cyclohexylamino-methyl)-benzonitrile

Under a nitrogen atmosphere, add sodium cyanoborohydride (9.6 g, 152 mmol) to a solution of 4-cyanobenzaldehyde (5 g, 38 mmol), cyclohexylamine (3.8 g, 38 mmol) and acetic acid (0.46 g, 7.6 mmol) in methanol (100 mL) at 0° C. Warm the mixture to room temperature and stir overnight. Add water (100 mL) and adjust the pH to 10 with 3N aqueous NaOH. Extract with DCM and wash the organic phase with water and brine. Dry the organic phase over $Na_2SO_4$, filter and concentrate in vacuo. Purify by chromatography on silica gel (500 g) eluting with hexane/EtOAc (1:0 to 1:1 gradient) to obtain the desired intermediate (6.9 g, 86%). MS (APCI+) m/z: 215 $(M+H)^+$.

4-[N-(tert-Butoxycarbonyl)-N-(cyclohexyl)-aminomethyl]-benzonitrile

Add 4-(cyclohexylamino-methyl)-benzonitrile (3.5 g, 16.3 mmol), triethylamine (2.26 mL, 16.3 mmol), and di-tert-butyl-dicarbonate (3.55 g, 16.3 mmol) to DCM (20 mL). Stir the mixture at room temperature overnight and concentrate in vacuo. Purify by chromatography on silica gel (150 g) eluting with hexane/EtOAc (1:0 to 9:1 gradient) to obtain the desired intermediate (3.7 g, 72%). MS (APCI+) m/z: 215 (M-Boc+H)$^+$.

4-[N-(tert-Butoxycarbonyl)-N-(cyclohexyl)-aminomethyl]-benzylamine

Under a nitrogen atmosphere, add borane-dimethylsulfide complex (29.3 mL, 58.7 mmol, 2M solution in THF) to 4-[N-(tert-butoxycarbonyl)-N-(cyclohexyl)-aminomethyl]-benzonitrile (3.7 g, 11.7 mmol) in THF (100 mL) at 0° C. Warm to room temperature and stir overnight. Heat the mixture under reflux for 30 min. Cool the mixture in an ice-bath, and add methanol (20 mL). Warm to room temperature, and add $KHSO_4$ (20 g in 100 mL of water). Stir the mixture for 2 h and adjust the pH to 10 with 3N aqueous NaOH. Extract the mixture with DCM. Dry the organic phase over $Na_2SO_4$, filter, and concentrate in vacuo. Purify by chromatography on silica gel (150 g) eluting with a gradient of DCM to 1:1 DCM/(chloroform:methanol:concentrated $NH_4OH$ 80:18:2) to obtain the title compound as an oil (2.43 g, 65%). MS (ES+) m/z: 319 $(M+H)^+$.

Preparation 51

4-[N-(tert-Butoxycarbonyl)-N-(iso-butyl)-aminomethyl]-benzylamine

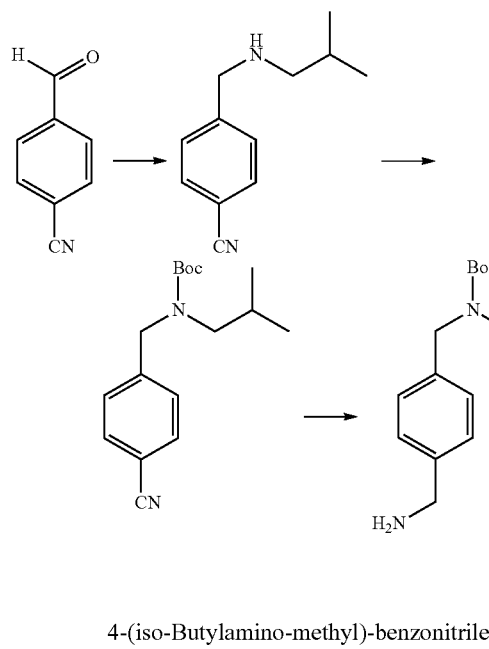

4-(iso-Butylamino-methyl)-benzonitrile

Under a nitrogen atmosphere add sodium cyanoborohydride (5.77 g, 91.6 mmol) to 4-cyanobenzaldehyde (3 g, 22.9 mmol), iso-butylamine (3.34 g, 45.8 mmol) and acetic acid (1.37 g, 22.9 mmol) in methanol (30 mL) at 0° C. Warm the mixture to room temperature and stir overnight. Add water (40 mL), saturated aqueous $K_2CO_3$ (30 mL) and extract with DCM. Wash the combined organic extracts with water and brine. Dry the organic phase over $Na_2SO_4$, filter and concentrate in vacuo. Purify the residue by chromatography on silica gel (500 g) eluting with 9:1 DCM/(chloroform:methanol:concentrated $NH_4OH$ 80:18:2) to obtain the desired intermediate (3.63 g, 84%). MS (APCI+) m/z: 189 (M+H)$^+$.

4-[N-(tert-Butoxycarbonyl)-N-(iso-butyl)-aminomethyl]-benzonitrile

Add 4-(iso-butylamino-methyl)-benzonitrile (2 g, 10.6 mmol), triethylamine (3 mL, 21.2 mmol), and di-tert-butyl-dicarbonate (2.44 g, 11.2 mmol) to DCM (30 mL). Stir the mixture at room temperature for 1 h and concentrate in vacuo. Purify by chromatography on silica gel (80 g) eluting with hexane/EtOAc (1:0 to 9:1 gradient) to obtain the desired intermediate as a clear oil (3.01 g, 98%). MS (ES+) m/z: 189 (M-Boc+H)$^+$.

4-[N-(tert-Butoxycarbonyl)-N-(iso-butyl)-aminomethyl]-benzylamine

Under a nitrogen atmosphere, add borane-dimethylsulfide complex (13 mL, 26 mmol, 2M solution in THF) to 4-[N-(tert-butoxycarbonyl)-N-(iso-butyl)-aminomethyl]-benzonitrile (1.5 g, 5.2 mmol) in THF (20 mL) at 0° C. Heat the mixture under reflux overnight. Cool the mixture in an ice-bath and add methanol (20 mL). Warm to room temperature and add $KHSO_4$ (7 g in 50 mL of water). Stir for 2 h at room temperature and basify with 3N aqueous NaOH. Extract with DCM, dry the organic phase over $Na_2SO_4$, and concentrate in vacuo. Purify by chromatography on silica gel (150 g) eluting with a gradient of DCM to 4:1 DCM/(chloroform:methanol:concentrated $NH_4OH$ 80:18:2) to obtain the title compound as an oil (0.72 g, 47%). MS (APCI+) m/z: 293 (M+H)$^+$.

Preparation 52

4-[N-(tert-Butoxycarbonyl)-N-(iso-propyl)-aminomethyl]-benzylamine

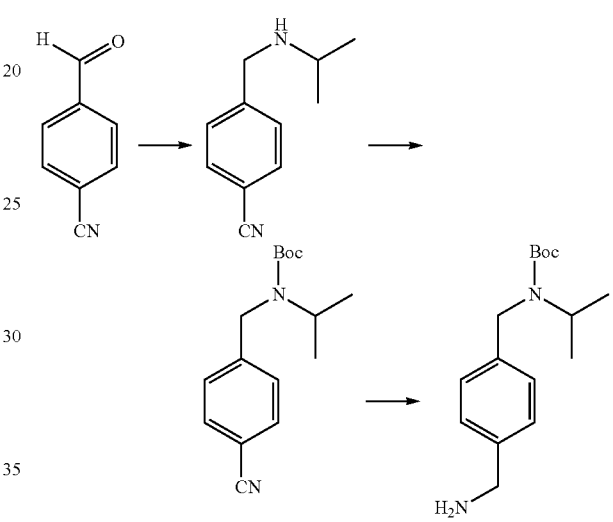

4-(iso-Propylamino-methyl)-benzonitrile

Under a nitrogen atmosphere, add sodium cyanoborohydride (5.77 g, 91.6 mmol) to a solution of 4-cyanobenzaldehyde (3 g, 22.9 mmol), iso-propylamine (2.03 g, 34.4 mmol) and acetic acid (1.37 g, 22.9 mmol) in methanol (30 mL) at 0° C. with stirring. Warm the mixture to room temperature and stir overnight. Add water (100 mL), saturated aqueous $K_2CO_3$ (50 mL), and extract with DCM. Wash the combined organic extracts with water and brine. Dry the organic phase over $Na_2SO_4$, filter and concentrate in vacuo. Purify by chromatography on silica gel (300 g) eluting with 9:1 DCM/(chloroform:methanol:concentrated $NH_4OH$ 80:18:2) to obtain the desired intermediate (1.53 g, 38%). MS (APCI+) m/z: 175 (M+H)$^+$.

4-[N-(tert-Butoxycarbonyl)-N-(iso-propyl)-aminomethyl]-benzonitrile

Add 4-(iso-propylamino-methyl)-benzonitrile (1.53 g, 8.9 mmol), triethylamine (2.48 mL, 17.8 mmol) and di-tert-butyl-dicarbonate (2.01 g, 9.23 mmol) to DCM (30 mL). Stir the mixture at room temperature for 2 h and concentrate in vacuo. Purify by chromatography on silica gel (100 g) eluting with hexane/EtOAc (1:0 to 9:1 gradient) to obtain the desired intermediate as a clear oil (2.3 g, 95%). MS (ES+) m/z: 175 (M-Boc+H)$^+$.

4-[N-(tert-Butoxycarbonyl)-N-(iso-propyl)-aminomethyl]-benzylamine

Under a nitrogen atmosphere add borane-dimethylsulfide complex (13.7 mL, 27.4 mmol, 2M solution in THF) to 4-[N-(tert-butoxycarbonyl)-N-(iso-propyl)-aminomethyl]-benzonitrile (1.5 g, 5.5 mmol) in THF (20 mL) at 0° C. Warm to room temperature and stir overnight. Heat the mixture under reflux for 2 h. Cool the mixture in an ice-bath and add methanol (20 mL). Warm to room temperature and add $KHSO_4$ (7 g in 50 mL of water). Stir for 2 h at room temperature and basify with 3N aqueous NaOH. Extract with DCM, dry the organic phase over $Na_2SO_4$ and concentrate in vacuo. Purify by chromatography on silica gel (150 g) eluting with a gradient of DCM to 4:1 DCM/(chloroform:methanol:concentrated $NH_4OH$ 80:18:2) to obtain the title compound as an oil (1.3 g, 85%). MS (APCI+) m/z: 279 (M+H)$^+$.

Preparation 53

4-[(N-methyl-iso-propylamino)-methyl]-benzyl amine

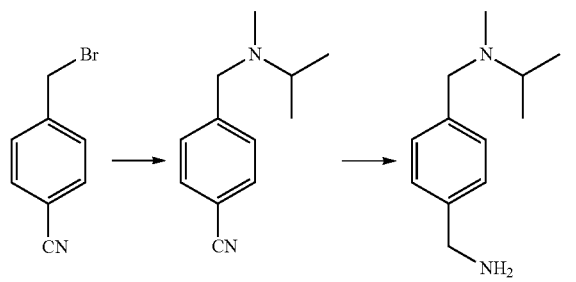

4-[(N-methyl-iso-propylamino)-methyl]-benzonitrile

Add 4-bromomethyl-benzonitrile (784 mg, 4 mmol) to a stirring mixture of N-isopropyl-methylamine (730 mg, 10 mmol), triethylamine (1.4 mL, 10 mmol) and THF (20 mL) at room temperature, and stir for 12 h. Dilute the mixture with water and EtOAc. Extract the aqueous layer with EtOAc and wash the organic phase with water and brine. Dry the organic solution over $Na_2SO_4$, filter, and concentrate in vacuo. Purify by chromatography on silica gel (12 g) eluting with a gradient of DCM to 9:1 DCM/(chloroform:methanol:concentrated $NH_4OH$ 80:18:2) to obtain the desired compound (660 mg, 88%). MS (APCI+) m/z: 189 (M+H)$^+$.

4-[(N-methyl-iso-propylamino)-methyl]-benzylamine

Under a nitrogen atmosphere, add borane-dimethyl sulfide complex (8.7 mL, 17.4 mmol, 2M solution in THF) to a solution of 4-[(N-methyl-iso-propylamino)-methyl]-benzonitrile (660 mg, 3.51 mmol) in THF (20 mL) at room temperature then heat to reflux for 30 min. Cool the mixture in an ice-bath and carefully add methanol (10 mL). Warm the mixture to room temperature and add concentrated HCl (10 mL). Stir the mixture for 12 h, and concentrate in vacuo. Purify by chromatography on silica gel (25 g) eluting with a gradient of DCM to 1:1 DCM/(chloroform:methanol:concentrated $NH_4OH$ 80:18:2) to obtain the title compound (550 mg, 82%). MS (ES+) m/z: 193 (M+H)$^+$.

Preparation 54

6-Aminomethyl-3-[N-(cyclohexyl)-N-(2,2,2-trifluoroacetyl)-aminomethyl]-pyridine

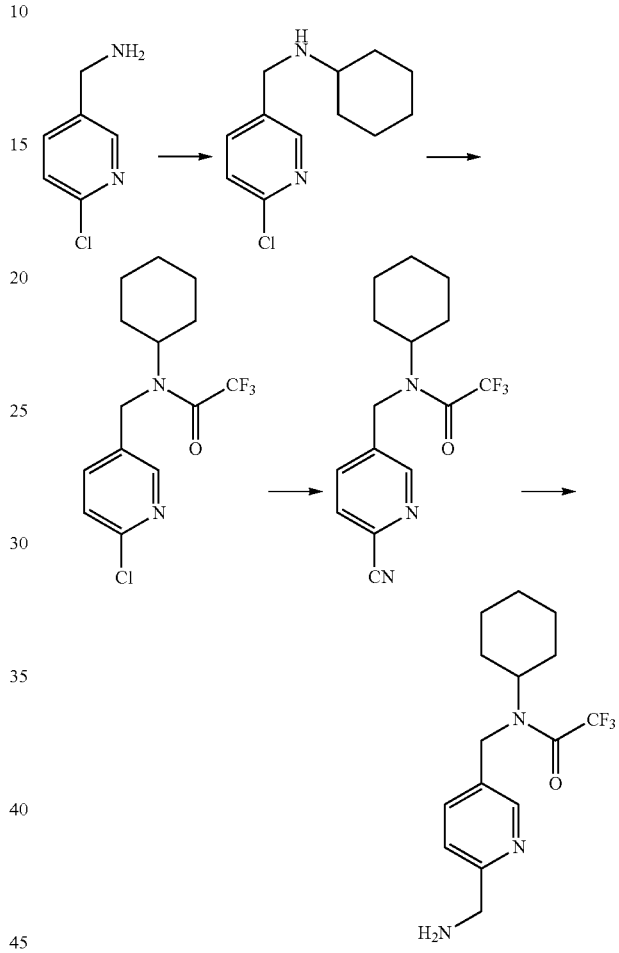

6-Chloro-3-(cyclohexylamino-methyl)-pyridine

Under a nitrogen atmosphere, add sodium cyanoborohydride (3.53 g, 56 mmol) to a solution of 3-aminomethyl-6-chloropyridine (2 g, 14 mmol), cyclohexanone (1.38 g, 14 mmol) and acetic acid (168 mg, 0.2 mmol) in methanol (20 mL) at 0° C. Warm the mixture to room temperature and stir overnight. Add water (100 mL) and saturated aqueous $K_2CO_3$. Extract three times with DCM and wash the combined organic extracts with water and brine. Dry over $Na_2SO_4$, filter, and concentrate in vacuo. Purify by chromatography on silica gel (150 g) eluting with 9:1 DCM/(chloroform:methanol:concentrated $NH_4OH$ 80:18:2) to obtain the desired intermediate (2.86 g, 91%). MS (APCI+) m/z: 225 (M+H)$^+$.

6-Chloro-3-[N-(cyclohexyl)-N-(2,2,2-trifluoroacetyl)-aminomethyl]-pyridine

Add trifluoroacetic anhydride (4 g, 19.1 mmol) to 6-chloro-3-(cyclohexylamino-methyl)-pyridine (2.86 g, 12.7 mmol)

and triethylamine (2.66 mL, 19.1 mmol) in DCM (20 mL) at 0° C. Warm to room temperature and stir for 12 h. Concentrate in vacuo and dilute with water and EtOAc. Separate the layers and extract the aqueous layer with EtOAc. Wash the combined organic extracts with water and brine. Dry over Na$_2$SO$_4$, filter and concentrate in vacuo. Purify by chromatography on silica gel (400 g) eluting with hexane/EtOAc (1:0 to 4:1 gradient) to obtain the desired intermediate as a white solid (3.7 g, 91%). MS (APCI+) m/z: 321 (M+H)$^+$.

6-Cyano-3-[N-(cyclohexyl)-N-(2,2,2-trifluoro-acetyl)-aminomethyl]-pyridine

Under a nitrogen atmosphere add 6-chloro-3-[N-(cyclohexyl)-N-(2,2,2-trifluoroacetyl)-aminomethyl]-pyridine (3.7 g, 11.5 mmol), zinc cyanide (2.02 g, 17.3 mmol), tris(dibenzylideneacetone)dipalladium(0) (0.48 g, 0.57 mmol) and DPPF (0.63 g, 1.15 mmol) to DMF (40 mL). Heat the mixture at 95° C. for 2 h. Cool the mixture to room temperature and dilute with water and EtOAc. Separate the layers and extract the aqueous layer with EtOAc. Wash the combined organic extracts with water and brine. Dry the organic phase over Na$_2$SO$_4$, filter and concentrate in vacuo. Purify by chromatography on silica gel (400 g) eluting with hexane/EtOAc (1:0 to 3:2 gradient) to obtain the desired intermediate (3.33 g, 93%). MS (APCI+) m/z: 312 (M+H)$^+$.

6-Aminomethyl-3-[N-(cyclohexyl)-N-(2,2,2-trifluoroacetyl)-aminomethyl]-pyridine

Add 6-cyano-3-[N-(cyclohexyl)-N-(2,2,2-trifluoroacetyl)-aminomethyl]-pyridine (1.5 g, 4.8 mmol), 2M hydrogen chloride in ether (7.2 mL, 14.4 mmol) and 10% Pd/C (0.3 g) to methanol (30 mL) in a pressure vessel. Flush the vessel three times with hydrogen and charge to 50 psi with hydrogen. Stir at room temperature for 4 h. Filter the mixture through Whatman® GF/B glass microfiber filter paper, and concentrate in vacuo. Purify the residue by chromatography on silica gel (100 g) eluting with a gradient of DCM to 4:1 DCM/(chloroform:methanol:concentrated NH$_4$OH 80:18:2) to obtain the title compound as a clear oil (1.6 g, 99%). MS (ES+) m/z: 316 (M+H)$^+$.

Preparation 55

5-Aminomethyl-2-(piperidin-1-ylmethyl)-pyridine

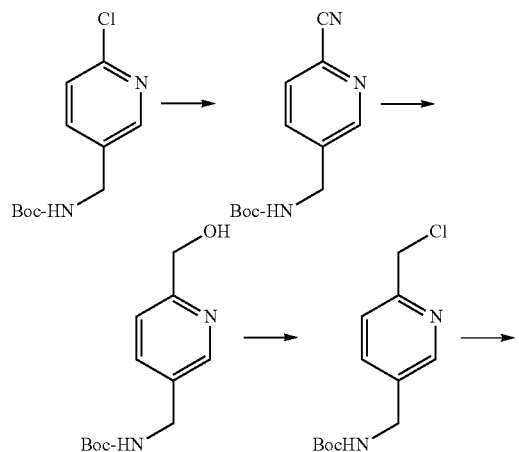

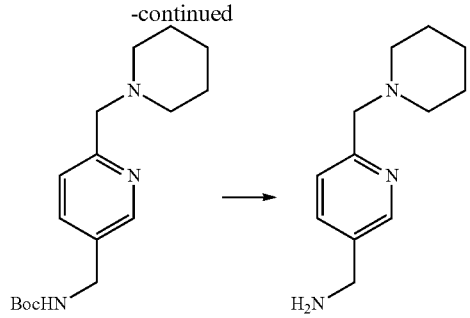

3-(tert-Butoxycarbonylamino-methyl)-6-cyano-pyridine

Under a nitrogen atmosphere, add 3-(tert-butoxycarbonylamino-methyl)-6-chloropyridine (13.1 g, 54 mmol), zinc cyanide (9.5 g, 81 mmol), tris(dibenzylideneacetone)dipalladium(0) (494 mg, 0.54 mmol), and dppf (550 mg, 0.81 mmol) to DMF (130 mL). Heat the mixture at 70° C. overnight. Cool the mixture to room temperature and dilute with water and EtOAc. Separate the layers, and extract the aqueous layer with EtOAc. Wash the combined organic extracts with water and brine. Dry the organic solution over Na$_2$SO$_4$, filter, and concentrate in vacuo. Purify by chromatography on silica gel (500 g) eluting with hexane/EtOAc (1:0 to 7:3 gradient) to provide the desired intermediate as a white solid (11.3 g, 90%). MS (ES+) m/z: 234 (M+H)$^+$.

3-(tert-Butoxycarbonylamino-methyl)-6-hydroxymethyl-pyridine

Add 3-(tert-butoxycarbonylamino-methyl)-6-cyano-pyridine (10.81 g, 46.4 mmol), KHSO$_4$ (18.9 g, 16.2 mmol), 5% Pd/C (Degussa type E101, 4 g) to a mixture of methanol (250 mL) and water (20 mL) in a pressure vessel. Flush the vessel three times with hydrogen and charge with hydrogen to 50 psi. Stir at room temperature, recharging to 50 psi hydrogen as necessary, until no change in pressure is observed. Add an aqueous NaOH solution (6.11 g of NaOH in 20 mL of water) to the mixture and stir for 15 min. Filter the mixture through glass microfiber filter paper. Dilute the filtrate with water and DCM. Separate the layers, and extract the aqueous layer with DCM. Wash the combined organic extracts with water and brine. Dry the organic solution over Na$_2$SO$_4$, filter and concentrate in vacuo. Purify by chromatography on silica gel (600 g) eluting with DCM/(chloroform:methanol:concentrated NH$_4$OH 80:18:2) (1:0 to 7:3 gradient) to obtain 6-aminomethyl-3-(tert-butoxycarbonylamino-methyl)-pyridine as a clear oil [3.4 g, 31%, MS (ES+) m/z: 238 (M+H)$^+$] and the desired intermediate 3-(tert-butoxycarbonylamino-methyl)-6-hydroxymethyl-pyridine as colorless oil (5.6 g, 52%). MS (ES+) m/z: 239 (M+H)$^+$.

3-(tert-Butoxycarbonylamino-methyl)-6-chloromethyl-pyridine

Add 3-(tert-butoxycarbonylamino-methyl)-6-hydroxymethyl-pyridine (2.3 g, 9.65 mmol) and triethylamine (2.05 mL, 14.5 mmol) to DCM (30 mL). Cool the mixture to 0° C. and add methanesulfonyl chloride (0.83 mL, 10.6 mmol) to the mixture. Allow the mixture to warm to room temperature and stir overnight. Dilute the mixture with water (10 mL) and saturated aqueous NaHCO$_3$ (10 mL). Separate the layers, and extract the aqueous layer with DCM (3×20 mL). Dry the combined organic extracts over Na$_2$SO$_4$, filter and concentrate in vacuo. Purify by chromatography on silica gel (80 g) eluting with hexane/EtOAc (1:0 to 1:1 gradient over 60 min, 80 mL/min) to obtain the desired intermediate as a colorless oil (1.14 g, 46%). MS (APCI+) m/z: 257 (M+H)+.

3-(tert-Butoxycarbonylamino-methyl)-6-(piperidin-1-ylmethyl)-pyridine

Add 3-(tert-butoxycarbonylamino-methyl)-6-chloromethyl-pyridine (500 mg, 1.95 mmol) to a solution of piperidine (0.58 mL, 5.84 mmol) and saturated aqueous NaHCO$_3$ (2.5 mL) in acetonitrile (15 mL). Stir the mixture at room temperature overnight. Dilute the mixture with water (20 mL) and DCM (25 mL), separate the layers and extract the aqueous layer with DCM (3×20 mL). Dry the combined organic extracts over Na$_2$SO$_4$, filter and concentrate in vacuo. Purify by chromatography on silica gel (80 g pre-packed cartridge) eluting with hexane/EtOAc (1:0 to 1:1 gradient over 60 min, 80 mL/min) to obtain the desired intermediate as a colorless oil (547 mg, 92%). MS (APCI+) m/z: 306 (M+H)+.

5-Aminomethyl-2-(piperidin-1-ylmethyl)-pyridine

Dissolve 3-(tert-butoxycarbonylamino-methyl)-6-(piperidin-1-ylmethyl)-pyridine (540 mg, 1.76 mmol) in methanol (10 mL) and cool to 0° C. Bubble hydrogen chloride through the vigorously stirred solution for 30 min. Concentrate in vacuo. Partition the residue between 3N aqueous NaOH (10 mL) and DCM (20 mL). Separate the two layers and extract the aqueous layer with DCM (2×20 mL). Wash the combined organic extracts with brine (20 mL). Dry over Na$_2$SO$_4$, filter and concentrate in vacuo to obtain the desired intermediate as a colorless oil (351 mg, 95%). MS (APCI+) m/z: 206 (M+H)+.

Preparation 56

4-(2,2-Dimethyl-propionylamino)-benzylamine

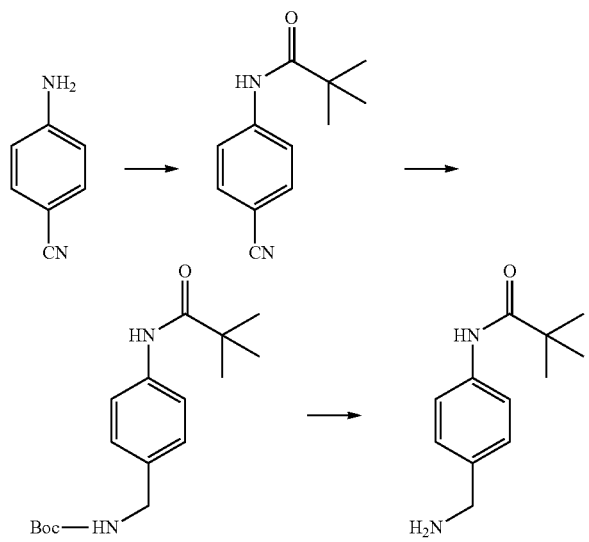

4-(2,2-Dimethyl-propionylamino)-benzonitrile

Add dropwise trimethylacetyl chloride (3.3 mL, 27 mmol) to a mixture of 4-aminobenzonitrile (2.92 g, 24.7 mmol) and triethylamine (3.8 mL, 27 mmol) in anhydrous DCM (25 mL) at 0° C. Stir the mixture to room temperature overnight. Partition the reaction mixture between DCM (500 mL) and water (250 mL) and extract the aqueous phase with DCM (250 mL). Wash the combined organic extracts with water (3×250 mL), dry over Na$_2$SO$_4$, filter and concentrate in vacuo to obtain the desired intermediate (5 g, 100%). MS (ES+) m/z: 203.2 (M+H)+.

N-(tert-Butoxycarbonyl)-4-(2,2-dimethyl-propionylamino)-benzylamine

Add a solution of 4-(2,2-dimethyl-propionylamino)-benzonitrile (5 g, 24.7 mmol) in THF/iso-propanol (1:2, 60 mL) to 10% Pd/C (Degussa type E101, 3 g, 1.41 mmol) via cannula under nitrogen. Add a solution of di-tert-butyl-dicarbonate (6.74 g, 30.9 mmol) in THF (19 mL) to the reaction mixture via cannula under nitrogen. Purge the reaction mixture with nitrogen and then submit to hydrogenation at 50 psi overnight. Filter the catalyst through Celite® and wash thoroughly with iso-propanol (500 mL) and THF (500 mL). Concentrate in vacuo to obtain a solid. Recrystallize from EtOAc, cool to 0° C., filter and wash with cold EtOAc to obtain the desired intermediate as a white solid (5.748 g, 76%). MS (ES+) m/z: 307.3 (M+H)+.

4-(2,2-Dimethyl-propionylamino)-benzylamine

Add 4M hydrogen chloride in dioxane (20 mL) to a solution of N-(tert-butoxycarbonyl)-4-(2,2-dimethyl-propionylamino)-benzylamine (2 g, 6.53 mmol) in anhydrous 1,4-dioxane (50 mL) at room temperature. Stir overnight and partition the reaction mixture between saturated aqueous NaHCO$_3$ (200 mL) and DCM (500 mL). Extract the aqueous phase with DCM/iso-propanol (85:15, 2×100 mL) and then with DCM/iso-propanol (3:1, 2×100 mL). Dry the combined organic extracts over Na$_2$SO$_4$, filter and concentrate in vacuo. Purify by SCX chromatography eluting with DCM and DCM/2M ammonia in methanol (1:1) to obtain the title compound as a waxy colorless oil (1.13 g, 84%). MS (ES−) m/z: 205.1 (M−H)−.

Preparations 57-58

The compounds of Preparations 57-58 may be prepared essentially as described in Preparation 56 using 4-aminobenzonitrile and the appropriate acid chloride. Overall yields and MS (ES+) data are shown in the Table below. Step 1 of Preparation 58 was purified by chromatography on silica gel eluting with hexane/EtOAc (1:0 to 67:33 gradient over 71 min and 67:33 to 0:1 gradient over 71 min; 50 mL/min).

| Prep. | Structure | Compound | Yield (%) | MS (ES+) m/z |
|---|---|---|---|---|
| 57 | ![structure] | 4-(Cyclo-propane-carbonyl-amino)-benzylamine | 39 | 191 (M + H)+ |

-continued

| Prep. | Structure | Compound | Yield (%) | MS (ES+) m/z |
|---|---|---|---|---|
| 58 | 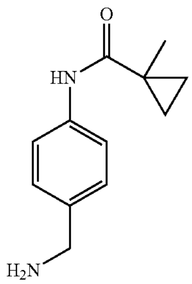 | 4-[(1-Methyl-cyclo-propane-carbonyl)-amino]-benzylamine | 34 | 205 (M + H)+ |

Preparation 59

4-[(2,2,3,3-Tetramethyl-cyclopropanecarbonyl)-amino]-benzylamine

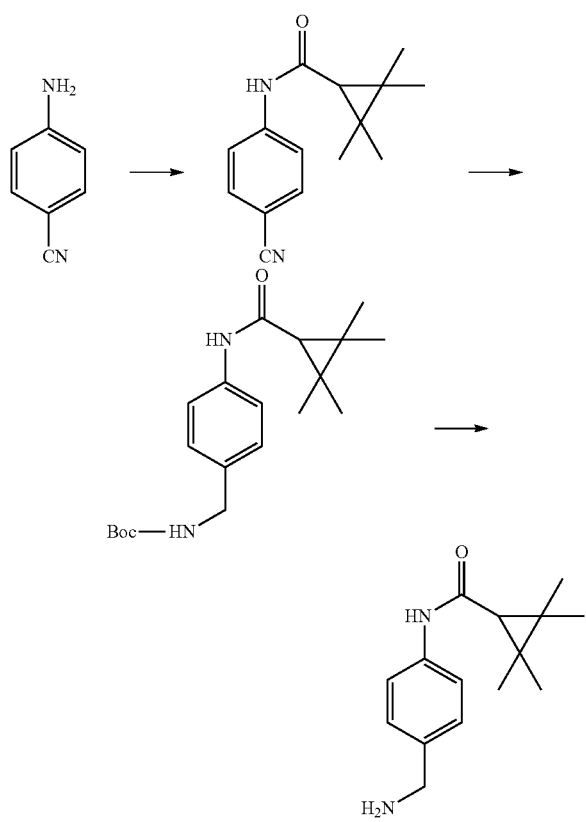

4-[(2,2,3,3-Tetramethyl-cyclopropanecarbonyl)-amino]-benzonitrile

Add a solution of 2,2,3,3-tetramethyl-cyclopropane-carbonyl chloride (5 g, 31.1 mmol) in anhydrous DCM to a mixture of 4-aminobenzonitrile (3.34 g, 28.3 mmol) and triethylamine (4.3 mL, 31 mmol) in anhydrous DCM (20 mL) at 0° C. After stirring at 0° C. for 20 min, warm the mixture to room temperature and stir overnight. Partition the reaction mixture between DCM (500 mL) and water (250 mL) and extract the aqueous phase with DCM (250 mL). Wash combined organic extracts with water (3×250 mL), dry over Na$_2$SO$_4$, filter and concentrate in vacuo. Purify the crude mixture by chromatography on silica gel eluting with hexane/EtOAc (1:0 over 36 min; 1:0 to 3:1 gradient over 36 min; 3:1 to 1:1 gradient over 71 min; 50 mL/min) to obtain the desired intermediate as a solid (2.31 g, 34%). MS (ES+) m/z: 243.2 (M+H)+.

N-(tert-Butoxycarbonyl)-4-[(2,2,3,3-tetramethyl-cyclopropanecarbonyl)-amino]-benzylamine Add a solution of di-tert-butyl-dicarbonate (1.8 g, 82.6 mmol) in methanol (7 mL) and nickel(II) chloride hexahydrate (0.098 g, 0.41 mmol) to a cooled solution of 4-[(2,2,3,3-tetramethyl-cyclopropanecarbonyl)-amino]-benzonitrile (1 g, 41.3 mmol) in methanol (30 mL) at 0° C. Add sodium borohydride (0.89 g, 23.5 mmol) in portions over 25 min under a nitrogen atmosphere at a rate to keep gas evolution under control. Stir the reaction mixture at 0° C. for 6 h and then slowly warm the reaction mixture in cooling bath until the reaction is complete. Concentrate in vacuo and partition the residue between EtOAc (250 mL) and saturated aqueous NaHCO$_3$ (100 mL). Extract the aqueous phase with EtOAc (3×50 mL). Dry the combined organic extracts over Na$_2$SO$_4$, filter and concentrate in vacuo. Slurry the residue in enough DCM and filter undissolved solid product (0.58 g). Concentrate in vacuo and purify by chromatography on silica gel eluting with hexane/EtOAc (1:0 to 3:1 gradient over 30 min; 3:1 over 3 min; 3:1 to 1:1 gradient over 30 min and 1:1 over 3 min; 35 mL/min) to obtain crude product. Dissolve the undissolved solid filtered above (0.58 g) in EtOAc (5.8 mL). Add hexane (11.6 mL) to precipitate out solid. Heat the slurry to reflux until homogeneous and then cool to room temperature and 0° C. Filter and wash solid with cold hexane (10 mL) and dry to obtain 0.173 g (12%) of the desired intermediate as a white solid. Combine the filtrate with the crude product isolated from the chromatography and concentrate in vacuo to obtain 1.766 g. Dissolve this material in EtOAc (12.6 mL) and add hexane (25.2 mL) to precipitate out solid. Heat the slurry to reflux until homogeneous and then cool to room temperature and store in freezer overnight. Filter and wash solid with cold hexane (10 mL) and dry to obtain the desired intermediate as a white solid (0.548 g, 50% overall). MS (ES+) m/z: 347.3 (M+H)+.

4-[(2,2,3,3-Tetramethyl-cyclopropanecarbonyl)-amino]-benzylamine

Add 4M hydrogen chloride in dioxane (6.1 mL) to a solution of N-(tert-butoxycarbonyl)-4-[(2,2,3,3-tetramethyl-cyclopropanecarbonyl)-amino]-benzylamine (0.678 g, 1.958 mmol) in anhydrous 1,4-dioxane (12.2 mL) at room temperature. After stirring at room temperature for 3 h, the reaction is a solid mass. Add more 1,4-dioxane (12.2 mL), DCM (24.4 mL) and more 4M hydrogen chloride in dioxane (6.1 mL), and stir overnight. Concentrate in vacuo and partition the residue between saturated aqueous NaHCO$_3$ (200 mL) and DCM (500 mL). Dry the organic phase over Na$_2$SO$_4$, filter and concentrate in vacuo. The aqueous phase was extracted with DCM/iso-propanol (3:1, 4×200 mL). Dry the combined organic extracts over Na$_2$SO$_4$, filter, combine with the organic fraction isolated above and concentrate in vacuo. Purify by SCX chromatography eluting with DCM and DCM/2M ammonia in methanol (1:1) to obtain the title compound (0.519 g, 100%). MS (ES+) m/z: 247.2 (M+H)+.

Preparation 60

(±)-trans-4-[(2-Methyl-cyclopropanecarbonyl)-amino]-benzylamine

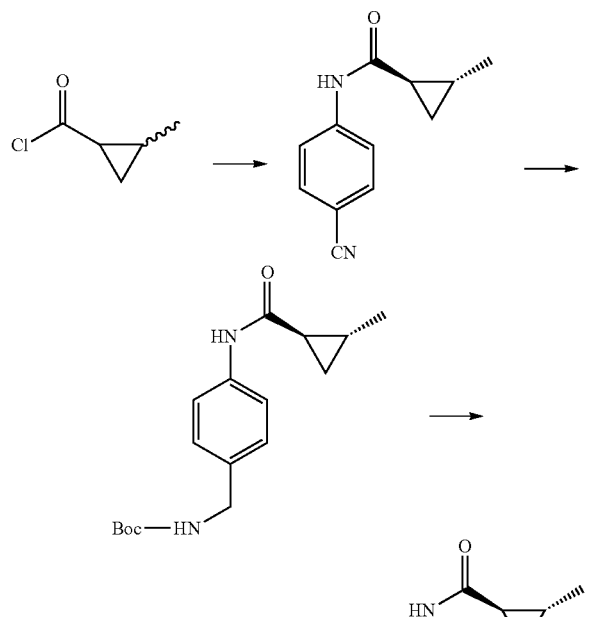

(±)-cis- and
(±)-trans-2-Methyl-cyclopropanecarbonyl chloride

Add thionyl chloride (39.3 mL, 539 mmol) at room temperature to a mixture of (±)-cis- and (±)-trans-2-methyl-cyclopropanecarboxylic acid (5 g, 49.9 mmol). Heat the reaction mixture at reflux overnight. Cool reaction mixture to room temperature and remove thionyl chloride by short-path distillation to afford a mixture of (±)-cis- and (±)-trans-2-methyl-cyclopropanecarbonyl chloride (5.53 g, 93%) as an amber oil. Trans/cis ratio is 16.7/1.0 by $^1$H NMR.

(±)-trans-4-[(2-Methyl-cyclopropanecarbonyl)-amino]-benzonitrile

To a mixture of 4-aminobenzonitrile (4.53 g, 38.4 mmol) and triethylamine (5.9 mL, 42 mmol) in anhydrous DCM (38.4 mL), add dropwise at 0° C. a solution of (±)-cis- and (±)-trans-2-methyl-cyclopropanecarbonyl chloride (5 g, 42.2 mmol) in anhydrous DCM (9 mL). Stir at 0° C. for 20 min, warm the mixture to room temperature and stir overnight. Partition the reaction mixture between DCM (500 mL) and water (250 mL) and extract the aqueous layer with DCM (250 mL). Wash the combined organic extracts with water (3×250 mL), dry over Na$_2$SO$_4$, filter and concentrate in vacuo. Purify by chromatography on silica gel eluting with hexane/EtOAc (1:0 to 3:1 over 71 min; 3:1 to 1:1 over 71 min; 50 mL/min) to afford (±)-trans-4-[(2-methyl-cyclopropanecarbonyl)-amino]-benzonitrile as a solid (2.31 g, 30%) and a fraction containing a mixture of both isomers.

(±)-trans-N-(tert-Butoxycarbonyl)-4-[(2-methyl-cyclopropanecarbonyl)-amino]-benzylamine Add a solution of (±)-trans-4-[(2-methyl-cyclopropanecarbonyl)-amino]-benzonitrile (2.316 g, 11.6 mmol) in THF/iso-propanol (1.0:1.8, 28 mL) to 10% Pd/C (Degussa type E101, 1.41 g, 0.66 mmol) via cannula under nitrogen. Add a solution of di-tert-butyl dicarbonate (3.16 g, 14.5 mmol) in THF (8 mL) via cannula under N$_2$. Purge the reaction mixture with nitrogen and then with hydrogen. Stir under 50 psi of hydrogen overnight. Filter the mixture over Celite®, wash with iso-propanol (100 mL) and THF (100 mL), and concentrate in vacuo to give a solid. Recrystallize the crude mixture in EtOAc (89 mL) and cool to 0° C. Filter and wash the solid with cold hexane (2×10 mL) to afford the desired intermediate as a white solid (1.893 g, 54%). More material can be obtained by recrystallizing again the compound remaining in filtrate.

(±)-trans-4-[(2-Methyl-cyclopropanecarbonyl)-amino]-benzylamine

Add 4M hydrogen chloride in dioxane (17.7 mL) to a solution of (±)-trans-N-(tert-butoxycarbonyl)-4-[(2-methyl-cyclopropanecarbonyl)-amino]-benzylamine (1.72 g, 5.65 mmol) in dioxane (35.4 mL). Stir at room temperature overnight, add diethyl ether and concentrate in vacuo several times. Partition the residue between saturated aqueous NaHCO$_3$ (200 mL) and DCM (500 mL). Extract the aqueous phase with DCM/iso-propanol (3:1, 4×200 mL). Dry the combined organic extracts over Na$_2$SO$_4$, filter and concentrate in vacuo. Load the compound into a SCX column (10 g), wash the column with DCM (100 mL), and then elute with 2M ammonia in methanol/DCM (1:1, 100 mL) to afford the title compound (0.935 g, 81%) as a waxy colorless oil.

Preparation 61

4-(N-Methyl-2,2-dimethyl-propionylamino)-benzylamine

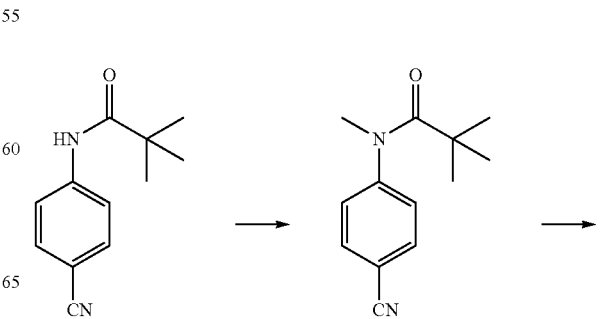

4-(N-Methyl-2,2-dimethyl-propionylamino)-benzonitrile

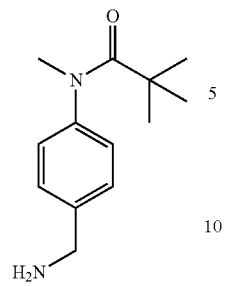

Add sodium hydride (0.21 g, 8.6 mmol, 95%) to a solution of 4-(2,2-dimethyl-propionylamino)-benzonitrile (1.589 g, 7.857 mmol) in anhydrous DMF (16 mL) at 0° C. under nitrogen. Add methyl iodide (0.54 mL, 8.6 mmol) after bubbling ceased (~20 min) Stir the mixture to room temperature overnight. Partition the reaction mixture between DCM (250 mL) and water (100 mL). Wash the organic phase with water (2×100 mL). Dry over Na$_2$SO$_4$, filter and concentrate in vacuo. Purify the crude mixture by chromatography on silica gel eluting with hexane/EtOAc (1:0 to 1:1 gradient over 71 min; 50 mL/min) to obtain the desired intermediate as a white solid (1.201 g, 71%).

4-(N-Methyl-2,2-dimethyl-propionylamino)-benzylamine

Add a solution of 4-(N-methyl-2,2-dimethyl-propionylamino)-benzonitrile (55 mg, 0.25 mmol) in THF/iso-propanol (1:1, 8 mL) to 10% Pd/C (Degussa type E101, 31 mg, 0.15 mmol) under nitrogen. Purge the reaction mixture with nitrogen and then submit to hydrogenation at 50 psi for 1 h. Filter the catalyst through Celite® and wash thoroughly with THF (100 mL) and iso-propanol (100 mL). Concentrate in vacuo and purify the crude mixture by chromatography on silica gel eluting with DCM/2M ammonia in methanol (1:0 to 9:1 gradient over 30 min and 9:1 over 3 min; 35 mL/min) to obtain the title compound as a colorless oil (41 mg, 73%). MS (ES+) m/z: 221.2 (M+H)$^+$.

Preparation 62

6-(4-Amino-benzylamino)-7-chloro-3-(2,2,2-trifluoroacetyl)-2,3,4,5-tetrahydro-1H-benzo[d]-azepine Hydrochloride

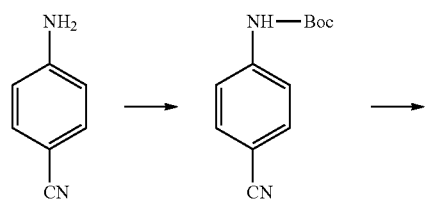

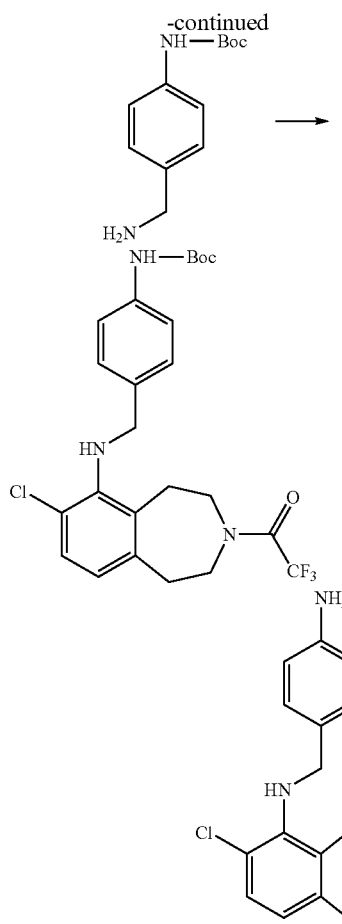

4-(tert-Butoxycarbonylamino)-benzonitrile

Add a solution of di-tert-butyl-dicarbonate (9.23, 42.3 mmol) in anhydrous toluene (2.3 mL) to 4-aminobenzonitrile (5 g, 42.3 mmol) in anhydrous toluene (20 mL) and heat the mixture at 100° C. for 3 days. Concentrate in vacuo and purify the crude mixture by chromatography on silica gel eluting with hexane/EtOAc (1:0 to 4:1 gradient over 71 min and 4:1 to 1:1 gradient over 71 min; 50 mL/min) to obtain the desired intermediate as a white solid (5.43 g, 59%). MS (ES+) m/z: 219.2 (M+H)$^+$.

4-(tert-Butoxycarbonylamino)-benzylamine

Add a solution of 4-(tert-butoxycarbonylamino)-benzonitrile (1 g, 4.58 mmol) in THF/iso-propanol (1:1, 142 mL) to 10% Pd/C (Degussa type E101, 0.56 g, 0.26 mmol) via syringe under N$_2$. Purge the reaction mixture with nitrogen and submit the mixture to hydrogenation at 50 psi overnight. Filter the catalyst through Celite® and wash thoroughly with iso-propanol (100 mL) and THF (100 mL). Concentrate in vacuo and purify the crude mixture by chromatography on silica gel eluting with DCM/2M ammonia in methanol (1:0 to 95:5 gradient over 30 min; 95:5 over 3 min; 95:5 to 9:1 gradient over 30 min and 9:1 over 30 min) to obtain the desired intermediate (0.364 g, 36%). MS (ES−) m/z: 220.1 (M−2H)$^-$.

6-(4-tert-Butoxycarbonylamino-benzylamino)-7-chloro-3-(2,2,2-trifluoroacetyl)-2,3,4,5-tetrahydro-1H-benzo[d]-azepine Use a method similar to the General Procedure 1-3 to couple 7-chloro-3-(2,2,2-trifluoroacetyl)-6-trifluoromethanesulfonyloxy-2,3,4,5-tetrahydro-1H-benzo[d]azepine (0.32 g, 0.76 mmol) with a solution of 4-(tert-butoxycarbonylamino)-benzylamine (0.338 g, 1.524 mmol) in anhydrous toluene/dioxane (4:1, 10 mL). Purify the crude mixture by chromatography on silica gel eluting with hexane/EtOAc (1:0 to 3:1 gradient over 30 min; 3:1 over 3 min; 3:1 to 1:1 gradient over 30 min and 1:1 over 3 min; 35 mL/min) to obtain the desired intermediate as a yellow oil (0.338 g, 89%). MS (ES+) m/z: 498.2 (M+H)$^+$.

6-(4-Amino-benzylamino)-7-chloro-3-(2,2,2-trifluoroacetyl)-2,3,4,5-tetrahydro-1H-benzo[d]-azepine Hydrochloride Add 4M hydrogen chloride in dioxane (20 mL, 20 mmol) to a solution of 6-(4-tert-butoxycarbonylamino-benzylamino)-7-chloro-3-(2,2,2-trifluoroacetyl)-2,3,4,5-tetrahydro-1H-benzo[d]-azepine (0.219, 0.44 mmol) in 1,4-dioxane/DCM (1:1, 40 mL). Stir overnight at room temperature, add diethyl ether and concentrate in vacuo to obtain the title compound (0.219 g, 100%) that was dried in vacuo.

Preparation 63

4-[(2,2-Dimethyl-propionylamino)-methyl]-benzylamine

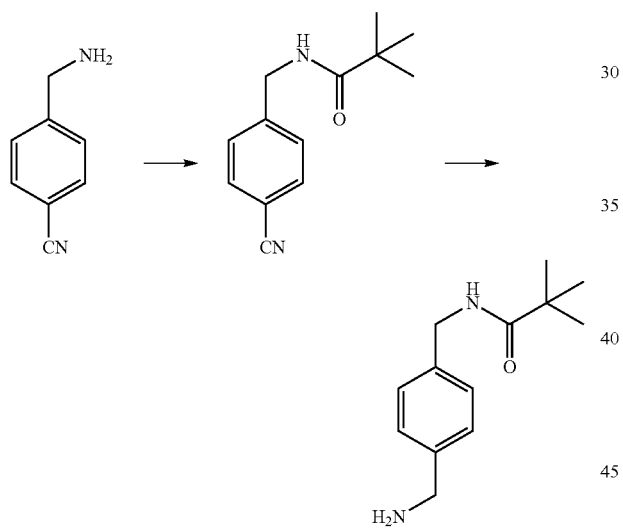

4-[(2,2-Dimethyl-propionylamino)-methyl]-benzonitrile

Add triethylamine (0.3 mL, 2.12 mmol) to a solution of 4-cyano-benzylamine (1.0 g, 7.58 mmol) in DCM (11 mL) and cool the mixture at 0° C. Add 2,2-dimethyl-propionyl chloride (0.93 mL, 7.58 mmol) dropwise and allow to stir the mixture at 0° C. for 15 min and at room temperature for 2 h. Add water, separate the organic phase and extract the aqueous phase twice with DCM. Dry the combined organic extracts over Na$_2$SO$_4$, filter and concentrate in vacuo to obtain the desired intermediate (1.23 g, 75%).

4-[(2,2-Dimethyl-propionylamino)-methyl]-benzylamine

Bubble nitrogen for 15 min into a solution of 4-[(2,2-dimethyl-propionylamino)-methyl]-benzonitrile (0.4 g, 1.85 mmol) in methanol (50 mL) with concentrated HCl (8 drops). Add 10% Pd/C (Degussa type E101, 40 mg) and submit the mixture to hydrogenation at atmospheric pressure overnight. Filter the catalyst through Celite® and concentrate in vacuo to obtain the hydrochloride salt of the title compound. Add saturated aqueous NaHCO$_3$ and extract twice with EtOAc. Dry the combined organic extracts over MgSO$_4$, filter and concentrate in vacuo to obtain the title compound as a yellow oil (315 mg, 77%). MS (ES+) m/z: 221 (M+H)$^+$.

Preparation 64

4-[(Cyclopropanecarbonyl-amino)-methyl]-benzylamine

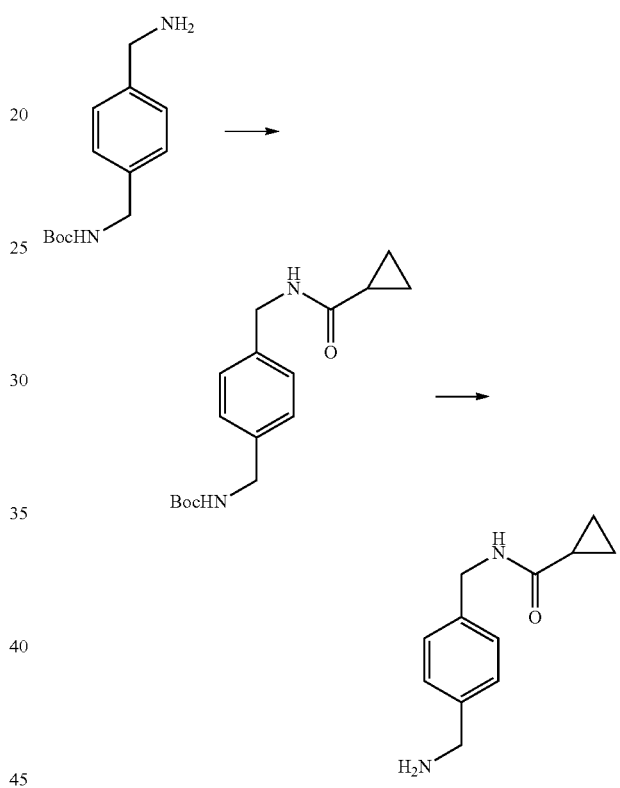

N-(tert-Butoxycarbonyl)-4-[(cyclopropanecarbonyl-amino)-methyl]-benzylamine

Add cyclopropane carbonyl chloride (0.3 mL, 3.3 mmol) to a stirred solution of ethyldiisopropylamine (1.35 mL, 7.73 mmol) and 4-(tert-butoxycarbonyl-aminomethyl)-benzylamine (0.6 g, 2.54 mmol) in DCM (12 mL). Stir the mixture for 1 h at room temperature. Partition the mixture between DCM and water. Extract the aqueous phase twice with DCM. Dry the combined organic extracts over MgSO$_4$, filter and concentrate in vacuo. Purify by chromatography on silica gel (120 g) eluting with DCM/(chloroform:methanol:concentrated NH$_4$OH 80:18:2) (1:0 over 5 min, 19:1 over 5 min, 9:1 over 5 min, 85:15; 50 mL/min) to obtain the desired intermediate (529 mg, 68%). MS (APCI+) m/z: 249 [M−(t-Bu)+H]$^+$ 4-[(Cyclopropanecarbonyl-amino)-methyl]-benzylamine Dissolve N-(tert-butoxycarbonyl)-4-[(cyclopropanecarbonyl-amino)-methyl]-benzylamine (529 mg, 1.74 mmol) in EtOAc (20 mL) and MeOH (15 mL). Bubble hydrogen chloride through the solution for 15 min, and stir the mixture overnight at room temperature. Concentrate the mixture in vacuo and dissolve the resulting solid in water. Adjust the pH to 9-11 with 20% aqueous $K_2CO_3$ (w/w %) and extract three times with chloroform/iso-propanol (3:1). Dry the combined organic extracts over $MgSO_4$, filter and concentrate in vacuo. Purify the crude mixture by chromatography on silica gel (40 g, pre-packed cartridge) eluting with DCM/(chloroform: methanol:concentrated $NH_4OH$ 80:18:2) (1:0 over 5 min, 19:1 over 5 min, 9:1 over 5 min, 4:1 over 5 min, 1:1 over 10 min, 1:3; 50 mL/min) to obtain the desired intermediate (275 mg, 77%). MS (APCI+) m/z: 188 $(M-NH_3+H)^+$.

Preparation 65

4-[2-(2,2-Dimethyl-propionylamino)-ethyl]-benzylamine

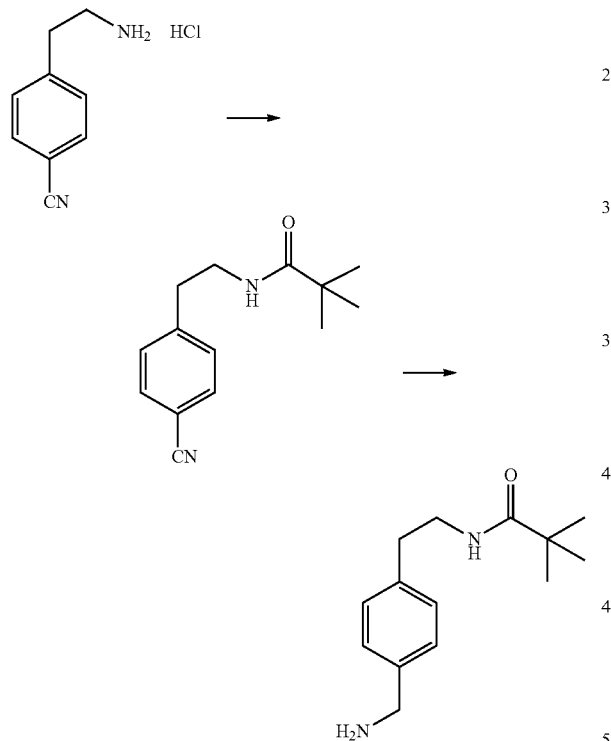

4-[2-(2,2-Dimethyl-propionylamino)-ethyl]-benzonitrile

Dissolve 4-(2-amino-ethyl)-benzonitrile hydrochloride (300 mg, 1.65 mmol) into saturated aqueous $NaHCO_3$ and extract twice with EtOAc. Dry the combined organic extracts over $Na_2SO_4$ and concentrate in vacuo to obtain 4-(2-amino-ethyl)-benzonitrile (205 mg, 85%). Dissolve 4-(2-amino-ethyl)-benzonitrile (200 mg, 1.37 mmol) in DCM (2 mL), add triethylamine (54 µL, 0.38 mmol) and cool the mixture at 0° C. Add 2,2-dimethyl-propionyl chloride (169 µL, 1.37 mmol) dropwise and allow to stir the mixture at 0° C. for 15 min and at room temperature for 2 h. Add water, separate the organic phase and extract the aqueous phase twice with DCM. Dry the combined organic extracts over $Na_2SO_4$, filter and concentrate in vacuo to obtain the desired intermediate (182 mg, 58%).

4-[2-(2,2-Dimethyl-propionylamino)-ethyl]-benzylamine

Bubble nitrogen for 15 min into a solution of 4-[2-(2,2-dimethyl-propionylamino)-ethyl]-benzonitrile (175 mg, 0.76 mmol) in methanol (31 mL) with concentrated HCl (3 drops). Add 10% Pd/C (Degussa type E101, 18 mg) and submit the mixture to hydrogenation at atmospheric pressure for 64 h. Filter the catalyst through Celite® and concentrate in vacuo to obtain the hydrochloride salt of the title compound. Add saturated aqueous $NaHCO_3$ and extract twice with EtOAc. Dry the combined organic extracts over $MgSO_4$, filter and concentrate in vacuo to obtain the title compound as a yellow oil (110 mg, 62%). MS (ES+) m/z: 235 $(M+H)^+$.

Preparation 66

4-(iso-Propylcarbamoyl-methyl)-benzylamine

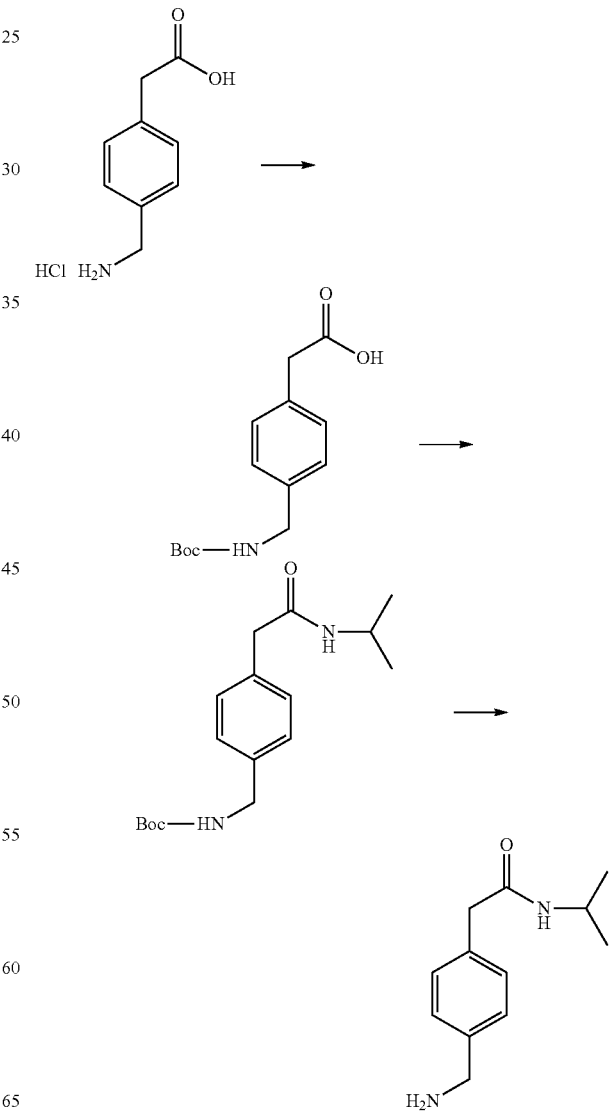

103

[4-(tert-Butoxycarbonylaminomethyl)-phenyl]-acetic acid

Add NaOH (0.992 g, 24.8 mmol) and di-tert-butyl-dicarbonate (5.4 g, 24.8 mmol) to a solution of (4-aminomethyl-phenyl)-acetic acid hydrochloride (5.0 g, 24.8 mmol) in dioxane/water (1:1, 40 mL) and stir for 24 h. Remove dioxane in vacuo and acidify the aqueous phase with 10% aqueous citric acid. Extract twice with EtOAc, dry the combined organic extracts over $Na_2SO_4$, filter and concentrate in vacuo to obtain a solid. Wash the solid with hexane, filter and dry to obtain the desired intermediate (3.3 g, 50%).

N-(tert-Butoxycarbonyl)-4-(iso-propylcarbamoyl-methyl)-benzylamine

Combine [4-(tert-butoxycarbonylaminomethyl)-phenyl]-acetic acid (400 mg, 1.5 mmol), isopropylamine (0.14 mL, 1.65 mmol), EDC (345 mg, 1.8 mmol), HOBt (243 mg, 1.8 mmol), triethylamine (0.63 mL, 4.5 mmol) and DMAP (18.3 mg, 0.15 mmol) in anhydrous DCM (15 mL). Stir at room temperature for 1 day under nitrogen. Concentrate in vacuo and purify the crude mixture by chromatography on silica gel eluting with hexane/EtOAc (1:1) to obtain the desired intermediate as a white solid (426 mg, 92%). MS (ES+) m/z: 324 $(M+NH_4^+)^+$.

4-(iso-Propylcarbamoyl-methyl)-benzylamine

Dissolve N-(tert-butoxycarbonyl)-4-(iso-propylcarbamoyl-methyl)-benzylamine (426 mg, 1.4 mmol) in DCM (5 mL). Add 4M hydrogen chloride in dioxane (3.5 mL, 14 mmol) and stir at room temperature for 1 h. Concentrate in vacuo and elute the compound through a SCX column to obtain the title compound as a white solid (281 mg, 98%). MS (ES+) m/z: 207 $(M+H)^+$.

Preparation 67

The compound of Preparation 67 may be prepared essentially as described in Preparation 66 by using [4-(tert-butoxycarbonylaminomethyl)-phenyl]-acetic acid and 2,2-dimethyl-propylamine. Overall yield and MS (ES) data are shown in the Table below.

104

Preparation 68

4-(2-Oxo-2-pyrrolidin-1-yl-ethyl)-benzylamine

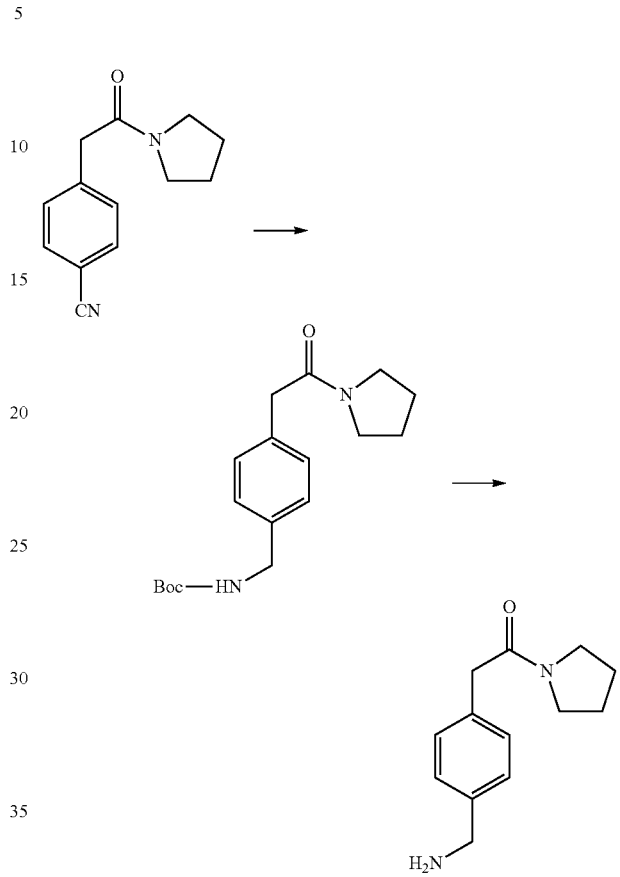

N-(tert-Butoxycarbonyl)-4-(2-oxo-2-pyrrolidin-1-yl-ethyl)-benzylamine

Combine 4-(2-oxo-2-pyrrolidin-1-yl-ethyl)-benzonitrile (200 mg, 0.93 mmol), di-tert-butyl-dicarbonate (244 mg, 1.1 mmol) and 10% Pd/C (Degussa type E101, 100 mg) in methanol (18 mL). Submit the mixture to hydrogenation at atmospheric pressure for 40 h. Filter the catalyst through Celite® and concentrate the filtrate in vacuo. Purify by chromatogra-

| Prep. | Structure | Compound | Yield (%) | MS (ES) m/z |
|---|---|---|---|---|
| 67 | | 4-[(2,2-Dimethyl-propylcarbamoyl)-methyl]-benzylamine | 83 | 235 $(M + H)^+$ | phy on silica gel eluting with hexane/EtOAc (1:1) to obtain the desired intermediate as a white solid (267 mg, 90%).

4-(2-Oxo-2-pyrrolidin-1-yl-ethyl)-benzylamine

Dissolve N-(tert-butoxycarbonyl)-4-(2-oxo-2-pyrrolidin-1-yl-ethyl)-benzylamine (267 mg, 0.8 mmol) in DCM (4 mL). Add 4M hydrogen chloride in dioxane (2 mL, 8 mmol) and stir at room temperature for 1 h. Concentrate in vacuo and elute the compound through a SCX column to obtain the title compound (179 mg, 98%). MS (ES+) m/z: 219 (M+H)+.

Preparation 69

(R)-4-[(1-Methyl-2,2,2-trifluoro-ethylcarbamoyl)-methyl]-benzylamine

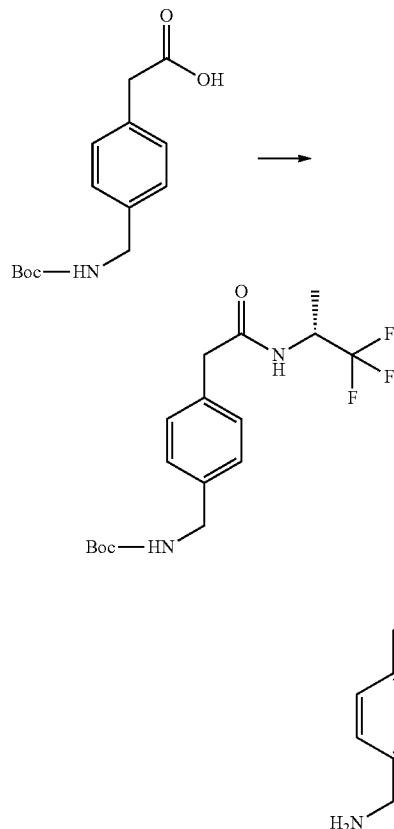

(R)—N-(tert-Butoxycarbonyl)-4-[(1-methyl-2,2,2-trifluoro-ethylcarbamoyl)-methyl]-benzylamine Dissolve [4-(tert-butoxycarbonylamino-methyl)-phenyl]-acetic acid (190 mg, 0.63 mmol) in DCM (12.4 mL) and add triethylamine (354 μL, 2.5 mmol), DMAP (8 mg, 0.063 mmol), EDC (145 mg, 0.756 mmol), HOBt (102 mg, 0.756 mmol) and (R)-1-methyl-2,2,2-trifluoro-ethylamine hydrochloride (71 mg, 0.63 mmol) under nitrogen atmosphere. Stir the reaction overnight at room temperature. Concentrate in vacuo and purify by chromatography on silica gel eluting with hexane/EtOAc (1:1 and 0:1) to obtain the desired intermediate (155 mg, 68%).

(R)-4-[(1-Methyl-2,2,2-trifluoro-ethylcarbamoyl)-methyl]-benzylamine

Dissolve (R)—N-(tert-butoxycarbonyl)-4-[(1-methyl-2,2,2-trifluoro-ethylcarbamoyl)-methyl]-benzylamine (155 mg, 0.43 mmol) in DCM (8 mL). Add 4M hydrogen chloride in dioxane (0.85 mL) and stir at room temperature overnight. Concentrate in vacuo and partition the hydrochloride salt between saturated aqueous NaHCO₃ and EtOAc. Extract the aqueous phase twice with EtOAc. Dry the combined organic extracts over Na₂SO₄, filter and concentrate in vacuo to obtain the title compound (105 mg, 91%). MS (ES+) m/z: 261 (M+H)+.

Preparation 70

(±)-4-[1-(2,2-Dimethylpropyl-carbamoyl)-ethyl]-benzylamine

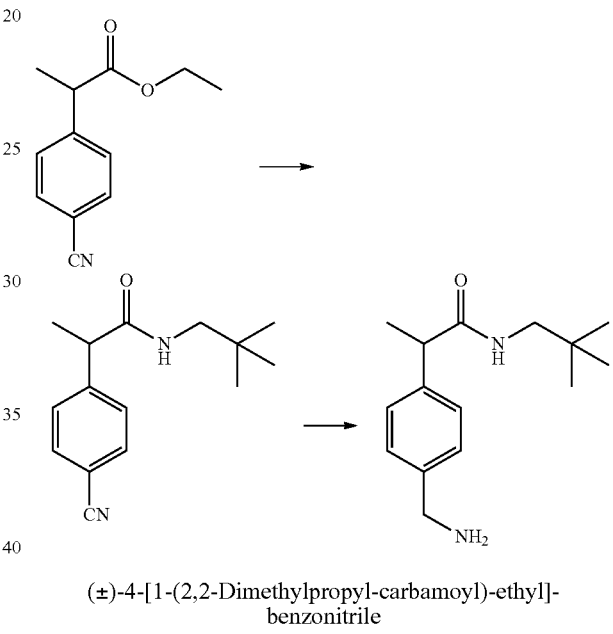

(±)-4-[1-(2,2-Dimethylpropyl-carbamoyl)-ethyl]-benzonitrile

Add AlMe₃ (1.72 mL, 3.44 mmol, 2M solution in hexane) to a solution of 2,2-dimethyl-propylamine (402 μL, 3.44 mmol) in DCM (0.5 mL) under nitrogen atmosphere. Stir the mixture for 15 min at room temperature and add ethyl 2-(4-cyanophenyl)propanoate. Heat the mixture at 40° C. overnight. Quench the reaction with 10N aqueous HCl and extract twice with DCM. Dry the combined organics extracts over Na₂SO₄, filter and concentrate in vacuo. Purify by chromatography on silica gel eluting with hexane/EtOAc (7:3) to obtain the desired intermediate (170 mg, 41%).

(±)-4-[1-(2,2-Dimethylpropyl-carbamoyl)-ethyl]-benzylamine

Bubble nitrogen into a solution of (±)-4-[1-(2,2-dimethylpropyl-carbamoyl)-ethyl]-benzonitrile (80 mg, 0.33 mmol) in methanol (9 mL) with 2 drops of concentrated HCl for 10 min. Add 10% Pd/C (Degussa type E101, 8 mg) and submit the mixture to hydrogenation at atmospheric pressure overnight. Filter the catalyst over Celite® and concentrate the filtrate in vacuo. Partition the solid between saturated aqueous NaHCO₃ and EtOAc, and extract again with EtOAc. Dry the combined organics extracts over MgSO₄, filter and concentrate in vacuo to afford the title compound as a yellow oil (69 mg, 85%). MS (ES+) m/z: 249 (M+H)+.

Preparation 71

The compound of Preparation 71 may be prepared essentially as described in Preparation 70 using methyl (4-cyanophenyl)acetate and cyclohexylmethyl amine Overall yield and MS (ES+) data are shown in the Table below.

| Prep. | Structure | Compound | Yield (%) | MS (ES) m/z |
|---|---|---|---|---|
| 71 | 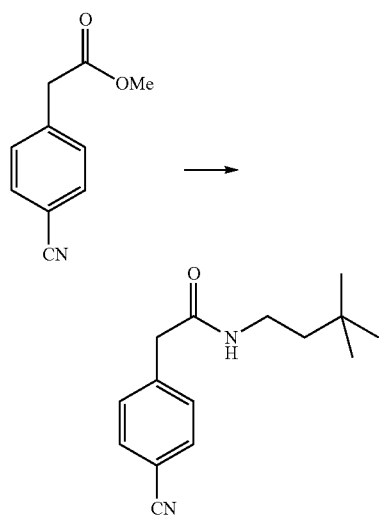 | 4-[(Cyclohexylmethyl-carbamoyl)-methyl]-benzylamine | 48 | 261 (M + H)+ |

Preparation 72

4-[(3,3-Dimethylbutyl-carbamoyl)-methyl]-benzylamine

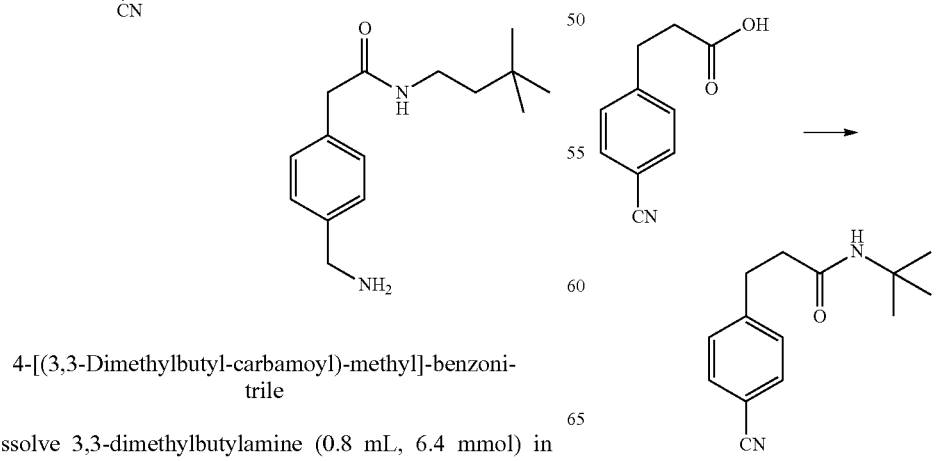

4-[(3,3-Dimethylbutyl-carbamoyl)-methyl]-benzonitrile

Dissolve 3,3-dimethylbutylamine (0.8 mL, 6.4 mmol) in anhydrous THF (2 mL) under nitrogen. Cool the solution at 0° C. and add DIBAL-H (6.2 mL, 6.2 mmol, 1M solution in toluene). Allow the mixture to warm up to room temperature and stir for 2 h. Add this complex to a solution of methyl (4-cyanophenyl)acetate (192 mg, 1.1 mmol) in THF (4 mL) and stir at room temperature overnight. Dilute with EtOAc and quench with 5% KHSO$_4$. Dry the organic phase over MgSO$_4$, filter and concentrate in vacuo. Purify by chromatography on silica gel eluting with hexane/EtOAc (7:3) to obtain the desired intermediate (160 mg, 60%). MS (ES+) m/z: 245 (M+H)+.

4-[(3,3-Dimethylbutyl-carbamoyl)-methyl]-benzylamine

Bubble nitrogen into a solution of 4-[(3,3-dimethylbutyl-carbamoyl)-methyl]-benzonitrile (240 mg, 0.9 mmol) in methanol (20 mL) with 3 drops of concentrated HCl for 10 min. Add 10% Pd/C (Degussa type E101, 48 mg) and submit the mixture to hydrogenation at atmospheric pressure overnight. Filter the catalyst over Celite® and concentrate the filtrate in vacuo. Elute the compound through a SCX column to obtain the title compound (240 mg, 98%). MS (ES+) m/z: 249 (M+H)+.

Preparation 73

4-[2-(tert-Butylcarbamoyl)-ethyl]-benzylamine

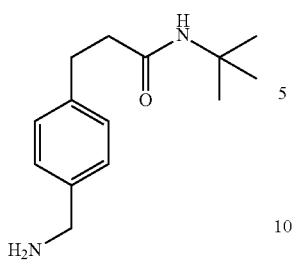

4-[2-(tert-Butylcarbamoyl)-ethyl]-benzonitrile

Dissolve 3-(4-cyanophenyl)-propionic acid (0.4 g, 2.48 mmol) and thionyl chloride (1.1 mL, 14.9 mmol) in toluene (2 mL) and reflux the mixture for 2 h. Concentrate in vacuo, dissolve the residue in DCM (1.5 mL) and add the solution to a cold solution (0° C.) of tert-butylamine (300 µL, 2.85 mmol) in DCM (1.5 mL) and triethylamine (97 µL, 0.69 mmol). Allow the mixture to stir at 0° C. for 15 min and at room temperature for 16 h. Add water, separate the organic phase and extract the aqueous phase twice with DCM. Dry the combined organic extracts over $Na_2SO_4$, filter and concentrate in vacuo. Purify by chromatography on silica gel eluting with hexane/EtOAc (65:35) to obtain the desired intermediate (306 mg, 54%).

4-[2-(tert-Butylcarbamoyl)-ethyl]-benzylamine

Add 10% Pd/C (Degussa type E101, 62 mg) to a solution of ethanol/water/acetic acid (10:5.6:0.6 mL). Add a solution of 4-[2-(tert-butylcarbamoyl)-ethyl]-benzonitrile (306 mg, 1.33 mmol) in ethanol (3.5 mL) and submit the mixture to hydrogenation at 60 psi overnight. Filter the catalyst through Celite® and concentrate in vacuo to obtain the acetate salt of the title compound. Wash with diethyl ether and filter the solid in vacuo. Add saturated aqueous $NaHCO_3$ and extract twice with EtOAc. Dry the combined organic extracts over $MgSO_4$, filter and concentrate in vacuo to obtain the title compound as a yellow oil (70 mg, 26%). MS (ES+) m/z: 235 (M+H)⁺.

Preparation 74

4-[2-(2,2-Dimethylpropyl-carbamoyl)-ethyl]-benzylamine

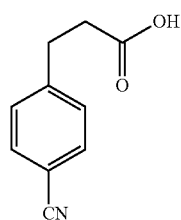

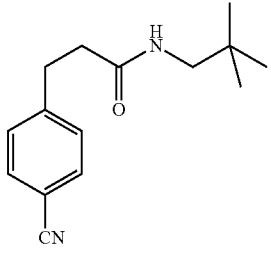

4-[2-(2,2-Dimethylpropyl-carbamoyl)-ethyl]-benzonitrile

Combine 3-(4-cyanophenyl)-propionic acid (870 mg, 4.9 mmol), 2,2-dimethylpropylamine (0.6 mL, 5.4 mmol), EDCI (1.0 g, 5.4 mmol), HOBT (804 mg, 5.9 mmol), triethylamine (2 mL, 14.8 mmol) and DMAP (60.5 mg, 0.5 mmol) in anhydrous DCM (50 mL). Stir at room temperature for 1 day under nitrogen. Concentrate the mixture in vacuo and purify by chromatography on silica gel eluting with hexane/EtOAc (1:1) to obtain the desired intermediate as a white solid (740 mg, 61%). MS (ES+) m/z: 245 (M+H)⁺.

4-[2-(2,2-Dimethylpropyl-carbamoyl)-ethyl]-benzylamine

Bubble nitrogen into a solution of 4-[2-(2,2-dimethylpropyl-carbamoyl)-ethyl]-benzonitrile (740 mg, 3.0 mmol) in methanol (60 mL) with 3 drops of concentrated HCl for 10 min. Add 10% Pd/C (Degussa type E101, 148 mg) and submit the mixture to hydrogenation at atmospheric pressure overnight. Filter the catalyst over Celite® and concentrate the filtrate in vacuo. Elute the compound through a SCX column to obtain the title compound (717 mg, 95%). MS (ES+) m/z: 249 (M+H)⁺.

Preparation 75

4-Cyclohexanesulfonyl-benzylamine

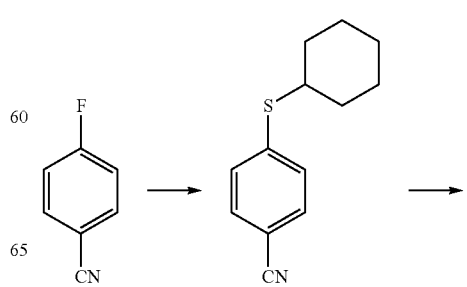

Preparation 76

3-Aminomethyl-6-[(2-methyl-2-propane)sulfonylmethyl]-pyridine

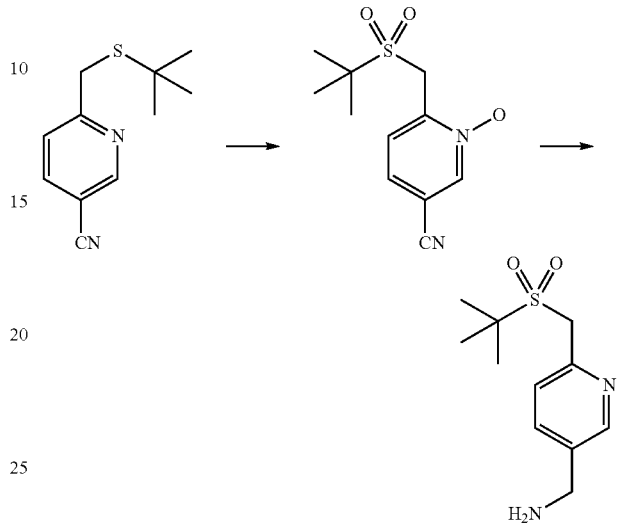

4-Cyclohexylthio-benzonitrile

Dissolve sodium metal (343 mg, 14.9 mmoles) in anhydrous ethanol (20 mL) at room temperature under nitrogen atmosphere. Then add cyclohexyl mercaptan (2 mL, 16.37 mmoles) and stir at room temperature for 30 min. Add then neat 4-fluoro-benzonitrile (1.8 g, 14.9 mmol) and heat the resulting solution at 80° C. overnight. Cool the reaction to room temperature and quench the reaction by adding 1N aqueous HCl (100 mL). Concentrate the mixture in vacuo and take up the residue with EtOAc (100 mL). Wash the organic layer with saturated aqueous NaHCO$_3$ (100 mL) and brine (100 mL). Dry the organic phase over MgSO$_4$ and concentrate in vacuo. Purify the crude mixture by chromatography on silica gel (120 g, pre-packed cartridge) eluting with cyclohexane/EtOAc (98:2 to 80:20 gradient) to afford the desired intermediate (2.2 g, 68%). GC-MS m/z: 217 (M$^+$).

4-Cyclohexanesulfonyl-benzonitrile

Dissolve 4-cyclohexylthio-benzonitrile (1.17 g, 5.4 mmol) in acetone (10 mL) and add water until the sulfide starts to come out of solution. Then add a drop of acetone to rehomogenize the solution. Cool the mixture to 0° C. and then add oxone (4.2 g, 6.73 mmol) in one portion while stirring vigorously at 0° C. for h. Concentrate in vacuo, take up the residue in DCM and filter the suspension through a frit. Concentrate in vacuo to obtain the desired intermediate (1.27 g, 94%) as a white solid.

4-Cyclohexanesulfonyl-benzylamine

Dissolve 4-cyclohexanesulfonyl-benzonitrile (1.27 g, 5.1 mmol) in anhydrous THF (15 mL) at 0° C. under nitrogen and then add a solution of borane-THF complex (15.3 mL, 15.3 mL, 1M solution in THF). Stir overnight while warming to room temperature. Add the reaction to a mixture of 5N aqueous HCl (50 mL), THF (50 mL) and ice and stir for 1 hour. Concentrate the mixture in vacuo and take up the resulting white residue through a SCX-2 column eluting with methanol followed by 3N ammonia in methanol to obtain the title compound as a white solid (625 mg, 50%). MS (ES+) m/z: 254.1 (M+H)$^+$

1-Hydroxy-6-[(2-methyl-2-propane)sulfonylmethyl]-pyridine-3-carbonitrile

To a solution of 6-(tert-butylthio)methyl-pyridine-3-carbonitrile (2.5 g, 12.13 mmol) in TFA (17 mL) at 0° C. add dropwise a solution of hydrogen peroxide in water (16.8 mL, 30% sol.) and warm the reaction to room temperature overnight. Concentrate in vacuo and take-up the resulting crude into saturated aqueous NaHCO$_3$ (50 mL). Extract the aqueous layer several times with EtOAc (100 mL each). Dry the combined organic extracts over MgSO$_4$, filter and concentrate in vacuo to obtain the desired intermediate as a white solid (2.8 g, 100%). MS (ES+) m/z: 255 (M+H)$^+$, 277 (M+Na)$^+$.

3-Aminomethyl-6-[(2-methyl-2-propane)sulfonylmethyl]-pyridine

Add a solution of 1-hydroxy-6-[(2-methyl-2-propane)sulfonylmethyl]-pyridine-3-carbonitrile (150 mg, 0.59 mmol) in ethanol (12 mL) to an aqueous slurry of Raney Ni (50%, 1 g). Submit the suspension to hydrogenation at 60 psi for 10 h and then filtrate the mixture through Celite® to provide an inseparable mixture of the title compound and the corresponding N-oxide. Take this mixture up in DCM (5 mL), add di-tert-butyl-dicarbonate (196 mg, 0.9 mmol) and stir overnight at room temperature. Concentrate in vacuo and purify by chromatography on silica gel eluting with DCM/EtOAc (7:3 to 0:1 gradient) to obtain 3-(tert-butoxycarbonylamino-methyl)-6-[(2-methyl-2-propane)sulfonylmethyl]-pyridine as a white solid (93 mg). Dilute this material in DCM (5 mL), add trifluoroacetic acid at room temperature and stir for 30 min. Concentrate in vacuo, take the residue up in methanol and filter through a SCX-2 column eluting with methanol followed by 3N ammonia in methanol to obtain the title compound as a colourless oil (66 mg, 46%). MS (ES+) m/z: 243 (M+H)$^+$.

Preparation 77

3-Aminomethyl-6-[(2,2-dimethylpropane)sulfonylmethyl]-pyridine

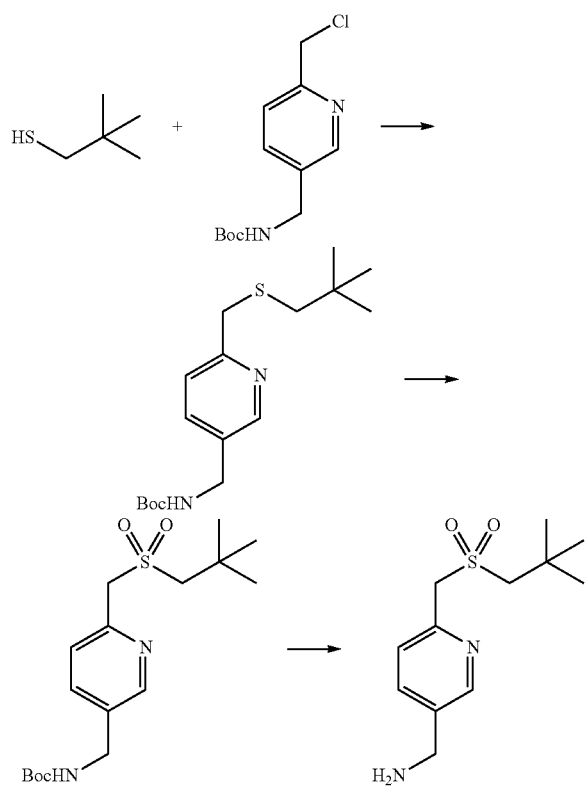

2,2-Dimethyl-propane-1-thiol

Add sulfur (3.05 g, 95 mmol) and ether (60 mL) to 2,2-dimethylpropylmagnesium chloride (95 mL, 95 mmol, 1M solution in diethyl ether) under nitrogen at 0° C. Warm the mixture to room temperature and stir for 2 h. Cool to 0° C. and add 1N aqueous HCl (120 mL). Extract into diethyl ether (~100 mL) by continuous extraction. Distill diethyl ether through a 22 cm long Vigreux column by heating with an oil bath (50-120° C.) under nitrogen. Cool and remove the Vigreux column and install a short path distillation head. Distill the product (60-100° C.) with the oil bath at −140° C. to obtain the desired intermediate (8.5 g, 86%).

3-(tert-Butoxycarbonylamino-methyl)-6-[(2,2-dimethylpropyl)thiomethyl]-pyridine Under a nitrogen atmosphere, add sodium methoxide (630 mg, 3.51 mmol, 30% w/w in methanol) to a stirring mixture of 2,2-dimethyl-propane-1-thiol (365 mg, 3.51 mmol) and methanol (10 mL) at room temperature and stir for 30 min. Add 3-(tert-butoxycarbonylamino-methyl)-6-chloromethyl-pyridine (450 mg, 1.76 mmol) in methanol (5 mL) and stir the mixture for 2 h. Dilute the mixture with water and ethyl acetate. Separate the layers and extract the aqueous layer with ethyl acetate. Wash the combined organic extracts with water and brine. Dry the organic phase over $Na_2SO_4$, filter, and concentrate in vacuo to obtain the desired intermediate suitable for use without additional purification. MS (APCI+) m/z: 325 $(M+H)^+$.

3-(tert-Butoxycarbonylamino-methyl)-6-[(2,2-dimethyl-propane)-sulfonylmethyl]-pyridine Add m-CPBA (977 mg, 4.36 mmol, 70-77% pure) to a solution of 3-(tert-butoxycarbonylamino-methyl)-6-[(2,2-dimethylpropyl)thiomethyl]-pyridine (700 mg, 2.16 mmol) in DCM (20 mL) at 0° C. Warm the mixture to room temperature and stir overnight. Dilute the mixture with 10% aqueous $K_2CO_3$ (30 mL) and DCM. Separate the layers and extract the aqueous phase with DCM. Wash the combined organic extracts with water and brine. Dry the organic phase over $Na_2SO_4$, filter and concentrate in vacuo. Purify the residue by chromatography on silica gel (45 g, pre-packed cartridge) eluting with hexane/EtOAc (1:0 to 1:1 gradient) to obtain the desired intermediate (480 mg, 62%). MS (APCI+) m/z: 357 $(M+H)^+$.

3-Aminomethyl-6-[(2,2-dimethyl-propane)sulfonylmethyl]-pyridine

Bubble hydrogen chloride into a mixture of 3-(tert-butoxycarbonylamino-methyl)-6-[(2,2-dimethyl-propane)sulfonylmethyl]-pyridine (480 mg, 1.35 mmol), methanol (10 mL) and EtOAc (10 mL) at room temperature until saturated. After stirring for 1 h, concentrate the mixture in vacuo. Purify by chromatography on silica gel (25 g, pre-packed cartridge) eluting with DCM/(chloroform:methanol:concentrated $NH_4OH$ 80:18:2) (1:0 to 1:1 gradient) to obtain the title compound (325 mg, 94%). MS (APCI+) m/z: 257 $(M+H)^+$.

Preparation 78

The compound of Preparation 78 may be prepared essentially as described in Preparation 77 by using 3-(tert-butoxycarbonylamino-methyl)-6-chloromethyl-pyridine and cyclohexanethiol. Overall yield and MS (ES) data are shown in the Table below.

| Prep. | Structure | Compound | Yield (%) | MS (ES) m/z |
|---|---|---|---|---|
| 78 | (structure shown) | 3-Aminomethyl-6-(cyclohexanesulfonyl)methyl-pyridine | 43 | 269 $(M + H)^+$ |

Preparation 79

4-(2,2-Dimethylpropane-sulfonylmethyl)-benzylamine

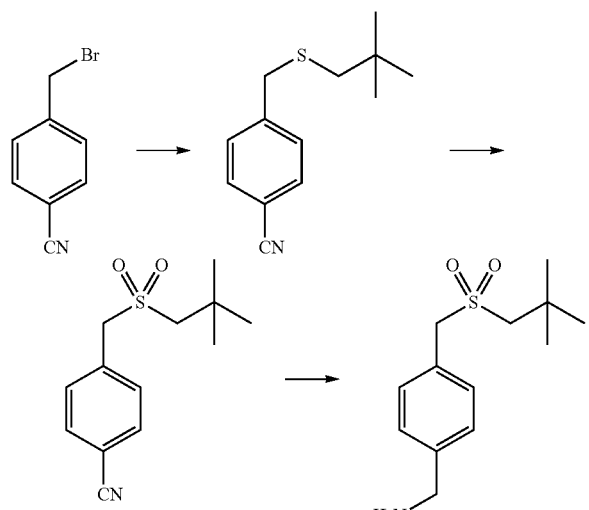

4-(2,2-Dimethylpropane-thiomethyl)-benzonitrile

Add sodium hydride (317 mg, 7.92 mmol, 60% dispersion in mineral oil) to a solution of 2,2-dimethyl-propane-1-thiol (635 mg, 6.09 mmol) in anhydrous DMF (50 mL) under nitrogen at 0° C. Stir the mixture for 15 min, add 4-(bromomethyl)-benzonitrile (597 mg, 3.04 mmol) and stir the resulting mixture overnight at room temperature. Add water and extract the aqueous phase twice with EtOAc. Wash the combined organic extracts twice with water, dry over $Mg_2SO_4$, filter, and concentrate in vacuo to obtain the desired compound (867 mg, 100%) suitable for use without further purification. MS (ES+) m/z: 220 $(M+H)^+$.

4-(2,2-Dimethylpropane-sulfonylmethyl)-benzonitrile

Dissolve 4-(2,2-dimethylpropane-thiomethyl)-benzonitrile (867 mg, 3.95 mmol) in DCM (20 mL). Cool the mixture to 0° C., and add m-CPBA (1.95 g, 8.69 mmol, 70-77% pure) slowly. Allow the mixture to warm to room temperature and stir overnight. Dilute the mixture with DCM and wash with saturated aqueous $Na_2SO_3$ followed by saturated aqueous $NaHCO_3$ (2×). Dry over $MgSO_4$, filter, and concentrate in vacuo to obtain the desired compound (966 mg, 97%) suitable for use without further purification. MS (APCI+) m/z: 252 $(M+H)^+$.

4-(2,2-Dimethylpropane-sulfonylmethyl)-benzylamine

Add cobalt(II) chloride hexahydrate (1.83 mg, 7.7 mmol) to a solution of 4-(2,2-dimethylpropane-sulfonylmethyl)-benzonitrile (966 mg, 3.85 mmol) in methanol (25 mL). Cool the mixture to 0° C. and stir for 15 min. Carefully add sodium borohydride (1.46 g, 38.49 mmol) in small batches, allow the mixture to warm to room temperature and stir for 2 h. Dilute the mixture with water and partition between water and chloroform. Extract the aqueous phase three times with chloroform/iso-propanol (3:1). Dry the combined organic extracts over $MgSO_4$, filter and concentrate in vacuo. Purify by chromatography on silica gel (80 g) eluting with DCM/(chloroform:methanol:concentrated $NH_4OH$ 80:18:2) (1:0 over 5 min, 19:1 over 5 min, 9:1 over 35 min, 85:15; 50 mL/min) to give the title compound (181 mg, 49%). MS (APCI+) m/z: 256 $(M+H)^+$.

Preparation 80

3-(tert-Butoxycarbonyl)-7-chloro-6-(4-dimethylcarbamoylthio-benzylamino)-2,3,4,5-tetrahydro-1H-benzo[d]azepine

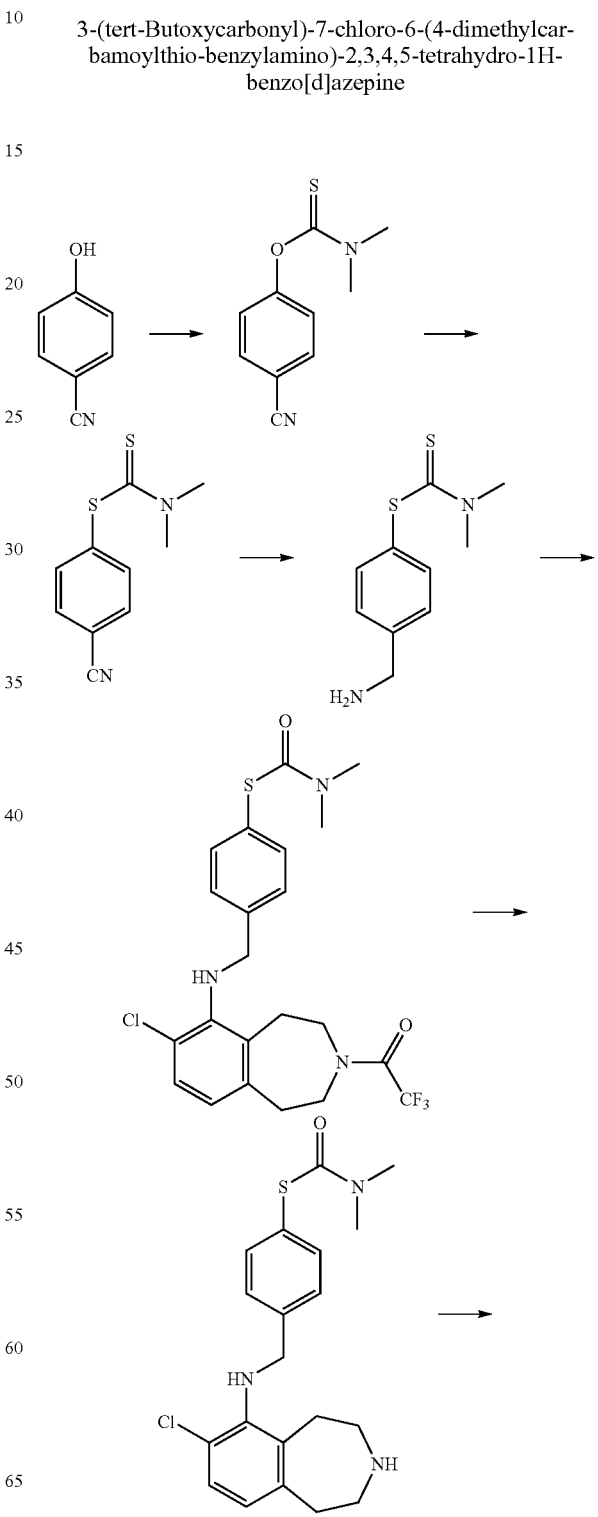

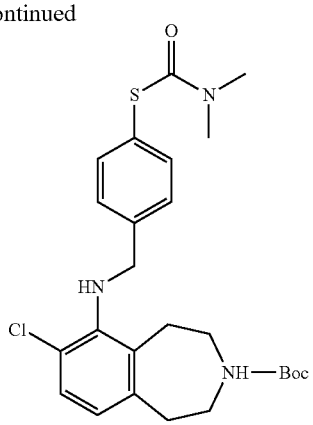

4-Dimethylthiocarbamoyloxy-benzonitrile

Add sodium hydride (1.21 g, 95%) to a solution of 4-cyanophenol (5.71 g, 47.98 mmol) in anhydrous TI-IF (70 mL) and stir the mixture for 5 min. Add dimethylthiocarbamoyl chloride (5.93 g, 47.98 mmol) and heat the mixture at reflux for 3 h. Cool the mixture to room temperature and add water. Extract the aqueous phase with EtOAc, dry the organic phase over MgSO₄, filter and concentrate in vacuo to obtain a solid. Wash the solid with diethyl ether, filter and dry in vacuo to obtain the desired intermediate as a solid (4.41 g, 75%).

4-Dimethylcarbamoylthio-benzonitrile

Place 4-dimethylthiocarbamoyloxy-benzonitrile (8.3 g, 40.29 mmol) into a sealed tube equipped with a magnetic stirrer. Immerse the tube in a preheated oil bath at 210° C. and stir at this temperature for 2 h. Cool to room temperature, dissolve the content in DCM and transfer the solution to a round bottom flask. Concentrate in vacuo to obtain a solid. Wash the solid with hexane and then with cold diethyl ether. Filter and dry in vacuo to obtain the desired intermediate as a beige solid (7.5 g, 90%).

4-Dimethylcarbamoylthio-benzylamine

Dissolve 4-dimethylcarbamoylthio-benzonitrile (3.07 g, 14.9 mmol) in anhydrous THF (30 mL). Add borane-dimethylsulfide complex (4.24 mL, 44.7 mmol, 1M solution in diethyl ether) and stir the mixture at room temperature for 3 h. Add methanol dropwise until hydrogen evolution ceases. Concentrate the mixture in vacuo and purify the crude mixture by SCX chromatography eluting with methanol and 2M ammonia in methanol to obtain the title compound as a slightly impure oil (2.9 g). Dissolve the oil (2.9 g) in DCM and add 2M hydrogen chloride in ether. Stir the mixture for 1 h and concentrate in vacuo to obtain a solid. Suspend the solid in DCM and add diethyl ether to precipitate the salt. Filter and dry the solid in vacuo to obtain the hydrochloride salt of the title compound as a white solid (2.33 g, 64%). Elute the compound through a SCX column to obtain the desired intermediate as an oil. MS (ES+) m/z: 211 (M+H)⁺.

7-Chloro-6-(4-dimethylcarbamoylthio-benzylamino)-3-(2,2,2-trifluoroacetyl)-2,3,4,5-tetrahydro-1H-benzo[d]azepine Use a method similar to the General Procedure 1-2 to couple 7-chloro-3-(2,2,2-trifluoroacetyl)-6-trifluoromethanesulfonyloxy-2,3,4,5-tetrahydro-1H-benzo[d]azepine (348 mg, 0.8 mmol) with 4-dimethylcarbamoylthio-benzylamine (345 mg, 1.6 mmol). Purify by chromatography on silica gel eluting with hexane/EtOAc (4:1) to obtain the desired intermediate (170 mg, 43%).

7-Chloro-6-(4-dimethylcarbamoylthio-benzylamino)-2,3,4,5-tetrahydro-1H-benzo[d]azepine Use a method similar to the General Procedure 2-1, using 7-chloro-6-(4-dimethylcarbamoylthio-benzylamino)-3-(2,2,2-trifluoroacetyl)-2,3,4,5-tetrahydro-1H-benzo[d]azepine (151 mg, 0.3 mmol), to obtain the desired intermediate as an oil (114 mg, 94%) suitable for use without additional purification.

3-(tert-Butoxycarbonyl)-7-chloro-6-(4-dimethylcarbamoylthio-benzylamino)-2,3,4,5-tetrahydro-1H-benzo[d]azepine Dissolve 7-chloro-6-(4-dimethylcarbamoylthio-benzylamino)-2,3,4,5-tetrahydro-1H-benzo[d]azepine (114 mg, 0.29 mmol) in anhydrous DCM (3 mL). Cool the solution at 0° C. and add di-tert-butyl-dicarbonate (64 mg, 0.29 mmol) and triethylamine (0.12 mL, 0.88 mmol). Stir at room temperature overnight. Concentrate in vacuo and purify the crude mixture by chromatography on silica gel eluting with hexane/EtOAc (4:1) to obtain the title compound (130 mg, 91%).

Preparation 81

3-Aminomethyl-6-(3,3-dimethyl-2-oxo-butoxy)-pyridine

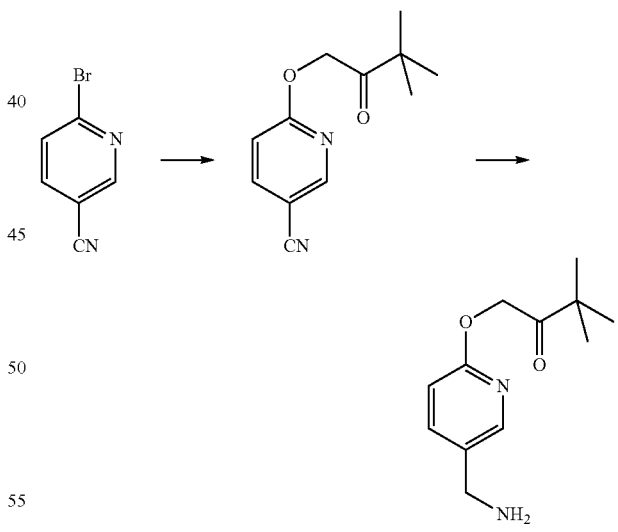

6-(3,3-Dimethyl-2-oxo-butoxy)-pyridine-3-carbonitrile

Dissolve sodium hydride (380 mg, 9.5 mmol) in anhydrous DMF (7 mL). Cool at 0° C., add dropwise 1-hydroxy-3,3-dimethylbutan-2-one (1.1 g, 9.5 mmol) and stir at this temperature for 30 min. Add a solution of 6-bromo-nicotinonitrile in DMF (7 mL) and heat at 70° C. overnight. Cool the reaction mixture with ice/water and work-up sequentially with EtOAc and water. Dry the organic fraction over MgSO$_4$, filter and concentrate in vacuo. Purify by chromatography on silica gel eluting with hexane/EtOAc (4:1) to obtain the desired intermediate (424 mg, 50%). MS (ES+) if/A: 219 (M+H)$^+$.

3-Aminomethyl-6-(3,3-dimethyl-2-oxo-butoxy)-pyridine

Bubble nitrogen into a solution of 6-(3,3-dimethyl-2-oxo-butoxy)-pyridine-3-carbonitrile (400 mg, 1.8 mmol) in methanol (36 mL) with 3 drops of concentrated HCl for 10 min. Add 10% Pd/C (Degussa type E101, 80 mg) and submit the mixture to hydrogenation at atmospheric pressure overnight. Filter the reaction mixture over Celite®. Concentrate the filtrate in vacuo and purify by SCX chromatography to obtain the title compound (223 mg, 55%). MS (ES+) m/z: 223 (M+H)$^+$.

Preparation 82

3-Aminomethyl-6-[(2,2-dimethyl-propylcarbamoyl)-methoxy]-pyridine

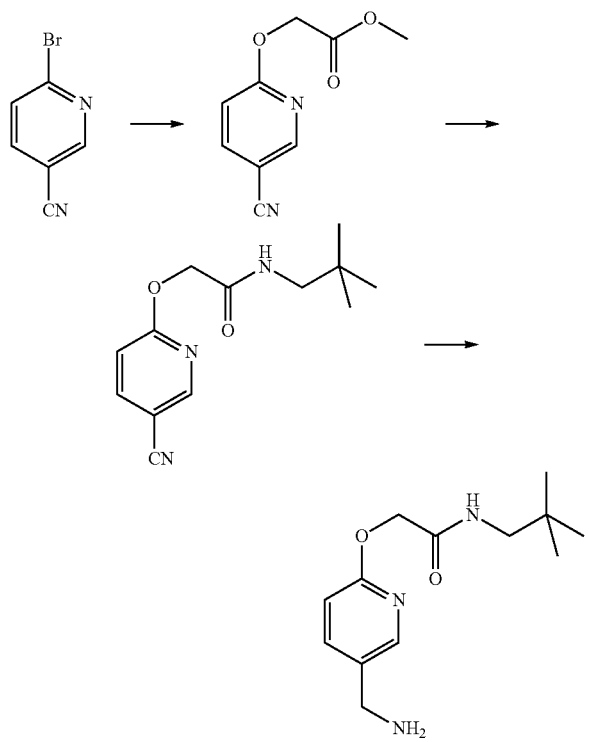

6-Methoxycarbonylmethoxy-pyridine-3-carbonitrile

Dissolve sodium hydride (380 mg, 9.5 mmol) in anhydrous DMF (7 mL). Cool at 0° C., add dropwise methyl 2-hydroxy-acetate (0.7 mL, 9.5 mmol) and stir at this temperature for 30 min. Add a solution of 6-bromo-nicotinonitrile in DMF (7 mL) and heat at 70° C. overnight. Cool the reaction mixture with ice/water and work-up sequentially with EtOAc and water. Dry the organic phase over MgSO$_4$, filter and concentrate in vacuo. Purify by chromatography on silica gel eluting with hexane/EtOAc (4:1) to obtain the desired intermediate (461 mg, 63%). MS (ES+) m/z: 193 (M+H)$^+$.

6-[(2,2-Dimethyl-propylcarbamoyl)-methoxy]-pyridine-3-carbonitrile

Dissolve under nitrogen 2,2-dimethylpropylamine (1.7 mL, 14.1 mmol) in anhydrous THF (10 mL). Cool the solution at 0° C. and add DIBAL-H (13.6 mL, 13.6 mmol, 1M solution in toluene). Allow the mixture to warm up to room temperature and stir for 1 h. Add this complex to a solution of 6-methoxy-carbonylmethoxy-pyridine-3-carbonitrile (461 mg, 2.4 mmol) in THF (10 mL) and stir at room temperature overnight. Dilute with EtOAc, and quench with 5% KHSO$_4$. Dry the organic phase over MgSO$_4$, filter and concentrate in vacuo. Purify by chromatography on silica gel eluting with hexane/EtOAc (1:1) to obtain the desired intermediate (320 mg, 54%). MS (ES+) m/z: 248 (M+H)$^+$.

3-Aminomethyl-6-[(2,2-dimethyl-propylcarbamoyl)-methoxy]-pyridine

Bubble nitrogen into a solution of 6-[(2,2-dimethyl-propyl-carbamoyl)-methoxy]-pyridine-3-carbonitrile (320 mg, 1.3 mmol) in methanol (26 mL) with 3 drops of concentrated HCl for 10 min. Add 10% Pd/C (Degussa type E101, 64 mg) and submit the mixture to hydrogenation at atmospheric pressure overnight. Filter the reaction mixture over Celite®, concentrate the filtrate in vacuo and purify by SCX chromatography to obtain the title compound (314 mg, 96%). MS (ES+) m/z: 252 (M+H)$^+$.

Preparation 83

4-[5-(Cyclopropylmethyl-amino)-isothiazol-3-yl]-benzylamine

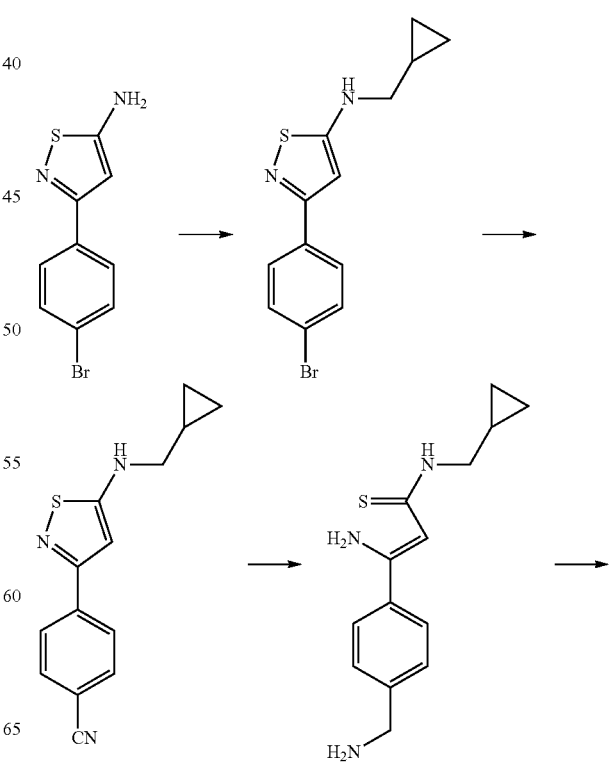

4-[5-(Cyclopropylmethyl-amino)-isothiazol-3-yl]-benzylamine

Add 30% hydrogen peroxide solution (0.13 mL, 1.1 mmol) to a solution of 4-[1-amino-2-(cyclopropylmethyl-thiocarbamoyl)-vinyl]-benzylamine (150 mg, 0.57 mmol) in methanol (5 mL). Stir the solution for 16 h at room temperature. Quench the reaction with aqueous saturated sodium hydrogensulfite (1 mL). Extract the mixture with EtOAc (2×30 mL), collect the organic layer and concentrate in vacuo. Purify the residue by chromatography on silica gel (4 g) eluting with DCM/ammonia in methanol (97:3) to obtain the title compound as a yellow solid (68 mg, 46%). MS (ES+) m/z: 243.1 (M-NH$_3$+H)$^+$.

Preparation 84

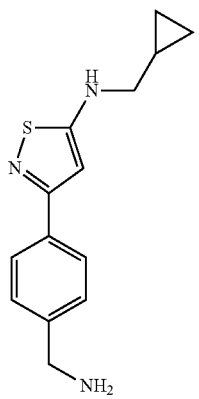

3-[(4-Bromo-phenyl)-isothiazol-5-yl]-cyclopropylmethyl-amine

Add acetic acid (1.4 mL, 23.5 mmol) to a slurry 3-(4-bromo-phenyl)-isothiazol-5-ylamine (1.0 g, 3.9 mmol), sodium triacetoxyborohydride (2.5 g, 11.8 mmol) and cyclopropane carboxaldehyde (275 mg, 3.9 mmol) at room temperature under a nitrogen atmosphere. Stir the resulting solution for 3 h at ambient temperature. Dilute the solution with DCM (40 mL) and wash with saturated aqueous NaHCO$_3$ (50 mL). Collect the organic layer, dry over Na$_2$SO$_4$, filter and concentrate in vacuo. Purify the residue by chromatography on silica gel (40 g) eluting with hexane/EtOAc (9:1 to 3:2 gradient) to obtain the desired intermediate (800 mg, 66%). MS (ES+) m/z: 309.1 (M$^+$).

4-[5-(Cyclopropylmethyl-amino)-isothiazol-3-yl]-benzonitrile

Slurry 3-[(4-bromo-phenyl)-isothiazol-5-yl]-cyclopropylmethyl-amine (800 mg, 2.6 mmol), tris(dibenzylideneacetone)-dipalladium(0) (119 mg, 0.13 mmol), DPPF (172 mg, 0.31 mmol) and zinc cyanide (182 mg, 1.6 mmol) in DMF at room temperature. Stir the mixture for 16 h at 120° C. under a nitrogen atmosphere. Cool the mixture to room temperature, add EtOAc (50 mL) and wash with 5% aqueous NaCl (20 mL). Collect the organic layer and back extract the aqueous layer with EtOAc (20 mL). Dry the combined organic extracts over Na$_2$SO$_4$, and concentrate in vacuo. Purify the residue by chromatography on silica gel (25 g) eluting with hexane/EtOAc (9:1 to 3:2 gradient) to obtain the desired intermediate (450 mg, 68%). MS (ES+) m/z: 256.1 (M+H)$^+$.

4-[1-Amino-2-(cyclopropylmethyl-thiocarbamoyl)-vinyl]-benzylamine

Add 1M lithium aluminum hydride in THF (3.0 mL, 3.0 mmol) to a solution of 4-[5-(cyclopropylmethyl-amino)-isothiazol-3-yl]-benzonitrile (210 mg, 0.82 mmol) in THF (8 mL) at room temperature under a nitrogen atmosphere. Stir the mixture at ambient temperature for 45 min, then quench the reaction sequentially with water (0.3 mL) and 5N aqueous NaOH (0.3 mL). Filter the slurry through Celite®, dry the filtrate over Na$_2$SO$_4$, filter and concentrate in vacuo. Purify the residue by chromatography on silica gel (8 g) eluting with DCM/2M ammonia in methanol (20:1) to obtain the desired intermediate (110 mg, 51%). MS (ES+) m/z: 245.1 (M-NH$_3$+H)$^+$.

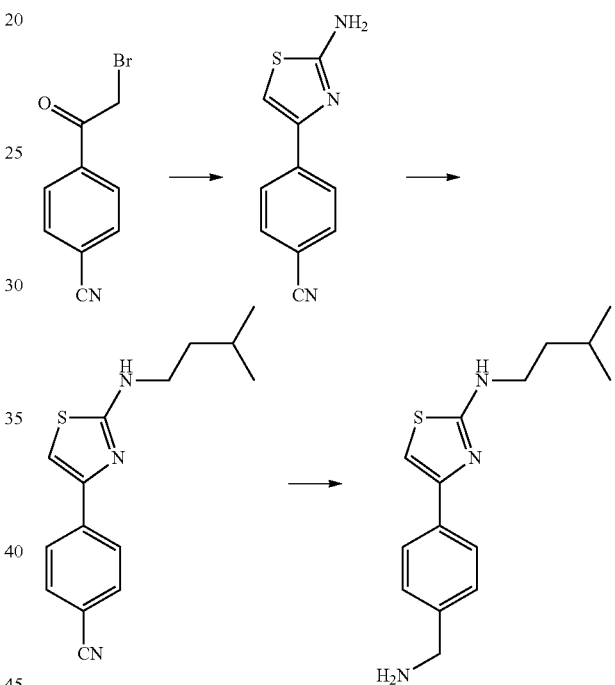

4-(2-Amino-thiazol-4-yl)-benzonitrile

Slurry 4-cyanophenacyl bromide (40 g, 179 mmol), thiourea (13.6 g, 181 mmol) and sodium bicarbonate (15.3 g, 181 mmol) in absolute ethanol (560 mL). Stir the mixture at reflux for 20 h under a nitrogen atmosphere. Cool the slurry to room temperature, filter, wash the solids with ethanol (100 mL), water (3×75 mL) and hexane (3×75 mL). Collect the yellow solid, add water (200 mL) and stir the slurry for 30 min at room temperate. Filter and wash the solid with hexane (excess). Slurry the solid in EtOAc (50 mL) and concentrate in vacuo twice to remove residual water. Collect the desired intermediate as a light yellow solid (36 g, 99%). MS (ES+) m/z: 202.1 (M+H)$^+$.

4-[2-(3-Methyl-butylamino)-thiazol-4-yl]-benzonitrile

Slurry 4-(2-amino-thiazol-4-yl)-benzonitrile (2.0 g, 9.9 mmol), sodium triacetoxyborohydride (6.3 g, 29.7 mmol), isovaleraldehyde (1.7 g, 19.8 mmol) and acetic acid (3.6 mL) in 1,2-dichloroethane (100 mL) at room temperature under a nitrogen atmosphere. Stir the mixture for 16 h at room temperature. Quench the reaction with saturated aqueous $NaHCO_3$ (75 mL, pH to 7.0-7.5). Extract the mixture twice with DCM (100 mL) and concentrate in vacuo. Purify the crude mixture by chromatography on silica gel (40 g) eluting with hexane/EtOAc (20:1 to 3:2 gradient) to obtain the desired intermediate (1.8 g, 67%). MS (ES+) m/z: 272 (M−H)+.

4-[2-(3-Methyl-butylamino)-thiazol-4-yl]-benzylamine

Add lithium aluminum hydride (210 mg, 5.5 mmol) portionwise over 3 min to a solution of 4-[2-(3-methyl-butylamino)-thiazol-4-yl]-benzonitrile (500 mg, 1.8 mmol) in THF (20 mL) at room temperature under a nitrogen atmosphere. Stir the mixture for 1 h at 60° C. Cool the mixture, quench slowly with water (0.2 mL) and 1N NaOH (0.2 mL). Add sodium sulfate to absorb residual water, filter the mixture through Celite®, wash with DCM (50 mL) and concentrate in vacuo. Purify the residue by SCX chromatography to obtain the desired intermediate (493 mg, 97%). MS (ES+) m/z: 276 (M+H)+.

Preparations 85-88

The compounds of Preparations 85-88 may be prepared essentially as described in Preparation 84 using 4-(2-amino-thiazol-4-yl)-benzonitrile and the appropriate aldehyde. Overall yields and MS (ES+) data are shown in the Table below.

| Prep. | Structure | Compound | Yield (%) | MS (ES+) m/z |
|---|---|---|---|---|
| 85 | 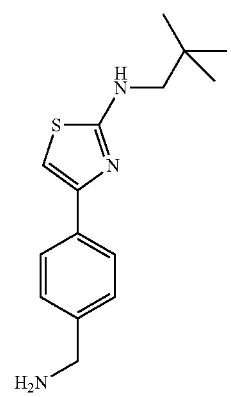 [SMILES: CC(C)(C)CNc1nc(-c2ccc(CN)cc2)cs1] | 4-[2-(2,2-Dimethyl-propylamino)-thiazol-4-yl]-benzylamine | 26 | 276 |
| 86 | 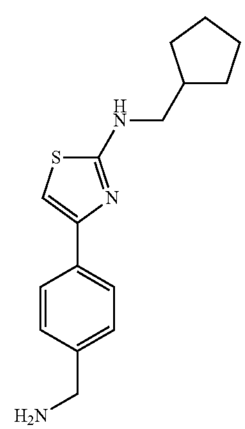 [SMILES: NCc1ccc(-c2csc(NCC3CCCC3)n2)cc1] | 4-(2-Cyclopentylmethylamino-thiazol-4-yl)-benzylamine | 18 | 288 |

-continued

| Prep. | Structure | Compound | Yield (%) | MS (ES+) m/z |
|---|---|---|---|---|
| 87 | 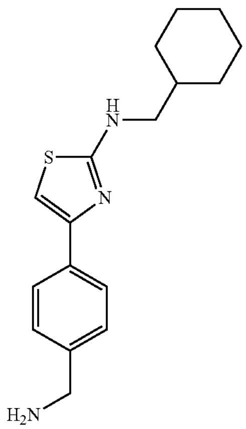 [SMILES: NCc1ccc(-c2csc(NCC3CCCCC3)n2)cc1] | 4-(2-Cyclohexylmethylamino-thiazol-4-yl)-benzylamine | 38 | 302.3 |
| 88 | 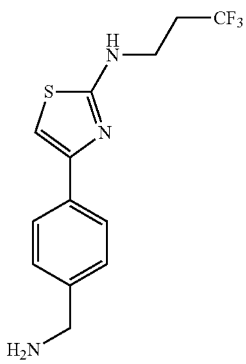 [SMILES: NCc1ccc(-c2csc(NCCC(F)(F)F)n2)cc1] | 4-[2-(3,3,3-Trifluoropropylamino)-thiazol-4-yl]-benzylamine | 14 | 302 |

Preparation 89

The compound of Preparation 89 may be prepared essentially as described in Preparation 4 by using 4-cyanophenacyl bromide and benzylthiourea. Overall yield and MS (ES+) data are shown in the Table below.

| Prep. | Structure | Compound | Yield (%) | MS (ES+) m/z |
|---|---|---|---|---|
| 89 | 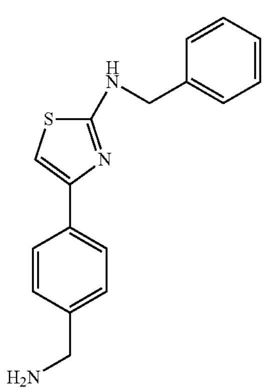 [SMILES: NCc1ccc(-c2csc(NCc3ccccc3)n2)cc1] | 4-(2-Benzylamino-thiazol-4-yl)-benzylamine | 25 | 296 (M + H)+ |

Preparation 90

4-(2-Cyclopropylmethylamino-5-methyl-thiazol-4-yl)-benzylamine

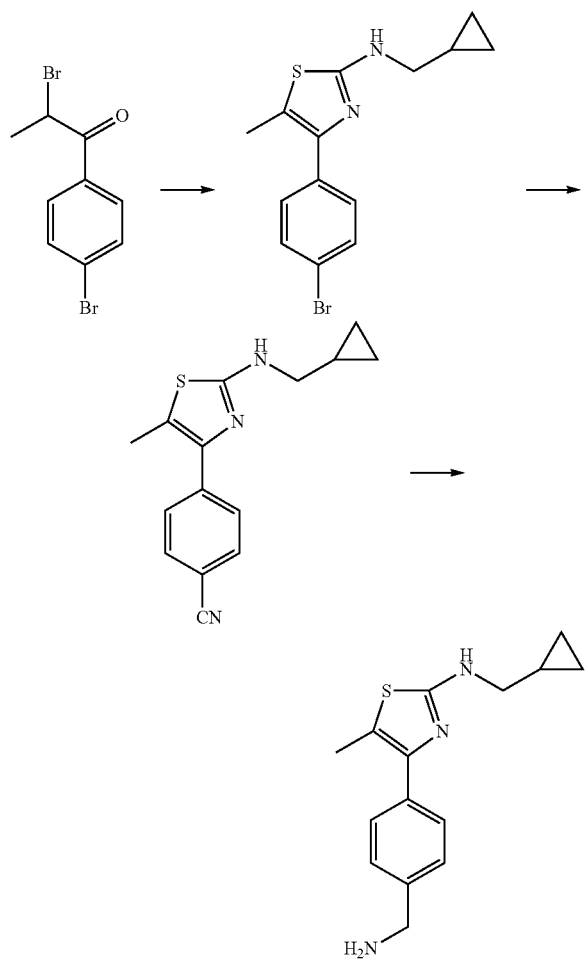

1-Bromo-4-(2-cyclopropylmethylamino-5-methyl-thiazol-4-yl)-benzene

Slurry 2,4'-dibromopropiophenone (2.92 g, 10 mmol), cyclopropopylmethyl-thiourea (1.3 g, 10 mmol) and sodium bicarbonate (840 mg, 10 mmol) in absolute ethanol (50 mL). Stir the mixture at reflux overnight under a nitrogen atmosphere. Cool to room temperature and pour into water (400 mL) and filter the resulting off-white solid. Wash the solid with hexane (10 mL) and dry in vacuo to obtain the desired intermediate as a white solid (2.4 g, 74%). MS (ES−) m/z: 321 (M−H)⁻.

4-(2-Cyclopropylmethylamino-5-methyl-thiazol-4-yl)-benzonitrile

Slurry 1-bromo-4-(2-cyclopropylmethylamino-5-methyl-thiazol-4-yl)-benzene (1.0 g, 3.09 mmol), 1,1'-bis-(diphenylphosphino)ferrocene (275 mg, 0.494 mmol), zinc cyanide (325 mg, 2.75 mmol) and tris(dibenzylideneacetone)dipalladium(0) (254 mg, 0.28 mmol) in DMF (6 mL) and heat in a sealed tube at 110° C. overnight. Cool the mixture to room temperature, dilute with dichloromethane (100 mL) and filter over Celite®. Concentrate in vacuo and purify the crude mixture by chromatography on silica gel (40 g) eluting with hexane/EtOAc (19:1 to 7:3 gradient over 30 min; 40 mL/min) to obtain the desired intermediate (416 mg, 52%) as a yellow solid. MS (ES+) m/z: 270 (M+H)⁺.

4-(2-Cyclopropylmethylamino-5-methyl-thiazol-4-yl)-benzylamine

Add a solution of 1M lithium aluminum hydride in THF (4.6 mL, 4.6 mmol) over 5 min to a solution of 4-(2-cyclopropylmethylamino-5-methyl-thiazol-4-yl)-benzonitrile (410 mg, 1.52 mmol) in anhydrous THF (10 mL). Heat to reflux for 30 min, cool to room temperature and quench by dropwise addition of water (5 mL), ether (50 mL), 3N NaOH (5 mL) and additional water (15 mL). Stir vigorously for 30 min and filter over a bed of Celite®. Wash the filtrate with water (2×100 mL) and brine (100 mL). Dry the organic phase over MgSO₄, filter and concentrate in vacuo to obtain the title compound as a yellow oil (340 mg, 82%) that was used without further purification. MS (ES+) m/z: 274 (M+H)⁺.

Preparation 91

4-[2-(2,2,2-Trifluoroethylamino)-thiazol-4-yl]-benzylamine

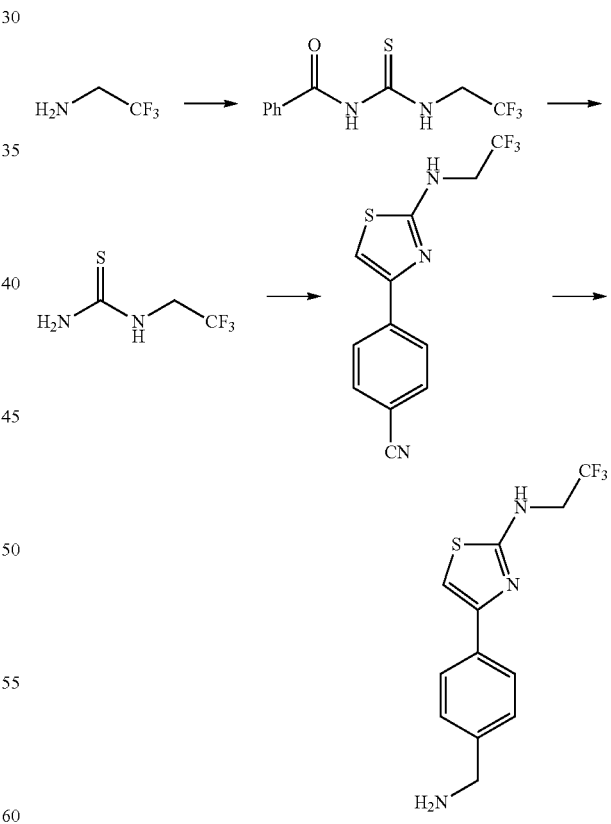

1-Benzoyl-3-(2,2,2-trifluoroethyl)-thiourea

Dissolve trifluoroethylamine (2.2 g, 22 mmol) in chloroform (20 mL) and add the solution to a mixture of benzoyl isothiocyanate (3.5 g, 22 mmol) in chloroform (20 mL) at room temperature. Stir the mixture in a sealed flask for 16 h at room temperature. Concentrate the mixture in vacuo to obtain the desired intermediate as a solid (5.5 g, 95%). MS (ES+) m/z: 263 (M+H)+.

2,2,2-Trifluoroethyl-thiourea

Slurry 1-benzoyl-3-(2,2,2-trifluoroethyl)-thiourea (5.5 g, 21.2 mmol) and potassium carbonate (11.7 g, 84.7 mmol) in methanol (180 mL) and water (40 mL). Stir the mixture at room temperature for 16 h. Concentrate the solution in vacuo to a paste. Triturate with hot water (20 mL, 60° C.), filter off the solids, wash with water (20 mL, 25° C.) and hexane (excess). Collect the solids, slurry in EtOAc and concentrate in vacuo twice to remove residual water. Dry the material in a vacuum oven at 45° C. for 16 h to obtain the desired intermediate as an off-white solid (2.2 g, 66%). MS (ES+) m/z: 159.1 (M+H)+.

4-[2-(2,2,2-Trifluoroethylamino)-thiazol-4-yl]-benzonitrile

Slurry 4-cyanophenacyl bromide (1.4 g, 6.3 mmol), 2,2,2-trifluoroethyl-thiourea (1.0 g, 6.3 mmol) and sodium bicarbonate (529 mg, 6.3 mmol) in absolute ethanol (30 mL). Stir the mixture at reflux for 1 h under a nitrogen atmosphere. Cool to room temperature and concentrate in vacuo. Partition the residue between DCM (100 mL) and water (20 mL). Dry the organic layer over Na2SO4 and concentrate in vacuo to obtain the desired intermediate (1.7 g, 95%). MS (ES+) m/z: 284 (M+H)+.

4-[2-(2,2,2-Trifluoroethylamino)-thiazol-4-yl]-benzylamine

Add lithium aluminum hydride (402 mg, 10.6 mmol) portionwise over 3 min to a solution of 4-[2-(2,2,2-trifluoroethylamino)-thiazol-4-yl]-benzonitrile (1.0 g, 3.5 mmol) in THF (40 mL) at room temperature under a nitrogen atmosphere. Stir the mixture for 1 h at 55° C. Cool the mixture to room temperature, quench slowly with water (0.4 mL) and 1N NaOH (0.4 mL). Add sodium sulfate to absorb residual water, filter through Celite®, wash with DCM (50 mL) and concentrate in vacuo. Purify the residue by SCX chromatography to obtain the desired intermediate (902 mg, 90%). MS (ES+) m/z: 288 (M+H)+.

Preparation 92

(R)-4-[2-(1-Methyl-2,2,2-trifluoroethylamino)-thiazol-4-yl]-benzyl amine

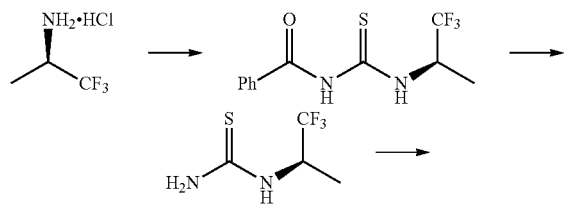

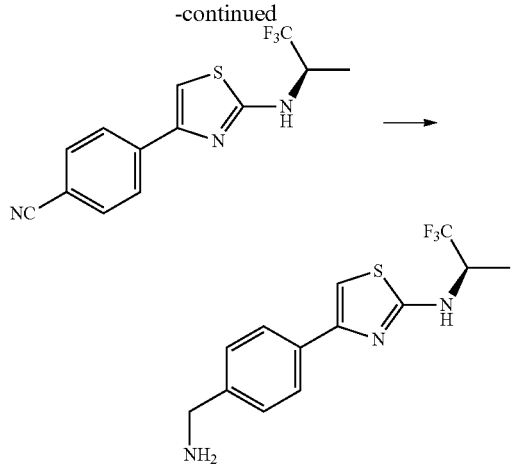

(R)-1-Benzoyl-3-(1-methyl-2,2,2-trifluoroethyl)-thiourea

Dissolve (R)-1-methyl-2,2,2-trifluoroethylamine hydrochloride (3.73 g, 25 mmol) in chloroform (50 mL) containing triethylamine (3.5 mL, 25 mmol). Cool to 0° C. in an ice bath and dropwise add benzoyl isothiocyanate (3.35 mL, 25 mmol) over 10 min. Warm the mixture to room temperature and stir overnight. Concentrate in vacuo and purify by chromatography on silica gel (200 g) eluting with hexane/EtOAc (19:1 to 4:1 over 40 min; 50 mL/min) to afford the desired intermediate as a light yellow oil (6.2 g, 90%).

(R)-(1-Methyl-2,2,2-trifluoroethyl)-thiourea

Dissolve (R)-1-benzoyl-3-(1-methyl-2,2,2-trifluoroethyl)-thiourea (6.2 g, 22.5 mmol) in methanol and add a solution of potassium carbonate (13.8 g, 100 mmol) in water (30 mL). Stir vigorously at room temperature overnight. Evaporate to dryness, dissolve residue in hot water (ca. 100 mL) and filter the resulting white crystals. Cool filtrate to 0° C., seed with crystals from hot water filtration, filter and collect resulting white crystals to obtain the desired intermediate (2.9 g, 74%). MS (ES+) m/z: 173 (M+H)+.

(R)-4-[2-(1-Methyl-2,2,2-trifluoroethylamino)-thiazol-4-yl]-benzonitrile

Dissolve 4-cyanophenacyl bromide (1.82 g, 8.14 mmol), (R)-(1-methyl-2,2,2-trifluoroethyl)-thiourea (1.4 g, 8.14 mmol) and sodium bicarbonate (0.68 g, 8.14 mmol) in absolute ethanol. Heat at reflux 2 h, cool to room temperature and let stand over 2 days. Filter and collect the resulting crude product as a tan solid. Purify by chromatography on silica gel (34 g) eluting with hexane/EtOAc (19:1 to 4:1 over 30 min, 4:1 over 10 min; 40 mL/min) to obtain the desired intermediate as a white solid (1.23 g, 52%). MS (ES+) m/z: 298 (M+H)+.

(R)-4-[2-(1-Methyl-2,2,2-trifluoroethylamino)-thiazol-4-yl]-benzylamine

Add a solution of 1M lithium aluminum hydride in THF (12 mL, 12 mmol) dropwise to an ice-cooled solution of (R)-4-[2-(1-methyl-2,2,2-trifluoroethylamino)-thiazol-4-yl]-benzonitrile in anhydrous THF (10 mL). Heat to reflux for 1 h, cool to room temperature, quench by slow addition of water (12 mL), ether (50 mL), 1N NaOH (12 mL) and additional water (36 mL). Add EtOAc (50 mL), stir vigorously for 20 min and filter over a bed of Celite®. Dry the organic phase over MgSO4, filter and concentrate in vacuo to obtain the title compound (765 mg, 64%). MS (ES+) m/z: 302 (M+H)+.

Preparation 93

The compound of Preparation 93 may be prepared essentially as described in Preparation 92 by using (S)-1-methyl-2,2,2-trifluoroethylamine hydrochloride. Overall yield and MS (ES+) data are shown in the Table below.

| | Structure | Compound | Yield | MS (ES+) m/z |
|---|---|---|---|---|
| 93 | 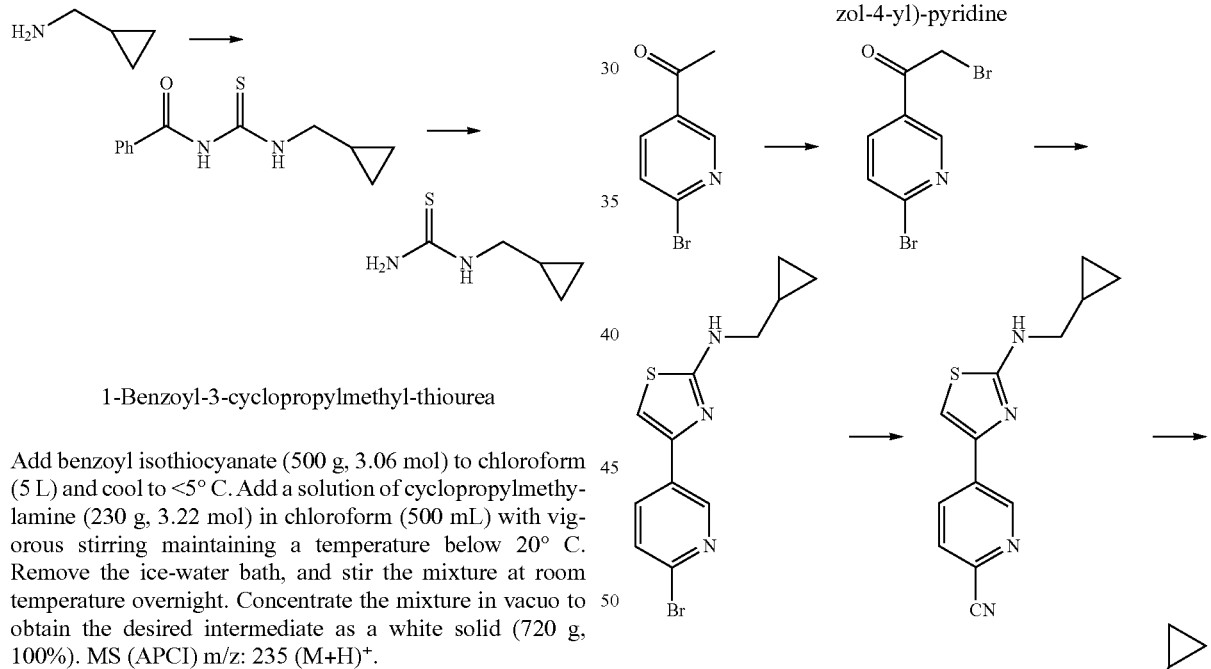 | (S)-4-[2-(1-Methyl-2,2,2-trifluoroethylamino)-thiazol-4-yl]-benzylamine | 51 | 302 (M + H)+ |

Preparation 94

Cyclopropylmethyl-thiourea

1-Benzoyl-3-cyclopropylmethyl-thiourea

Add benzoyl isothiocyanate (500 g, 3.06 mol) to chloroform (5 L) and cool to <5° C. Add a solution of cyclopropylmethylamine (230 g, 3.22 mol) in chloroform (500 mL) with vigorous stirring maintaining a temperature below 20° C. Remove the ice-water bath, and stir the mixture at room temperature overnight. Concentrate the mixture in vacuo to obtain the desired intermediate as a white solid (720 g, 100%). MS (APCI) m/z: 235 (M+H)+.

Cyclopropylmethyl-thiourea

Add 1-benzoyl-3-cyclopropylmethyl-thiourea (718 g, 3.06 mol) to methanol (6 L) and heat gently to dissolve. Add a solution of potassium carbonate (1.70 kg, 12.3 mol) in water (2 L) and stir overnight at room temperature. Filter any solids that form and concentrate the filtrate in vacuo until 10% of the volume. Dilute the residue with water (2 L) and EtOAc (~3.5 L) and extract the aqueous phase with EtOAc (4×2.5 L). Wash the combined organic extracts with aqueous 1N NaOH (2×1 L) and brine (2 L). Dry the organic layer over Na$_2$SO$_4$, filter, and concentrate in vacuo. Redissolve the residue in warm EtOAc (4 L), concentrate in vacuo until ~20% of the volume and filter the precipitate, rinsing with cold (~5° C.) EtOAc (~500 mL). Dry the solid under high vacuum to obtain the title compound as an off-white solid (220 g, 55%). Concentrate the filtrate in vacuo until ~10% of the volume and filter the precipitate, rinsing with cold EtOAc. Dry the solid under high vacuum to provide a second crop of cyclopropylmethyl-thiourea as an off-white solid (103 g, 26%). Total yield (323 g, 81%). MS (APCI) m/z: 131 (M+H)+.

Preparation 95

2-Aminomethyl-5-(2-cyclopropylmethylamino-thiazol-4-yl)-pyridine

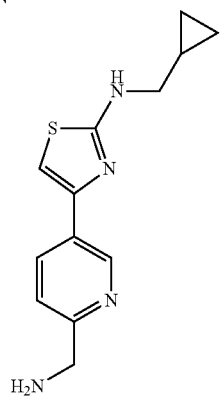

2-Bromo-5-(2-bromo-acetyl)-pyridine

Add pyridinium tribromide (7.0 g, 22 mmol) to a solution of 5-acetyl-2-bromo-pyridine (4.0 g, 20 mmol) in THF (100 mL) at room temperature. Stir the mixture for 16 h at room temperature under a nitrogen atmosphere. Quench the mixture with saturated aqueous NaHCO$_3$ (50 mL, pH to 7.8). Extract the mixture with EtOAc (150 mL). Wash the organic layer with brine (50 mL) and concentrate in vacuo to obtain the desired intermediate as a dark brown oil (11.5 g) that was used without further purification. MS (ES+) m/z: 280 (M+H)$^+$.

6-Bromo-3-(2-cyclopropylmethylamino-thiazol-4-yl)-pyridine

Slurry crude 2-bromo-5-(2-bromo-acetyl)-pyridine (11.5 g, ca. 48%), cyclopropylmethyl-thiourea (2.2 g, 16.9 mmol) and sodium bicarbonate (1.7 g, 20 mmol) in ethanol (100 mL) at room temperature. Stir the mixture at reflux for 1 h under a nitrogen atmosphere. Turn off heat and stir the mixture for 16 h at room temperature. Filter the slurry, then wash the solids with ethanol (50 mL), water (2×50 mL) and hexane (excess). Dry the solid in a vacuum oven for 20 h at 50° C. to obtain the desired intermediate as a tan solid (3.2 g, 61% over 2 steps). MS (ES+) m/z: 312 (M+2)$^+$.

5-(2-Cyclopropylmethylamino-thiazol-4-yl)-pyridine-2-carbonitrile

Slurry 6-bromo-3-(2-cyclopropylmethylamino-thiazol-4-yl)-pyridine (1.1 g, 3.6 mmol), 1,1'-bis-(diphenylphosphino) ferrocene (320 mg, 0.6 mmol), zinc cyanide (337 mg, 2.9 mmol) and tris(dibenzylideneacetone)dipalladium(0) (231 mg, 0.25 mmol) in wet DMF (6 mL). Stir the mixture in a sealed tube at 115° C. for 6 h. Cool the mixture to room temperature, dilute with EtOAc (50 mL) and wash with 5% aqueous sodium chloride (3×30 mL). Collect the organic layer and concentrate in vacuo. Purify the residue by chromatography on silica gel (40 g) eluting with hexane/(THF with 1% methanol) (4:1) to obtain the desired intermediate (350 mg, 38%). MS (ES+) m/z: 257.3 (M+H)$^+$.

2-Aminomethyl-5-(2-cyclopropylmethylamino-thiazol-4-yl)-pyridine

Add lithium aluminum hydride (75 mg, 2.0 mmol) portion-wise over 1 minute to a solution of 5-(2-cyclopropylmethylamino-thiazol-4-yl)-pyridine-2-carbonitrile (340 mg, 1.3 mmol) in THF (20 mL) at room temperature under a nitrogen atmosphere. Stir the mixture for 10 min at room temperature. Quench the mixture successively with water (0.1 mL) and 1N NaOH (0.1 mL). Add sodium sulfate to absorb residual water, filter through Celite®, wash with DCM (30 mL) and concentrate in vacuo. Purify the residue by chromatography on silica gel (12 g) eluting with DCM/2M ammonia in methanol (97:3) to obtain the title compound (180 mg, 52%). MS (ES+) m/z: 261.3 (M+H)$^+$.

Preparation 96

3-Aminomethyl-6-(2-cyclopropylmethylamino-thiazol-4-yl)-pyridine

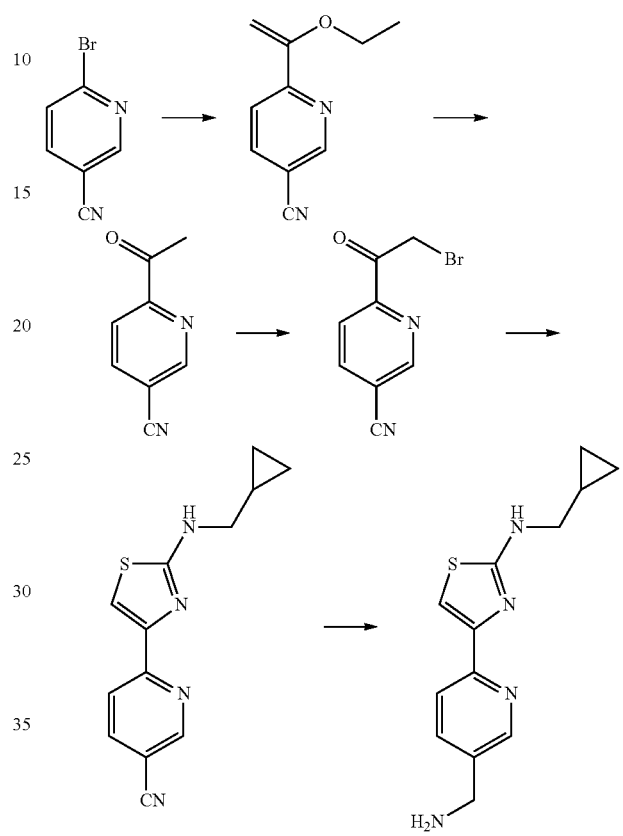

6-(1-Ethoxy-vinyl)-nicotinonitrile

Slurry 6-bromo-nicotinonitrile (8.0 g, 43.7 mmol), 1-ethoxyvinyl-tributylstannane (17.4 g, 48 mmol), and dichlorobis(triphenylphosphine)-palladium (1.5 g, 2.2 mmol) in acetonitrile (680 mL) at room temperature. Stir the mixture at reflux for 16 h under a nitrogen atmosphere. Cool the mixture to room temperature, add aqueous saturated potassium fluoride (100 mL), stir 30 min then filter and wash with EtOAc (200 mL). Wash the organic phase with water (250 mL). Dry the organic layer over Na$_2$SO$_4$, filter and concentrate in vacuo to obtain the desired intermediate (14.5 g) that was used without further purification. MS (ES+) m/z: 175 (M+H)$^+$.

6-Acetyl-nicotinonitrile

Dissolve crude 6-(1-ethoxy-vinyl)-nicotinonitrile (14.5 g, ca. 80%) in THF (120 mL) and 2.5 N hydrochloric acid (40 mL). Stir the solution for 16 h at room temperature. Quench the reaction with saturated aqueous NaHCO$_3$ (pH to 7.5). Extract the mixture with EtOAc (200 mL). Dry the organic layer over Na$_2$SO$_4$, filter and concentrate in vacuo. Purify the crude mixture by chromatography on silica gel (120 g) eluting with hexane/EtOAc (9:1 to 3:1 gradient) to obtain the desired intermediate (4.2 g, 65%).

6-(2-Bromo-acetyl)-nicotinonitrile

Add pyridinium tribromide (9.2 g, 28.7 mmol) to a solution of 6-acetyl-nicotinonitrile (4.2 g, 28.7 mmol) in THF (200 mL) at room temperature. Filter off the solids and wash with minimal THF. Recrystallize the solid from EtOAc/hexane to obtain the desired intermediate as a light orange solid (5.2 g, 80%) that was used without further purification. MS (ES–) m/z: 223 (M–H)⁻.

6-[2-(Cyclopropylmethylamino)-thiazol-4-yl]-nicotinonitrile

Slurry crude 6-(2-bromo-acetyl)-nicotinonitrile (5.2 g), cyclopropylmethyl-thiourea (2.7 g, 20.8 mmol) and sodium bicarbonate (1.95 g, 23.1 mmol) in ethanol (135 mL) at room temperature. Stir the mixture at reflux for 1 h under a nitrogen atmosphere. Cool the mixture to room temperature and concentrate in vacuo. Recrystallize from ethanol (20 mL) and water (100 mL) at 5° C. to obtain the desired intermediate as a tan solid (4.8 g, 81%). MS (ES+) m/z: 257 (M+H)⁺.

3-Aminomethyl-6-(2-cyclopropylmethylamino-thiazol-4-yl)-pyridine

Add 6-[2-(cyclopropylmethylamino)-thiazol-4-yl]-nicotinonitrile (2.0 g, 7.8 mmol), Raney Nickel (2.0 mL), and 2M ammonia in methanol (200 mL) to a pressure vessel under a nitrogen atmosphere. Pressurize the vessel to 60 psi with hydrogen, and stir the mixture for 6 h at 40° C. Filter the mixture through Celite® and concentrate in vacuo to an oil. Dissolve the oil in EtOAc (300 mL) and saturated ammonium hydroxide (50 mL). Stir the solution for 20 h in a sealed flask at room temperature. Collect the organic layer and concentrate in vacuo. Purify the crude mixture by SCX chromatography followed by chromatography on silica gel (150 g) eluting with DCM/2M ammonia in methanol (99:1 to 85:15 gradient) to obtain the title compound (1.05 g, 51%). MS (ES+) m/z: 261 (M+H)⁺.

Preparation 97

4-[(2-Cyclopropanecarbonyl-amino)-thiazol-4-yl]-benzylamine

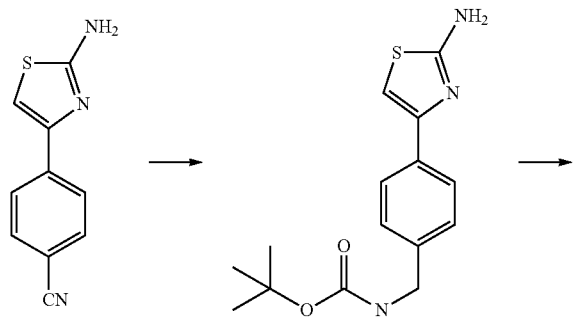

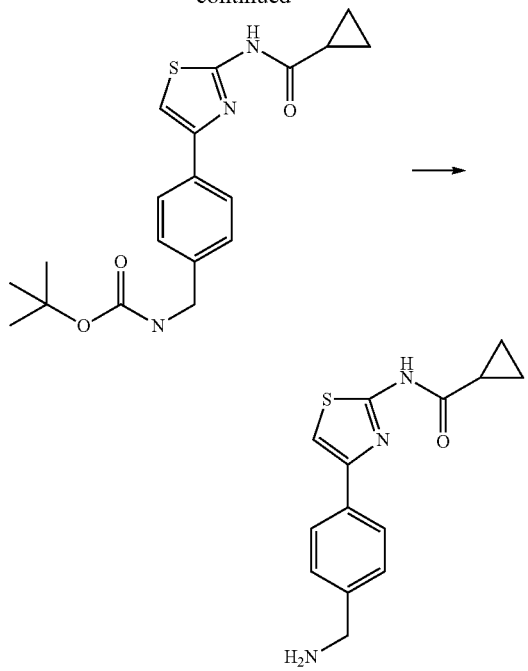

4-(2-Aminothiazol-4-yl)-N-(tert-butoxycarbonyl)-benzylamine

To a mechanically-stirred slurry of lithium aluminum hydride (2.64 g, 69.7 mmol) in anhydrous dioxane (150 mL) at room temperature, add a warmed slurry of 4-(2-amino-thiazol-4-yl)-benzonitrile (4 g, 19.9 mmol) in dioxane (200 mL) in portions. Heat the reaction mixture at 75° C. for 4 h and then cool the mixture to 0° C. Quench the reaction with water (2.6 mL) dropwise. Add 15% aqueous NaOH (2.6 mL) and water (8 mL). Stir the mixture for 2 h at room temperature and filter the slurry over Celite®. Wash the Celite® filter pad with dioxane (500 mL) and concentrate the filtrate. Dissolve the residue in dioxane (300 mL) and then add a solution of di-tert-butyl dicarbonate (5.2 g, 23.8 mmol) in dioxane (100 mL). Stir at room temperature for 24 h and concentrate the reaction mixture in vacuo. Dissolve the residue in EtOAc (500 mL) and wash the solution with saturated aqueous NaHCO₃ (250 mL). Dry the organic phase over Na₂SO₄, filter and concentrate in vacuo. Dissolve the residue in dichloromethane, add silica gel (12 g) and concentrate the mixture to a powder. Load the powder on to a dry column attached to an Analogix® column (330 g) and elute by preparative liquid chromatography (0:1 to 2:3 EtOAc/hexane over 33 min, 2:3 EtOAc/hexane over 33 min, 2:3 to 1:0 EtOAc/hexane over 33 min, 1:1 EtOAc/DCM over 99 min; 35 mL/min) to afford the desired intermediate (2.98 g, 49%) as a yellow solid. MS (ES+) m/z: 306.2 (M+H)⁺.

4-[(2-Cyclopropanecarbonyl-amino)-thiazol-4-yl]-N-(tert-butoxycarbonyl)-benzylamine To a mixture of 4-(2-aminothiazol-4-yl)-N-(tert-butoxycarbonyl)-benzylamine (2.98 g, 9.76 mmol) in DCM/dioxane (2:1, 150 mL) at room temperature, add triethylamine (2.0 mL, 15 mmol) and cyclopropanecarbonyl chloride (1.1 mL, 12 mmol). Stir at room temperature overnight and partition the reaction mixture between EtOAc (500 mL) and saturated aqueous NaHCO₃ (250 mL). Dry the organic extract over Na₂SO₄, filter and concentrate in vacuo. Combine the residue with DCM and silica gel (12 g) and concentrate to a powder. Load powder on to a dry column attached to an Analogix® column (330 g) and purify by preparative liquid chromatography (0:1 to 1:4 EtOAc/hexane over 33 min, 1:4 EtOAc/hexane over 33 min, 1:4 to 1:1 EtOAc/hexane over 33 min, 1:1 EtOAc/hexane over 66 min; 35 mL/min) to afford the desired intermediate (2.381 g, 65%) as a yellow solid. MS (ES+) m/z: 374.2 (M+H)⁺.

4-[(2-Cyclopropanecarbonyl-amino)-thiazol-4-yl]-benzylamine

To a solution of 4-[(2-cyclopropanecarbonyl-amino)-thiazol-4-yl]-N-(tert-butoxycarbonyl)-benzylamine (2.381 g, 6.376 mmol) in anhydrous DCM (53 mL), add trifluoroacetic acid (45 mL) at room temperature and stir overnight. Concentrate the reaction mixture in vacuo and elute the residue through a SCX column (20 g). Dissolve the residue in DCM, add silica gel (14 g) and concentrate to a powder. Load the powder on to a dry column attached to an Analogix® column (150 g) and purify by preparative liquid chromatography (0:1 to 1:4 2M ammonia in methanol/DCM over 33 min, 1:4 2M ammonia in methanol/DCM over 33 min; 35 mL/min) to afford the title compound (1.668 g, 96%) as an off-white solid. MS (ES+) m/z: 274.1 (M+H)⁺.

Preparation 98

4-[3-(Cyclopropylmethyl-amino)-pyrazol-1-yl]-benzylamine

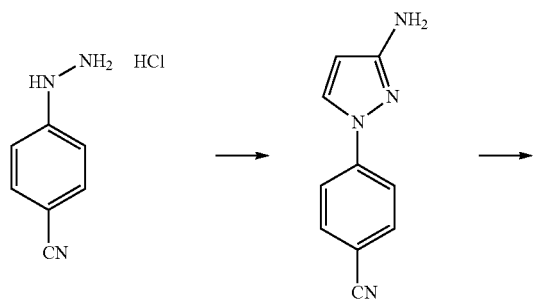

4-(3-Amino-pyrazol-1-yl)-benzonitrile

Suspend 4-cyanophenyl hydrazine hydrochloride (5 g, 29.58 mmol) in tert-butanol (60 mL). Add methoxyacrylonitrile (2.458 g, 29.58 mmol) and potassium tert-butoxide (3.975 g, 35.49 mmol) and heat the mixture at 90° C. overnight. Concentrate in vacuo and partition the residue between EtOAc/water. Extract the organic phase with 10% hydrochloric acid. Neutralize the aqueous phase with saturated aqueous NaHCO₃ and extract twice with EtOAc. Dry the combined organic extracts over MgSO₄, filter and concentrate in vacuo to obtain a solid that was washed with ether/hexane. Filter and dry the solid in vacuo to obtain the desired intermediate.

4-[3-(Cyclopropylmethyl-amino)-pyrazol-1-yl]-benzonitrile

Dissolve 4-(3-amino-pyrazol-1-yl)-benzonitrile (200 mg) in 1,2-dichloroethane (12 mL). Add acetic acid (0.36 mL) and cyclopropanecarboxaldehyde (0.08 mL, 1.06 mmol) and stir the mixture at room temperature under a nitrogen atmosphere for 40 min. Add sodium triacetoxyborohydride (674 mg, 3.18 mmol) and stir for 3 h at room temperature. Quench the reaction with water. Extract the mixture three timed with EtOAc. Dry the combined organic extracts over Na₂SO₄, filter and concentrate in vacuo to obtain the desired intermediate (136 mg, 54%) that was used without further purification.

4-[3-(Cyclopropylmethyl-amino)-pyrazol-1-yl]-benzylamine

Add a solution of 1M lithium aluminum hydride in THF (1.4 mL, 1.4 mmol) to a solution of 4-[3-(cyclopropylmethyl-amino)-pyrazol-1-yl]-benzonitrile (136 mg, 0.57 mmol) in THF (10 mL) at room temperature under a nitrogen atmosphere. Stir the mixture for 1 h at 60° C. Cool the mixture to room temperature and quench slowly with water, 1N NaOH and additional water. Dilute with EtOAc, stir vigorously for 20 min and filter through Celite®. Dry the organic phase over Na₂SO₄, filter and concentrate in vacuo. Purify the residue by SCX chromatography to obtain the desired intermediate that was used without further purification (130 mg, 94%). MS (ES+) m/z: 243 (M+H)⁺.

Preparation 99

4-(1-Cyclopropylmethyl-1H-pyrazol-3-yl)-benzylamine

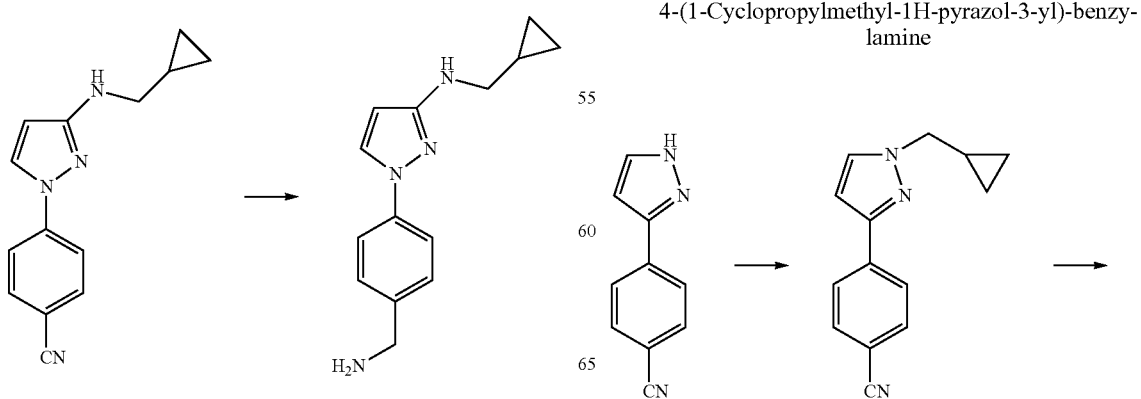

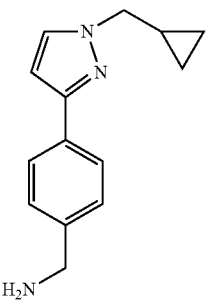

4-(1-Cyclopropylmethyl-1H-pyrazol-3-yl)-benzonitrile

Add sodium hydride (64 mg, 2.65 mmol) to a solution of 4-(1H-pyrazol-3-yl)-benzonitrile (300 mg, 1.77 mmol) in DMF (5 mL) under nitrogen atmosphere. Stir the mixture for 15 min at 0° C. and add (bromomethyl)cyclopropane (206 □l, 2.12 mmol). Stir the mixture for 5 min at 0° C. and then at room temperature overnight. Quenck the reaction mixture with water and extract twice with EtOAc. Dry the combined organics extracts over Na$_2$SO$_4$, filter and concentrate in vacuo. Purify the crude mixture by chromatography on silica gel eluting with hexane/EtOAc (75:25) to obtain the desired intermediate (256 mg, 65%).

4-(1-Cyclopropylmethyl-1H-pyrazol-3-yl)-benzylamine

Bubble nitrogen into a solution of 4-(1-cyclopropylmethyl-1H-pyrazol-3-yl)-benzonitrile (256 mg, 1.15 mmol) in methanol (48 mL) with 5 drops of concentrated hydrochloric acid for 10 min. Add 10% Pd/C (Degussa type, 48 mg) and submit the mixture to hydrogenation at atmospheric pressure overnight. Filter the mixture over Celite® and concentrate in vacuo. Add saturated aqueous NaHCO$_3$ and extract twice with AcOEt. Dry the combined organic extracts over MgSO$_4$, filter and concentrate in vacuo to give the title compound as a yellow oil (207 mg, 80%). MS (ES+) m/z: 228 (M+H)$^+$.

Preparation 100

4-[6-(Cyclopropylmethyl-amino)-pyrimidin-4-yl]-benzylamine

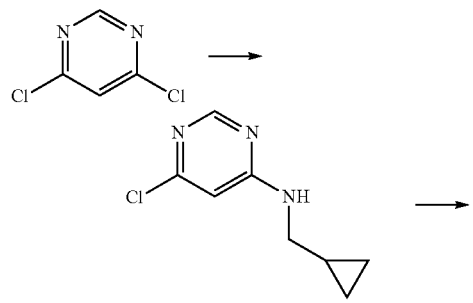

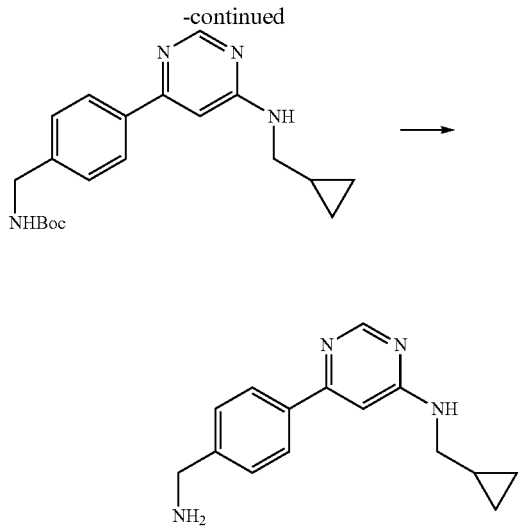

6-Chloro-4-(cyclopropylmethyl-amino)-pyrimidine

In a microwave reaction vessel, slurry 4,6-dichloropyrimidine (540 mg, 3.6 mmol), cyclopropylmethylamine (2800 L, 3.24 mmol), and diisopropylethylamine (1.25 mL, 7.2 mmol) in iso-propanol (3 mL). Irradiate in microwave (300 watts) at 140° C. for 40 min. Cool to room temperature and concentrate in vacuo. Purify by chromatography on silica gel (40 g) eluting with hexane/EtOAc (9:1 to 3:1 over 30 min; 40 mL/min) to obtain the desired intermediate (567 mg, 86%) as an off-white solid. MS (ES+) m/z: 184 (M+H)$^+$.

4-[6-(Cyclopropylmethyl-amino)-pyrimidin-4-yl]-N-(tert-butoxycarbonyl)-benzylamine In a microwave reaction vessel, slurry 6-chloro-4-(cyclopropylmethyl-amino)-pyrimidine (560 mg, 3 mmol), [4-(N-tert-butoxycarbonyl-aminomethyl)phenyl]boronic acid (1.1 g, 4 mmol), and tetrakis(triphenylphosphine)palladium(0) (190 mg, 0.15 mmol) in toluene (4 mL). Add ethanol (1 mL) followed by potassium carbonate (0.9 g, 6 mmol) dissolved in water (300 □L). Irradiate in microwave (300 watts) at 120° C. for 60 min. Cool to room temperature, pour reaction mixture into 1N NaOH (250 mL) and extract with DCM (3×100 mL). Wash the combined organic extracts with brine, dry over MgSO$_4$, filter and concentrate in vacuo. Purify by chromatography on silica gel (40 g) eluting with hexane/EtOAc (4:1 to 2:3 over 45 min; 40 mL/min) to obtain the desired intermediate (450 mg, 38%) as a yellow solid. MS (ES+) m/z: 355 (M+H)$^+$.

4-[6-(Cyclopropylmethyl-amino)-pyrimidin-4-yl]-benzylamine

Dissolve 4-[6-(cyclopropylmethyl-amino)-pyrimidin-4-yl]-N-(tert-butoxycarbonyl)-benzylamine (450 mg, 1.2 mmol) in DCM (5 mL). Add trifluoroacetic acid (3 mL) and stir under nitrogen for 3 h. Concentrate in vacuo and purify the crude mixture by SCX chromatography (5 g) to obtain the title compound (305 mg, 93%) suitable for use without additional purification. MS (ES+) m/z: 255 (M+H)⁺.

Preparation 101

4-[4-(Cyclopropylmethyl-amino)-pyrimidin-2-yl]-benzylamine

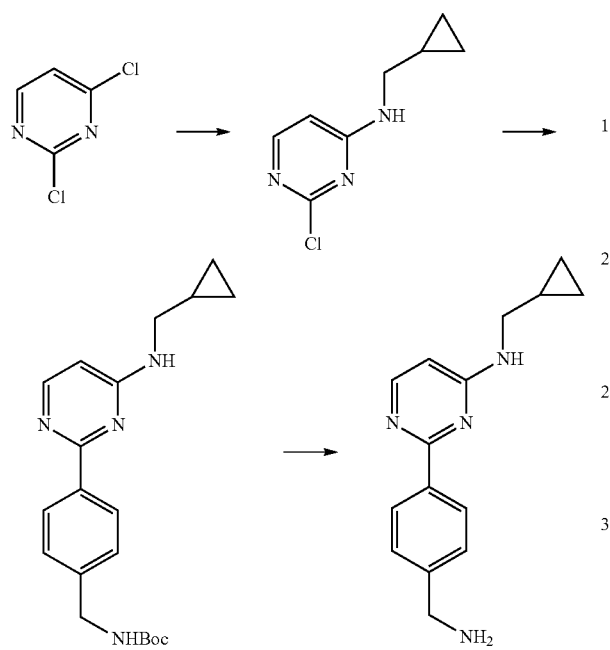

2-Chloro-4-(cyclopropylmethyl-amino)-pyrimidine

In a microwave reaction vessel, slurry 2,4-dichloropyrimidine (0.5 g, 3.36 mmol), cyclopropylmethylamine (275 µL, 3.18 mmol), and diisopropylethylamine (1.17 mL, 6.72 mmol) in iso-propanol (2 mL). Irradiate in microwave (300 watts) at 130° C. for 15 min. Cool to room temperature and concentrate in vacuo. Purify by chromatography on silica gel (40 g) eluting with hexane/EtOAc (4:1 to 1:3 over 45 min; 40 mL/min) to obtain the desired intermediate (374 mg, 65%) as a colorless oil.

4-[4-(Cyclopropylmethyl-amino)-pyrimidin-2-yl]-N-(tert-butoxycarbonyl)-benzylamine Slurry 2-chloro-4-(cyclopropylmethyl-amino)-pyrimidine (370 mg, 2 mmol), [4-(N-tert-butoxycarbonyl-aminomethyl)phenyl]boronic acid (710 mg, 2.83 mmol), and tetrakis(triphenylphosphine)palladium(0) (116 mg, 0.10 mmol) in toluene (3 mL). Add ethanol (0.5 mL) followed by potassium carbonate (550 mg, 4 mmol) dissolved in water (300 µL). Irradiate in microwave (300 watts) at 120° C. for 90 min. Cool to room temperature, pour reaction mixture into water (100 mL) containing 1N NaOH (25 mL) and extract with DCM (3×50 mL). Wash the combined organic extracts with brine, dry over MgSO4, filter and concentrate in vacuo. Purify by chromatography on silica gel (40 g) eluting with hexane/EtOAc (4:1 to 1:4 over 45 min; 40 mL/min) to obtain the desired intermediate (105 mg, 20%) as a yellow solid. MS (ES+) m/z: 355 (M+H)⁺. Additionally recovered unreacted 2-chloro-4-(cyclopropylmethyl-amino)-pyrimidine (100 mg).

4-[4-(Cyclopropylmethyl-amino)-pyrimidin-2-yl]-benzylamine

Dissolve 4-[4-(cyclopropylmethyl-amino)-pyrimidin-2-yl]-N-(tert-butoxycarbonyl)-benzylamine (100 mg, 0.28 mmol) in DCM (3 mL) containing trifluoroacetic acid (2 mL). Stir under nitrogen for 3 h. Concentrate in vacuo and purify the crude mixture by SCX chromatography (5 g) to obtain the title compound (68.5 mg, 90%) suitable for use without additional purification. MS (ES+) m/z: 255 (M+H)⁺.

Preparation 102

4-[2-(Cyclopropylmethyl-amino)-pyrimidin-4-yl]-benzylamine

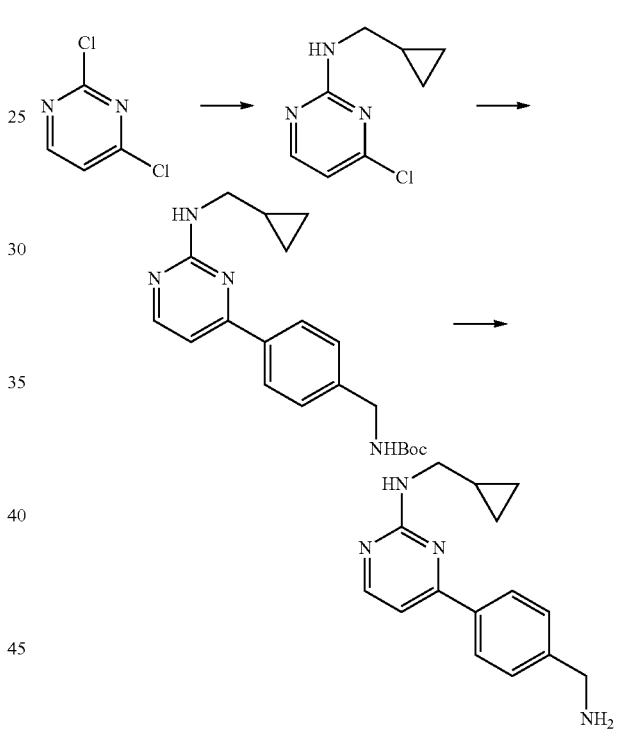

4-Chloro-2-(cyclopropylmethyl-amino)-pyrimidine

In a microwave reaction vessel, slurry 2,4-dichloropyrimidine (1.0 g, 6.7 mmol), cyclopropylmethylamine (550 µL, 6.0 mmol), and diisopropylethylamine (2.35 mL, 13.4 mmol) in toluene (3 mL). Irradiate in microwave (300 watts) at 120° C. for 30 min. Cool to room temperature and concentrate in vacuo. Purify by chromatography on silica gel (40 g) eluting with hexane/EtOAc (4:1 to 3:7 over 30 min; 40 mL/min) to obtain the desired intermediate (157.5 mg, 15%) as a colorless oil.

4-[2-(Cyclopropylmethyl-amino)-pyrimidin-4-yl]-N-(tert-butoxycarbonyl)-benzylamine Slurry 4-chloro-2-(cyclopropylmethyl-amino)-pyrimidine (155 mg, 0.62 mmol), [4-(N-tert-butoxycarbonyl-aminomethyl)phenyl]boronic acid (160 mg, 0.86 mmol), and tetrakis(triphenylphosphine)palladium(0) (36 mg, 0.031 mmol) in toluene (3 mL). Add ethanol (0.5 mL) followed by potassium carbonate (175 mg, 1.24 mmol) dissolved in water (300 µL). Irradiate in microwave (300 watts) at 120° C. for 60 min. Cool to room temperature, pour reaction mixture into water (100 mL) containing 1N NaOH (25 mL) and extract with DCM (3×50 mL). Wash the combined organic extracts with brine, dry over MgSO4, filter and concentrate in vacuo. Purify by chromatography on silica gel (12 g) eluting with hexane/EtOAc (4:1 to 3:7 over 30 min; 30 mL/min) to obtain the desired intermediate (200 mg, 90%) as a light yellow solid. MS (ES+) m/z: 355 (M+H)+.

4-[2-(cyclopropylmethyl-amino)-pyrimidin-4-yl]-benzylamine

Dissolve 4-[2-(cyclopropylmethyl-amino)-pyrimidin-4-yl]-N-(tert-butoxycarbonyl)-benzylamine (195 mg, 0.55 mmol) in DCM (3 mL) and add trifluoroacetic acid (1.5 mL). Stir at room temperature for 3 h. Concentrate in vacuo and purify the crude mixture by SCX chromatography (5 g) to obtain the title compound (140 mg, 93%) suitable for use without additional purification. MS (ES+) m/z: 255 (M+H)+.

Preparation 103

4-[5-(3,3-Dimethylbutyryltiophen-2-yl]-benzylamine

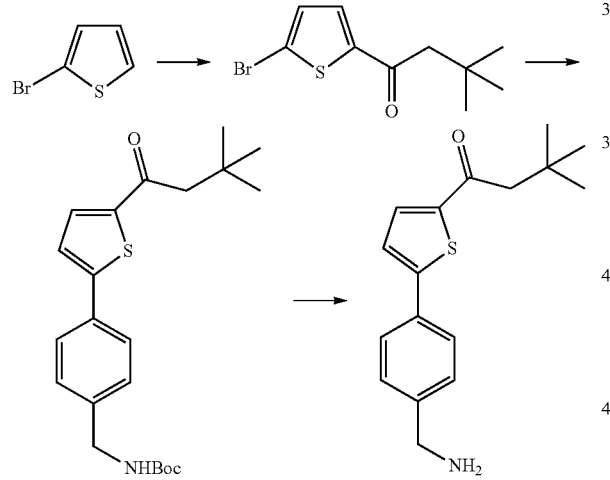

2-Bromo-5-(3,3-dimethylbutyryl)-thiophene

Stir overnight at room temperature a mixture of 5-bromothiophene (1 g, 6.1 mmol), 3,3-dimethylbutyryl chloride (1.3 mL, 9.1 mmol) and ytterbium(III) trifluoromethanesulfonate (378 mg, 0.6 mmol) in nitromethane (15 mL). Wash the mixture sequentially with water, saturated aqueous NaHCO3 and water. Extract with chloroform, dry over MgSO4, filter and concentrate in vacuo. Purify the crude mixture by chromatography on silica gel eluting with hexane to obtain the desired intermediate (1.3 g, 80%).

N-(tert-Butoxycarbonyl)-4-[5-(3,3-dimethylbutyryl)tiophen-2-yl]-benzylamine

To a solution of 2-bromo-5-(3,3-dimethylbutyryl)-thiophene (187 mg, 0.7 mmol) in dioxane (7 mL) add a solution of aqueous 2M Na2CO3 (0.9 mL), [4-(N-tert-butoxycarbonyl-aminomethyl)phenyl]boronic acid (216 mg, 0.8 mmol) and tetrakis(triphenylphosphine)-palladium(0) (41 mg, 0.03 mmol). Heat the mixture at 90° C. overnight. Cool at room temperature, add water and extract with EtOAc. Dry the organic phase over MgSO4, filter and concentrate in vacuo. Purify the crude mixture by chromatography on silica gel eluting with hexane/EtOAc (4:1) to obtain the desired intermediate (174 mg, 63%).

4-[5-(3,3-Dimethylbutyryl)tiophen-2-yl]-benzylamine

To a solution of N-(tert-butoxycarbonyl)-4-[5-(3,3-dimethyl-butyryptiophen-2-yl]-benzylamine (174 mg, 0.4 mmol) in anhydrous dichloromethane (0.3 mL) add a solution of 4M hydrogen chloride in dioxane (1.7 mL, 6.7 mmol) and stir for 2 h at room temperature. Concentrate in vacuo and purify the crude mixture by SCX chromatography to obtain the title compound (128 mg, 99%). MS (ES+) m/z: 288 (M+H)+.

Preparation 104

3-Aminomethyl-6-[(2,2-dimethylpropane)sulfonyl]-pyridine

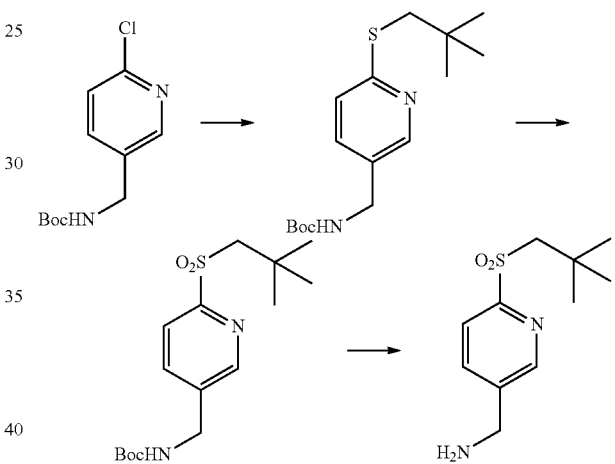

N-(tert-Butoxycarbonyl)-3-aminomethyl-6-[(2,2-dimethylpropane)thio]-pyridine

Add sodium hydride (590 mg, 15.5 mmol, 60% in mineral oil) to DMF (50 mL) and cool to 0° C. Add 2,2-dimethyl-propane-1-thiol (966 mg, 9.27 mmol) and stir the mixture for 1 h at 0° C. Add 3-(tert-butoxycarbonylamino-methyl)-6-chloropyridine (1.5 g, 6.18 mmol) to the mixture and heat to 70° C. overnight. Cool the mixture to room temperature and carefully dilute with water (50 mL). Extract the mixture with EtOAc (5×25 mL). Wash the combined organic extracts with water (3×20 mL) and brine (50 mL). Dry the organic layer over Na2SO4, filter, and concentrate in vacuo. Purify the residue by chromatography on silica gel (120 g) eluting with hexane:EtOAc (1:0 to 1:1 over 1 h, 80 mL/min) to provide the desired intermediate as a light yellow oil (915 mg, 48%). MS (APCI) m/z: 211 (M-C5H8O2+H)+.

N-(tert-Butoxycarbonyl)-3-aminomethyl-6-[(2,2-dimethylpropane)sulfonyl]-pyridine Add 3-chloroperbenzoic acid (1.83 g, ~70%, 7.44 mmol) to DCM (25 mL) and cool to 0° C. Slowly add a solution of N-(tert-butoxycarbonyl)-3-aminomethyl-6-[(2,2-dimethyl-propane)thio]-pyridine (924 mg, 2.98 mmol) in DCM (10 mL) maintaining the temperature below 10° C. Allow the mixture to warm to room temperature and stir for 3 h. Wash the mixture with aqueous 3N NaOH (3×25 mL), water (25 mL), and brine (25 mL). Dry the organic layer over $Na_2SO_4$, filter, and concentrate in vacuo. Purify the crude mixture by chromatography on silica gel (120 g), eluting with DCM/ (chloroform:methanol:concentrated $NH_4OH$) (1:1 over 1.5 h, 80 mL/min) to provide the desired intermediate as a light yellow oil (961 mg, 94%). MS (APCI) m/z: 243 (M-$O_5H_8O_2$+H)$^+$.

3-Aminomethyl-6-[(2,2-dimethylpropane)sulfonyl]-pyridine

Add N-(tert-butoxycarbonyl)-3-aminomethyl-6-[(2,2-dimethylpropane)sulfonyl]-pyridine (1.13 g, 3.21 mmol) to methanol (25 mL) and cool to 0° C. Bubble anhydrous hydrogen chloride gas into the mixture until saturated and stir for 1 h. Concentrate the mixture in vacuo. Purify the residue by chromatography on silica gel (45 g), eluting with DCM/ (chloroform:methanol:concentrated $NH_4OH$) (1:3 over 30 min; 80 mL/min) to provide the desired intermediate as a light yellow oil (344 mg, 42%). MS (APCI) m/z: 243 (M+H)$^+$.

Preparation 105

4-[2-(2,2,2-Trifluoroethylthio)-1,1-(ethylenedioxy)ethyl]-benzylamine

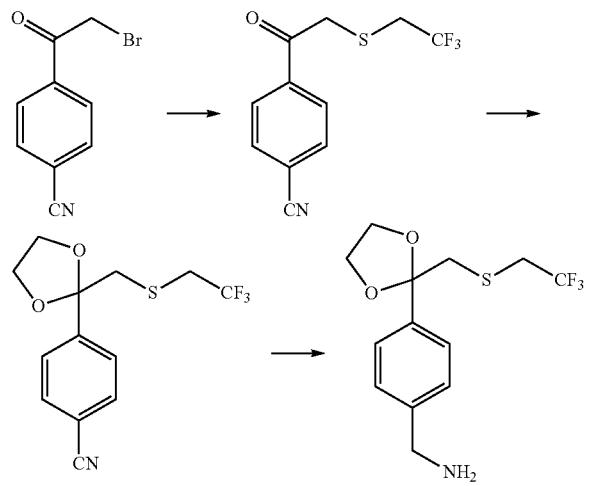

4-(2,2,2-Trifluoroethylthiomethylcarbonyl)-benzonitrile

To a solution of 2,2,2-trifluoroethanethiol (1.5 mL, 17.2 mmol) in anhydrous THF (28 mL) at 0° C. under nitrogen, add sodium hydride (629 mg, 15.7 mmol) and stir for 15 min. Then, add 4-cyanophenacyl bromide (3.2 g, 14.3 mmol) and stir at ambient temperature overnight. Quench with water and extract with EtOAc. Dry the combined organics extracts over $MgSO_4$, filter and concentrate in vacuo. Purify the crude mixture by chromatography on silica gel eluting with hexane/ EtOAc (7:3) to obtain the desired intermediate (3.1 mg, 84%).

4-[1-(2,2,2-Trifluoroethylthio)-1,1-(ethylenedioxy)ethyl]-benzonitrile

To a solution of 4-(2,2,2-trifluoroethylthiomethylcarbonyl)-benzonitrile (770 mg, 2.9 mmol) in anhydrous toluene (15 mL), add ethyleneglycol (0.33 mL, 5.9 mmol) and p-toluenesulfonic acid (564 mg, 2.9 mmol) and reflux with a Dean-Stark apparatus overnight. Cool to room temperature, wash with saturated aqueous $NaHCO_3$ and brine. Dry the combined organic extracts over $MgSO_4$, filter and concentrate in vacuo. Purify the crude mixture by chromatography on silica gel eluting with hexane/EtOAc (4:1), to obtain the desired intermediate (459 mg, 51%).

4-[2-(2,2,2-Trifluoroethylthio)-1,1-(ethylenedioxy)ethyl]-benzylamine

To a solution of 4-[2-(2,2,2-trifluoroethylthio)-1,1-(ethylenedioxy)ethyl]-benzonitrile (248 mg, 0.8 mmol) in anhydrous THF (8 mL) under nitrogen, add borane-tetrahydrofurane complex (9.8 mL, 9.8 mmol) and heat at 60° C. for 3 h. Cool to room temperature and quench with methanol dropwise. Concentrate in vacuo and purify by SCX chromatography to obtain the title compound (250 mg, 99%). MS (ES+) m/z: 308 (M+H)$^+$.

EXAMPLE 1

7-Chloro-6-[4-(1-methoxyimino-ethyl)-benzylamino]-2,3,4,5-tetrahydro-1H-benzo[d]azepine Succinate

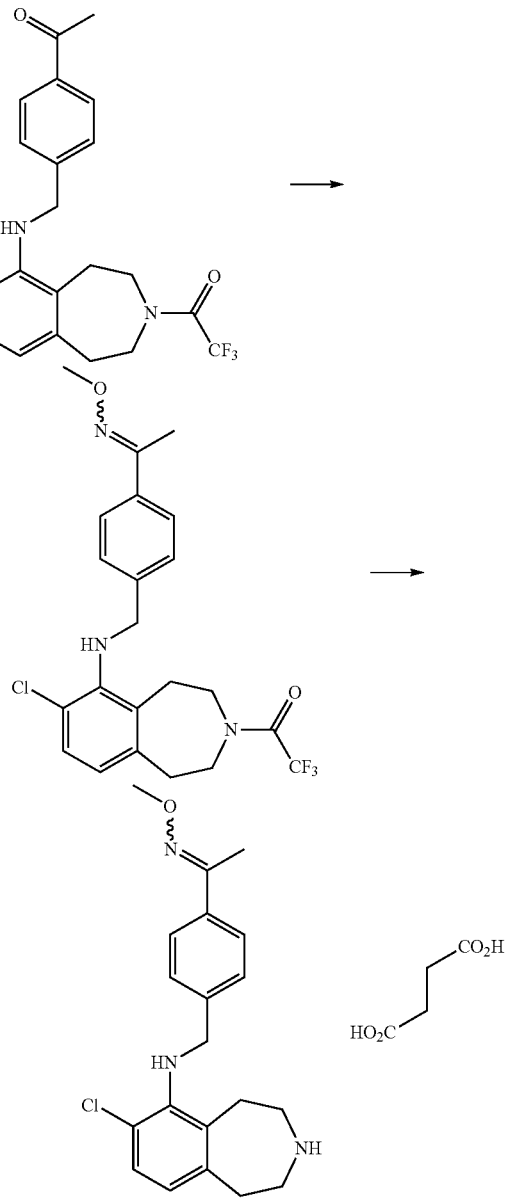

Add O-methylhydroxylamine hydrochloride (10 mg, 0.12 mmol) and pyridine (0.02 mL, 0.24 mmol) to a solution of 6-(4-acetyl-benzylamino)-7-chloro-3-(2,2,2-trifluoro-acetyl)-2,3,4,5-tetrahydro-1H-benzo[d]azepine (50 mg, 0.12 mmol) in ethanol (10 mL). Heat the mixture to reflux for 1.5 h. Remove the solvent in vacuo and partition the residue between DCM and 0.1N aqueous HCl. Dry the organic phase over $Na_2SO_4$, filter and concentrate in vacuo. Purify by chromatography on silica gel eluting with hexane/EtOAc (95:5 to 1:1 gradient over 30 min). Concentrate in vacuo to obtain 7-chloro-6-[4-(1-methoxyimino-ethyl)-benzylamino]-3-(2,2,2-trifluoroacetyl)-2,3,4,5-tetrahydro-1H-benzo[d]azepine as a colorless oil (45 mg, 83%). MS (ES+) m/z: 454 (M+H)$^+$.

Use a method similar to the General Procedure 2-1, using 7-chloro-6-[4-(1-methoxyimino-ethyl)-benzylamino]-3-(2,2,2-trifluoroacetyl)-2,3,4,5-tetrahydro-1H-benzo[d]azepine (45 mg, 0.099 mmol), to obtain 7-chloro-6-[4-(1-methoxyiminoethyl)-benzylamino]-2,3,4,5-tetrahydro-1H-benzo[d]azepine as a colorless oil (30 mg, 85%) suitable for use without additional purification.

Use a method similar to the General Procedure 3-1, using 7-chloro-6-[4-(1-methoxyiminoethyl)-benzylamino]-2,3,4,5-tetrahydro-1H-benzo[d]azepine (30 mg, 0.084 mmol) to obtain the title compound, a mixture of E- and Z-isomers, as a white solid (35.7 mg, 89%). MS (ES+) m/z: 358 (M+H)$^+$.

EXAMPLES 2-3

Examples 2-3 may be prepared essentially as described in Example 1 by using 6-(4-acetyl-benzylamino)-7-chloro-3-(2,2,2-trifluoroacetyl)-2,3,4,5-tetrahydro-1H-benzo[d]azepine and the appropriate O-alkylhydroxylamine hydrochloride. Overall yields and MS (ES+) data are shown in the Table below.

| Ex. | R | Compound | Yield (%) | MS (ES+) m/z |
|---|---|---|---|---|
| 2 | Ethyl | 7-Chloro-6-[4-(1-ethoxyimino-ethyl)-benzylamino]-2,3,4,5-tetrahydro-1H-benzo[d]azepine Succinate | 55 | 372 (M + H)$^+$ |
| 3 | iso-Butyl | 7-Chloro-6-[4-(1-iso-butoxyimino-ethyl)-benzylamino]-2,3,4,5-tetrahydro-1H-benzo[d]azepine Succinate | 45 | 400 (M + H)$^+$ |

EXAMPLE 4

7-Chloro-6-[4-(1-hydroxyimino-3-methyl-butyl)-benzylamino]-2,3,4,5-tetrahydro-1H-benzo[d]azepine Succinate

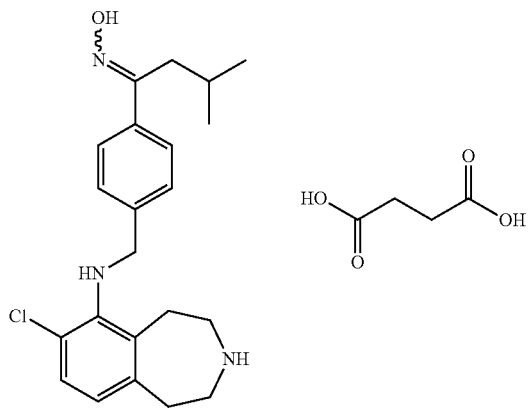 [SMILES: CC(C)CC(=NO)c1ccc(CNc2c(Cl)ccc3c2CCNCC3)cc1 ; O=C(O)CCC(=O)O]

Add hydroxylamine hydrochloride (6.3 mg, 0.091 mmol) and pyridine (15 uL, 0.182 mmol) to a solution of 7-chloro-6-[4-(3-methyl-butyryl)-benzylamino]-3-(2,2,2-trifluoroacetyl)-2,3,4,5-tetrahydro-1H-benzo[d]azepine (42 mg, 0.091 mmol) in ethanol (1 mL). Heat the mixture to reflux for 18 h. Remove the solvent in vacuo and partition the residue between DCM and 0.1N aqueous HCl. Dry the organic phase over $Na_2SO_4$, filter and concentrate in vacuo. Purify by chromatography on silica gel eluting with hexane/EtOAc (95:5 to 1:1 gradient over 30 min). Concentrate in vacuo to obtain 7-chloro-6-[4-(1-hydroxyimino-3-methyl-butyl)-benzylamino]-3-(2,2,2-trifluoroacetyl)-2,3,4,5-tetrahydro-1H-benzo[d]azepine as an off-white solid (19.1 mg, 44%). MS (ES+) m/z: 482 (M+H)$^+$.

Use a method similar to the General Procedure 2-1, using 7-chloro-6-[4-(1-hydroxyimino-3-methyl-butyl)-benzylamino]-3-(2,2,2-trifluoroacetyl)-2,3,4,5-tetrahydro-1H-benzo[d]azepine (45 mg, 0.099 mmol), to obtain 7-chloro-6-[4-(1-hydroxyimino-3-methyl-butyl)-benzylamino]-2,3,4,5-tetrahydro-1H-benzo[d]azepine as a colorless oil (14.5 mg, 42%).

Use a method similar to the General Procedure 3-1, using 7-chloro-6-[4-(1-hydroxyimino-3-methyl-butyl)-benzylamino]-2,3,4,5-tetrahydro-1H-benzo[d]azepine (14.5 mg, 0.084 mmol) to obtain the title compound, a mixture of E- and Z-isomers, as an off-white solid (15 mg, 90%). MS (ES+) m/z: 386 (M+H)$^+$.

EXAMPLE 5

Example 5 may be prepared essentially as described in Example 4 using 7-chloro-6-[4-(3-methyl-butyryl)-benzylamino]-3-(2,2,2-trifluoroacetyl)-2,3,4,5-tetrahydro-1H-benzo[d]azepine and O-methylhydroxylamine hydrochloride. Example 5 was obtained as a mixture of E- and Z-isomers.

| Ex. | Structure | Compound | Yield (%) | MS (ES+) m/z |
|---|---|---|---|---|
| 5 | 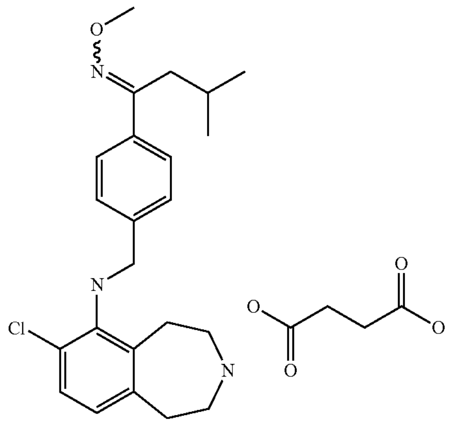 | 7-Chloro-6-[4-(1-methoxyimino-3-methyl-butyl)-benzylamino]-2,3,4,5-tetrahydro-1H-benzo[d]azepine Succinate | 44 | 400 (M + H)+ |

EXAMPLE 6

7-Chloro-6-[4-(2-methylamino-thiazol-4-yl)-benzylamino]-2,3,4,5-tetrahydro-1H-benzo[d]azepine Succinate

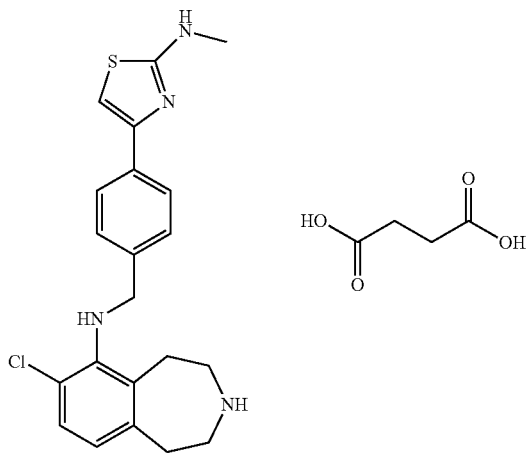 [SMILES: CNc1nc(-c2ccc(CNc3c(Cl)ccc4c3CCNCC4)cc2)cs1 ; O=C(O)CCC(=O)O]

Use a method similar to the General Procedure 1-3, using 7-chloro-3-(2,2,2-trifluoroacetyl)-6-trifluoromethanesulfonyloxy-2,3,4,5-tetrahydro-1H-benzo[d]azepine (0.48 g, 1.14 mmol) and 4-(2-methylamino-thiazol-4-yl)-benzylamine (0.4 g, 1.8 mmol), to obtain 7-chloro-6-[4-(2-methylamino-thiazol-4-yl)-benzylamino]-3-(2,2,2-trifluoroacetyl)-2,3,4,5-tetrahydro-1H-benzo[d]azepine as an off-white solid (0.12 g, 21%). MS (ES+) m/z: 495 (M+H)+.

Use a method similar to the General Procedure 2-1 to deprotect 7-chloro-6-[4-(2-methylamino-thiazol-4-yl)-benzylamino]-3-(2,2,2-trifluoroacetyl)-2,3,4,5-tetrahydro-1H-benzo[d]azepine (112 mg, 0.227 mmol) to obtain 7-chloro-6-[4-(2-methylamino-thiazol-4-yl)-benzylamino]-2,3,4,5-tetrahydro-1H-benzo[d]azepine as an off-white foam (70 mg, 78%).

Use a method similar to the General Procedure 3-1, using 7-chloro-6-[4-(2-methylamino-thiazol-4-yl)-benzylamino]-2,3,4,5-tetrahydro-1H-benzo[d]azepine (69 mg, 0.17 mmol) to obtain the title compound as an off-white foam (76.6 mg, 85%). MS (ES+) m/z: 399 (M+H)+.

EXAMPLES 7-12

Examples 7-12 may be prepared essentially as described in Example 6 using 7-chloro-3-(2,2,2-trifluoroacetyl)-6-trifluoromethanesulfonyloxy-2,3,4,5-tetrahydro-1H-benzo[d]azepine and the appropriately substituted benzylamine. For Examples 11-12, deprotection to obtain the free base was performed using a method similar to the General Procedure 2-2. Overall yields and MS (ES+) data are shown in the Table below.

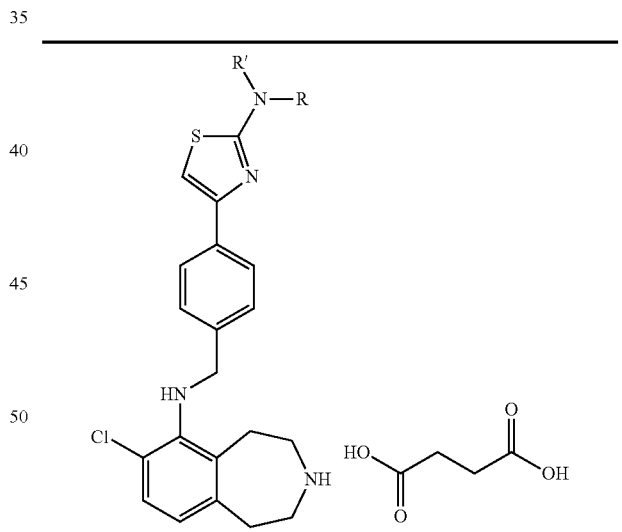

| Ex. | R, R' | Compound | Yield (%) | MS (ES+) m/z |
|---|---|---|---|---|
| 7 | Ethyl, H | 7-Chloro-6-[4-(2-ethylamino-thiazol-4-yl)-benzylamino]-2,3,4,5-tetrahydro-1H-benzo[d]azepine Succinate | 16 | 413 (M + H)+ |
| 8 | iso-Propyl, H | 7-Chloro-6-[4-(2-iso-propylamino-thiazol-4-yl)-benzylamino]-2,3,4,5-tetrahydro-1H-benzo[d]azepine Succinate | 48 | 427 (M + H)+ |

-continued

| | | | | |
|---|---|---|---|---|
| 9 | n-Propyl, H | 7-Chloro-6-[4-(2-n-propylamino-thiazol-4-yl)-benzylamino]-2,3,4,5-tetrahydro-1H-benzo[d]azepine Succinate | 64 | 427 (M + H)⁺ |
| 10 | —(CH₂)₅— | 7-Chloro-6-[4-(2-piperidin-1-yl-thiazol-4-yl)-benzylamino]-2,3,4,5-tetrahydro-1H-benzo[d]azepine Succinate | 77 | 453 (M + H)⁺ |
| 11 | Cyclopropyl-methyl, H | 7-Chloro-6-[4-(2-cyclopropylmethylamino-thiazol-4-yl)-benzylamino]-2,3,4,5-tetrahydro-1H-benzo[d]azepine Succinate | 82 | 439 (M + H)⁺ |
| 12 | iso-Butyl, H | 7-Chloro-6-[4-(2-iso-butylamino-thiazol-4-yl)-benzylamino]-2,3,4,5-tetrahydro-1H-benzo[d]azepine Succinate | 36 | 441 (M + H)⁺ |

EXAMPLE 13

7-Chloro-6-[4-(2-methylamino-oxazol-4-yl)-benzylamino]-2,3,4,5-tetrahydro-1H-benzo[d]azepine (L)-Tartrate

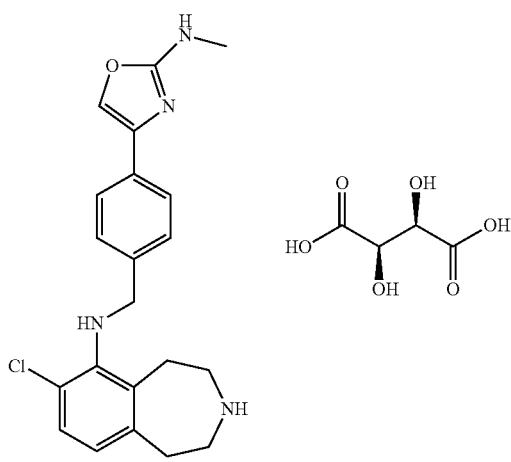 [SMILES: CNc1nc(-c2ccc(CNc3c(Cl)ccc4c3CCNCC4)cc2)co1 ; O=C(O)[C@H](O)[C@@H](O)C(=O)O]

Slurry 4-(2-methylamino-oxazol-4-yl)-benzylamine hydrochloride (485 mg, 1.8 mmol) in toluene (10 mL) and DMF (1 mL) at 90° C. under a nitrogen atmosphere. Degass and place under vacuum then purge with nitrogen three times. Add 7-chloro-3-(2,2,2-trifluoroacetyl)-6-trifluoromethanesulfonyloxy-2,3,4,5-tetrahydro-1H-benzo[d]azepine (0:5 g, 1.17 mmol), tris(dibenzylideneacetone)dipalladium(0) (161 mg, 0.18 mmol), BINAP (219 mg, 0.35 mmol) and cesium carbonate (1.6 g, 4.9 mmol) to the slurry at 90° C. Stir the mixture at 95° C. for 16 h in a sealed flask. Cool the reaction to room temperature, dilute with EtOAc (100 mL), filter through Celite®, and concentrate in vacuo to an oil. Purify by chromatography on silica gel (10 g, pre-packed cartridge) eluting with hexane/THF (40:1 to 4:1 gradient) followed by SCX chromatography (10 g) eluting with DCM and DCM/2M ammonia in methanol (1:1, 50 mL) to obtain 7-chloro-6-[4-(2-methylamino-oxazol-4-yl)-benzylamino]-3-(2,2,2-trifluoroacetyl)-2,3,4,5-tetrahydro-1H-benzo[d]azepine (110 mg, 20%). MS (ES+) m/z: 479.2 (M+H)⁺.

Use a method similar to the General Procedure 2-2 to deprotect 7-chloro-6-[4-(2-methylamino-oxazol-4-yl)-benzylamino]-3-(2,2,2-trifluoroacetyl)-2,3,4,5-tetrahydro-1H-benzo[d]azepine. Purify by chromatography on silica gel eluting with DCM/2M ammonia in methanol (1:0 to 30:1 gradient) to obtain 7-chloro-6-[4-(2-methylamino-oxazol-4-yl)-benzylamino]-2,3,4,5-tetrahydro-1H-benzo[d]azepine. Dissolve 7-chloro-6-[4-(2-methylamino-oxazol-4-yl)-benzylamino]-2,3,4,5-tetrahydro-1H-benzo[d]azepine (27 mg, 0.07 mmol) and (L)-tartaric acid (11 mg) in methanol. Concentrate in vacuo to an oil. Triturate oil with diethyl ether and remove solvent in vacuo to obtain the title compound as a solid (30 mg, 24%). MS (ES+) m/z: 383.1 (M+H)⁺.

EXAMPLE 14

7-Chloro-6-[4-(cyclopentylthiomethyl)-benzylamino]-2,3,4,5-tetrahydro-1H-benzo[d]azepine (L)-Tartrate

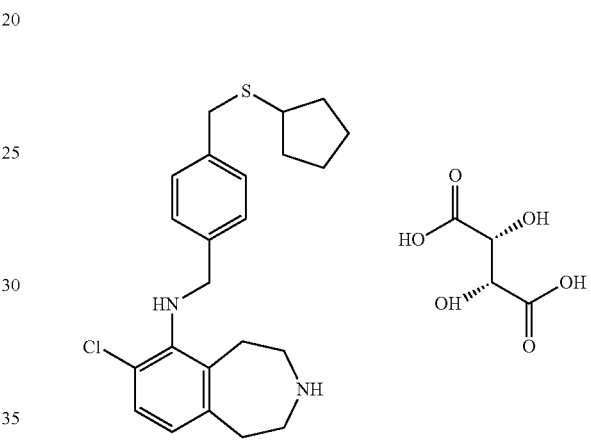

Use a method similar to the General Procedure 1-2 to couple 7-chloro-3-(2,2,2-trifluoroacetyl)-6-trifluoromethanesulfonyloxy-2,3,4,5-tetrahydro-1H-benzo[d]azepine (0.4 g, 0.94 mmol) with 4-(cyclopentylthiomethyl)-benzylamine (229 mg, 1.03 mmol) in toluene (10 mL). Purify the crude mixture by chromatography on silica gel eluting with isohexane/EtOAc (1:0 to 4:1 gradient) to obtain 7-chloro-6-[4-(cyclopentylthiomethyl)-benzylamino]-3-(2,2,2-trifluoroacetyl)-2,3,4,5-tetrahydro-1H-benzo[d]azepine (190 mg, 41%). MS (ES+) m/z: 498 (M+H)⁺.

Use a method similar to the General Procedure 2-1 to deprotect 7-chloro-6-[4-(cyclopentylthiomethyl)-benzylamino]-3-(2,2,2-trifluoroacetyl)-2,3,4,5-tetrahydro-1H-benzo[d]azepine (190 mg, 0.38 mmol). Purify by SCX chromatography eluting with methanol and 3N ammonia in methanol to obtain 7-chloro-6-[4-(cyclopentylthio-methyl)-benzylamino]-2,3,4,5-tetrahydro-1H-benzo[d]azepine (142 mg). Use a method similar to the General Procedure 3-2 to obtain the title compound (195.4 mg, 93% over two steps). MS (ES+) m/z: 402 (M+H)⁺.

EXAMPLE 15

Example 15 may be prepared essentially as described in Example 14 using 7-chloro-3-(2,2,2-trifluoroacetyl)-6-trifluoromethanesulfonyloxy-2,3,4,5-tetrahydro-1H-benzo[d]azepine and 4-(cyclohexylthiomethyl)-benzylamine. Overall yield and MS (ES+) data are shown in the Table below.

| Ex. | Structure | Compound | Yield (%) | MS (ES+) m/z |
|---|---|---|---|---|
| 15 | 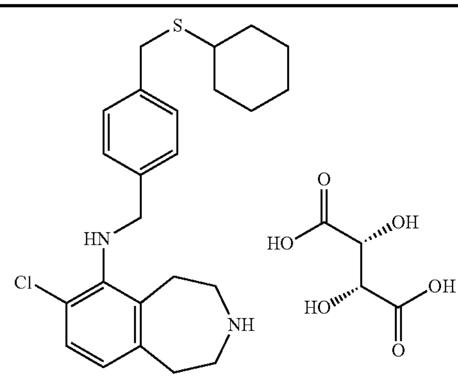 | 7-Chloro-6-[4-(cyclohexylthiomethyl)-benzylamino]-2,3,4,5-tetrahydro-1H-benzo[d]azepine (L)-Tartrate | 53 | 416 (M + H)+ |

EXAMPLE 16

7-Chloro-6-[(5-cyclopentylthiomethyl-pyridin-2-ylmethyl)-amino]-2,3,4,5-tetrahydro-1H-benzo[d]azepine (L)-Tartrate

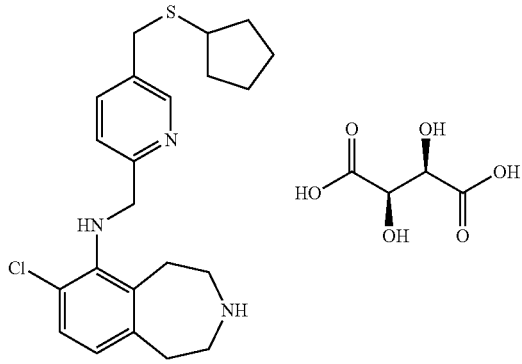 [SMILES: Clc1ccc2c(c1NCc1ccc(CSC3CCCC3)cn1)CCNCC2 ; O=C(O)[C@H](O)[C@@H](O)C(=O)O]

Use a method similar to the General Procedure 1-2 to couple 7-chloro-3-(2,2,2-trifluoroacetyl)-6-trifluoromethanesulfonyloxy-2,3,4,5-tetrahydro-1H-benzo[d]azepine (245 mg, 0.58 mmol) with 2-aminomethyl-5-cyclopentylthiomethyl-pyridine (230 mg, 1 mmol) in toluene (5 mL). Purify the crude mixture by chromatography on silica gel eluting with hexane/THF (49:1 to 7:3 gradient) to obtain 7-chloro-6-[(5-cyclopentylthiomethyl-pyridin-2-ylmethyl)-amino]-3-(2,2,2-trifluoroacetyl)-2,3,4,5-tetrahydro-1H-benzo[d]azepine (170 mg, 59%). MS (ES+) m/z: 498.1 (M+H)+.

Use a method similar to the General Procedure 2-3 to deprotect 7-chloro-6-[(5-cyclopentylthiomethyl-pyridin-2-ylmethyl)-amino]-3-(2,2,2-trifluoroacetyl)-2,3,4,5-tetrahydro-1H-benzo[d]azepine. Purify by chromatography on silica gel eluting with DCM/2M ammonia in methanol (99:1 to 9:1 gradient) to obtain 7-chloro-6-[(5-cyclopentylthiomethyl-pyridin-2-ylmethyl)-amino]-2,3,4,5-tetrahydro-1H-benzo[d]azepine. Dissolve 7-chloro-6-[(5-cyclopentylthiomethyl-pyridin-2-ylmethyl)-amino]-2,3,4,5-tetrahydro-1H-benzo[d]azepine (68 mg, 0.14 mmol) and (L)-tartaric acid (21 mg, 0.14 mmol) in methanol. Concentrate in vacuo to an oil. Triturate oil with diethyl ether and remove solvent in vacuo to obtain the title compound as a solid (85 mg, 48%). MS (ES+) m/z: 402.1 (M+H)+.

EXAMPLES 17-19

Examples 17-19 may be prepared essentially as described in Example 16 by using 7-chloro-3-(2,2,2-trifluoroacetyl)-6-trifluoromethanesulfonyloxy-2,3,4,5-tetrahydro-1H-benzo[d]azepine and the appropriately substituted 2-aminomethyl-pyridine. Overall yields and MS (ES+) data are shown in the Table below.

| Ex. | Structure | Compound | Yield (%) | MS (ES+) m/z |
|---|---|---|---|---|
| 17 | 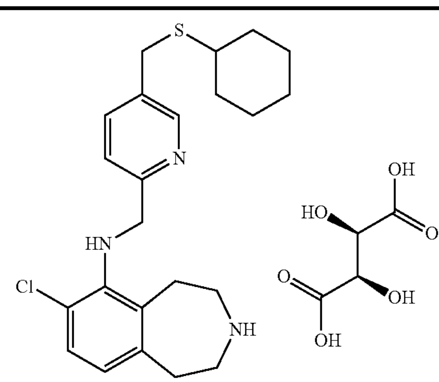 | 7-Chloro-6-[(5-cyclohexylthiomethyl-pyridin-2-ylmethyl)-amino]-2,3,4,5-tetrahydro-1H-benzo[d]azepine (L)-Tartrate | 10 | 416.1 (M + H)+ |

-continued

| Ex. | Structure | Compound | Yield (%) | MS (ES+) m/z |
|---|---|---|---|---|
| 18 | 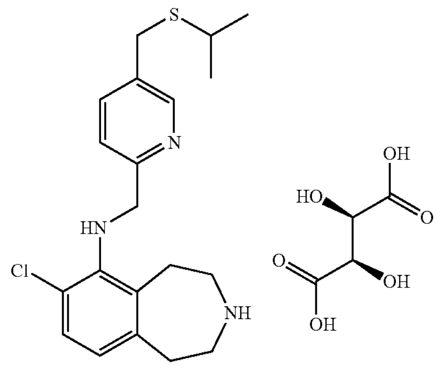 [SMILES: CC(C)SCc1ccc(CNc2c(Cl)ccc3c2CCNCC3)nc1 ; O=C(O)[C@H](O)[C@@H](O)C(=O)O] | 7-Chloro-6-[(5-iso-propylthio-methyl-pyridin-2-ylmethyl)-amino]-2,3,4,5-tetrahydro-1H-benzo[d]azepine (L)-Tartrate | 12 | 376.1 (M + H)+ |
| 19 | 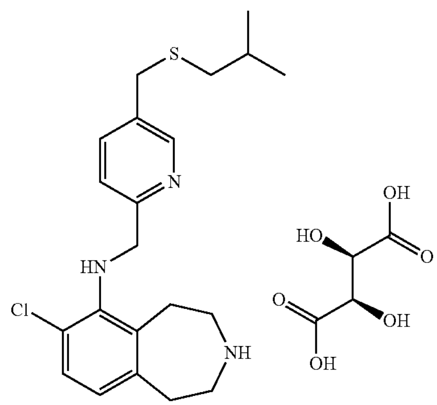 [SMILES: CC(C)CSCc1ccc(CNc2c(Cl)ccc3c2CCNCC3)nc1 ; O=C(O)[C@H](O)[C@@H](O)C(=O)O] | 7-Chloro-6-[(5-iso-butylthio-methyl-pyridin-2-ylmethyl)-amino]-2,3,4,5-tetrahydro-1H-benzo[d]azepine (L)-Tartrate | 10 | 390.1 (M + H)+ |

EXAMPLE 20

7-Chloro-6-[6-(2,2-dimethyl-propylthiomethyl)-pyridin-3-ylmethyl-amino]-2,3,4,5-tetrahydro-1H-benzo[d]azepine (L)-Tartrate

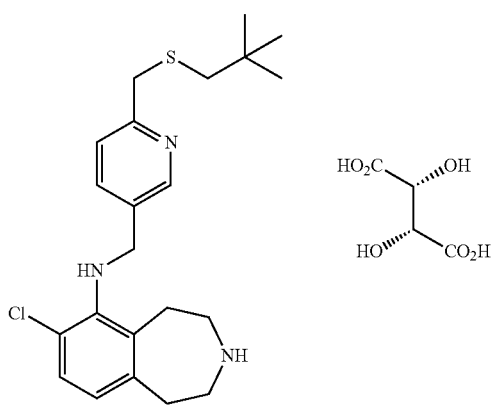 [SMILES: CC(C)(C)CSCc1ccc(CNc2c(Cl)ccc3c2CCNCC3)cn1 ; O=C(O)[C@H](O)[C@@H](O)C(=O)O]

Use a method similar to the General Procedure 1-3 to couple 7-chloro-3-(2,2,2-trifluoroacetyl)-6-trifluoromethanesulfonyloxy-2,3,4,5-tetrahydro-1H-benzo[d]azepine (586 mg, 1.37 mmol) with 3-aminomethyl-6-[(2,2-dimethylpropyl)thiomethyl]-pyridine (340 mg, 1.51 mmol) in 1,4-dioxane (15 mL). Purify by chromatography on silica gel eluting with hexane/EtOAc (10:1, 5:1 and 3:1) followed by SCX chromatography eluting with DCM and DCM/2M ammonia in methanol (1:1). Concentrate in vacuo to obtain 7-chloro-6-{6-[(2,2-dimethyl-propylthiomethyl)-pyridin-3-ylmethyl]-amino}trifluoroacetyl)-2,3,4,5-tetrahydro-1H-benzo[d]azepine as a yellow oil (0.2 g, 29%).

Use a method similar to the General Procedure 2-1 to deprotect 7-chloro-6-{6-[(2,2-dimethyl-propylthiomethyl)-pyridin-3-ylmethyl]-amino}-3-(2,2,2-trifluoroacetyl)-2,3,4,5-tetrahydro-1H-benzo[d]azepine (0.2 g, 0.4 mmol). Purify by chromatography on silica gel eluting with DCM/2M ammonia in methanol (99:1 to 90:10) to obtain 7-chloro-6-{6-[(2,2-dimethyl-propylthiomethyl)-pyridin-3-ylmethyl]-amino}-2,3,4,5-tetrahydro-1H-benzo[d]azepine. Use a method similar to the General Procedure 3-2 to obtain the title compound (103 mg, 62%). MS (ES+) m/z: 405 (M+H)+.

EXAMPLES 21-23

Examples 21-23 may be prepared essentially as described in Example 20 by using 7-chloro-3-(2,2,2-trifluoroacetyl)-6-trifluoromethanesulfonyloxy-2,3,4,5-tetrahydro-1H-benzo[d]azepine and the appropriately substituted amine. Overall yields and MS (ES+) data are shown in the Table below.

| Ex. | Structure | Compound | Yield (%) | MS (ES+) m/z |
|---|---|---|---|---|
| 21 | 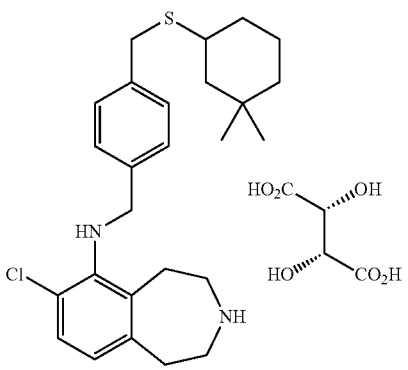 | 7-Chloro-6-[4-(3,3-dimethyl-cyclohexylthiomethyl)-benzylamino]-2,3,4,5-tetrahydro-1H-benzo[d]azepine (L)-Tartrate | 59 | 443 (M + H)+ |
| 22 | 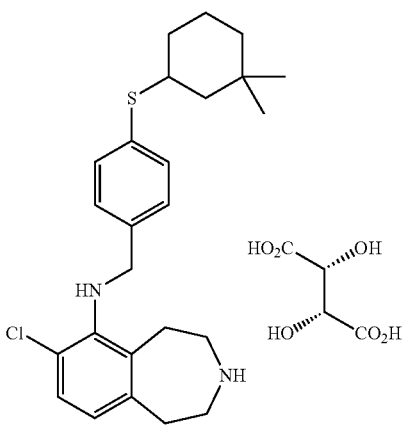 [SMILES: CC1(C)CCCC(Sc2ccc(CNc3c(Cl)ccc4c3CCNCC4)cc2)C1 ; O=C(O)[C@H](O)[C@@H](O)C(=O)O] | 7-Chloro-6-[4-(3,3-dimethyl-cyclohexylthio)-benzylamino]-2,3,4,5-tetrahydro-1H-benzo[d]azepine (L)-Tartrate | 67 | 429 (M + H)+ |
| 23 | 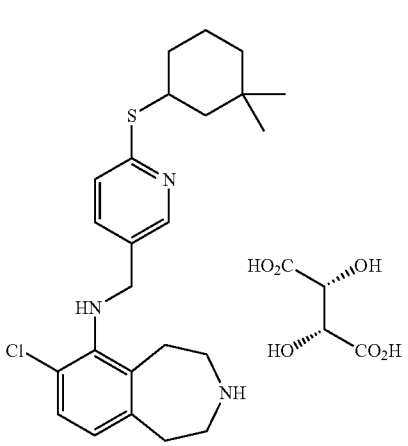 [SMILES: CC1(C)CCCC(Sc2ccc(CNc3c(Cl)ccc4c3CCNCC4)cn2)C1 ; O=C(O)[C@H](O)[C@@H](O)C(=O)O] | 7-Chloro-6-[6-(3,3-dimethyl-cyclohexylthio)-pyridin-3-ylmethyl]-amino]-2,3,4,5-tetrahydro-1H-benzo[d]azepine (L)-Tartrate | 71 | 430 (M + H)+ |

EXAMPLE 24

6-[6-(tert-Butylthiomethyl)-pyridin-3-ylmethyl-amino]-7-chloro-2,3,4,5-tetrahydro-1H-benzo[d]azepine (L)-Tartrate

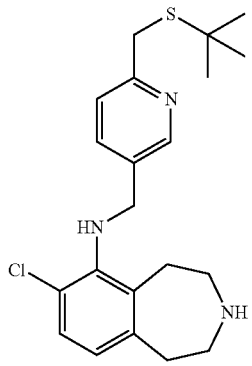

EXAMPLE 25

7-Chloro-6-[6-(3,3-dimethyl-cyclohexyloxy)-pyridin-3-ylmethyl-amino]-2,3,4,5-tetrahydro-1H-benzo[d]azepine (L)-Tartrate Isomer 1

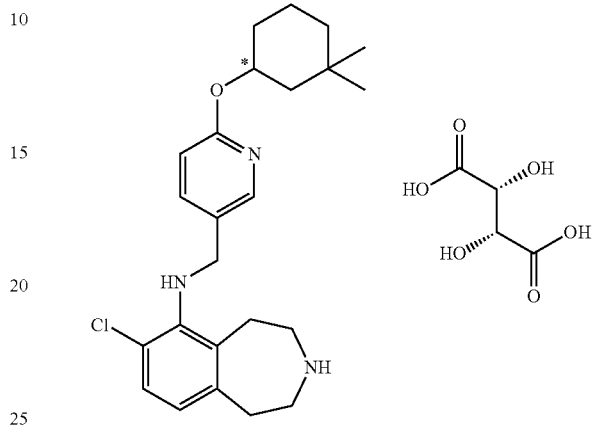

Use a method similar to the General Procedure 1-3. Add 3-aminomethyl-6-(tert-butylthio)methyl-pyridine (2.99 g, 14.2 mmol), 7-chloro-3-(2,2,2-trifluoroacetyl)-6-trifluoromethanesulfonyloxy-2,3,4,5-tetrahydro-1H-benzo[d]azepine (5.05 g, 11.9 mmol), tris(dibenzylideneacetone)dipalladium(0) (275 mg, 0.3 mmol), palladium(II) acetate (133 mg, 0.6 mmol), BINAP (560 mg, 0.9 mmol) and cesium carbonate (5.82 g, 17.9 mmol) to toluene (100 mL) under a nitrogen atmosphere. Heat the mixture at 90° C. for 12 h. Cool the mixture to room temperature. Purify by chromatography on silica gel eluting with hexane/EtOAc (100:0 to 85:15 gradient) to obtain 6-[(6-tert-butylthiomethyl-pyridin-3-ylmethyl)-amino]-7-chloro-3-(2,2,2-trifluoroacetyl)-2,3,4,5-tetrahydro-1H-benzo[d]azepine (4.1 g, 71%). MS (APCI+) m/z: 486 (M+H)$^+$.

Dissolve 6-[(6-tert-butylthiomethyl-pyridin-3-ylmethyl)-amino]-7-chloro-3-(2,2,2-trifluoroacetyl)-2,3,4,5-tetrahydro-1H-benzo[d]azepine (4.46 g, 9.24 mmol) in methanol (20 mL). Add a solution of potassium carbonate (5.1 g, 37 mmol) in water (10 mL) and stir at room temperature for 12 h. Remove methanol in vacuo, dilute the residue with water, and extract the aqueous phase with DCM. Purify the crude mixture by SCX chromatography (20 g) eluting with methanol and a solution of NH$_4$OH (40 mL) in methanol (140 mL). Concentrate in vacuo to obtain pure 6-[(6-tert-butylthiomethyl-pyridin-3-ylmethyl)-amino]-7-chloro-2,3,4,5-tetrahydro-1H-benzo[d]azepine (3.6 g, 100%). MS (APCI+) m/z: 390 (M+H)$^+$.

Dissolve 6-[(6-tert-butylthiomethyl-pyridin-3-ylmethyl)-amino]-7-chloro-2,3,4,5-tetrahydro-1H-benzo[d]azepine (3.6 g, 9.24 mmol) in methanol and add (L)-tartaric acid (1.25 g, 8.32 mmol). Stir the mixture until homogeneous. Concentrate the mixture in vacuo, dissolve in water, and freeze dry to provide the title compound as a solid (4.4 g, 88%). MS (APCI+) m/z: 390 (M+H)$^+$.

Use a method similar to the General Procedure 1-3 to couple 7-chloro-3-(2,2,2-trifluoroacetyl)-6-trifluoromethanesulfonyloxy-2,3,4,5-tetrahydro-1H-benzo[d]azepine (1 g, 2.54 mmoles) with 3-aminomethyl-6-(3,3-dimethyl-cyclohexyloxy)-pyridine isomer 1 (596 mg, 2.54 mmoles). Purify by chromatography on silica gel (40 g, pre-packed cartridge) eluting with cyclohexane/EtOAc (1:0 to 7:3 gradient) to afford 7-chloro-6-{6-[(3,3-dimethyl-cyclohexyloxy)-pyridin-3-ylmethyl]-amino}-3-(2,2,2-trifluoroacetyl)-2,3,4,5-tetrahydro-1H-benzo[d]azepine isomer 1 as an oil (870 mg, 62%).

Use a method similar to the General Procedure 2-2, using 7N ammonia in methanol/water/THF (10:1:1 ratio) as solvent, to deprotect 7-chloro-6-{6-[(3,3-dimethyl-cyclohexyloxy)-pyridin-3-ylmethyl]-amino}-3-(2,2,2-trifluoroacetyl)-2,3,4,5-tetrahydro-1H-benzo[d]azepine isomer 1. Purify by SCX-2 chromatography eluting with methanol followed by 3N ammonia in methanol to obtain 7-chloro-6-{6[(3,3-dimethyl-cyclohexyloxy)-pyridin-3-ylmethyl]-amino}-2,3,4,5-tetrahydro-1H-benzo[d]azepine isomer 1 (673 mg). [α]$_D$=−15.5° (c=0.23, EtOH).

Use a method similar to the General Procedure 3-2 to obtain the title compound as a solid (916 mg, 69% three steps). MS (ES+) m/z: 414.2 (M+H)$^+$.

EXAMPLES 26-32

Examples 26-32 may be prepared essentially as described in Example 25 using 7-chloro-3-(2,2,2-trifluoroacetyl)-6-trifluoromethanesulfonyloxy-2,3,4,5-tetrahydro-1H-benzo[d]azepine and the appropriately substituted amine. Overall yields and MS (ES+) data are shown in the Table below. Optical rotation for Example 26 is also shown in the Table below.

| Ex. | Structure | Compound | Yield (%) | MS (ES+) m/z |
|---|---|---|---|---|
| 26 | 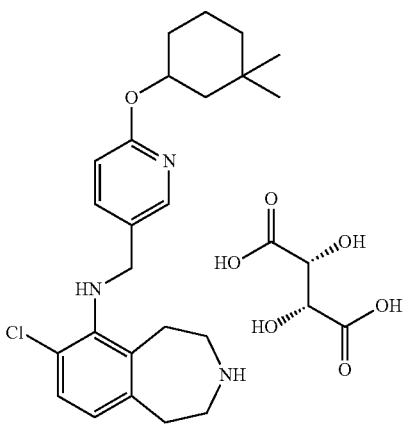 [SMILES: CC1(C)CCCC(Oc2ccc(CNc3c(Cl)ccc4c3CCNCC4)cn2)C1 ; O=C(O)[C@H](O)[C@@H](O)C(=O)O] | 7-Chloro-6-[6-(3,3-dimethyl-cyclohexyloxy)-pyridin-3-ylmethyl]-amino]-2,3,4,5-tetrahydro-1H-benzo[d]azepine (L)-Tartrate Isomer 2 | 35 | 414 (M + H)+ Free base: $[\alpha]_D$ = +19° (c = 0.25, EtOH) |
| 27 | 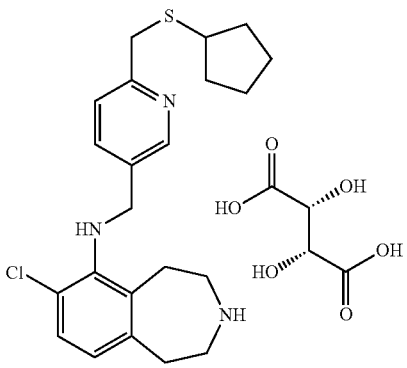 | 7-Chloro-6-[6-(cyclo-pentylthiomethyl)-pyridin-3-ylmethyl-amino]-2,3,4,5-tetrahydro-1H-benzo[d]azepine (L)-Tartrate | 30 | 402 (M + H)+ |
| 28 | 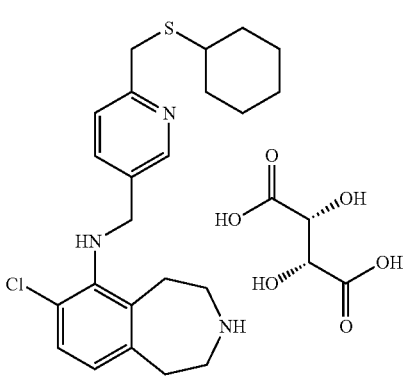 | 7-Chloro-6-[6-(cyclo-hexylthiomethyl)-pyridin-3-ylmethyl-amino]-2,3,4,5-tetrahydro-1H-benzo[d]azepine (L)-Tartrate | 21 | 416 (M + H)+ |

-continued
| Ex. | Structure | Compound | Yield (%) | MS (ES+) m/z |
|---|---|---|---|---|
| 29 | 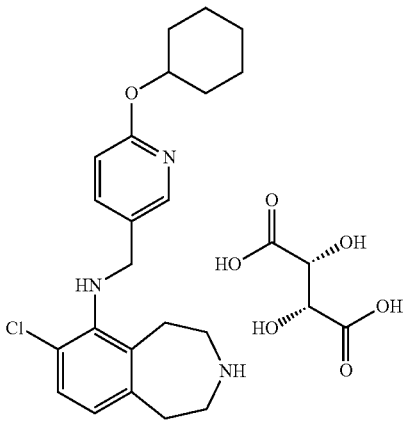 [SMILES: Clc1ccc2c(c1NCc1ccc(OC3CCCCC3)nc1)CCNCC2 ; O=C(O)[C@H](O)[C@@H](O)C(=O)O] | 7-Chloro-6-[6-(cyclohexyloxy)-pyridin-3-ylmethyl-amino]-2,3,4,5-tetrahydro-1H-benzo[d]azepine (L)-Tartrate | 45 | 386 (M + H)+ |
| 30 | 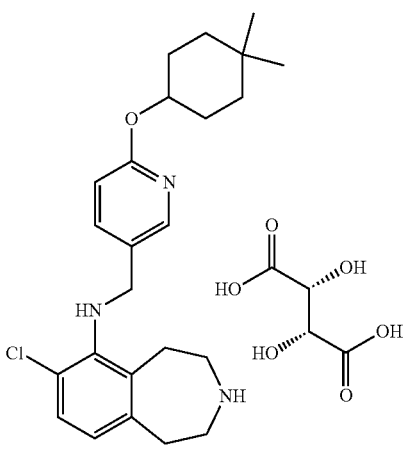 [SMILES: CC1(C)CCC(Oc2ccc(CNc3c(Cl)ccc4c3CCNCC4)cn2)CC1 ; O=C(O)[C@H](O)[C@@H](O)C(=O)O] | 7-Chloro-6-[6-(4,4-dimethyl-cyclohexyloxy)-pyridin-3-ylmethyl-amino]-2,3,4,5-tetrahydro-1H-benzo[d]azepine (L)-Tartrate | 60 | 414 (M + H)+ |
| 32 | 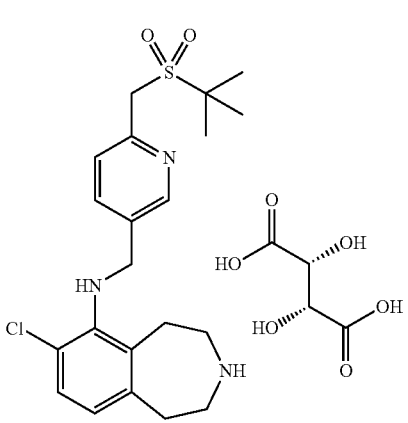 [SMILES: CC(C)(C)S(=O)(=O)Cc1ccc(CNc2c(Cl)ccc3c2CCNCC3)cn1 ; O=C(O)[C@H](O)[C@@H](O)C(=O)O] | 7-Chloro-6-[6-(2-methyl-2-propane-sulfonylmethyl)-pyridin-3-ylmethyl-amino]-2,3,4,5-tetrahydro-1H-benzo[d]azepine (L)-Tartrate | 55 | 422 (M + H)+ |

EXAMPLE 33

7-Chloro-6-[6-(iso-propoxymethyl)-pyridin-3-ylmethyl-amino]-2,3,4,5-tetrahydro-1H-benzo[d]azepine (L)-Tartrate

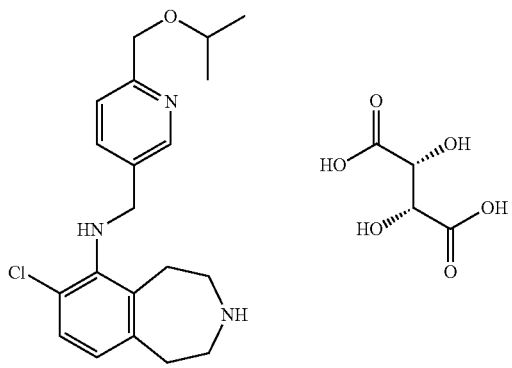 [SMILES: CC(C)OCc1ccc(CNc2c(Cl)ccc3c2CCNCC3)cn1 ; O=C(O)[C@H](O)[C@@H](O)C(=O)O]

Use a method similar to the General Procedure 1-2 to couple 7-chloro-3-(2,2,2-trifluoroacetyl)-6-trifluoromethanesulfonyloxy-2,3,4,5-tetrahydro-1H-benzo[d]azepine (408 mg, 0.96 mmol) with 3-aminomethyl-6-(iso-propoxy)methyl-pyridine (190 mg, 1.05 mmol) in toluene (8 mL). Purify the crude mixture by chromatography on silica gel eluting with isohexane/EtOAc (1:0 to 1:1 gradient) to obtain 7-chloro-6-[(6-iso-propoxymethyl-pyridin-3-ylmethyl)-amino]-3-(2,2,2-trifluoroacetyl)-2,3,4,5-tetrahydro-1H-benzo[d]azepine. MS (ES+) m/z: 456 (M+H)⁺.

Use a method similar to the General Procedure 2-1 to deprotect 7-chloro-6-[(6-iso-propoxymethyl-pyridin-3-ylmethyl)-amino]-3-(2,2,2-trifluoroacetyl)-2,3,4,5-tetrahydro-1H-benzo[d]azepine. Purify by SCX chromatography eluting with methanol and 3N ammonia in methanol and then by reverse phase HPLC (Princeton SPHER-C₁₈ 100 Å column 5 □m, 100×20 mm; 20-95% of solvent B in 11 min then 95% of solvent B in 4 min; solvent A: water, 0.1% acetic acid; solvent B: acetonitrile, 0.1% acetic acid; 20 mL/min). Use a method similar to the General Procedure 3-2 to obtain the title compound (76 mg, 22%). MS (ES+) m/z: 361 (M+H)⁺.

EXAMPLES 34-36

Examples 34-36 may be prepared essentially as described in Example 33 using 7-chloro-3-(2,2,2-trifluoroacetyl)-6-trifluoromethanesulfonyloxy-2,3,4,5-tetrahydro-1H-benzo[d]azepine and the appropriately substituted 3-aminomethyl-pyridine. Overall yields and MS (ES+) data are shown in the Table below.

| Ex. | R | Compound | Yield (%) | MS (ES+) m/z |
|---|---|---|---|---|
| 34 | 2,2-Dimethylpropyl | 7-Chloro-6-[6-(2,2-dimethylpropoxymethyl)-pyridin-3-ylmethyl-amino]-2,3,4,5-tetrahydro-1H-benzo[d]azepine (L)-Tartrate | 9 | 388 (M + H)⁺ |
| 35 | Cyclopentyl | 7-Chloro-6-[6-(cyclopentyloxymethyl)-pyridin-3-ylmethyl-amino]-2,3,4,5-tetrahydro-1H-benzo[d]azepine (L)-Tartrate | 50 | 387 (M + H)⁺ |
| 36 | Cyclohexyl | 7-Chloro-6-[6-(cyclohexyloxymethyl)-pyridin-3-ylmethyl-amino]-2,3,4,5-tetrahydro-1H-benzo[d]azepine (L)-Tartrate | 11 | 401 (M + H)⁺ |

EXAMPLE 37

7-Chloro-6-[5-(cyclohexyloxy)-pyridin-2-ylmethyl-amino]-2,3,4,5-tetrahydro-1H-benzo[d]azepine Succinate

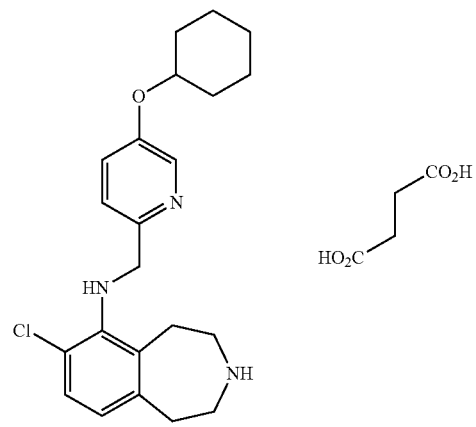 [SMILES: Clc1ccc2c(c1NCc1ccc(OC3CCCCC3)cn1)CCNCC2 ; O=C(O)CCC(=O)O]

Use a method similar to the General Procedure 1-2 to couple 7-chloro-3-(2,2,2-trifluoroacetyl)-6-trifluoromethanesulfonyloxy-2,3,4,5-tetrahydro-1H-benzo[d]azepine (705 mg, 1.66 mmol) and 2-aminomethyl-5-cyclohexyloxy-pyridine (410 mg, 1.99 mmol). Purify the crude mixture by chromatography on silica gel (150 g, pre-packed cartridge) eluting with hexane/EtOAc (1:0 to 9:1 gradient) to obtain 7-chloro-6-[(5-cyclohexyloxy-pyridin-2-ylmethyl)-amino]-3-(2,2,2-trifluoroacetyl)-2,3,4,5-tetrahydro-1H-benzo[d]azepine (520 mg, 65%). MS (APCI+) m/z: 482 (M+H)⁺.

Use a method similar to the General Procedure 2-1 to deprotect 7-chloro-6-[(5-cyclohexyloxy-pyridin-2-ylmethyl)-amino]-3-(2,2,2-trifluoroacetyl)-2,3,4,5-tetrahydro-1H-benzo[d]azepine (520 mg). Purify the crude mixture by SCX chromatography to obtain 7-chloro-6-[(5-cyclohexyloxy-pyridin-2-ylmethyl)-amino]-2,3,4,5-tetrahydro-1H-benzo[d]azepine (510 mg, 92%).

Use a method similar to the General Procedure 3-1, using 7-chloro-6-[(5-cyclohexyloxy-pyridin-2-ylmethyl)-amino]-2,3,4,5-tetrahydro-1H-benzo[d]azepine (510 mg) to obtain the title compound as a white solid (590 mg, 82%). MS (APCI+) m/z: 386 (M+H)+.

EXAMPLE 38

Example 38 may be prepared essentially as described in Example 37 using 7-chloro-3-(2,2,2-trifluoroacetyl)-6-trifluoromethanesulfonyloxy-2,3,4,5-tetrahydro-1H-benzo[d]azepine and 2-aminomethyl-5-cycloheptyloxy-pyridine. Deprotection to obtain the free base was performed using a method similar to the General Procedure 2-3. Overall yields and MS (ES+) data are shown in the Table below.

Use a method similar to the General Procedure 1-1 to couple 7-chloro-3-(2,2,2-trifluoroacetyl)-6-trifluoromethanesulfonyloxy-2,3,4,5-tetrahydro-1H-benzo[d]azepine (378 mg, 0.888 mmol) and 2-aminomethyl-5-(3,3-dimethylcyclohexyloxy)-pyridine (260 mg, 1.11 mmol). Purify by chromatography on silica gel eluting with hexane/EtOAc (1:0 to 2:1 gradient) to obtain 7-chloro-6-{5-[(3,3-dimethylcyclohexyloxy)-pyridin-2-ylmethyl]-amino}-3-(2,2,2-trifluoroacetyl)-2,3,4,5-tetrahydro-1H-benzo[d]azepine as a light yellow oil (107 mg, 24%). MS (APCI+) m/z: 510 (M+H)+.

Use a method similar to the General Procedure 2-1, using 7-chloro-6-{5-[(3,3-dimethylcyclohexyloxy)-pyridin-2-ylmethyl]-amino}-3-(2,2,2-trifluoroacetyl)-2,3,4,5-tetrahydro-1H-benzo[d]azepine (106 mg, 0.208 mmol) to obtain 7-chloro-6-{5-[(3,3-dimethylcyclohexyloxy)-pyridin-2-ylmethyl]-amino}-2,3,4,5-tetrahydro-1H-benzo[d]azepine as a colorless oil (68 mg; 79%). MS (APCI+) m/z: 482 (M+H)+.

Use a method similar to the General Procedure 3-1, using 7-chloro-6-{5-[(3,3-dimethylcyclohexyloxy)-pyridin-2-ylmethyl]-amino}-2,3,4,5-tetrahydro-1H-benzo[d]azepine (65 mg, 0.157 mmol) to obtain the title compound as an off-white solid (71 mg, 85%). MS (APCI+) m/z: 414 (M+H)+.

| Ex. | Structure | Compound | Yield (%) | MS (ES+) m/z |
|---|---|---|---|---|
| 38 | 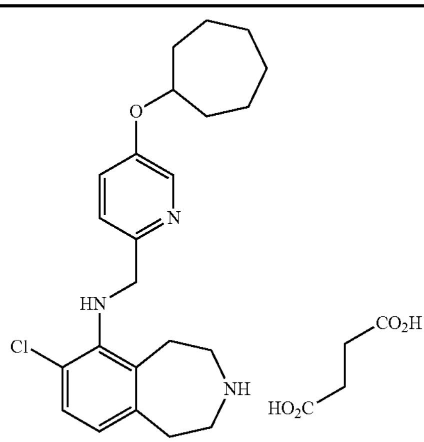 | 7-Chloro-6-[5-(cycloheptyloxy)-pyridin-2-ylmethyl-amino]-2,3,4,5-tetrahydro-1H-benzo[d]azepine Succinate | 32 | 400 (M + H)+ |

EXAMPLE 39

7-Chloro-6-[5-(3,3-dimethyl-amino]-2,3,4,5-tetrahydro-1H-benzo[d]azepine Succinate

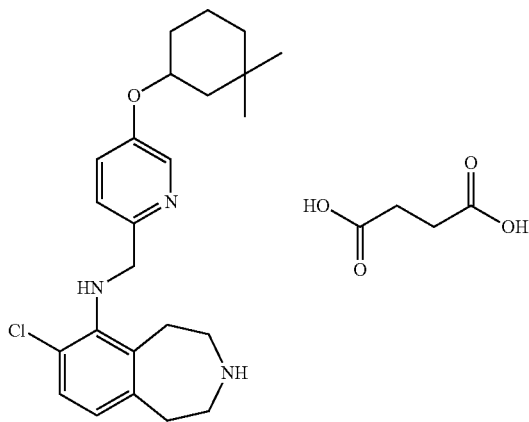 [SMILES: CC1(C)CCCC(Oc2ccc(CNc3c(Cl)ccc4c3CCNCC4)nc2)C1 ; O=C(O)CCC(=O)O]

EXAMPLE 40
(E)-7-Chloro-6-[6-(2-cyclohexyl-vinyl-pyridin-3-ylmethyl-amino]-2,3,4,5-tetrahydro-1H-benzo[d]azepine Succinate

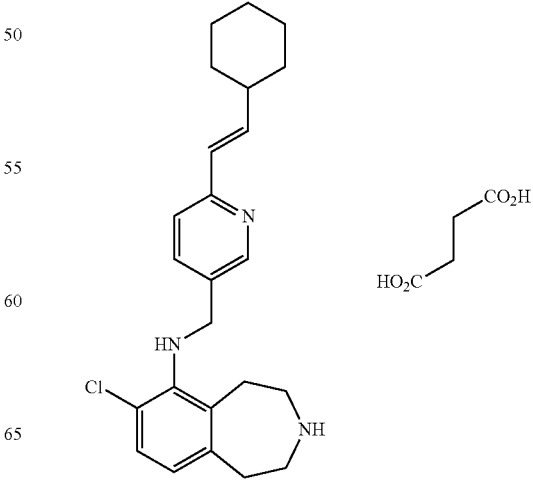

Use a method similar to the General Procedure 1-2 to couple 7-chloro-3-(2,2,2-trifluoroacetyl)-6-trifluoromethanesulfonyloxy-2,3,4,5-tetrahydro-1H-benzo[d]azepine (579 mg, 1.361 mmol) and (E)-3-aminomethyl-6-(2-cyclohexylvinyl)-pyridine (368 mg, 1.701 mmol). Purify by chromatography on silica gel (80 g, pre-packed cartridge) eluting sequentially with hexane/EtOAc (1:0, 49:1, 19:1, 93:7, 9:1 and 85:15) to obtain (E)-7-chloro-6-{6-[(2-cyclohexyl-vinyl)-pyridin-3-ylmethyl]-amino}-3-(2,2,2-trifluoroacetyl)-2,3,4,5-tetrahydro-1H-benzo[d]azepine (445 mg, 66%). MS (APCI+) m/z: 492 (M+H)+.

Use a method similar to the General Procedure 2-3 to deprotect (E)-7-chloro-6-{6-[(2-cyclohexyl-vinyl)-pyridin-3-ylmethyl]-amino}-3-(2,2,2-trifluoroacetyl)-2,3,4,5-tetrahydro-1H-benzo[d]azepine (607 mg, 1.234 mmol) using lithium hydroxide monohydrate (525 mg, 12.52 mmol) in methanol (15 mL) for 2 h. Purify by chromatography on silica gel (120 g, pre-packed cartridge) eluting sequentially with DCM/(chloroform:methanol:concentrated NH$_4$OH 80:18:2) (49:1, 19:1, 9:1 and 17:3) to obtain (E)-7-chloro-6-{6-[(2-cyclohexyl-vinyl)-pyridin-3-ylmethyl]-amino}-2,3,4,5-tetrahydro-1H-benzo[d]azepine (481 mg, 98%). MS (APCI+) m/z: 396 (M+H)+.

Use a method similar to the General Procedure 3-1, using (E)-7-chloro-6-{6-[(2-cyclohexyl-vinyl)-pyridin-3-ylmethyl]-amino}-2,3,4,5-tetrahydro-1H-benzo[d]azepine (481 mg, 1.215 mmol) to obtain the title compound (605 mg, 97%). MS (APCI+) m/z: 396 (M+H)+.

EXAMPLES 41-44

Examples 41-44 may be prepared essentially as described in Example 40 by using 7-chloro-3-(2,2,2-trifluoroacetyl)-6-trifluoromethanesulfonyloxy-2,3,4,5-tetrahydro-1H-benzo[d]azepine and the appropriately substituted amine. For Example 44, (L)-Tartrate salt was prepared essentially as described in General Procedure 3-2. Overall yields and MS (ES+) data are shown in the Table below.

| Ex. | Structure | Compound | Yield (%) | MS (ES+) m/z |
|---|---|---|---|---|
| 41 | 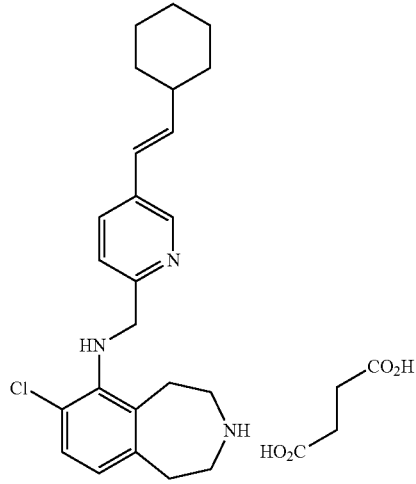 [SMILES: Clc1ccc2c(c1NCc1ccc(/C=C/C3CCCCC3)cn1)CCNCC2 ; O=C(O)CCC(=O)O] | (E)-7-Chloro-6-[5-(2-cyclohexyl-vinyl)-pyridin-2-ylmethyl-amino]-2,3,4,5-tetrahydro-1H-benzo[d]azepine Succinate | 3 | 396 (M + H)+ |
| 42 | 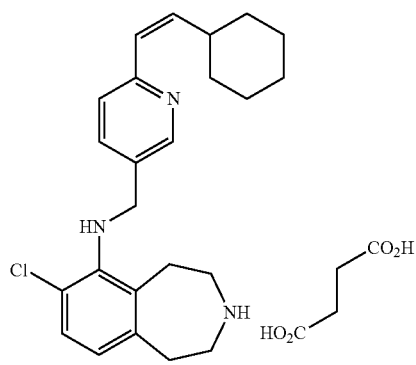 [SMILES: Clc1ccc2c(c1NCc1ccc(/C=C\C3CCCCC3)nc1)CCNCC2 ; O=C(O)CCC(=O)O] | (Z)-7-Chloro-6-[6-(2-cyclohexyl-vinyl)-pyridin-3-ylmethyl-amino]-2,3,4,5-tetrahydro-1H-benzo[d]azepine Succinate | 50 | 396 (M + H)+ |

-continued

| Ex. | Structure | Compound | Yield (%) | MS (ES+) m/z |
|---|---|---|---|---|
| 43 | 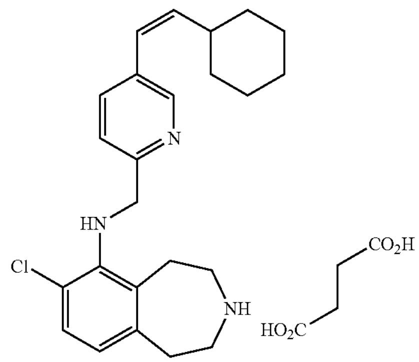 [SMILES: Clc1ccc2c(c1NCc1ccc(/C=C\C3CCCCC3)cn1)CCNCC2 ; O=C(O)CCC(=O)O] | (Z)-7-Chloro-6-[5-(2-cyclohexyl-vinyl)-pyridin-2-ylmethyl-amino]-2,3,4,5-tetrahydro-1H-benzo[d]azepine Succinate | 4 | 396 (M + H)+ |
| 44 | 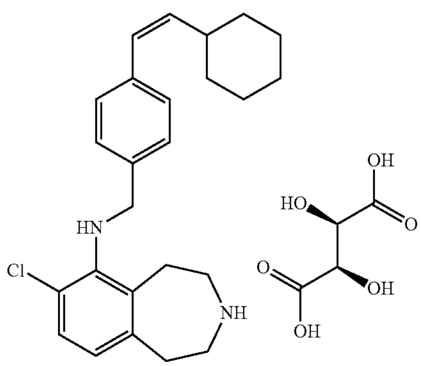 | (Z)-7-Chloro-6-[4-(2-cyclohexyl-vinyl)-benzylamino]-2,3,4,5-tetrahydro-1H-benzo[d]azepine (L)-Tartrate | 12 | 395.2 (M + H)+ |

EXAMPLE 45

7-Chloro-6-[4-(2-cyclohexyl-2-oxo-ethyl)-benzylamino]-2,3,4,5-tetrahydro-1H-benzo[d]azepine (L)-Tartrate

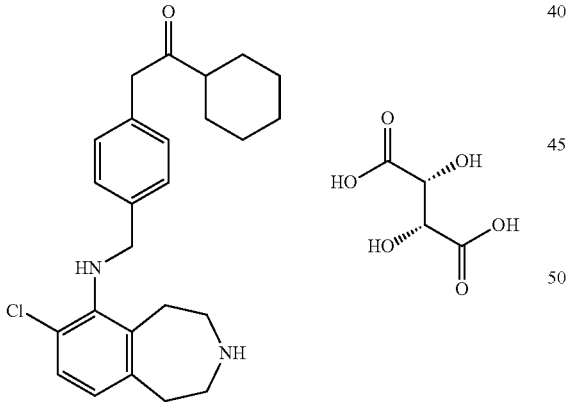

Use a method similar to the General Procedure 1-2 to couple 7-chloro-3-(2,2,2-trifluoroacetyl)-6-trifluoromethanesulfonyloxy-2,3,4,5-tetrahydro-1H-benzo[d]azepine (137 mg, 0.325 mmol) and 4-(2-cyclohexyl-2-oxo-ethyl)-benzylamine (150 mg, 0.65 mmol). Purify by chromatography on silica gel eluting with hexane/EtOAc (95:5) to obtain 7-chloro-6-[4-(2-cyclohexyl-2-oxo-ethyl)-benzylamino]-3-(2,2,2-trifluoroacetyl)-2,3,4,5-tetrahydro-1H-benzo[d]azepine as a yellow oil (76 mg, 46%). MS (ES+) m/z: 507 (M+H)+.

Use a method similar to the General Procedure 2-1, using 7-chloro-6-[4-(2-cyclohexyl-2-oxo-ethyl)-benzylamino]-3-(2,2,2-trifluoroacetyl)-2,3,4,5-tetrahydro-1H-benzo[d]azepine (76 mg, 0.150 mmol) to obtain 7-chloro-6-[4-(2-cyclohexyl-2-oxo-ethyl)-benzylamino]-2,3,4,5-tetrahydro-1H-benzo azepine (59 mg, 93%) as a yellow oil suitable for use without additional purification.

Use a method similar to the General Procedure 3-2, using 7-chloro-6-[4-(2-cyclohexyl-2-oxo-ethyl)-benzylamino]-2,3,4,5-tetrahydro-1H-benzo[d]azepine (59 mg, 0.142 mmol) to obtain the title compound as a white solid (79 mg, 99%). MS (ES+) m/z: 411 (M+H)+.

EXAMPLE 46

7-Chloro-6-[4-(morpholin-4-ylmethyl)-benzylamino]-2,3,4,5-tetrahydro-1H-benzo[d]azepine Succinate

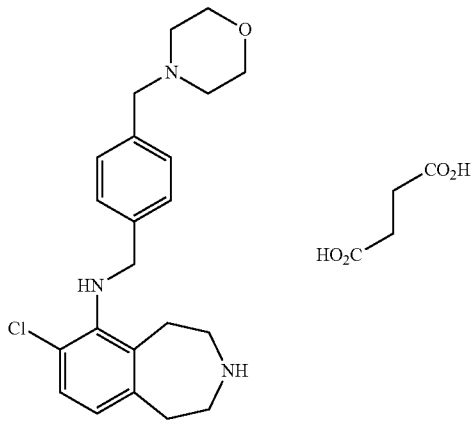 [SMILES: Clc1ccc2c(c1NCc1ccc(CN3CCOCC3)cc1)CCNCC2 ; O=C(O)CCC(=O)O]

Use a method similar to the General Procedure 1-2 to couple 7-chloro-3-(2,2,2-trifluoroacetyl)-6-trifluoromethanesulfonyloxy-2,3,4,5-tetrahydro-1H-benzo[d]azepine (400 mg, 0.94 mmol) with 4-(morpholin-4-ylmethyl)-benzylamine (291 mg, 1.41 mmol). Purify by chromatography on silica gel (80 g, pre-packed cartridge) eluting with hexane/EtOAc (1:0 to 2:1 gradient) to obtain 7-chloro-6-[4-(morpholin-4-ylmethyl)-benzylamino]-3-(2,2,2-trifluoroacetyl)-2,3,4,5-tetrahydro-1H-benzo[d]azepine (304 mg, 67%). MS (APCI+) m/z: 482 (M+H)+.

Use a method similar to the General Procedure 2-2, using 7-chloro-6-[4-(morpholin-4-ylmethyl)-benzylamino]-3-(2,2,2-trifluoroacetyl)-2,3,4,5-tetrahydro-1H-benzo[d]azepine (294 mg, 0.61 mmol) to obtain 7-chloro-6-[4-(morpholin-4-ylmethyl)-benzylamino]-2,3,4,5-tetrahydro-1H-benzo[d]azepine as a colorless oil (230 mg, 98%). MS (APCI+) m/z: 386 (M+H)+.

Use a method similar to the General Procedure 3-1, using 7-chloro-6-[4-(morpholin-4-ylmethyl)-benzylamino]-2,3,4,5-tetrahydro-1H-benzo[d]azepine (230 mg, 0.596 mmol) to obtain the title compound as an off-white solid (295 mg, 98%). MS (APCI+) m/z: 386 (M+H)+.

EXAMPLES 47-48

Examples 47-48 may be prepared essentially as described in Example 46 by using 7-chloro-3-(2,2,2-trifluoroacetyl)-6-trifluoromethanesulfonyloxy-2,3,4,5-tetrahydro-1H-benzo[d]azepine and the appropriately substituted benzylamine. Enantiomeric excess of Example 47 was 92.7% [Analytical chiral conditions: Chiralpak® AD column; 250×4.6 mm, eluting with hexane/iso-propanol (95:5 with 0.1% diethylamine)]. Overall yields and MS (ES+) data are shown in the Table below.

EXAMPLE 49

7-Chloro-6-[4-(piperidin-1-ylmethyl)-benzylamino]-2,3,4,5-tetrahydro-1H-benzo[d]azepine Succinate

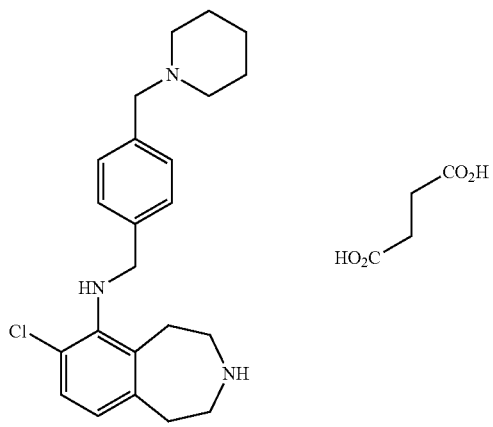

Use a method similar to the General Procedure)-2 to couple 7-chloro-3-(2,2,2-trifluoroacetyl)-6-trifluoromethansulfonyloxy-2,3,4,5-tetrahydro-1H-benzo[d]azepine (300 mg, 0.69 mmol) and 4-(piperidin-1-ylmethyl)-benzylamine (174 mg, 0.84 mmol). Purify by chromatography on silica gel (150 g) eluting with a gradient of DCM to 4:1 DCM/(chloroform:methanol:concentrated NH4OH 80:18:2) to obtain 7-chloro-

| Ex. | Structure | Compound | Yield (%) | MS (ES+) m/z; [α]$_D$ (c, solvent) |
|---|---|---|---|---|
| 47 | 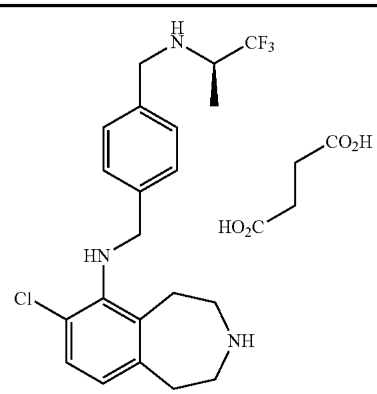 | (R)-7-Chloro-6-[4-(1-methyl-2,2,2-trifluoro-ethylamino)-methyl-benzylamino]-7-chloro-2,3,4,5-tetrahydro-1H-benzo[d]azepine Succinate | 38 | 412 (M + H)+; [α]$_D$ = −8.2° (c = 0.5, MeOH) |
| 48 | 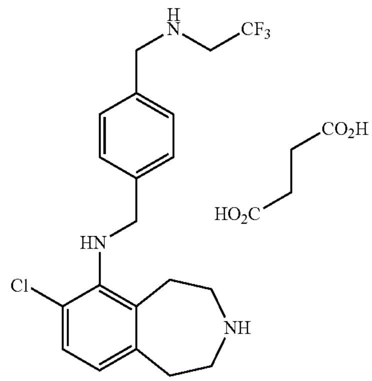 [SMILES: FC(F)(F)CNCc1ccc(CNc2c(Cl)ccc3c2CCNCC3)cc1 ; O=C(O)CCC(=O)O] | 7-Chloro-6-[4-(2,2,2-trifluoroethylamino-methyl)-benzylamino]-7-chloro-2,3,4,5-tetrahydro-1H-benzo[d]azepine Succinate | 43 | 398 (M + H)+ |

6-[4-(piperidin-1-ylmethyl)-benzylamino]-3-(2,2,2-trifluoroacetyl)-2,3,4,5-tetrahydro-1H-benzo[d]azepine as an oil (240 mg, 71%). MS (ES+) m/z: 480 (M+H)+.

Use a method similar to the General Procedure 2-2, using 7-chloro-6-[4-(piperidin-1-ylmethyl)-benzylamino]-3-(2,2,2-trifluoroacetyl)-2,3,4,5-tetrahydro-1H-benzo[d]azepine (370 mg, 0.77 mmol). Purify by chromatography on silica gel (12 g, pre-packed cartridge) eluting with a gradient of DCM to 4:1 DCM/(chloroform:methanol:concentrated NH4OH 80:18:2) to obtain 7-chloro-6-[4-(piperidin-1-ylmethyl)-benzylamino]-2,3,4,5-tetrahydro-1H-benzo[d]azepine as a clear oil (270 mg, 95%). MS (APCI+) m/z: 384 (M+H)+.

Use a method similar to the General Procedure 3-1, using 7-chloro-6-[4-(piperidin-1-ylmethyl)-benzylamino]-2,3,4,5-tetrahydro-1H-benzo[d]azepine (270 mg, 0.7 mmol) to obtain the title compound as an off-white solid (335 mg, 96%). MS (APCI+) m/z: 384 (M+H)+.

EXAMPLES 50-52

Examples 50-52 may be prepared essentially as described in Example 49 by using 7-chloro-3-(2,2,2-trifluoroacetyl)-6-trifluoromethanesulfonyloxy-2,3,4,5-tetrahydro-1H-benzo[d]azepine and the appropriately substituted benzylamine. Overall yields and MS (ES+) data are shown in the Table below.

| Ex. | Structure | Compound | Yield (%) | MS (APCI+) m/z |
|---|---|---|---|---|
| 50 | 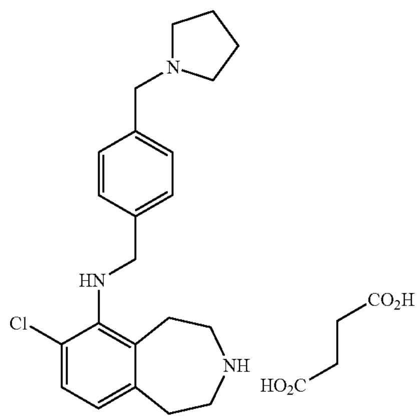 [SMILES: Clc1ccc2c(c1NCc1ccc(CN3CCCC3)cc1)CCNCC2 ; O=C(O)CCC(=O)O] | 7-Chloro-6-[4-(pyrrolidin-1-ylmethyl)-benzylamino]-2,3,4,5-tetrahydro-1H-benzo[d]azepine Succinate | 51 | 370 (M + H)+ |
| 51 | 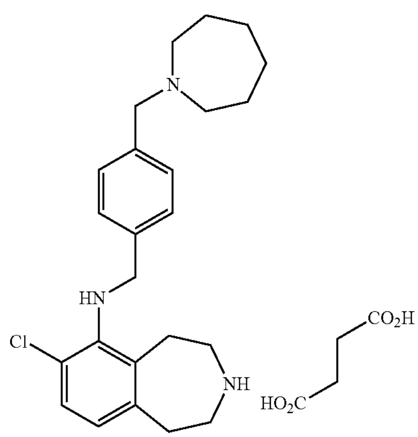 [SMILES: Clc1ccc2c(c1NCc1ccc(CN3CCCCCC3)cc1)CCNCC2 ; O=C(O)CCC(=O)O] | 7-Chloro-6-[4-(azepan-1-ylmethyl)-benzylamino]-2,3,4,5-tetrahydro-1H-benzo[d]azepine Succinate | 12 | 398 (M + H)+ |
| 52 | 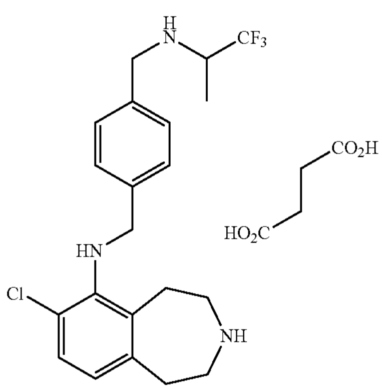 [SMILES: CC(NCc1ccc(CNc2c(Cl)ccc3c2CCNCC3)cc1)C(F)(F)F ; O=C(O)CCC(=O)O] | 7-Chloro-6-[4-(1-methyl-2,2,2-trifluoro-ethylamino-methyl)-benzylamino]-7-chloro-2,3,4,5-tetrahydro-1H-benzo[d]azepine Succinate | 40 | 412 (M + H)+ |

EXAMPLE 53

7-Chloro-6-[4-(N-cyclohexyl-aminomethyl)-benzylamino]-2,3,4,5-tetrahydro-1H-benzo[d]azepine Succinate

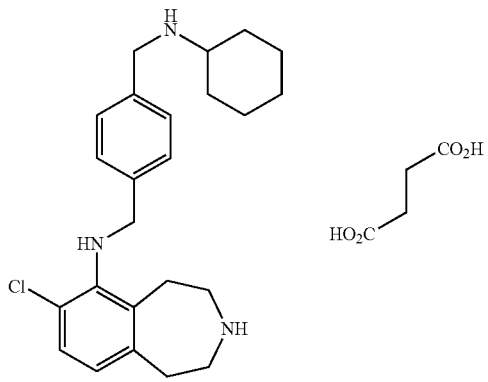 [SMILES: Clc1ccc2c(c1NCc1ccc(CNC3CCCCC3)cc1)CCNCC2 ; O=C(O)CCC(=O)O]

Use a method similar to the General Procedure 1-2 to couple 7-chloro-3-(2,2,2-trifluoroacetyl)-6-trifluoromethanesulfonyloxy-2,3,4,5-tetrahydro-1H-benzo[d]azepine (300 mg, 0.71 mmol) and 4-[N-(tert-butoxycarbonyl)-N-(cyclohexyl)-aminomethyl]-benzylamine (335 mg, 1.05 mmol). Purify by chromatography on silica gel (150 g) eluting with hexane/EtOAc (1:0 to 9:1 gradient) to obtain 6-{-4-[N-(tert-butoxycarbonyl)-N-(cyclohexyl)-aminomethyl]-benzylamino}-7-chloro-3-(2,2,2-trifluoroacetyl)-2,3,4,5-tetrahydro-1H-benzo[d]azepine (320 mg, 76%). MS (ES+) m/z: 494 (M-Boc+H)+.

Bubble hydrogen chloride into a solution of 6-{-4-[N-(tert-butoxycarbonyl)-N-(cyclohexyl)-aminomethyl]-benzylamino}-7-chloro-3-(2,2,2-trifluoroacetyl)-2,3,4,5-tetrahydro-1H-benzo[d]azepine (355 mg, 0.6 mmol) in EtOAc (5 mL) at room temperature. Stir the mixture for 1 h, and concentrate in vacuo. Dissolve the residue in methanol (5 mL) and add water (2 mL) and $K_2CO_3$ (1 g, 7.2 mmol). Stir the mixture at room temperature overnight. Concentrate the mixture in vacuo and partition the residue between water (20 mL) and DCM (20 mL). Extract the aqueous phase with DCM (2×20 mL). Dry the combined organic extracts over $Na_2SO_4$, filter, and concentrate in vacuo. Purify by reverse phase chromatography [Phenomonex C18(2) column (5×25 cm) eluting with a gradient of water:acetonitrile (0.1% TFA in each) 9:1 through 2:3 over 50 min, 118 mL/min]. Concentrate pure fractions and apply to a SCX column (3.5 g) eluting with methanol and 3N ammonia in methanol to obtain 7-chloro-6-{4-[N-(cyclohexyl)-aminomethyl]-benzylamino}-2,3,4,5-tetrahydro-1H-benzo[d]azepine (204 mg, 86%).

Use a method similar to the General Procedure 3-1, using 7-chloro-6-{1-[4N-(cyclohexyl)-aminomethyl]-benzylamino}-2,3,4,5-tetrahydro-1H-benzo[d]azepine (204 mg, 0.51 mmol) to obtain the title compound as an off-white solid (245 mg, 93%). MS (APCI+) m/z: 398 (M+H)+.

EXAMPLES 54-55

Examples 54-55 may be prepared essentially as described in Example 53 by using 7-chloro-3-(2,2,2-trifluoroacetyl)-6-trifluoromethanesulfonyloxy-2,3,4,5-tetrahydro-1H-benzo[d]azepine and the appropriately substituted benzylamine. Overall yields and MS (ES+) data are shown in the Table below.

| Ex. | Structure | Compound | Yield (%) |
|---|---|---|---|
| 54 | 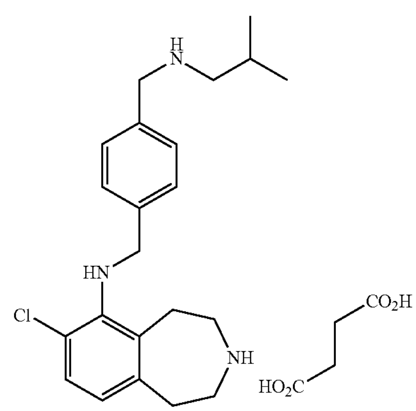 [SMILES: CC(C)CNCc1ccc(CNc2c(Cl)ccc3c2CCNCC3)cc1 ; O=C(O)CCC(=O)O] | 6-[4-(N-iso-Butyl-aminomethyl)-benzylamino]-7-chloro-2,3,4,5-tetrahydro-1H-benzo[d]azepine Succinate | 42 |

-continued

| Ex. | Structure | Compound | Yield (%) |
|---|---|---|---|
| 55 | 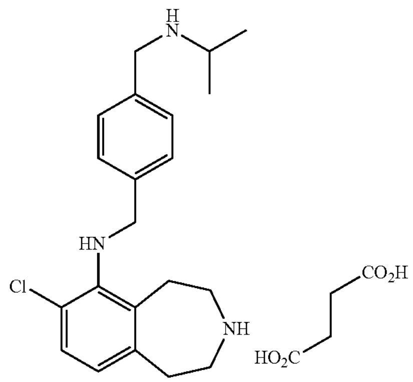 [SMILES: CC(C)NCc1ccc(CNc2c(Cl)ccc3c2CCNCC3)cc1 ; O=C(O)CCC(=O)O] | 7-Chloro-6-[4-(N-iso-propyl-aminomethyl)-benzylamino]-2,3,4,5-tetrahydro-1H-benzo[d]azepine Succinate | 52 |

EXAMPLE 56

7-Chloro-6-[4-(N-methyl-iso-propylamino-methyl)-benzylamino]-2,3,4,5-tetrahydro-1H-benzo[d]azepine Succinate

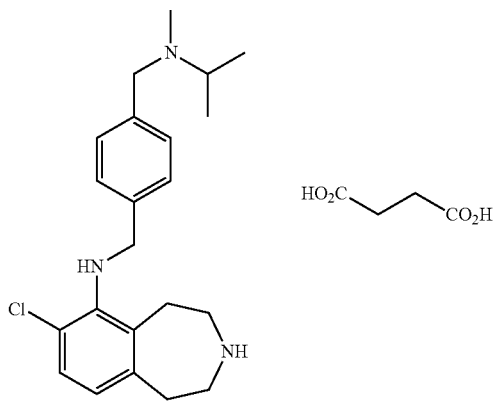 [SMILES: CC(C)N(C)Cc1ccc(CNc2c(Cl)ccc3c2CCNCC3)cc1 ; O=C(O)CCC(=O)O]

Use a method similar to the General Procedure 1-2 to couple 7-chloro-3-(2,2,2-trifluoroacetyl)-6-trifluoromethanesulfonyloxy-2,3,4,5-tetrahydro-1H-benzo[d]azepine (500 mg, 1.18 mmol) with 4-[(N-methyl-iso-propylamino)-methyl]-benzylamine (270 mg, 1.41 mmol) in toluene (10 mL). Purify by chromatography on silica gel (75 g) eluting with a gradient of 100% DCM to 9:1 DCM/(chloroform:methanol:concentrated NH₄OH 80:18:2) to obtain 7-chloro-6-{4-[(N-methyl-iso-propylamino)-methyl]-benzylamino}-3-(2,2,2-trifluoroacetyl)-2,3,4,5-tetrahydro-1H-benzo[d]azepine (350 mg, 64%). MS (APCI) m/z: 468 (M+H)⁺.

Dissolve 7-chloro-6-{4-[(N-methyl-iso-propylamino)-methyl]-benzylamino}-3-(2,2,2-trifluoroacetyl)-2,3,4,5-tetrahydro-1H-benzo[d]azepine (350 mg, 0.75 mmol) in concentrated NH₄OH. (10 mL) and MeOH (10 mL). Stir the reaction mixture overnight. Concentrate the mixture in vacuo. Purify by chromatography on silica gel (45 g) eluting with a gradient of 100% DCM to 1:1 DCM/(chloroform:methanol: concentrated NH₄OH 80:18:2) to obtain 7-chloro-6-{4-[(N-methyl-iso-propylamino)-methyl]-benzylamino}-2,3,4,5-tetrahydro-1H-benzo[d]azepine (260 mg, 93%). MS (APCI+) m/z: 372 (M+11)⁺.

Dissolve 7-chloro-6-{4-[(N-methyl-iso-propylamino)-methyl]-benzylamino}-2,3,4,5-tetrahydro-1H-benzo[d]azepine (250 mg, 0.67 mmol) in methanol and add succinic acid (75 mg, 0.63 mmol). Stir the mixture until homogeneous. Concentrate the mixture in vacuo, dissolve in water, and freeze dry the solution to obtain the title compound (325 mg, 95%). MS (APCI+) m/z: 372 (M+H)⁺.

EXAMPLE 57

7-Chloro-6-[5-(N-cyclohexyl-aminomethyl)-pyridin-2-yl-methyl-amino]-2,3,4,5-tetrahydro-1H-benzo[d]azepine Succinate

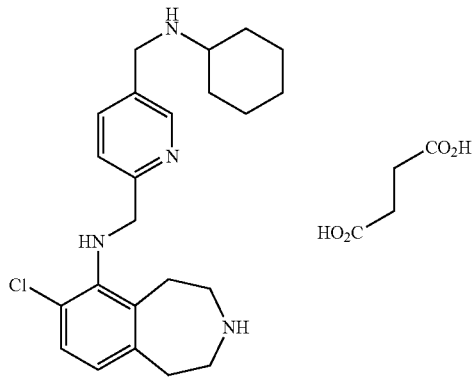 [SMILES: Clc1ccc2c(c1NCc1ccc(CNC3CCCCC3)cn1)CCNCC2 ; O=C(O)CCC(=O)O]

Use a method similar to the General Procedure 1-2 to couple 7-chloro-3-(2,2,2-trifluoroacetyl)-6-trifluoromethanesulfonyloxy-2,3,4,5-tetrahydro-1H-benzo[d]azepine (400 mg, 0.94 mmol) and 6-aminomethyl-3-[N-(cyclohexyl)-N-(2,2,2-trifluoroacetyl)-aminomethyl]-pyridine (440 mg, 1.41 mmol). Purify the crude mixture by chromatography on silica gel (150 g) eluting with hexane/EtOAc (1:0 to 7:3 gradient) to obtain 7-chloro-6-{5-[(N-cyclohexyl-N-(2,2,2-trifluoroacetyl)-aminomethyl)-pyridin-2-yl-methyl]-amino}-3-(2,2,2-trifluoroacetyl)-2,3,4,5-tetrahydro-1H-benzo[d]azepine as an oil (350 mg, 63%). MS (APCI+) m/z: 591 (M+H)⁺.

Dissolve 7-chloro-6-{5-[(N-cyclohexyl-N-(2,2,2-trifluoroacetyl)-aminomethyl)-pyridin-2-yl-methyl]-amino}-3-(2,2,2-trifluoroacetyl)-2,3,4,5-tetrahydro-1H-benzo[d]azepine (350 mg, 0.59 mmol) in K₂CO₃ (400 mg, 2.9 mmol), methanol (10 mL), and water (10 mL), and stir for 12 h at 60° C. Extract with DCM and purify the crude mixture by SCX chromatography (4 g) eluting with methanol and 3N ammonia in methanol to obtain 7-chloro-6-{5-[(N-cyclohexyl-aminomethyl)-pyridin-2-yl-methyl]-amino}-2,3,4,5-tetrahydro-1H-benzo[d]azepine as an oil (210 mg, 89%). MS (APCI+) m/z: 399 (M+H)$^+$.

Use a method similar to the General Procedure 3-1, using 7-chloro-6-{5-[(N-cyclohexyl-aminomethyl)-pyridin-2-yl-methyl]-amino}-2,3,4,5-tetrahydro-1H-benzo[d]azepine (210 mg, 0.53 mmol) to obtain the title compound as a yellow solid (260 mg, 96%). MS (APCI+) m/z: 399 (M+H)$^+$.

EXAMPLE 58

7-Chloro-6-[6-(piperidin-1-ylmethyl)-pyridin-3-yl-methyl-amino]-2,3,4,5-tetrahydro-1H-benzo[d]azepine Succinate

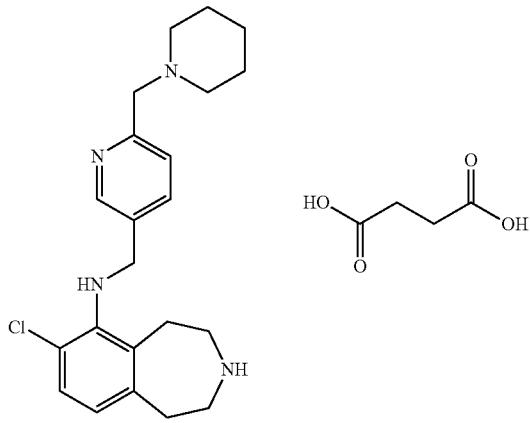 [SMILES: Clc1ccc2c(c1NCc1ccc(CN3CCCCC3)nc1)CCNCC2 ; O=C(O)CCC(=O)O]

Use a method similar to the General Procedure 1-2 to couple 7-chloro-3-(2,2,2-trifluoroacetyl)-6-trifluoromethanesulfonyloxy-2,3,4,5-tetrahydro-1H-benzo[d]azepine (340 mg, 0.799 mmol) and 5-aminomethyl-2-(piperidin-1-ylmethyl)-pyridine (246 mg, 1.19 mmol). Purify by chromatography on silica gel (80 g) eluting with hexane/EtOAc (1:0 to 1:2 gradient over 1.25 h, 80 mL/min) to obtain 7-chloro-6-{6-[(piperidin-1-ylmethyl)-pyridin-3-yl-methyl]-amino}-3-(2,2,2-trifluoroacetyl)-2,3,4,5-tetrahydro-1H-benzo[d]azepine as a light yellow oil (305 mg, 79%). MS (APCI+) m/z: 481 (M+H)$^+$.

Add 7-chloro-6-{6-[(piperidin-1-ylmethyl)-pyridin-3-yl-methyl]-amino}-3-(2,2,2-trifluoroacetyl)-2,3,4,5-tetrahydro-1H-benzo[d]azepine (300 mg, 0.623 mmol) in methanol (10 mL). Add lithium hydroxide hydrate (456 mg, 19.0 mmol) and stir at room temperature overnight. Concentrate in vacuo and dissolve the residue in water (10 mL). Extract the aqueous layer with DCM (3×15 mL). Dry the combined organic extracts over Na$_2$SO$_4$, filter and concentrate in vacuo to provide 7-chloro-6-{6-[(piperidin-1-ylmethyl)-pyridin-3-yl-methyl]-amino}-2,3,4,5-tetrahydro-1H-benzo[d]azepine as an off-white foam (234 mg, 96%). MS (APCI+) m/z: 385 (M+H)$^+$.

Use a method similar to the General Procedure 3-1, using 7-chloro-6-{6-[(piperidin-1-ylmethyl)-pyridin-3-yl-methyl]-amino}-2,3,4,5-tetrahydro-1H-benzo[d]azepine (230 mg, 0.597 mmol) to obtain the title compound as an off-white solid (303 mg, 100%). MS (APCI+) m/z: 385 (M+H)$^+$.

EXAMPLE 59

7-Chloro-6-[4-(2,2-dimethyl-propionylamino)-benzylamino]-2,3,4,5-tetrahydro-1H-benzo[d]-azepine Succinate

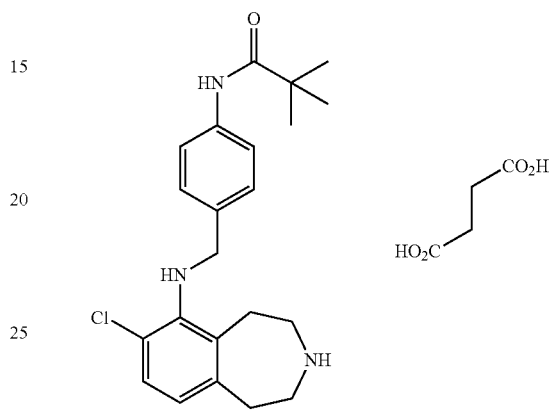

Use a method similar to the General Procedure 1-3 to couple 7-chloro-3-(2,2,2-trifluoroacetyl)-6-trifluoromethanesulfonyloxy-2,3,4,5-tetrahydro-1H-benzo[d]azepine (0.33 g, 0.78 mmol) with a solution of 4-(2,2-dimethyl-propionylamino)-benzylamine (0.32 g, 1.6 mmol) in anhydrous toluene/dioxane (4:1, 10 mL). Purify the crude mixture by chromatography on silica gel eluting with hexane/EtOAc (1:0 to 7:3 gradient over 30 min; 35 mL/min) and then by SCX chromatography to obtain 7-chloro-6-[4-(2,2-dimethyl-propionylamino)-benzylamino]-3-(2,2,2-trifluoroacetyl)-2,3,4,5-tetrahydro-1H-benzo[d]azepine as a yellow oil (0.266 g, 70%). MS (ES+) m/z: 482 (M+H)$^+$.

Use a method similar to the General Procedure 2-1 to deprotect 7-chloro-6-[4-(2,2-dimethyl-propionylamino)-benzylamino]-3-(2,2,2-trifluoroacetyl)-2,3,4,5-tetrahydro-1H-benzo[d]azepine (0.259 g, 0.538 mmol). Purify the crude mixture by chromatography on silica gel eluting with DCM/2M ammonia in methanol (1:0 to 9:1 gradient over 30 min; 9:1 over 3 min; 9:1 to 4:1 gradient over 30 min and 4:1 over 3 min; 35 mL/min) to obtain 7-chloro-6-[4-(2,2-dimethyl-propionylamino)-benzylamino]-2,3,4,5-tetrahydro-1H-benzo[d]-azepine as a white foam (0.173 g, 84%).

Use a method similar to the General Procedure 3-1, using 7-chloro-6-[4-(2,2-dimethyl-propionylamino)-benzylamino]-2,3,4,5-tetrahydro-1H-benzo[d]-azepine (0.171 g, 0.443 mmol) to obtain the title compound as a white solid (215.5 mg, 96%). MS (ES+) m/z: 386.2 (M+H)$^+$.

EXAMPLES 60-61

Examples 60-61 may be prepared essentially as described in Example 59 using 7-chloro-3-(2,2,2-trifluoroacetyl)-6-trifluoromethanesulfonyloxy-2,3,4,5-tetrahydro-1H-benzo[d]azepine and the appropriately substituted benzylamine. Overall yields and MS (ES+) data are shown in the Table below.

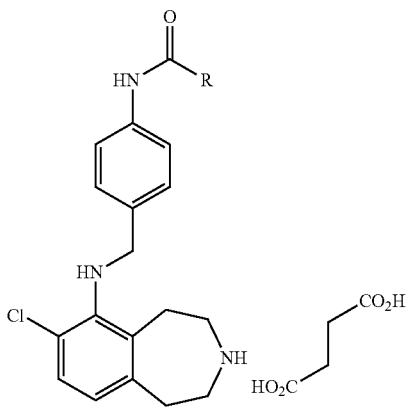

| Ex. | R | Compound | Yield (%) | MS (ES+) m/z |
|---|---|---|---|---|
| 60 | Cyclopropyl | 7-Chloro-6-[4-(cyclopropanecarbonyl-amino)-benzylamino]-2,3,4,5-tetrahydro-1H-benzo[d]-azepine Succinate | 47 | 370 (M + H)+ |
| 61 | 1-Methyl-cyclopropyl | 7-Chloro-6-[4-(1-methyl-cyclopropanecarbonyl]-amino)-benzylamino]-2,3,4,5-tetrahydro-1H-benzo[d]-azepine Succinate | 35 | 384 (M + H)+ |
| 62 | 2,2,3,3-Tetramethyl-cyclopropyl | 7-Chloro-6-[4-(2,2,3,3-tetramethyl-cyclopropanecarbonyl-amino)-benzylamino]-2,3,4,5-tetrahydro-1H-benzo[d]-azepine Succinate | 49 | 426 (M + H)+ |

EXAMPLES 63 AND 64

(+)-7-Chloro-6-[4-(2-methyl-cyclopropanecarbonyl-amino)-benzylamino]-2,3,4,5-tetrahydro-1H-benzo[d]-azepine Succinate and (−)-7-Chloro-6-[4-(2-methyl-cyclopropanecarbonyl-amino)-benzylamino]-2,3,4,5-tetrahydro-1H-benzo[d]-azepine Succinate

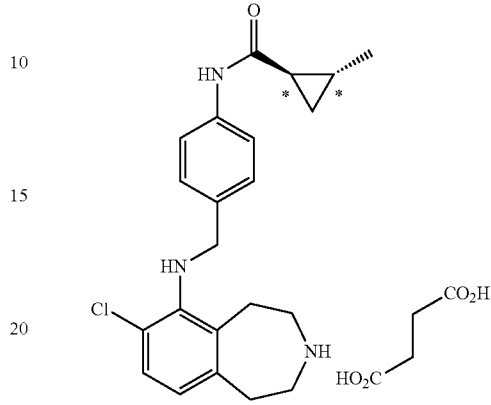

Use a method similar to the General Procedure 1-3 to couple 7-chloro-3-(2,2,2-trifluoroacetyl)-6-trifluoromethanesulfonyloxy-2,3,4,5-tetrahydro-1H-benzo[d]azepine (0.94 g, 2.2 mmol) with a solution of (±)-trans-4-[(2-methyl-cyclopropanecarbonyl)-amino]-benzylamine (0.899 g, 4.403 mmol) in anhydrous toluene (22 mL) and anhydrous dioxane (5.8 mL). Purify by chromatography on silica gel to afford (±)-trans-7-chloro-6-{4-[(2-methyl-cyclopropanecarbonyl)-amino]-benzylamino}-3-(2,2,2-trifluoroacetyl)-2,3,4,5-tetrahydro-1H-benzo[d]-azepine (0.834 g, 79%) as an orange oil.

Separate both enantiomers from the racemic mixture (0.747 g) by chiral chromatography (Chiralpak AD-H, 4.6× 150 mm column; elute with 2B-3 ethanol (100%); 0.6 mL/min) to afford Isomer 1 (330 mg, 62%) and Isomer 2 (265 mg, 50%).

Use a method similar to the General Procedure 2-1 to deprotect each isomer independently and a method similar to the General Procedure 3-1 to prepare independently the title compounds. MS (ES+) data and optical rotation for each enantiomer are shown in the Table below.

| Ex. | Structure | Compound | MS (ES+) m/z [α]$_D$ (c, solvent) |
|---|---|---|---|
| 63 | 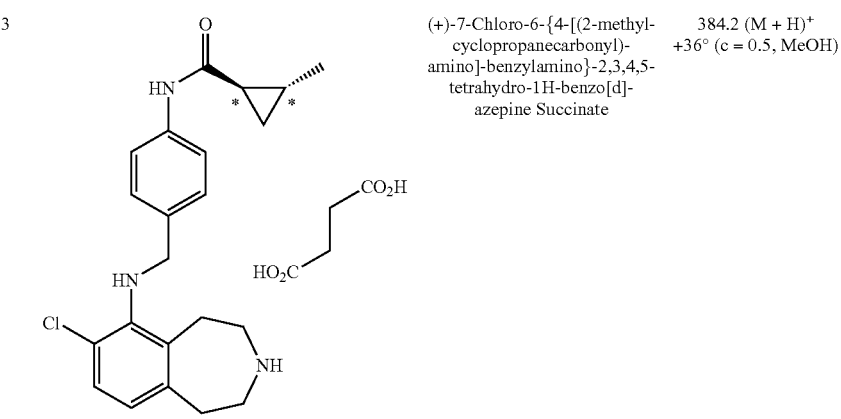 | (+)-7-Chloro-6-{4-[(2-methyl-cyclopropanecarbonyl)-amino]-benzylamino}-2,3,4,5-tetrahydro-1H-benzo[d]-azepine Succinate | 384.2 (M + H)+ +36° (c = 0.5, MeOH) |

| Ex. | Structure | Compound | MS (ES+) m/z [α]$_D$ (c, solvent) |
|---|---|---|---|
| 64 | 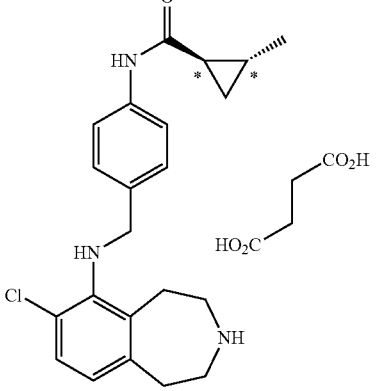 | (−)-7-Chloro-6-{4-[(2-methyl-cyclopropanecarbonyl)-amino]-benzylamino}-2,3,4,5-tetrahydro-1H-benzo[d]-azepine Succinate | 384.2 (M + H)$^+$ −40° (c = 0.5, MeOH) |

EXAMPLE 65

7-Chloro-6-[4-(N-methyl-2,2-dimethyl-propionylamino)-benzylamino]-2,3,4,5-tetrahydro-1H-benzo[d]-azepine Succinate

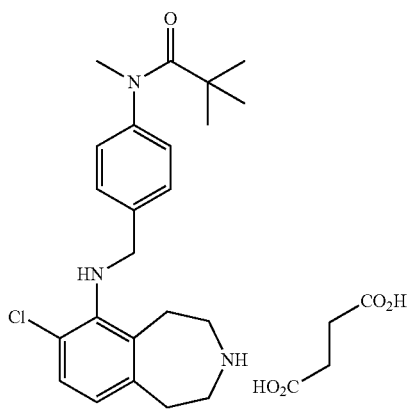 [SMILES: CN(C(=O)C(C)(C)C)c1ccc(CNc2c(Cl)ccc3c2CCNCC3)cc1 ; O=C(O)CCC(=O)O]

Use a method similar to the General Procedure 1-2 to couple 7-chloro-3-(2,2,2-trifluoroacetyl)-6-trifluoromethanesulfonyloxy-2,3,4,5-tetrahydro-1H-benzo[d]azepine (0.23 g, 0.53 mmol) with a solution of 4-(N-methyl-2,2-dimethyl-propionylamino)-benzylamine (0.23 g, 1.06 mmol) in anhydrous toluene/dioxane (4:1, 7 mL). Purify by chromatography on silica gel eluting with hexane/EtOAc (1:0 to 17:3 gradient over 30 min, 17:3 over 30 min, 17:3 to 7:3 gradient over 30 min and 7:3 over 30 min; 35 mL/min) to obtain 7-chloro-6-[4-(N-methyl-2,2-dimethyl-propionylamino)-benzylamino]-3-(2,2,2-trifluoroacetyl)-2,3,4,5-tetrahydro-1H-benzo[d]-azepine as a yellow oil (0.235 g, 90%).

Use a method similar to the General Procedure 2-1 to deprotect 7-chloro-6-[4-(N-methyl-2,2-dimethyl-propionylamino)-benzylamino]-3-(2,2,2-trifluoroacetyl)-2,3,4,5-tetrahydro-1H-benzo[d]-azepine (0.217 g, 0.437 mmol). Purify by chromatography on silica gel eluting with DCM/2M ammonia in methanol (1:0 to 9:1 over 30 min, 9:1 over 3 min; 35 mL/min) to obtain 7-chloro-6-[4-(N-methyl-2,2-dimethyl-ethyl-propionylamino)-benzylamino]-2,3,4,5-tetrahydro-1H-benzo[d]-azepine as a colorless oil (0.127 g, 73%). Use a method similar to the General Procedure 3-1, using 7-chloro-6-[4-(N-methyl-2,2-dimethyl-propionylamino)-benzylamino]-2,3,4,5-tetrahydro-1H-benzo[d]-azepine (0.124 g, 0.309 mmol) to obtain the title compound as a white solid (154 mg, 96%). MS (ES+) m/z: 400.2 (M+H)$^+$.

EXAMPLE 66

7-Chloro-6-[4-(cyclohexanecarbonyl-amino)-benzylamino]-2,3,4,5-tetrahydro-1H-benzo[d]-azepine Succinate

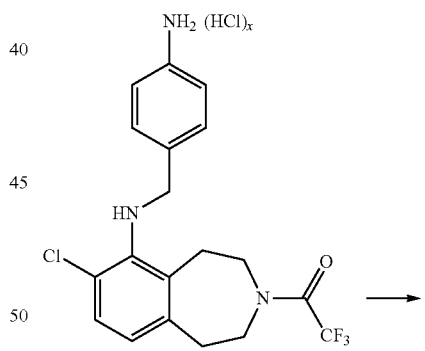

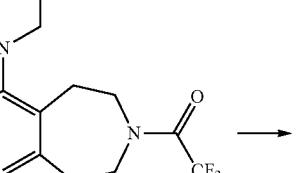

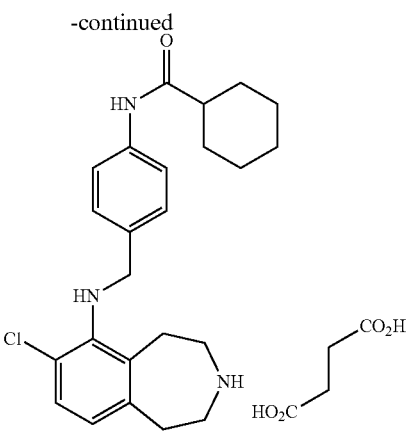

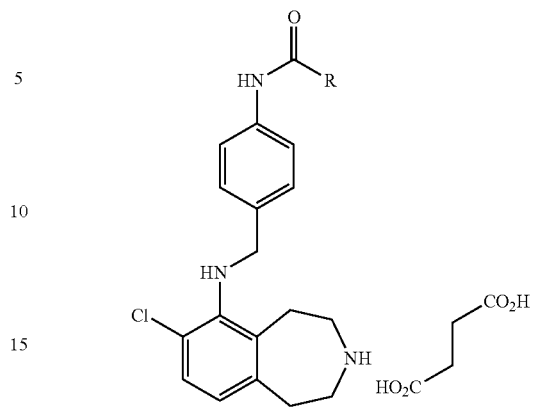

| Ex. | R | Compound | Yield (%) | MS (ES+) m/z |
|---|---|---|---|---|
| 67 | Cyclopentyl | 7-Chloro-6-[4-(cyclopentanecarbonyl-amino)-benzylamino]-2,3,4,5-tetrahydro-1H-benzo[d]-azepine Succinate | 59 | 398.3 (M + H)+ |
| 68 | Cycloheptyl | 7-Chloro-6-[4-(cycloheptanecarbonyl-amino)-benzylamino]-2,3,4,5-tetrahydro-1H-benzo[d]-azepine Succinate | 57 | 426.2 (M + H)+ |

Add a solution of triethylamine (24 mg, 0.117 mmol) in DCM (3.6 mL) to a heterogeneous mixture of 6-(4-aminobenzylamino)-7-chloro-3-(2,2,2-trifluoroacetyl)-2,3,4,5-tetrahydro-1H-benzo[d]-azepine hydrochloride (181 mg, 0.385 mmol) in anhydrous DCM (18.2 mL) at 0° C. Add a solution of cyclohexanecarbonyl chloride (56 mg, 0.39 mmol) in anhydrous DCM (3.6 mL). Stir at 0° C. for 15 min and then at room temperature overnight. Partition the reaction mixture between DCM (100 mL) and water (50 mL). Extract the aqueous phase with DCM (50 mL). Wash the combined organic extracts with water (3×25 mL), dry over Na$_2$SO$_4$, filter and concentrate in vacuo. Purify by chromatography on silica gel eluting with hexane/EtOAc (1:0 to 3:1 over 30 min; 3:1 over 3 min; 3:1 to 1:1 over 30 min and 1:1 over 3 min; 35 mL/min) to obtain 7-chloro-6-[4-(cyclohexanecarbonyl-amino)-benzylamino]-3-(2,2,2-triluoroacetyl)-2,3,4,5-tetrahydro-1H-benzo[d]-azepine (0.161 g, 83%). MS (ES+) m/z: 508.3 (M+H)+.

Use a method similar to the General Procedure 2-3, using 7-chloro-6-[4-(cyclohexanecarbonyl-amino)-benzylamino]-3-(2,2,2-triluoroacetyl)-2,3,4,5-tetrahydro-1H-benzo[d]-azepine (0.120 g, 0.236 mmol) to obtain 7-chloro-6-[4-(cyclohexanecarbonyl-amino)-benzylamino]-2,3,4,5-tetrahydro-1H-benzo[d]-azepine (74 mg, 76%). MS (ES+) m/z: 412.3 (M+H)+. Use a method similar to the General Procedure 3-1 to obtain the title compound as a white solid (95 mg, 100%). MS (ES+) m/z: 412.3 (M+H)+.

EXAMPLES 67-68

Examples 67-68 may be prepared essentially as described in Example 66 using 6-(4-amino-benzylamino)-7-chloro-3-(2,2,2-trifluoroacetyl)-2,3,4,5-tetrahydro-1H-benzo[d]-azepine hydrochloride and the appropriate carbonyl chloride. Overall yields and MS (ES+) data are shown in the Table below.

EXAMPLE 69

7-Chloro-6-[4-(2,2-dimethyl-propionylamino-methyl)-benzylamino]-2,3,4,5-tetrahydro-1H-benzo[d] azepine (L)-Tartrate

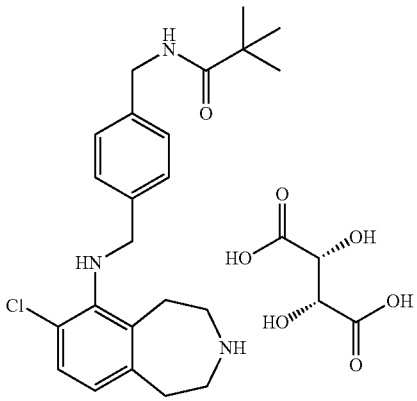 [SMILES: CC(C)(C)C(=O)NCc1ccc(CNc2c(Cl)ccc3c2CCNCC3)cc1 ; O=C(O)[C@H](O)[C@@H](O)C(=O)O]

Use a method similar to the General Procedure 1-2 to couple 7-chloro-3-(2,2,2-trifluoroacetyl)-6-trifluoromethanesulfonyloxy-2,3,4,5-tetrahydro-1H-benzo[d] azepine (299 mg, 0.704 mmol) and 4-[(2,2-dimethyl-propionylamino)-methyl]-benzylamine (310 mg, 1.41 mmol). Purify the crude mixture by chromatography on silica gel eluting with hexane/EtOAc (3:2) to obtain 7-chloro-6-{4-[(2,2-dimethyl-propionylamino)-methyl]-benzylamino}-3-(2,2,2-trifluoroacetyl)-2,3,4,5-tetrahydro-1H-benzo[d]azepine as a yellow oil (265 mg, 76%). MS (ES+) m/z: 496 (M+H)+.

Use a method similar to the General Procedure 2-1 to deprotect 7-chloro-6-{4-[(2,2-dimethyl-propionylamino)- methyl]-benzylamino}-3-(2,2,2-trifluoroacetyl)-2,3,4,5-tetrahydro-1H-benzo[d]azepine (265 mg, 0.53 mmol). Purify by reverse phase HPLC [Xterra MS C18 column, 100×19 mm, 5 ☐M; flow rate: 25 mL/min, eluting with 3:7 to 6:4 acetonitrile/ammonium bicarbonate (20 mM at pH=8)] to obtain 7-chloro-6-{4-[(2,2-dimethyl-propionylamino)-methyl]-benzylamino}-2,3,4,5-tetrahydro-1H-benzo[d]azepine as a yellow oil (155 mg, 73%). MS (ES+) m/z: 400 (M+H)$^+$.

Use a method similar to the General Procedure 3-2, using 7-chloro-6-{4-[(2,2-dimethyl-propionylamino)-methyl]-benzylamino}-2,3,4,5-tetrahydro-1H-benzo[d]azepine (150 mg, 0.375 mmol) to obtain the title compound as a white solid (206 mg, 99%). MS (ES+) m/z: 400 (M+H)$^+$.

EXAMPLE 70

7-Chloro-6-[4-(cyclopropanecarbonyl-amino-methyl)-benzylamino]-2,3,4,5-tetrahydro-1H-benzo[d]azepine Succinate

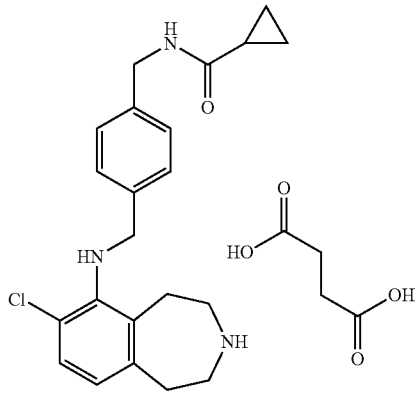 [SMILES: O=C(NCc1ccc(CNc2c(Cl)ccc3c2CCNCC3)cc1)C1CC1 ; O=C(O)CCC(=O)O]

Use a method similar to the General Procedure 1-2 to couple 7-chloro-3-(2,2,2-trifluoroacetyl)-6-trifluoromethanesulfonyloxy-2,3,4,5-tetrahydro-1H-benzo[d]azepine (458 mg, 1.076 mmol) with 4-[(cyclopropanecarbonyl-amino)-methyl]-benzylamine (275 mg, 1.346 mmol) using tris(dibenzylideneacetone)dipalladium(0) (99 mg, 0.108 mmol), BINAP (134 mg, 0.215 mmol) and cesium carbonate (710 mg, 2.17 mmol) in toluene (17 mL). Purify by chromatography on silica gel (80 g, pre-packed cartridge) eluting with hexane/EtOAc (1:0 over 5 min, 49:1 over 5 min, 19:1 over 5 min, 9:1 over 5 min, 85:15 over 5 min, 3:1 over 30 min, 1:1; 50 mL/min) to obtain 7-chloro-6-{4-[(cyclopropanecarbonyl-amino)-methyl]-benzylamino}-3-(2,2,2-trifluoroacetyl)-2,3,4,5-tetrahydro-1H-benzo[d]azepine (335 mg, 65%) as a white solid. MS (ES+) m/z: 480 (M+H)$^+$.

Dissolve 7-chloro-6-{4-[(cyclopropanecarbonyl-amino)-methyl]-benzylamino}-3-(2,2,2-trifluoroacetyl)-2,3,4,5-tetrahydro-1H-benzo[d]azepine (335 mg, 0.698 mmol) in MeOH (10 mL). Add LiOH.H$_2$O (293 mg, 6.98 mmol) and stir overnight. Partition the reaction mixture between chloroform and water. Separate the aqueous phase and extract three times with chloroform and once with chloroform/iso-propanol (3:1). Dry the combined organic extracts over MgSO$_4$, filter and concentrate in vacuo. Purify the crude mixture by chromatography on silica gel (40 g, pre-packed cartridge) eluting with DCM/(chloroform:methanol:concentrated NH$_4$OH 80:18:2) (1:0 over 5 min, 19:1 over 5 min, 9:1 over 5 min, 85:15; 50 mL/min) to obtain 7-chloro-6-{-4-[(cyclopropanecarbonyl-amino)-methyl]-benzylamino}-2,3,4,5-tetrahydro-1H-benzo[d]azepine (244 mg, 91%). MS (APCI+) m/z: 384 (M+H)$^+$.

Use a method similar to the General Procedure 3-1, using 7-chloro-6-{4-[(cyclopropanecarbonyl-amino)-methyl]-benzylamino}-2,3,4,5-tetrahydro-1H-benzo[d]azepine (240 mg, 0.625 mmol) to obtain the title compound (323 mg, 100%). MS (APCI+) m/z: 384 (M+H)$^+$.

EXAMPLE 71

7-Chloro-6-{4-[2-(2,2-dimethyl-propionylamino)-ethyl]-benzylamino}-2,3,4,5-tetrahydro-1H-benzo[d]azepine (L)-Tartrate

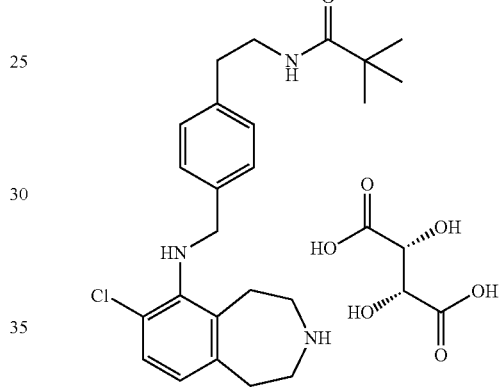

Use a method similar to the General Procedure 1-2 to couple 7-chloro-3-(2,2,2-trifluoroacetyl)-6-trifluoromethanesulfonyloxy-2,3,4,5-tetrahydro-1H-benzo[d]azepine (106 mg, 0.251 mmol) and 4-[2-(2,2-dimethyl-propionylamino)-ethyl]-benzylamine (110 mg, 0.427 mmol). Purify the crude mixture by chromatography on silica gel eluting with hexane/EtOAc (6:4) to obtain 7-chloro-6-{4-[2-(2,2-dimethyl-propionylamino)-ethyl]-benzylamino}-3-(2,2,2-trifluoroacetyl)-2,3,4,5-tetrahydro-1H-benzo[d]azepine as a yellow oil (90 mg, 70%). MS (ES+) m/z: 510 (M+H)$^+$.

Use a method similar to the General Procedure 2-1, using 7-chloro-6-{4-[2-(2,2-dimethyl-propionylamino)-ethyl]-benzylamino}-3-(2,2,2-trifluoroacetyl)-2,3,4,5-tetrahydro-1H-benzo[d]azepine (90 mg, 0.176 mmol) to obtain 7-chloro-6-{4-[2-(2,2-dimethyl-propionylamino)-ethyl]-benzylamino}-2,3,4,5-tetrahydro-1H-benzo[d]azepine (70 mg, 96%) as a yellow oil suitable for use without additional purification.

Use a method similar to the General Procedure 3-2, using 7-chloro-6-{-4-[2-(2,2-dimethyl-propionylamino)-ethyl]-benzylamino}-2,3,4,5-tetrahydro-1H-benzo[d]azepine (70 mg, 0.169 mmol) to obtain the title compound as a white solid (95 mg, 99%). MS (ES+) m/z: 414 (M+H)$^+$.

EXAMPLE 72

7-Chloro-6-[4-(iso-propylcarbamoyl-methyl)-benzylamino]-2,3,4,5-tetrahydro-1H-benzo[d]azepine (L)-Tartrate

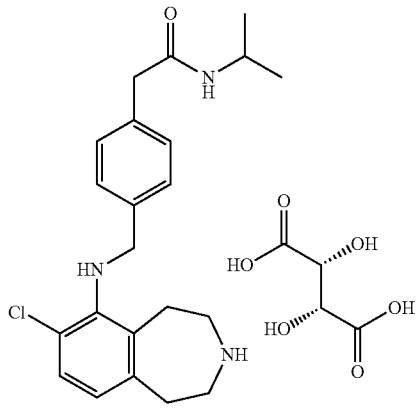 [SMILES: CC(C)NC(=O)Cc1ccc(CNc2c(Cl)ccc3c2CCNCC3)cc1 ; O=C(O)[C@H](O)[C@@H](O)C(=O)O]

Use a method similar to the General Procedure 1-2 to couple 7-chloro-3-(2,2,2-trifluoroacetyl)-6-trifluoromethanesulfonyloxy-2,3,4,5-tetrahydro-1H-benzo[d]azepine (162 mg, 0.38 mmol) and 4-(iso-propylcarbamoyl-methyl)-benzylamine (157 mg, 0.76 mmol). Purify by chromatography on silica gel eluting with hexane/EtOAc (9:1, 4:1, 2:1 and 1:1) to obtain 7-chloro-6-[4-(iso-propylcarbamoyl-methyl)-benzylamino]-3-(2,2,2-trifluoroacetyl)-2,3,4,5-tetrahydro-1H-benzo[d]azepine as an oil (117 mg, 64%).

Use a method similar to the General Procedure 2-1, using 7-chloro-6-[4-(iso-propylcarbamoyl-methyl)-benzylamino]-3-(2,2,2-trifluoroacetyl)-2,3,4,5-tetrahydro-1H-benzo[d]azepine (117 mg, 0.24 mmol) to obtain 7-chloro-6-[4-(iso-propylcarbamoyl-methyl)-benzylamino]-2,3,4,5-tetrahydro-1H-benzo[d]azepine as an oil (83 mg, 89%) suitable for use without additional purification.

Use a method similar to the General Procedure 3-2, using 7-chloro-6-[4-(iso-propylcarbamoyl-methyl)-benzylamino]-2,3,4,5-tetrahydro-1H-benzo[d]azepine (45 mg, 0.11 mmol) to obtain the title compound as a white solid (106 mg, 92%). MS (ES+) m/z: 386 (M+H)$^+$.

EXAMPLES 73-77

Examples 73-77 may be prepared essentially as described in Example 72 by using 7-chloro-3-(2,2,2-trifluoroacetyl)-6-trifluoromethanesulfonyloxy-2,3,4,5-tetrahydro-1H-benzo[d]azepine and the appropriately substituted benzylamine. Overall yields and MS (ES+) data are shown in the Table below.

| Ex. | Structure | Compound | Yield (%) | MS (ES+) m/z |
|---|---|---|---|---|
| 73 | 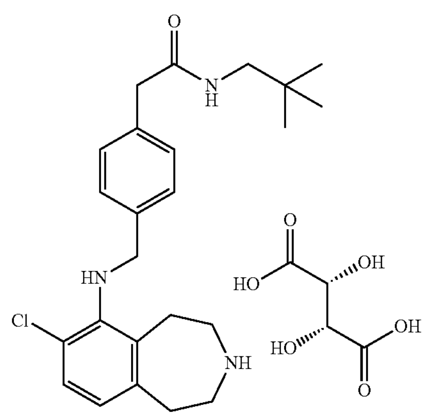 | 7-Chloro-6-{4-[(2,2-dimethylpropyl-carbamoyl)-methyl]-benzylamino}-2,3,4,5-tetrahydro-1H-benzo[d]azepine (L)-Tartrate | 41 | 414 (M + H)$^+$ |
| 74 | 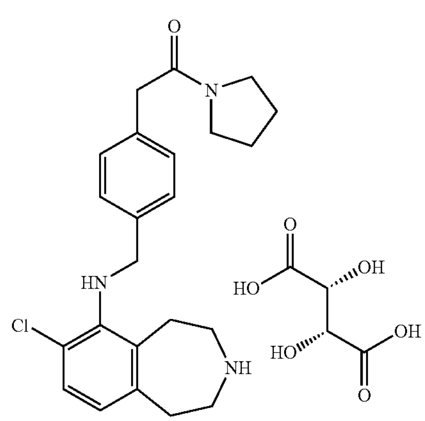 | 7-Chloro-6-[4-(2-oxo-2-pyrrolidin-1-yl-ethyl)-benzylamino]-2,3,4,5-tetrahydro-1H-benzo[d]azepine (L)-Tartrate | 64 | 398 (M + H)$^+$ |

| Ex. | Structure | Compound | Yield (%) | MS (ES+) m/z |
|---|---|---|---|---|
| 75 | 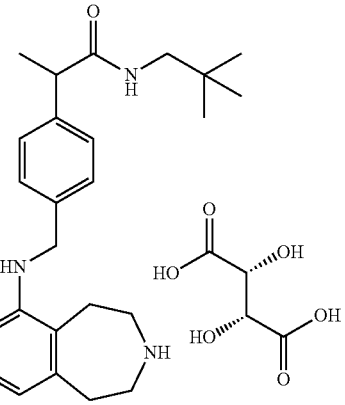 | (±)-7-Chloro-6-{4-[1-(2,2-dimethylpropyl-carbamoyl)-ethyl]-benzylamino}-2,3,4,5-tetrahydro-1H-benzo[d]azepine (L)-Tartrate | 50 | 428 (M + H)+ |
| 76 | 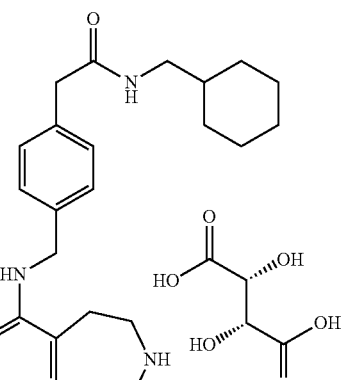 | 7-Chloro-6-{4-[(cyclohexylmethyl-carbamoyl)-methyl]-benzylamino}-2,3,4,5-tetrahydro-1H-benzo[d]azepine (L)-Tartrate | 21 | 440 (M + H)+ |
| 77 | 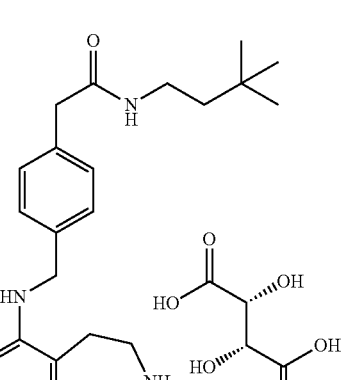 | 7-Chloro-6-{4-[(3,3-dimethylbutyl-carbamoyl)-methyl]-benzylamino}-2,3,4,5-tetrahydro-1H-benzo[d]azepine (L)-Tartrate | 44 | 428 (M + H)+ |

EXAMPLE 78

(R)-7-Chloro-6-{4-[(1-methyl-2,2,2-trifluoro-ethyl-carbamoyl)-methyl]-benzylamino}-2,3,4,5-tetrahydro-1H-benzo[d]azepine (L)-Tartrate

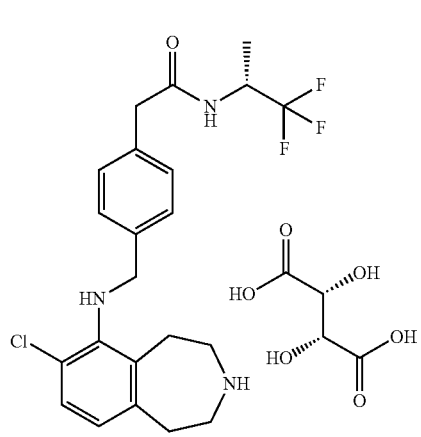 [SMILES: C[C@@H](NC(=O)Cc1ccc(CNc2c(Cl)ccc3c2CCNCC3)cc1)C(F)(F)F ; O=C(O)[C@H](O)[C@@H](O)C(=O)O]

Use a method similar to the General Procedure 1-2 to couple 7-chloro-3-(2,2,2-trifluoroacetyl)-6-trifluoromethanesulfonyloxy-2,3,4,5-tetrahydro-1H-benzo[d]azepine (84 mg, 0.196 mmol) and (R)-4-[(1-methyl-2,2,2-trifluoro-ethylcarbamoyl)-methyl]-benzylamine (102 mg, 0.39 mmol). Purify by chromatography on silica gel eluting with hexane/EtOAc (4:1) to obtain (R)-7-chloro-6-{4-[(1-methyl-2,2,2-trifluoro-ethylcarbamoyl)-methyl]-benzylamino}-3-(2,2,2-trifluoroacetyl)-2,3,4,5-tetrahydro-1H-benzo[d]azepine as a yellow oil (47 mg, 45%). MS (ES+) m/z: 536 (M+H)+.

Use a method similar to the General Procedure 2-1 to deprotect (R)-7-chloro-6-{4-[(1-methyl-2,2,2-trifluoro-ethylcarbamoyl)-methyl]-benzylamino}-3-(2,2,2-trifluoroacetyl)-2,3,4,5-tetrahydro-1H-benzo[d]azepine (45 mg, 0.08 mmol). Purify by reverse phase HPLC [Xterra MS C18 column, 100×19 mm, 5 µM; flow rate: 25 mL/min, eluting with 3:7 to 9:11 acetonitrile/ammonium bicarbonate (10 mM at pH=8)] to obtain (R)-7-chloro-6-{4-[(1-methyl-2,2,2-trifluoro-ethylcarbamoyl)-methyl]-benzylamino}-2,3,4,5-tetrahydro-1H-benzo[d]azepine as a yellow oil (15 mg, 42%).

Use a method similar to the General Procedure 3-2, using (R)-7-chloro-6-{4-[(1-methyl-2,2,2-trifluoro-ethylcarbamoyl)-methyl]-benzylamino}-2,3,4,5-tetrahydro-1H-benzo[d]azepine (15 mg, 0.03 mmol) to obtain the title compound as a white solid (20 mg, 99%). MS (ES+) m/z: 440 (M+H)+. $[\alpha]_D = -4°$ (c=0.225, MeOH).

EXAMPLE 79

6-{4-[2-(tert-Butylcarbamoyl)-ethyl]-benzylamino}-7-chloro-2,3,4,5-tetrahydro-1H-benzo[d]azepine (L)-Tartrate

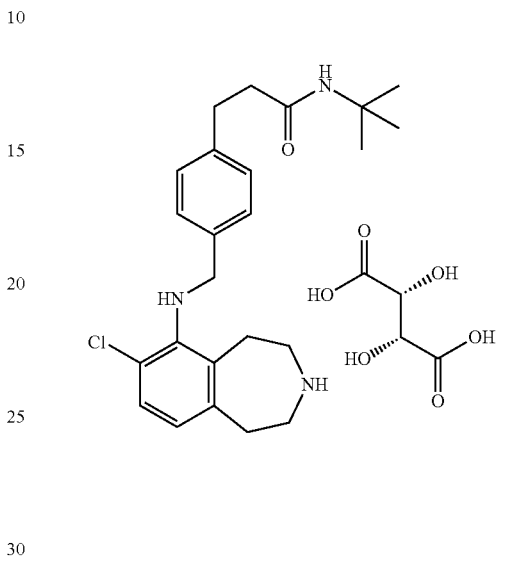

Use a method similar to the General Procedure 1-2 to couple 7-chloro-3-(2,2,2-trifluoroacetyl)-6-trifluoromethanesulfonyloxy-2,3,4,5-tetrahydro-1H-benzo[d]azepine (85 mg, 0.2 mmol) and 4-[2-(tert-butylcarbamoyl)-ethyl]-benzylamine (80 mg, 0.34 mmol). Purify the crude mixture by chromatography on silica gel eluting with hexane/EtOAc (95:5 to 1:1 gradient) to obtain 6-{4-[2-(tert-butylcarbamoyl)-ethyl]benzylamino}-7-chloro-3-(2,2,2-trifluoroacetyl)-2,3,4,5-tetrahydro-1H-benzo[d]azepine as a yellow oil (75 mg, 74%). MS (ES+) m/z: 510 (M+H)+.

Use a method similar to the General Procedure 2-1, using 6-{4-[2-(tert-butylcarbamoyl)-ethyl]-benzylamino}-7-chloro-3-(2,2,2-trifluoroacetyl)-2,3,4,5-tetrahydro-1H-benzo[d]azepine (71 mg, 0.14 mmol) to obtain 6-{4-[2-(tert-butylcarbamoyl)-ethyl]-benzylamino}-7-chloro-2,3,4,5-tetrahydro-1H-benzo[d]azepine (57 mg, 99%) as a yellow oil suitable for use without additional purification.

Use a method similar to the General Procedure 3-2, using 6-{4-[2-(tert-butylcarbamoyl)-ethyl]-benzylamino}-7-chloro-2,3,4,5-tetrahydro-1H-benzo[d]azepine (57 mg, 0.14 mmol) to obtain the title compound as a white solid (76 mg, 99%). MS (ES+) m/z: 414 (M+H)+.

EXAMPLE 80

Example 80 may be prepared essentially as described in Example 79 by using 7-chloro-3-(2,2,2-trifluoroacetyl)-6-trifluoromethanesulfonyloxy-2,3,4,5-tetrahydro-1H-benzo[d]azepine and 4-[2-(2,2-dimethylpropyl-carbamoyl)ethyl]-benzylamine. Overall yield and MS (ES+) data are shown in the Table below.

| Ex. | Structure | Compound | Yield (%) | MS (ES+) m/z |
|---|---|---|---|---|
| 80 | 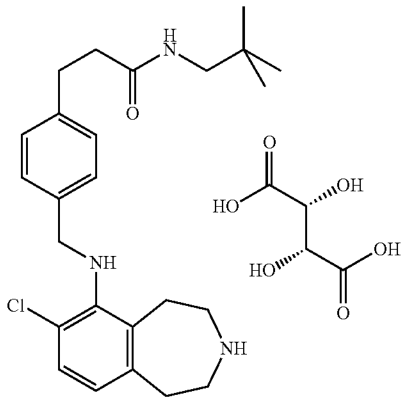 | 7-Chloro-6-{4-[2-(2,2-dimethylpropyl-carbamoyl)-ethyl]-benzylamino}-2,3,4,5-tetrahydro-1H-benzo[d]azepine (L)-Tartrate | 63 | 428 (M + H)+ |

EXAMPLE 81

7-Chloro-6-{6-[(2,2-dimethyl-propanesulfonylmethyl)-pyridin-3-ylmethyl]-amino}-2,3,4,5-tetrahydro-1H-benzo[d]azepine Succinate

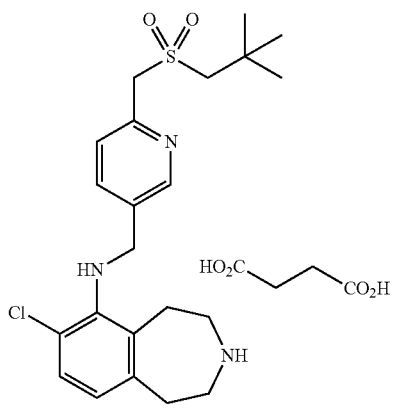

Use a method similar to the General Procedure 1-2 to couple 7-chloro-3-(2,2,2-trifluoroacetyl)-6-trifluoromethanesulfonyloxy-2,3,4,5-tetrahydro-1H-benzo[d]azepine (450 mg, 1.06 mmol) with 3-aminomethyl-6-[(2,2-dimethylpropane)sulfonylmethyl]-pyridine (325 mg, 1.27 mmol) using tris(dibenzylideneacetone)dipalladium(0) (95 mg, 0.1 mmol), BINAP (95 mg, 0.15 mmol) and cesium carbonate (520 mg, 1.5 mmol) in toluene (10 mL). Heat the mixture at 90° C. for 12 h. Cool the mixture to room temperature and purify by chromatography on silica gel (75 g) eluting with hexane/EtOAc (1:0 to 1:1 gradient) to obtain 7-chloro-6-{6-[(2,2-dimethyl-propanesulfonylmethyl)-pyridin-3-ylmethyl]-amino}-3-(2,2,2-trifluoroacetyl)-2,3,4,5-tetrahydro-1H-benzo[d]azepine (470 mg, 83%). MS (APCI+) m/z: 532 (M+H)+.

Dissolve 7-chloro-6-{6-[(2,2-dimethyl-propanesulfonylmethyl)-pyridin-3-ylmethyl]-amino}-3-(2,2,2-trifluoroacetyl)-2,3,4,5-tetrahydro-1H-benzo[d]azepine (470 mg, 0.88 mmol) in concentrated NH$_4$OH/methanol (1:1, 20 mL) and stir the mixture overnight at room temperature. Concentrate the mixture in vacuo. Purify by chromatography on silica gel (45 g, pre-packed cartridge) eluting with a gradient of DCM to 4:1 DCM/(chloroform:methanol:concentrated NH$_4$OH 80:18:2) to obtain 7-chloro-6-{6-[(2,2-dimethyl-propanesulfonylmethyl)-pyridin-3-ylmethyl]-amino}-2,3,4,5-tetrahydro-1H-benzo[d]azepine (380 mg, 99%). MS (APCI+) m/z: 436 (M+H)+.

Dissolve 7-chloro-6-{6-[(2,2-dimethyl-propanesulfonylmethyl)-pyridin-3-ylmethyl]-amino}-2,3,4,5-tetrahydro-1H-benzo[d]azepine (380 mg, 0.87 mmol) in methanol and add succinic acid (98 mg, 0.83 mmol). Stir the mixture until homogeneous. Concentrate the mixture in vacuo, dissolve in water, and freeze dry the solution to obtain the title compound (470 mg, 98%) as a light yellow solid. MS (APCI+) m/z: 436 (M+H)+.

EXAMPLE 82

Example 82 may be prepared essentially as described in Example 81 by using 7-chloro-3-(2,2,2-trifluoroacetyl)-6-trifluoromethanesulfonyloxy-2,3,4,5-tetrahydro-1H-benzo[d]azepine and 3-aminomethyl-6-(cyclohexanesulfonyl)methyl-pyridine. Overall yield and MS (ES+) data are shown in the Table below.

| Ex. | Structure | Compound | Yield (%) | MS (ES+) m/z |
|---|---|---|---|---|
| 82 | 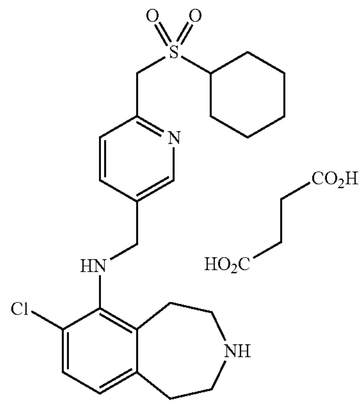 | 7-Chloro-6-[(6-cyclo hexanesulfonylmethyl-pyridin-3-ylmethyl)-amino]-2,3,4,5-tetrahydro-1H-benzo[d]azepine Succinate | 81 | 448 (M + H)+ |

EXAMPLE 83

7-Chloro-6-[4-(2,2-dimethyl-propanesulfonylmethyl)-benzylamino]-2,3,4,5-tetrahydro-1H-benzo[d]azepine Succinate

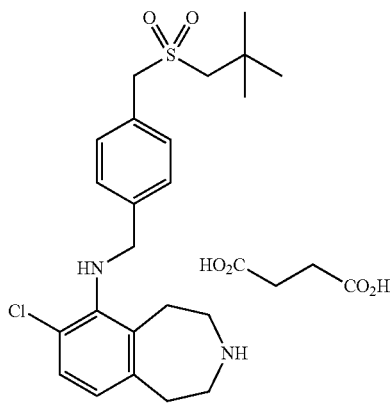

Use a method similar to the General Procedure 1-2 to couple 7-chloro-3-(2,2,2-trifluoroacetyl)-6-trifluoromethanesulfonyloxy-2,3,4,5-tetrahydro-1H-benzo[d]azepine (639 mg, 1.50 mmol) with 4-(2,2-dimethyl-propanesulfonylmethyl)-benzylamine (479 mg, 1.88 mmol), using tris(dibenzylideneacetone)dipalladium(0) (137 mg, 0.15 mmol), BINAP (187 mg, 0.3 mmol) and cesium carbonate (977 mg, 3 mmol) in toluene (20 mL). Heat the mixture at 90° C. overnight. Cool the mixture to room temperature and purify by chromatography on silica gel (80 g) eluting with hexane/EtOAc (1:0 to 4:1 gradient over 15 min; 50 mL/min) to give 7-chloro-6-[4-(2,2-dimethyl-propanesulfonyl-methyl)-benzylamino]-3-(2,2,2-trifluoroacetyl)-2,3,4,5-tetrahydro-1H-benzo[d]azepine (615 mg, 77%). MS (APCI+) m/z: 531 (M+H)+.

Dissolve 7-chloro-6-[4-(2,2-dimethyl-propanesulfonylmethyl)-benzylamino]-3-(2,2,2-trifluoroacetyl)-2,3,4,5-tetrahydro-1H-benzo[d]azepine (605 mg, 1.14 mmol) in methanol (8 mL) and add LiOH H2O (478 mg, 11.4 mmol). Stir the reaction mixture overnight. Partition the mixture between water and chloroform. Extract the aqueous phase three times with chloroform and chloroform/iso-propanol (3:1). Dry the combined organic extracts over MgSO4, filter and concentrate in vacuo. Purify by chromatography on silica gel (40 g) eluting with DCM/(chloroform:methanol:concentrated NH4OH 80:18:2) (1:0 over 5 min, 19:1 over 5 min, 9:1; 50 mL/min) to obtain 7-chloro-6-[4-(2,2-dimethyl-propanesulfonylmethyl)-benzylamino]-2,3,4,5-tetrahydro-1H-benzo[d]azepine (467 mg, 94%). MS (APCI+) m/z: 435 (M+H)+.

Dissolve 7-chloro-6-[4-(2,2-dimethyl-propanesulfonylmethyl)-benzylamino]-2,3,4,5-tetrahydro-1H-benzo[d]azepine (316 mg, 0.726 mmol) in methanol (10 mL) and add succinic acid (86 mg, 0.726 mmol). Stir the mixture for 2 h. Concentrate the mixture in vacuo and dry under high vacuum at 50° C. to obtain the title compound (380 mg, 94%). MS (APCI+) m/z: 435 (M+H)+.

EXAMPLE 84

7-Chloro-6-(4-dimethylcarbamoylthio-benzylamino)-2,3,4,5-tetrahydro-1,1-benzo[d]azepine Succinate

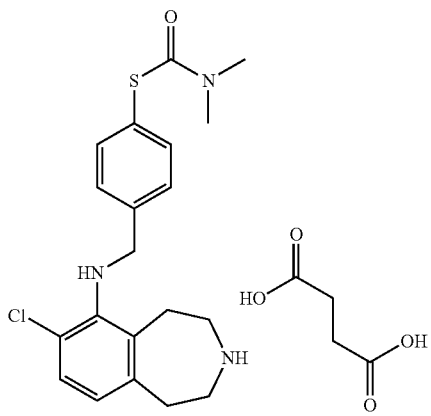

Use a method similar to the General Procedure 3-1, using 7-chloro-6-(4-dimethylcarbamoylthio-benzylamino)-2,3,4,5-tetrahydro-1H-benzo[d]azepine (56 mg, 0.14 mmol) to obtain the title compound as a solid (67 mg, 92%). MS (ES+) m/z: 390 (M+H)+.

EXAMPLE 85

7-Chloro-6-[4-(3,3-dimethyl-2-oxobutylthio)-benzylamino]-2,3,4,5-tetrahydro-1H-benzo[d]azepine (L)-Tartrate

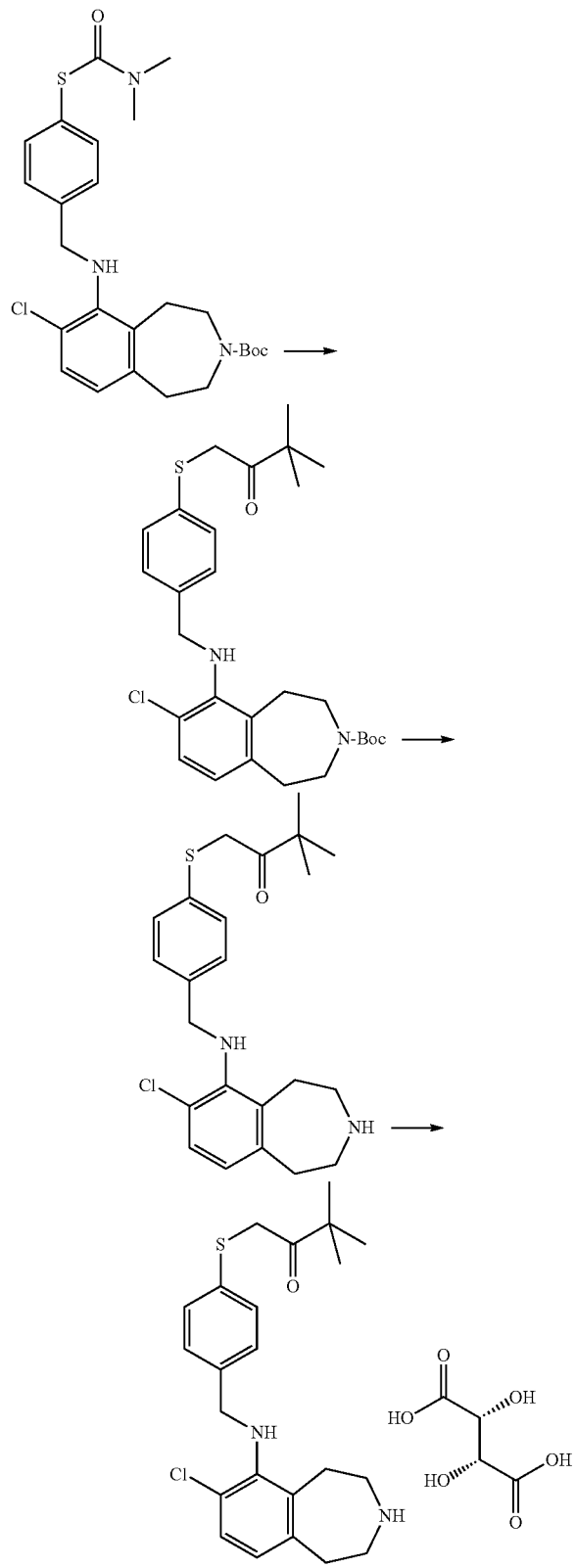

3-(tert-Butoxycarbonyl)-7-chloro-6-[4-(3,3-dimethyl-2-oxobutylthio)-benzylamino]-2,3,4,5-tetrahydro-1H-benzo[d]azepine Dissolve 3-(tert-butoxycarbonyl)-7-chloro-6-(4-dimethylcarbamoylthio-benzylamino)-2,3,4,5-tetrahydro-1H-benzo[d]azepine (57 mg, 0.1 mmol) in methanol (5 mL). Add potassium hydroxide (65 mg, 1.1 mmol) and heat the mixture for 3 h at 65° C. Then add 1-bromo-3,3-dimethyl-2-butanone and heat at 65° C. for 2 h. Cool the mixture and dilute with EtOAc. Wash the organic phase with water, dry over MgSO$_4$, filter and concentrate in vacuo. Purify by chromatography on silica gel eluting with hexane/diethyl ether (7:3) to obtain the desired intermediate as an oil (18 mg, 30%).

7-Chloro-6-[4-(3,3-dimethyl-2-oxobutylthio)-benzylamino]-2,3,4,5-tetrahydro-1H-benzo[d]azepine Dissolve 3-(tert-butoxycarbonyl)-7-chloro-6-[4-(3,3-dimethyl-2-oxobutylthio)-benzylamino]-2,3,4,5-tetrahydro-1H-benzo[d]azepine (35 mg, 0.06 mmol) in DCM (0.2 mL). Add 4M hydrogen chloride in dioxane (0.3 mL, 1.3 mmol) and stir at room temperature for 1 h. Concentrate in vacuo and purify by SCX chromatography to obtain the desired intermediate (26 mg, 93%).

7-Chloro-6-[4-(3,3-dimethyl-2-oxobutylthio)-benzylamino]-2,3,4,5-tetrahydro-1H-benzo[d]azepine (L)-Tartrate Use a method similar to the General Procedure 3-2, using 7-chloro-6-[4-(3,3-dimethyl-2-oxobutylthio)-benzylamino]-2,3,4,5-tetrahydro-1H-benzo[d]azepine (26 mg, 0.06 mmol) to obtain the title compound as a white solid (35 mg, 99%). MS (ES+) m/z: 418 (M+H)$^+$.

EXAMPLE 86

7-Chloro-6-{4-[(2,2-dimethyl-propylcarbamoyl)-methylthio]-benzylamino}-2,3,4,5-tetrahydro-1H-benzo[d]azepine (L)-Tartrate

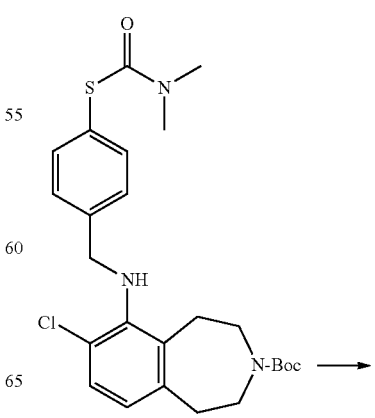

-continued

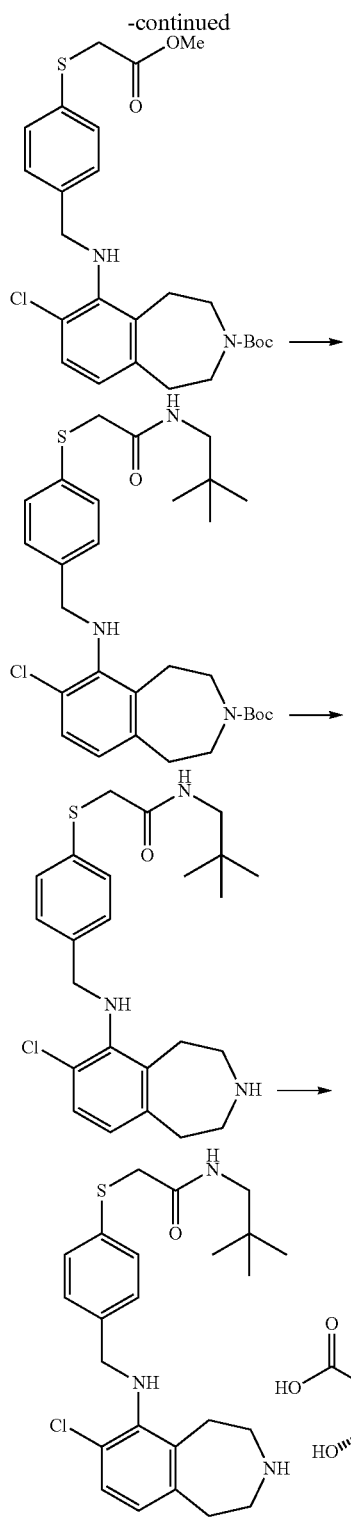

3-(tert-Butoxycarbonyl)-7-chloro-6-(4-methoxycarbonylmethylthio-benzylamino)-2,3,4,5-tetrahydro-1H-benzo[d]azepine Dissolve 3-(tert-butoxycarbonyl)-7-chloro-6-(4-dimethylcarbamoylthio-benzylamino)-2,3,4,5-tetrahydro-1H-benzo[d]azepine (270 mg, 0.5 mmol) in methanol (20 mL). Add potassium hydroxide (308 mg, 5.5 mmol) and heat the mixture for 3 h at 65° C. Add methyl bromoacetate (0.52 mL, 5.5 mmol) and heat at 65° C. for 3 h. Cool the mixture to room temperature and dilute with EtOAc. Wash the organic phase with water, dry over MgSO₄, filter and concentrate in vacuo. Purify by chromatography on silica gel eluting with hexane/EtOAc (4:1) to obtain the desired intermediate as an oil (203 mg, 75%).

3-(tert-Butoxycarbonyl)-7-chloro-6-{-4-[(2,2-dimethyl-propylcarbamoyl)-methylthio]-benzylamino}-2,3,4,5-tetrahydro-1H-benzo[d]azepine Dissolve 2,2-dimethyl-propylamine (0.1 mL, 0.84 mmol) in anhydrous THF (0.6 mL) under nitrogen. Cool the solution at 0° C. and add DIBAL-H (0.79 mL, 0.79 mmol, 1M solution in toluene). Allow the mixture warm up to room temperature and stir for 2 h. Add this complex to a solution of 3-(tert-butoxycarbonyl)-7-chloro-6-(4-methoxycarbonylmethylthio-benzylamino)-2,3,4,5-tetrahydro-1H-benzo[d]azepine (70 mg, 0.14 mmol) in THF (0.3 mL) and stir at room temperature overnight. Dilute with EtOAc and quench with 5% aqueous KHSO₄. Dry the organic phase over MgSO₄, filter and concentrate in vacuo. Purify the crude mixture by chromatography on silica gel eluting with hexane/EtOAc (4:1) to obtain the desired intermediate as an oil (51 mg, 65%).

7-Chloro-6-{4-[(2,2-dimethyl-propylcarbamoyl)-methylthio]-benzylamino}-2,3,4,5-tetrahydro-1H-benzo[d]azepine Dissolve 3-(tert-butoxycarbonyl)-7-chloro-6-{4-[(2,2-dimethyl-propylcarbamoyl)-methylthio]-benzylamino}-2,3,4,5-tetrahydro-1-H-benzo[d]azepine (51 mg, 0.09 mmol) in DCM (0.2 mL). Add 4M hydrogen chloride in dioxane (0.5 mL, 1.8 mmol) and stir at room temperature for 1 h. Concentrate in vacuo and purify by SCX chromatography to obtain the desired intermediate (39 mg, 93%).

7-Chloro-6-{4-[(2,2-dimethyl-propylcarbamoyl)-methylthio]-benzylamino}-2,3,4,5-tetrahydro-1H-benzo[d]azepine (L)-Tartrate Use a method similar to the General Procedure 3-2, using 7-chloro-6-{4-[(2,2-dimethyl-propylcarbamoyl)-methylthio]-benzylamino}-2,3,4,5-tetrahydro-1H-benzo[d]azepine (39 mg, 0.08 mmol) to obtain the title compound as a white solid (51 mg, 98%). MS (ES+) m/z: 446 (M+H)⁺.

EXAMPLE 87

7-Chloro-6-[6-(3,3-dimethyl-2-oxo-butoxy)-pyridin-3-ylmethyl-amino]-2,3,4,5-tetrahydro-1H-benzo[d]azepine (L)-Tartrate

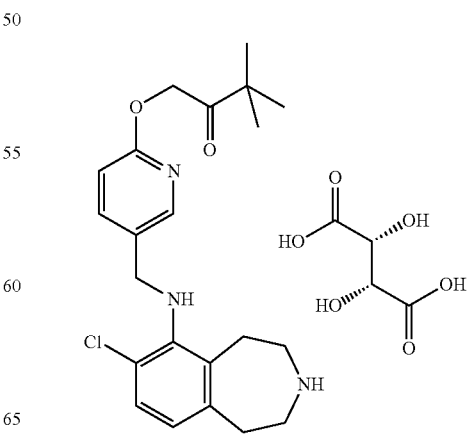

Use a method similar to the General Procedure 1-2 to couple 7-chloro-3-(2,2,2-trifluoroacetyl)-6-trifluoromethanesulfonyloxy-2,3,4,5-tetrahydro-1H-benzo[d]azepine (210 mg, 0.5 mmol) with 3-aminomethyl-6-(3,3-dimethyl-2-oxo-butoxy)-pyridine (220 mg, 1 mmol). Purify by chromatography on silica gel eluting with hexane/EtOAc (4:1) to give 7-chloro-6-{[6-(3,3-dimethyl-2-oxo-butoxy)-pyridin-3-ylmethyl]-amino}-3-(2,2,2-trifluoroacetyl)-2,3,4,5-tetrahydro-1H-benzo[d]azepine (122 mg, 50%). MS (ES+) m/z: 498 (M+H)⁺.

Use a method similar to the General Procedure 2-1, using 7-chloro-6-{[6-(3,3-dimethyl-2-oxo-butoxy)-pyridin-3-ylmethyl]-amino}-3-(2,2,2-trifluoroacetyl)-2,3,4,5-tetrahydro-1H-benzo[d]azepine (122 mg, 0.2 mmol) to give 7-chloro-6-{[6-(3,3-dimethyl-2-oxo-butoxy)-pyridin-3-ylmethyl]-amino}-2,3,4,5-tetrahydro-1H-benzo[d]azepine (80 mg, 81%) suitable for use without further purification.

Use a method similar to the General Procedure 3-2, using 7-chloro-6-{[6-(3,3-dimethyl-2-oxo-butoxy)-pyridin-3-ylmethyl]-amino}-2,3,4,5-tetrahydro-1H-benzo[d]azepine to afford the title compound as a white solid (108 mg, 99%). MS (ES+) m/z: 402 (M+H)⁺.

EXAMPLE 88

7-Chloro-6-({6-[(2,2-dimethyl-propylcarbamoyl)-methoxy]-pyridin-3-ylmethyl}-amino)-2,3,4,5-tetrahydro-1H-benzo[d]azepine (L)-Tartrate

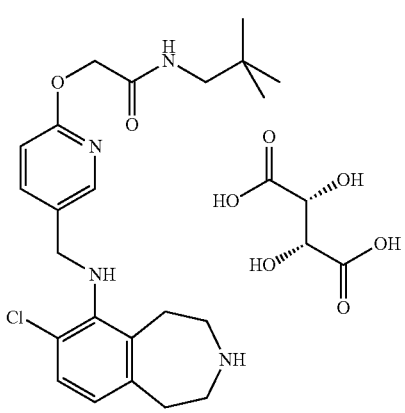

Use a method similar to the General Procedure 1-2 to couple 7-chloro-3-(2,2,2-trifluoroacetyl)-6-trifluoromethanesulfonyloxy-2,3,4,5-tetrahydro-1H-benzo[d]azepine (265 mg, 0.6 mmol) with 3-aminomethyl-6-[(2,2-dimethyl-propylcarbamoyl)-methoxy]-pyridine (314 mg, 1.2 mmol). Purify by chromatography on silica gel eluting with hexane/EtOAc (1:1) to give 7-chloro-6-({6-[(2,2-dimethyl-propylcarbamoyl)-methoxy]-pyridin-3-ylmethyl}-amino)-3-(2,2,2-trifluoroacetyl)-2,3,4,5-tetrahydro-1H-benzo[c]azepine (145 mg, 44%). MS (ES+) m/z: 527 (M+H)⁺.

Use a method similar to the General Procedure 2-1, using 7-chloro-6-({6-[(2,2-dimethyl-propylcarbamoyl)-methoxy]-pyridin-3-ylmethyl}-amino)-3-(2,2,2-trifluoroacetyl)-2,3,4,5-tetrahydro-1H-benzo[d]azepine (145 mg, 0.2 mmol) to give 7-chloro-6-({6-[(2,2-dimethyl-propylcarbamoyl)-methoxy]-pyridin-3-ylmethyl}-amino)-2,3,4,5-tetrahydro-1H-benzo[d]azepine (100 mg, 84%) suitable for use without further purification.

Use a method similar to the General Procedure 3-2, using 7-chloro-6-({6-[(2,2-dimethyl-propylcarbamoyl)-methoxy]-pyridin-3-ylmethyl}-amino)-2,3,4,5-tetrahydro-1H-benzo[d]azepine (100 mg, 0.2 mmol) to give the title compound as a white solid (125 mg, 92%). MS (ES+) m/z: 431 (M+H)⁺.

EXAMPLE 89

7-Chloro-6-{4-[5-(cyclopropylmethyl-amino)-isothiazol-3-yl]-benzylamino}-2,3,4,5-tetrahydro-1H-benzo[d]azepine Succinate

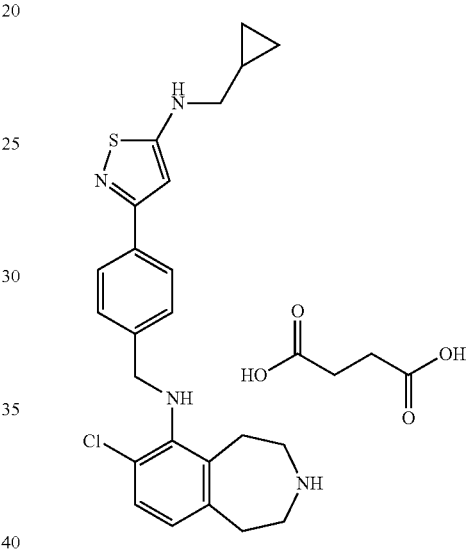

Use a method similar to the General Procedure 1-2 to couple 7-chloro-3-(2,2,2-trifluoroacetyl)-6-trifluoromethanesulfonyloxy-2,3,4,5-tetrahydro-1H-benzo[d]azepine (75 mg, 0.18 mmol) with 4-[5-(cyclopropylmethyl-amino)-isothiazol-3-yl]-benzylamine (68 mg, 0.26 mmol) in toluene (3 mL). Purify the crude mixture by chromatography on silica gel (4 g) eluting with hexane/EtOAc with 2% methanol (9:1 to 4:1 gradient) to obtain 7-chloro-6-{4-[5-(cyclopropylmethyl-amino)-isothiazol-3-yl]-benzylamino}-3-(2,2,2-trifluoroacetyl)-2,3,4,5-tetrahydro-1H-benzo[d]azepine (38 mg, 40%). MS (ES+) m/z: 535.3 (M+H)⁴.

Use a method similar to the General Procedure 2-2 to deprotect 7-chloro-6-{-4-[5-(cyclopropylmethyl-amino)-isothiazol-3-yl]-benzylamino}-3-(2,2,2-trifluoroacetyl)-2,3,4,5-tetrahydro-1H-benzo[d]azepine (38 mg). Purify by chromatography on silica gel (1 g) eluting with DCM/2M ammonia in methanol (1:0 to 9:1 gradient) to give 7-chloro-6-{4-[5-(cyclopropylmethyl-amino)-isothiazol-3-yl]-benzylamino}-2,3,4,5-tetrahydro-1H-benzo[d]azepine. Use a method similar to the General Procedure 3-1 to obtain the title compound (28 mg, 70%). MS (ES+) m/z: 439.2 (M+H)⁺.

EXAMPLE 90

7-Chloro-6-{4-[2-(2,2,2-trifluoroethylamino)-thiazol-4-yl]-benzylamino}-2,3,4,5-tetrahydro-1H-benzo[d]azepine Succinate

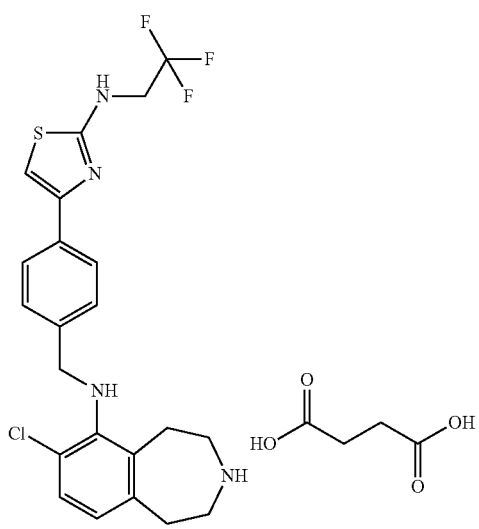

Dissolve 4-[2-(2,2,2-trifluoroethylamino)-thiazol-4-yl]-benzylamine (899 mg, 3.1 mmol) in toluene (16 mL) and DMF (2 mL) under nitrogen at 95° C. Add 7-chloro-3-(2,2,2-trifluoroacetyl)-6-trifluoromethanesulfonyloxy-2,3,4,5-tetrahydro-1H-benzo[d]azepine (665 mg, 1.56 mmol), tris(dibenzylideneacetone)dipalladium(0) (286 mg, 0.31 mmol), BINAP (389 mg, 0.62 mmol) and cesium carbonate (711 mg, 2.2 mmol). Stir the mixture for 12 h at 95° C. under a nitrogen atmosphere and check by GC to determine if the triflate is consumed. Add additional 7-chloro-3-(2,2,2-trifluoroacetyl)-6-trifluoromethanesulfonyloxy-2,3,4,5-tetrahydro-1H-benzo[d]azepine (500 mg, 1.17 mmol), tris(dibenzylideneacetone)dipalladium(0) (286 mg, 0.31 mmol), BINAP (389 mg, 0.62 mmol) and cesium carbonate (711 mg, 2.2 mmol) to the mixture and stir for 16 h at 95° C. (check by LC/MS to determine if the starting amine is consumed). Cool the mixture to room temperature, filter through Celite® and wash with DCM (50 mL). Concentrate in vacuo and purify the residue by chromatography on silica gel (25 g) eluting with hexane/(EtOAc with 1% methanol) (20:1 to 1:1 gradient) to obtain 7-chloro-3-(2,2,2-trifluoroacetyl)-6-{4-[2-(2,2,2-trifluoroethylamino-thiazol-4-yl)]-benzylamino}-2,3,4,5-tetrahydro-1H-benzo[d]azepine (250 mg, 16%). MS (ES+) m/z: 563.1 (M+H)$^+$.

Use a method similar to the General Procedure 2-2 to deprotect 7-chloro-3-(2,2,2-trifluoroacetyl)-6-{4-[2-(2,2,2-trifluoroethylamino-thiazol-4-yl)]-benzylamino}-2,3,4,5-tetrahydro-1H-benzo[d]azepine. Purify by chromatography on silica gel (40 g) eluting with DCM/2M ammonia in methanol (33:1) to give 7-chloro-6-{4-[2-(2,2,2-trifluoroethylamino-thiazol-4-yl)]- benzylamino}-2,3,4,5-tetrahydro-1H-benzo[d]azepine. Use a method similar to the General Procedure 4-1 to obtain the title compound (89 mg). MS (ES+) m/z: 467.3 (M+H)$^+$.

EXAMPLE 91

7-Chloro-6-{4-[2-(3-methyl-butylamino)-thiazol-4-yl]-benzylamino}-2,3,4,5-tetrahydro-1H-benzo[d]azepine Succinate

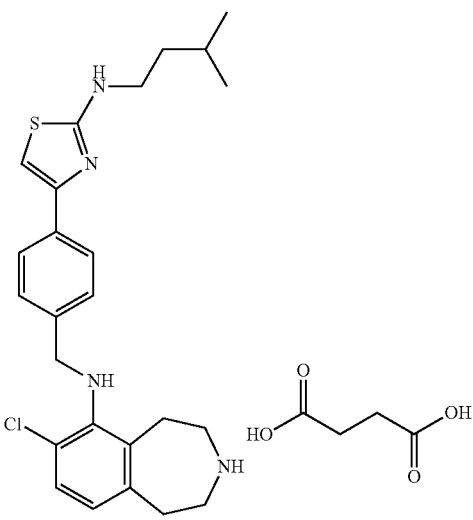

Use a method similar to the General Procedure 1-2 to couple 7-chloro-3-(2,2,2-trifluoroacetyl)-6-trifluoromethanesulfonyloxy-2,3,4,5-tetrahydro-1H-benzo[d]azepine (380 mg, 0.89 mmol) with 4-[2-(3-methyl-butylamino)-thiazol-4-yl]-benzylamine (443 mg, 1.6 mmol) in toluene (12 mL). Purify the crude mixture by chromatography on silica gel (25 g) eluting with hexane/(EtOAc with 1% methanol) (20:1 to 7:3 gradient) to obtain 7-chloro-6-{4-[2-(3-methyl-butylamino)-thiazol-4-yl]-benzylamino}-3-(2,2,2-trifluoroacetyl)-2,3,4,5-tetrahydro-1H-benzo[d]azepine (368 mg, 75%). MS (ES+) m/z: 551.4 (M+H)$^+$.

Use a method similar to the General Procedure 2-2 to deprotect 7-chloro-6-{-4-[2-(3-methyl-butylamino)-thiazol-4-yl]-benzylamino}-3-(2,2,2-trifluoroacetyl)-2,3,4,5-tetrahydro-1H-benzo[d]azepine. Purify by chromatography on silica gel (25 g) eluting with DCM/2M ammonia in methanol (20:1) to give 7-chloro-6-{4-[2-(3-methyl-butylamino)-thiazol-4-yl]-benzylamino}-2,3,4,5-tetrahydro-1H-benzo[d]azepine. Use a method similar to the General Procedure 3-1 to obtain the title compound (240 mg, 63%). MS (ES+) m/z: 455 (M+H)$^+$.

EXAMPLES 92-95

Examples 92-95 may be prepared essentially as described in Example 91 by using 7-chloro-3-(2,2,2-trifluoroacetyl)-6-trifluoromethanesulfonyloxy-2,3,4,5-tetrahydro-1H-benzo[d]azepine and the appropriate benzylamine. Overall yields and MS (ES+) data are as in the Table below.

| Ex. | Structure | Compound | Yield (%) | MS (ES+) m/z |
|---|---|---|---|---|
| 92 | 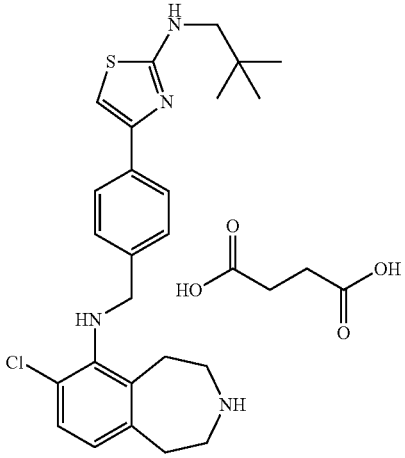 [SMILES: CC(C)(C)CNc1nc(-c2ccc(CNc3c(Cl)ccc4c3CCNCC4)cc2)cs1 ; O=C(O)CCC(=O)O] | 7-Chloro-6-{4-[2-(2,2-dimethyl-propylamino)-thiazol-4-yl]-benzylamino}-2,3,4,5-tetrahydro-1H-benzo[d]azepine Succinate | 45 | 455 (M + H)+ |
| 93 | 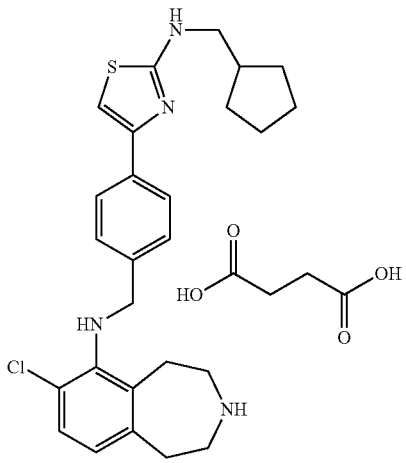 [SMILES: Clc1ccc2c(c1NCc1ccc(-c3csc(NCC4CCCC4)n3)cc1)CCNCC2 ; O=C(O)CCC(=O)O] | 7-Chloro-6-[4-(2-cyclo-pentylmethylamino-thiazol-4-yl)-benzylamino]-2,3,4,5-tetrahydro-1H-benzo[d]azepine Succinate | 50 | 467 (M + H)+ |
| 94 | 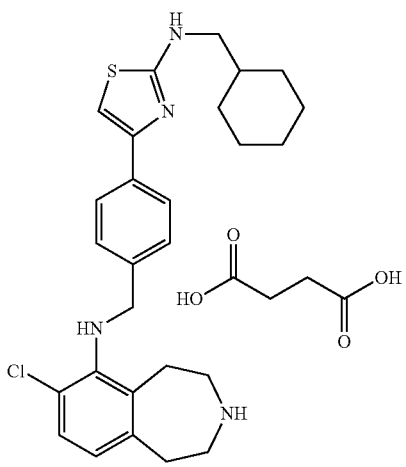 [SMILES: Clc1ccc2c(c1NCc1ccc(-c3csc(NCC4CCCCC4)n3)cc1)CCNCC2 ; O=C(O)CCC(=O)O] | 7-Chloro-6-[4-(2-cyclo-hexylmethylamino-thiazol-4-yl)-benzylamino]-2,3,4,5-tetrahydro-1H-benzo[d]azepine Succinate | 65 | 481 (M + H)+ |

| Ex. | Structure | Compound | Yield (%) | MS (ES+) m/z |
|---|---|---|---|---|
| 95 | 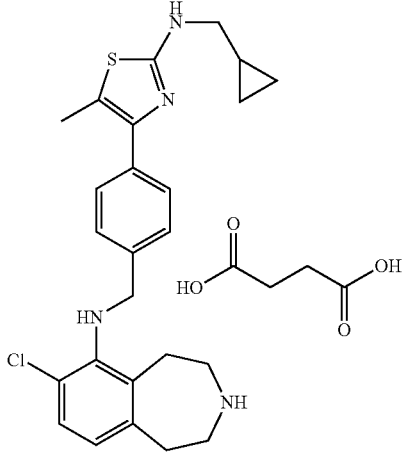 [SMILES: Cc1sc(NCC2CC2)nc1-c1ccc(CNc2c(Cl)ccc3c2CCNCC3)cc1 ; O=C(O)CCC(=O)O] | 7-Chloro-6-[4-(2-cyclo-propylmethylamino-5-methyl-thiazol-4-yl)-benzylamino]-2,3,4,5-tetrahydro-1H-benzo[d]azepine Succinate | 54 | 453 (M + H)+ |

EXAMPLES 96-99

Examples 96-99 may be prepared essentially as described in Example 6 using 7-chloro-3-(2,2,2-trifluoroacetyl)-6-trifluoromethanesulfonyloxy-2,3,4,5-tetrahydro-1H-benzo[d]azepine and the appropriate benzylamine. Examples 98-99 were prepared by using the General Procedure 2-2 for deprotection. Overall yields and MS (ES+) data are shown in the Table below.

| Ex. | Structure | Compound | Yield (%) | MS (ES+) m/z; $[\alpha]_D$ (c, solvent) |
|---|---|---|---|---|
| 96 | 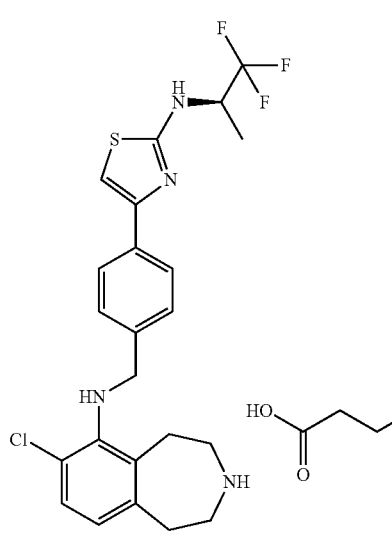 | (R)-7-Chloro-6-{4-[2-(1-methyl-2,2,2-trifluoroethyl-amino)-thiazol-4-yl]-benzylamino}-2,3,4,5-tetrahydro-1H-benzo[d]azepine Succinate | 25 | 481 (M + H)+ $[\alpha]_D = -20°$ (c = 0.5, MeOH) |

| Ex. | Structure | Compound | Yield (%) | MS (ES+) m/z; [α]$_D$ (c, solvent) |
|---|---|---|---|---|
| 97 | 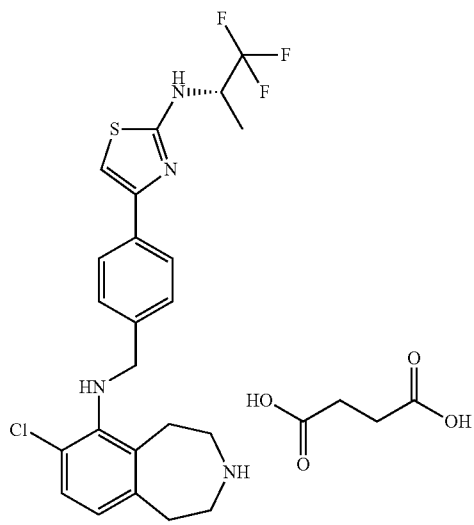 [SMILES: C[C@H](Nc1nc(-c2ccc(CNc3c(Cl)ccc4c3CCNCC4)cc2)cs1)C(F)(F)F ; O=C(O)CCC(=O)O] | (S)-7-Chloro-6-{4-[2-(1-methyl-2,2,2-trifluoroethyl-amino)-thiazol-4-yl]-benzylamino}-2,3,4,5-tetrahydro-1H-benzo[d]azepine Succinate | 40 | 481 (M + H)$^+$ [α]$_D$ = +18.6° (c = 0.5, MeOH) |
| 98 | 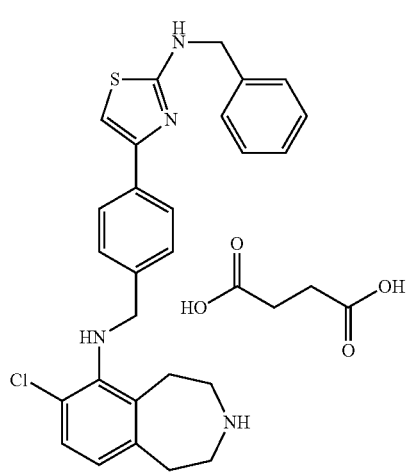 [SMILES: Clc1ccc2c(c1NCc1ccc(-c3csc(NCc4ccccc4)n3)cc1)CCNCC2 ; O=C(O)CCC(=O)O] | 6-[4-(2-Benzylamino-thiazol-4-yl)-benzylamino]-7-chloro-2,3,4,5-tetrahydro-1H-benzo[d]azepine Succinate | 12 | 475 (M + H)$^+$ |
| 99 | 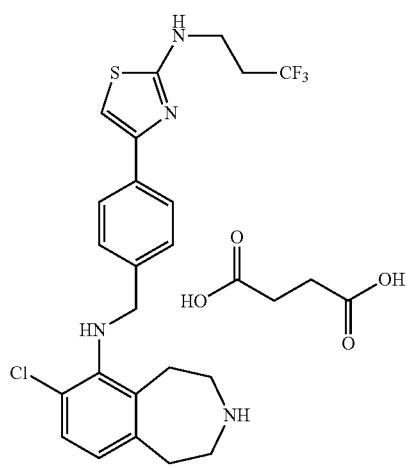 [SMILES: FC(F)(F)CCNc1nc(-c2ccc(CNc3c(Cl)ccc4c3CCNCC4)cc2)cs1 ; O=C(O)CCC(=O)O] | 7-Chloro-6-{4-[2-(3,3,3-trifluoropropylamino)-thiazol-4-yl]-benzylamino}-2,3,4,5-tetrahydro-1H-benzo[d]azepine Succinate | 67 | 427 (M + H)$^+$ |

EXAMPLE 100

7-Chloro-6-[5-(2-cyclopropylmethylamino-thiazol-4-yl)-pyridin-2-ylmethyl-amino]-2,3,4,5-tetrahydro-1H-benzo[d]azepine Succinate

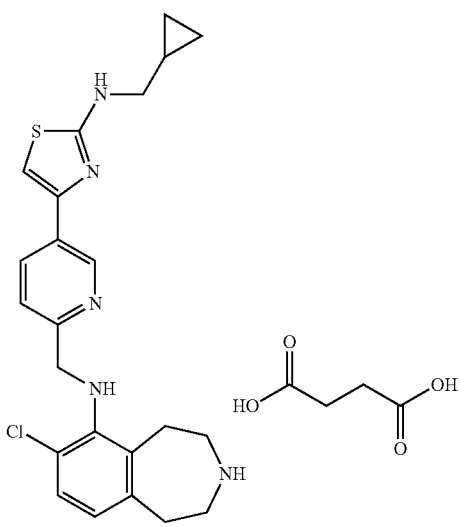

Use a method similar to the General Procedure 1-2 to couple 7-chloro-3-(2,2,2-trifluoroacetyl)-6-trifluoromethanesulfonyloxy-2,3,4,5-tetrahydro-1H-benzo[d]azepine (316 mg, 0.74 mmol) with 2-aminomethyl-5-(2-cyclopropylmethylamino-thiazol-4-yl)-pyridine (290 mg, 1.11 mmol) in toluene (8 mL). Filter the crude mixture over Celite®, followed by activated charcoal and wash with dichloromethane. Concentrate the filtrate in vacuo and purify the crude mixture by chromatography on silica gel (12 g) eluting with hexane/(EtOAc with 1% methanol) (20:1 to 3:2 gradient) to obtain 7-chloro-6-{[5-(2-cyclopropylmethylamino-thiazol-4-yl)-pyridin-2-ylmethyl]-amino}-3-(2,2,2-trifluoroacetyl)-2,3,4,5-tetrahydro-1H-benzo[d]azepine (120 mg, 30%). MS (ES+) m/z: 536.3 (M+H)⁺.

Use a method similar to the General Procedure 2-2 to deprotect 7-chloro-6-{[5-(2-cyclopropylmethylamino-thiazol-4-yl)-pyridin-2-ylmethyl]-amino}-3-(2,2,2-trifluoroacetyl)-2,3,4,5-tetrahydro-1H-benzo[d]azepine. Purify by chromatography on silica gel (4 g) eluting with DCM/2M ammonia in methanol (49:1 to 24:1) to give 7-chloro-6-{[5-(2-cyclopropylmethylamino-thiazol-4-yl)-pyridin-2-ylmethyl]-amino}-2,3,4,5-tetrahydro-1H-benzo[d]azepine. Use a method similar to the General Procedure 3-1 to obtain the title compound (63 mg, 50%). MS (ES+) m/z: 440 (M+H)⁺.

EXAMPLE 101

Example 101 may be prepared essentially as described in Example 100 using 7-chloro-3-(2,2,2-trifluoroacetyl)-6-trifluoromethanesulfonyloxy-2,3,4,5-tetrahydro-1H-benzo[d]azepine and 3-aminomethyl-6-(2-cyclopropylmethylamino-thiazol-4-yl)-pyridine. Overall yield and MS (ES+) data are shown in the Table below.

| Ex. | Structure | Compound | Yield (%) | MS (ES+) m/z |
|-----|-----------|----------|-----------|--------------|
| 101 | 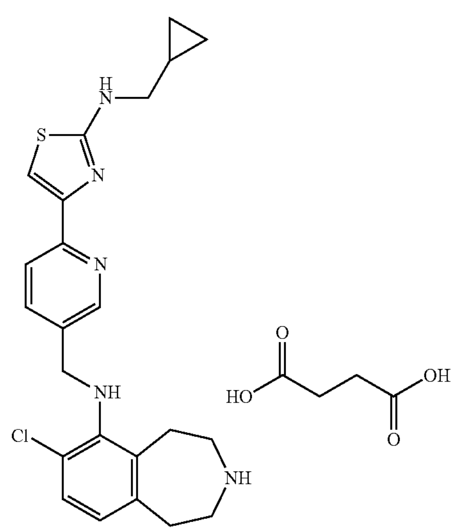 | 7-Chloro-6-[6-(2-cyclopropylmethylamino-thiazol-4-yl)-pyridin-3-ylmethyl-amino]-2,3,4,5-tetrahydro-1H-benzo[d]azepine Succinate | 29 | 440.3 (M + H)⁺ |

EXAMPLE 102

7-Chloro-6-{4-[2-(cyclopropanecarbonyl-amino)-thiazol-4-yl]-benzylamino}-2,3,4,5-tetrahydro-1H-benzo[d]azepine Succinate

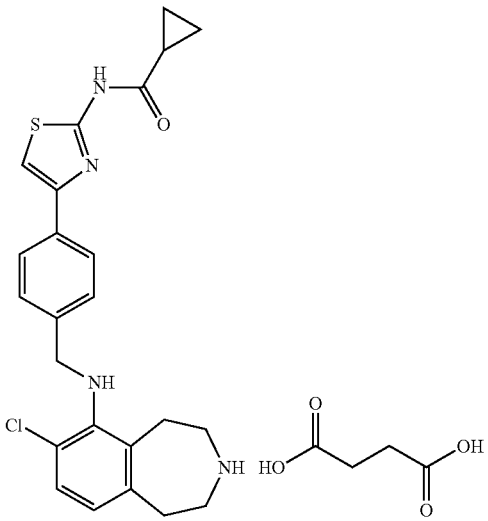

To a slurry of 4-[2-(cyclopropanecarbonyl-amino)-thiazol-4-yl]-benzylamine (1.654 g, 6.052 mmol) in toluene (30.2 mL)/dioxane (7.8 mL), at 100° C., add a solid mixture of 7-chloro-3-(2,2,2-trifluoroacetyl)-6-trifluoromethanesulfonyloxy-2,3,4,5-tetrahydro-1H-benzo[d]azepine (1.29 g, 3.03 mmol), tris(dibenzylideneacetone)-dipalladium(0) (0.55 g, 0.61 mmol), BINAP (0.75 g, 0.12 mmol) and cesium carbonate (3.45 g, 10.6 mmol) all at once. Purge the reaction mixture with nitrogen and heat at 100° C. overnight. After cooling to room temperature, filter the reaction mixture over Celite® and wash with DCM (500 mL). Concentrate in vacuo, dissolve the residue in DCM and load on to an Analogix® column (150 g). Purify by preparative liquid chromatography (0:1 to 1:9 2M ammonia in methanol/DCM over 33 min, 1:9 to 1:3 2M ammonia in methanol/DCM over 33 min, 1:3 to 1:1 2M ammonia in methanol/DCM over 33 min; 35 mL/min) to afford 7-chloro-6-{4-[2-(cyclopropanecarbonyl-amino)-thiazol-4-yl]-benzylamino}-3-(2,2,2-trifluoroacetyl)-2,3,4,5-tetrahydro-1H-benzo[d]azepine (0.318 g, 19%) as a yellow foam. MS (ES+) m/z: 549.1 (M+H)$^+$.

To 7-chloro-6-{4-[2-(cyclopropanecarbonyl-amino)-thiazol-4-yl]-benzylamino}-3-(2,2,2-trifluoroacetyl)-2,3,4,5-tetrahydro-1H-benzo[d]azepine (0.310 g, 5.648 mmol) at room temperature, add 2M ammonia in methanol (18 mL). After stirring for 30 min, add 7M ammonia in methanol (124 mL) to the reaction mixture. After stirring at room temperature overnight, concentrate the reaction mixture in vacuo and elute the residue through a SCX column (20 g). Dissolve the residue in DCM and load the solution on to a RediSep® column (40 g). Purify by preparative liquid chromatography (0:1 to 1:9 2M ammonia in methanol/DCM over 33 min, 1:9 to 1:4 2M ammonia in methanol/DCM over 33 min; 35 mL/min) to afford 7-chloro-6-{4-[2-(cyclopropanecarbonyl-amino)-thiazol-4-yl]-benzylamino}-2,3,4,5-tetrahydro-1H-benzo[d]azepine (0.140 g, 55%) as a white foam. MS (ES+) m/z: 453.1 (M+H)$^+$.

To a slurry of 7-chloro-6-{4-[2-(cyclopropanecarbonyl-amino)-thiazol-4-yl]-benzylamino}-2,3,4,5-tetrahydro-1H-benzo[d]azepine (0.136 g, 0.3 mmol) in absolute ethanol (5 mL) at room temperature, add dichloromethane (5 mL). Add succinic acid (0.035 g, 0.301 mmol) to the mixture and stir for 1 h. Concentrate in vacuo. Combine the residue with MTBE (5 mL) and concentrate three times to afford a white solid. Dry the white solid in a vacuum oven at 40° C. overnight to afford the title compound (160 mg, 93%) as a white solid. MS (ES+) m/z: 453 (M+H)$^+$.

EXAMPLE 103

7-Chloro-6-[4-(1-cyclopropylmethyl-1H-pyrazol-3-yl)-benzylamino]-2,3,4,5-tetrahydro-1H-benzo[d]azepine (L)-Tartrate

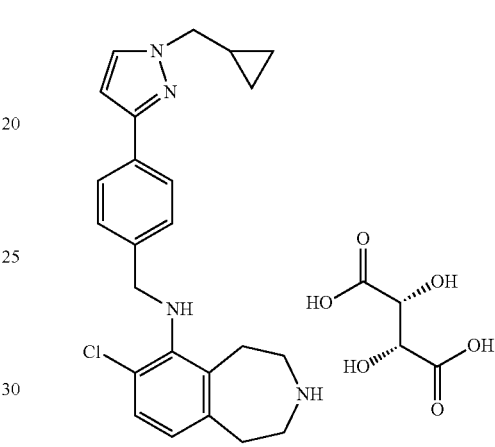

Use a method similar to the General Procedure 1-2 to couple 7-chloro-3-(2,2,2-trifluoroacetyl)-6-trifluoromethanesulfonyloxy-2,3,4,5-tetrahydro-1H-benzo[d]azepine (193 mg, 0.45 mmol) with 4-(1-cyclopropylmethyl-1H-pyrazol-3-yl)-benzylamine (207 mg, 0.91 mmol) using tris(dibenzylideneacetone)dipalladium(0) (83 mg, 0.091 mmol), BINAP (113 mg, 0.182 mmol) and cesium carbonate (207 mg, 0.627 mmol) in toluene (21 mL). Purify by chromatography on silica gel eluting with hexane:EtOAc (9:1) to give 7-chloro-6-[4-(1-cyclopropylmethyl-1H-pyrazol-3-yl)-benzylamino]trifluoroacetyl)-2,3,4,5-tetrahydro-1H-benzo[d]azepine as a yellow oil (135 mg, 59%). MS (ES+) m/z: 503 (M+H)$^+$.

Use a method similar to General Procedure 2-1, using 7-chloro-6-[4-(1-cyclopropylmethyl-1H-pyrazol-3-yl)-benzylamino]-3-(2,2,2-trifluoroacetyl)-2,3,4,5-tetrahydro-1H-benzo[d]azepine (135 mg, 0.27 mmol) to give 7-chloro-6-[4-(1-cyclopropylmethyl-1H-pyrazol-3-yl)-benzylamino]-2,3,4,5-tetrahydro-1H-benzo[d]azepine (97 mg, 89%) as a yellow oil.

Use a method similar to the General Procedure 4-2, using 7-chloro-6-[4-(1-cyclopropylmethyl-1H-pyrazol-3-yl)-benzylamino]-2,3,4,5-tetrahydro-1H-benzo[d]azepine (97 mg, 0.088 mmol) to give the title compound as a white solid (122 mg, 98%). MS (ES+) m/z: 407 (M+H)$^+$.

EXAMPLE 104

Example 104 may be prepared essentially as described in Example 103 using 7-chloro-3-(2,2,2-trifluoroacetyl)-6-trifluoromethanesulfonyloxy-2,3,4,5-tetrahydro-1H-benzo[d]azepine and 4-[3-(cyclopropylmethyl-amino)-pyrazol-1-yl]-benzylamine. Overall yield and MS (ES+) data are shown in the Table below.

| Ex. | Structure | Compound | Yield (%) | MS (ES+) m/z |
|---|---|---|---|---|
| 104 | 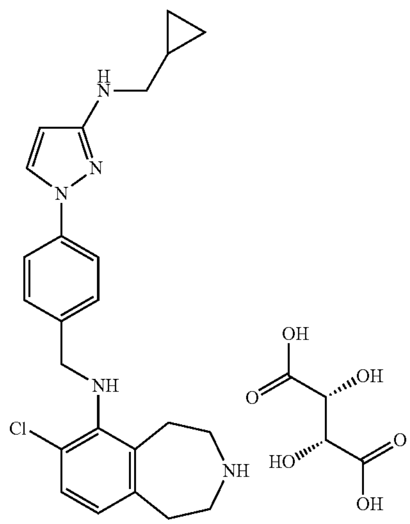 | 7-Chloro-6-[4-(3-cyclopropylmethylamino)-pyrazol-1-yl-benzylamino]-2,3,4,5-tetrahydro-1H-benzo[d]azepine (L)-Tartrate | 55 | 422 (M + H)+ |

EXAMPLE 105

7-Chloro-6-{4-[6-(cyclopropylmethyl-amino)-pyrimidin-4-yl]-benzylamino}-2,3,4,5-tetrahydro-1H-benzo[d]azepine Succinate

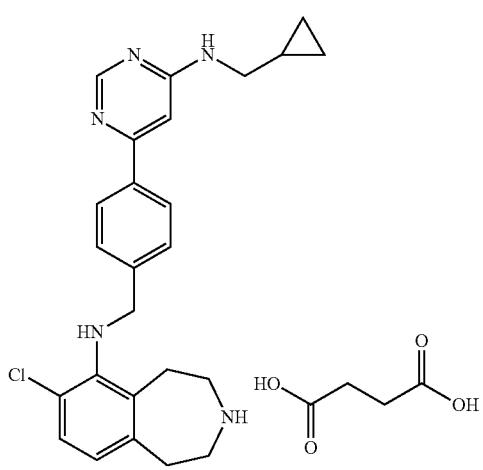

Use a method similar to the General Procedure 1-3, using 7-chloro-3-(2,2,2-trifluoroacetyl)-6-trifluoromethanesulfonyloxy-2,3,4,5-tetrahydro-1H-benzo[d]azepine (260 mg, 0.6 mmol) and 4-[6-(cyclopropylmethyl-amino)-pyrimidin-4-yl]-benzylamine (300 mg, 1.18 mmol), to give 7-chloro-6-{4-[6-(cyclopropylmethyl-amino)-pyrimidin-4-yl]-benzylamino}-3-(2,2,2-trifluoroacetyl)-2,3,4,5-tetrahydro-1H-benzo[d]azepine as an off-white foam (250 mg, 78%). MS (ES+) m/z: 530 (M+H)+.

Use a method similar to the General Procedure 2-1 to deprotect 7-chloro-6-{-4-[6-(cyclopropylmethyl-amino)-pyrimidin-4-yl]-benzylamino}-3-(2,2,2-trifluoroacetyl)-2,3,4,5-tetrahydro-1H-benzo[d]azepine (250 mg, 0.47 mmol) to give 7-chloro-6-{-4-[6-(cyclopropylmethyl-amino)-pyrimidin-4-yl]-benzylamino}-2,3,4,5-tetrahydro-1H-benzo[d]azepine (145 mg, 71%) as an off-white foam. MS (ES+) m/z: 434 (M+H)+.

Use a method similar to the General Procedure 4-1, using 7-chloro-6-{4-[6-(cyclopropylmethyl-amino)-pyrimidin-4-yl]-benzylamino}-2,3,4,5-tetrahydro-1H-benzo[d]azepine (175 mg, 0.4 mmol) to give the title compound (175 mg, 98%) as an off-white solid. MS (ES+) m/z: 434 (M+H)+.

EXAMPLES 106-107

Examples 106-107 may be prepared essentially as described in Example 105 using 7-chloro-3-(2,2,2-trifluoroacetyl)-6-trifluoromethanesulfonyloxy-2,3,4,5-tetrahydro-1H-benzo[d]azepine and the appropriate benzylamine. Overall yields and MS (ES+) data are shown in the Table below.

| Ex. | Structure | Compound | Yield (%) | MS (ES+) m/z |
|---|---|---|---|---|
| 106 | 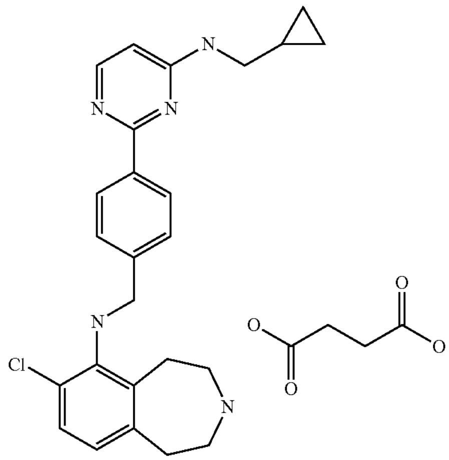 [SMILES: Clc1ccc2c(c1NCc1ccc(-c3nccc(NCC4CC4)n3)cc1)CCNCC2 ; O=C(O)CCC(=O)O] | 7-Chloro-6-{4-[4-(cyclopropylmethyl-amino)-pyrimidin-2-yl]-benzylamino}-2,3,4,5-tetrahydro-1H-benzo[d]azepine Succinate | 75 | 434 (M + H)⁺ |
| 107 | 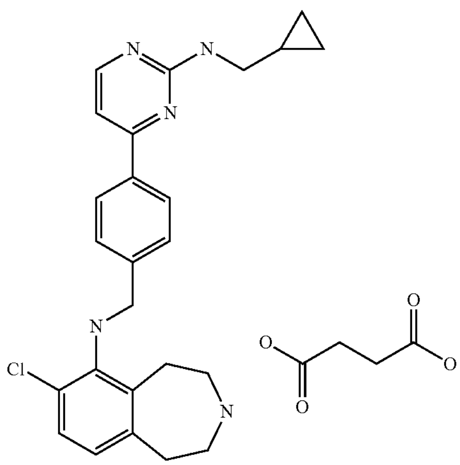 [SMILES: Clc1ccc2c(c1NCc1ccc(-c3ccnc(NCC4CC4)n3)cc1)CCNCC2 ; O=C(O)CCC(=O)O] | 7-Chloro-6-{4-[2-(cyclopropylmethyl-amino)-pyrimidin-4-yl]-benzylamino}-2,3,4,5-tetrahydro-1H-benzo[d]azepine Succinate | 22 | 434 (M + H)⁺ |

EXAMPLE 108

7-Chloro-6-{4-[5-(3,3-dimethylbutyryl)-tiophen-2-yl]-benzylamino}-2,3,4,5-tetrahydro-1H-benzo[d]azepine (L)-Tartrate

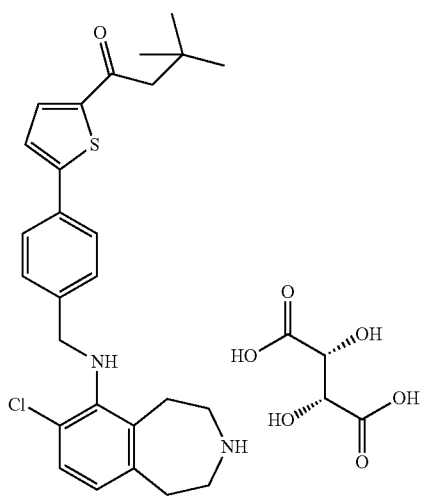 [SMILES: CC(C)(C)CC(=O)c1ccc(-c2ccc(CNc3c(Cl)ccc4c3CCNCC4)cc2)s1 ; O=C(O)[C@H](O)[C@@H](O)C(=O)O]

Use a method similar to the General Procedure 1-2 to couple 7-chloro-3-(2,2,2-trifluoroacetyl)-6-trifluoromethanesulfonyloxy-2,3,4,5-tetrahydro-1H-benzo[d]azepine (93.5 mg, 0.2 mmol) with 4-[5-(3,3-dimethylbutyryl)tiophen-2-yl]-benzylamine (129 mg, 0.4 mmol) using tris(dibenzylideneacetone)dipalladium(0) (40.3 mg, 0.04 mmol), BINAP (58.3 mg, 0.08 mmol) and cesium carbonate (100 mg, 0.3 mmol) in toluene/DMF (11:1, 12 mL). Purify by chromatography on silica gel eluting with hexane/EtOAc (4:1) to give 7-chloro-6-{4-[5-(3,3-dimethylbutyryl)-tiophen-2-yl]-benzylamino}trifluoroacetyl)-2,3,4,5-tetrahydro-1H-benzo[d]azepine as a yellow oil (77 mg, 62%). MS (ES+) m/z: 563 (M+H)⁺.

Use a method similar to the General Procedure 2-1, using 7-chloro-6-{4-[5-(3,3-dimethylbutyryl)-tiophen-2-yl]-benzylamino}-3-(2,2,2-trifluoroacetyl)-2,3,4,5-tetrahydro-1H-benzo[d]azepine (77 mg, 0.1 mmol) to give 7-chloro-6-{4-[5-(3,3-dimethylbutyryl)-tiophen-2-yl]-benzylamino}-2,3,4,5-tetrahydro-1H-benzo[d]azepine (55 mg, 87%) as a yellow oil.

Use a method similar to the General Procedure 3-2, using 7-chloro-6-{4-[5-(3,3-dimethylbutyryl)-tiophen-2-yl]-benzylamino}-2,3,4,5-tetrahydro-1H-benzo[d]azepine (55 mg, 0.1 mmol) to give the title compound as a white solid (70 mg, 96%). MS (ES+) m/z: 467 (M+H)+.

EXAMPLE 109

7-Chloro-6-[6-(2,2-dimethylpropane-sulfonyl)-pyridin-3-yl-methyl-amino]-2,3,4,5-tetrahydro-1H-benzo[d]azepine Succinate

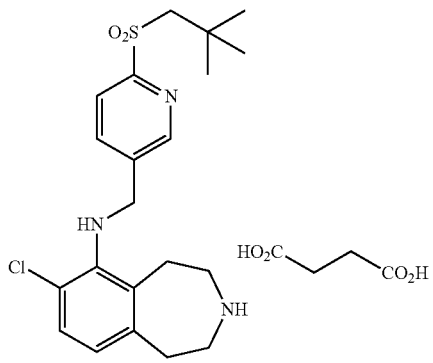 [SMILES: CC(C)(C)CS(=O)(=O)c1ccc(CNc2c(Cl)ccc3c2CCNCC3)cn1 ; O=C(O)CCC(=O)O]

Under a nitrogen atmosphere, add 3-aminomethyl-6-[(2,2-dimethylpropane)-sulfonyl]-pyridine (300 mg, 1.23 mmol), 7-chloro-3-(2,2,2-trifluoroacetyl)-6-trifluoromethansulfonyloxy-2,3,4,5-tetrahydro-1H-benzo[d]azepine (350 mg, 822 μmol), tris(dibenzylideneacetone)dipalladium(0) (75 mg, 82 μmol), BINAP (77 mg, 123 μmol), and cesium carbonate (402 mg, 1.23 mmol) to toluene (100 mL). Heat the mixture at 95° C. overnight. Cool the mixture to room temperature, and concentrate the mixture in vacuo. Purify the crude mixture by chromatography on silica gel eluting with DCM/(chloroform:methanol:concentrated NH$_4$OH) (1:0 to 1:1 over 1.5 h, 80 mL/min) to provide 7-chloro-6-{[6-(2,2-dimethylpropane-sulfonyl)-pyridin-3-yl-methyl]-amino}-3-(2,2,2-trifluoroacetyl)-2,3,4,5-tetrahydro-1H-benzo[d]azepine (142 mg, 33%) and additional impure product (150 mg, 33%). MS (ES+) m/z: 518 (M+H)+.

Dissolve 7-chloro-6-{[6-(2,2-dimethylpropane-sulfonyl)-pyridin-3-yl-methyl]-amino}-3-(2,2,2-trifluoroacetyl)-2,3,4,5-tetrahydro-1H-benzo[d]azepine (142 mg, 0.27 mmol) in methanol (5 mL). Add lithium hydroxide hydrate (23 mg, 0.54 mmol) and stir for 1 h. Mix with silica gel (1 g), concentrate in vacuo, and purify by chromatography on silica gel (12 g) eluting with DCM/(chloroform:methanol:concentrated NH$_4$OH) (1:0 to 9:1 gradient) to give 7-chloro-6-{[6-(2,2-dimethylpropane-sulfonyl)-pyridin-3-yl-methyl]-amino}-2,3,4,5-tetrahydro-1H-benzo[d]azepine (91 mg, 78%). MS (APCI) m/z: 422 (M+H)+.

Dissolve 7-chloro-6-{[6-(2,2-dimethylpropane-sulfonyl)-pyridin-3-yl-methyl]-amino}-2,3,4,5-tetrahydro-1H-benzo[d]azepine (171 mg, 0.4 mmol) in methanol and add succinic acid (45 mg, 0.38 mmol). Stir the mixture until homogeneous. Concentrate the mixture in vacuo, dissolve in water, and freeze dry the solution to provide the title compound (215 mg, 99%). MS (APCI) m/z: 422 (M+H)+.

EXAMPLE 110

7-Chloro-6-[4-(2,2,2-trifluoroethylthio-methylcarbonyl)-benzylamino]-2,3,4,5-tetrahydro-1H-benzo[d]azepine (L)-Tartrate

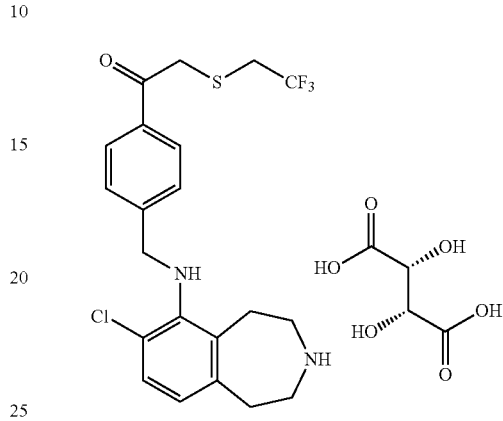

Use a method similar to the General Procedure 1-2 to couple 7-chloro-3-(2,2,2-trifluoroacetyl)-6-trifluoromethanesulfonyloxy-2,3,4,5-tetrahydro-1H-benzo[d]azepine (173 mg, 0.4 mmol) with 4-[2-(2,2,2-trifluoroethylthio)-1,1-(ethylenedioxy)ethyl]-benzylamine (250 mg, 0.8 mmol) using tris(dibenzylideneacetone)dipalladium(0) (73.2 mg, 0.08 mmol), BINAP (106 mg, 0.16 mmol) and cesium carbonate (182 mg, 0.6 mmol) in toluene (20 mL). Purify by chromatography on silica gel eluting with hexane/EtOAc (75:25) to give 7-chloro-3-(2,2,2-trifluoroacetyl)-6-{4-[2-(2,2,2-trifluoroethylthio)-1,1-(ethylenedioxy)ethyl]-benzylamino}-2,3,4,5-tetrahydro-1H-benzo[d]azepine (97 mg, 41%).

To a solution of 7-chloro-3-(2,2,2-trifluoroacetyl)-6-{4-[2-(2,2,2-trifluoroethylthio)-1,1-(ethylenedioxy)ethyl]-benzylamino}-2,3,4,5-tetrahydro-1H-benzo[d]azepine (97 mg, 0.16 mmol) in anhydrous dichloromethane (0.5 mL), add a solution of 4M hydrogen chloride in dioxane (1.2 mL) and reflux overnight. Dilute with dichloromethane and wash with saturated aqueous NaHCO$_3$. Dry the organics extracts over MgSO$_4$, filter and concentrate in vacuo. Purify the crude mixture by chromatography on silica gel eluting with hexane/EtOAc (4:1) to obtain 7-chloro-3-(2,2,2-trifluoroacetyl)-6-[4-(2,2,2-trifluoroethylthio-methylcarbonyl)-benzylamino]-2,3,4,5-tetrahydro-1H-benzo[d]azepine (37 mg, 41%). MS (ES+) m/z: 539 (M+H)+.

Use a method similar to the General Procedure 2-1, using 7-chloro-3-(2,2,2-trifluoroacetyl)-6-[4-(2,2,2-trifluoroethylthio-methylcarbonyl)-benzylamino]-2,3,4,5-tetrahydro-1H-benzo[d]azepine (37 mg, 0.07 mmol) to give 7-chloro-6-[4-(2,2,2-trifluoroethylthio-methylcarbonyl)-benzylamino]-2,3,4,5-tetrahydro-1H-benzo[d]azepine (16 mg, 53%).

Use a method similar to the General Procedure 3-2, using 7-chloro-6-[4-(2,2,2-trifluoroethylthio-methylcarbonyl)-benzylamino]-2,3,4,5-tetrahydro-1H-benzo[d]azepine (16 mg, 0.04 mmol) to give the title compound as a white solid (21 mg, 98%). MS (ES+) m/z: 443 (M+H)+.

The compounds of the present invention are relatively selective for the 5-HT$_{2C}$ receptor. The compounds of the present invention are particularly relatively selective for the 5-HT$_{2C}$ receptor in comparison to other 5-HT receptor subtypes and specifically the 5-HT$_{2A}$ and 5-HT$_{2B}$ receptors. This selectivity is demonstrated in the following agonist activity assays and receptor binding assays.

Agonist Activity Assays (G Alpha q-GTPγ[$^{35}$S] Binding Assays)

The 5-HT$_2$ receptors are functionally coupled to specific G-proteins. Agonist activation of 5-HT$_2$ G-protein-coupled receptors results in the release of GDP from the α-subunit (G alpha q or G alpha i) of the G-protein and the subsequent binding of GTP. The binding of the stable analog GTPγ[$^{35}$S] is an indicator of receptor activation (i.e. agonist activity).

The G alpha q-GTPγ[$^{35}$S] binding assay is used to determine the in vitro potency (EC$_{50}$) and maximal efficacy (E$_{max}$, normalized to the 5-HT response) of a test compound at the 5-HT$_{2A}$, 5-HT$_{2B}$, and 5-HT$_{2C}$ receptors. The area under the dose response curve (AUC) is also determined for each receptor subtype and used to measure the test compound's selectivity for the 5-HT$_{2C}$ receptor over the 5-HT$_{2A}$ and 5-HT$_{2B}$ receptors, expressed as Selectivity Ratios (AUC 2C/2A and AUC 2C/2B, respectively). The Selectivity Ratios allow the assessment of selectivity based on both potency and efficacy. A selectivity measure that incorporates both potency and efficacy at the 5-HT$_{2C}$ receptor, as compared to the 5-HT$_{2A}$ and 5-HT$_{2B}$ receptors, is considered important due to the adverse events associated with 5-HT$_{2A}$ and 5-HT$_{2B}$ agonist activity (see introduction).

Membrane Preparation:

Grow AV12 cells stably transfected with the human 5-HT$_{2A}$, 5-HT$_{2B}$, or 5-HT$_{2C}$ receptors in suspension, harvest by centrifugation, wash the cell pellet with phosphate buffered saline, pH 7.4, pellet the cells again, remove the supernatant, freeze the cell pellet on dry ice and store at −70° C. Thaw stock cell pellet and resuspend in 50 mM Tris, pH 7.4, aliquot into 1-2 mL volumes and refreeze at −70° C. for subsequent assays. (As is appreciated in the art, optimal cell quantities used per aliquot will vary with the individual transfected cell line used. In one embodiment, 5-HT$_{2A}$ and 5-HT$_{2C}$ transfected cells are typically used at about 6×10$^8$ cells per aliquot, while 5-HT$_{2B}$ cells are typically used at about 7.5×10$^8$ cells per aliquot).

On the day of assay, thaw membranes, wash the membranes with assay buffer (50 mM Tris-HCl (pH 7.4), 10 mM MgCl$_2$, 100 mM NaCl, and 0.2 mM EDTA), resuspend in assay buffer and incubate for 10 min. at 37° C. to hydrolyze any residual endogenous 5-HT. Wash the membranes again with assay buffer, and resuspend in assay buffer at a concentration to provide aliquots of about 1-4×10$^6$ cell equivalents per well (typically about 1-2×10$^6$ cell equivalents for assays with 5-HT$_{2A}$ or 5-HT$_{2C}$ receptor assays, and about 3-4×10$^6$ cell equivalents for assays with 5-HT$_{2B}$ receptor assays). Homogenize the cells with a tissue grinder and use the homogenate directly in the assay as described below.

G alpha q-GTPγ[$^{35}$] Binding Assays: The immunoadsorption scintillation proximity assay (ISPA) of [$^{35}$S]-GTPγS binding to G alpha q is modified from published conditions (DeLapp et al, JPET 289 (1999) 946-955). Dissolve test compounds in DMSO and dilute in assay buffer to provide a range of concentrations to generate a concentration response curve. In wells of a 96 well microtiter plate, mix diluted test compound, GDP (0.1 μM final concentration), and [$^{35}$S]-GTPγS (between 0.5 and 1.0 nM final concentration). Add an aliquot of membranes to the incubation mixture and mix the plates to initiate agonist stimulation of the nucleotide exchange (200 μl final volume). Incubate the microtiter plates for 30 min. at room temperature. Quench the incubation with IGEPAL® CA-630 detergent (0.27% final concentration). Add affinity purified polyclonal rabbit anti-G alpha q antibody (about 1-2 μg per well), and anti-rabbit Ig scintillation proximity assay beads (Amersham; about 1.25 mg per well; 300 μl final volume). Seal the plates and incubate the mixture for 3 h at room temperature. Centrifuge the microtiter plates briefly to pellet beads. Quantitate the GTPγ[$^{35}$S] binding by microtiter plate scintillation spectrometry (Wallac Trilux MicroBeta™ scintillation counter).

Data Analysis: For each concentration response curve for a test compound at a given receptor, analyze the data with GraphPad Prism™ software (v3.02; GraphPad Software, San Diego, Calif.) running on a personal computer with MicroSoft Windows OS®, using nonlinear regression analysis curve fitting to determine the EC$_{50}$ and E$_{max}$(normalized to 5-HT control curves). Determine the Area Under the agonist concentration-response Curve (AUC) with GraphPad Prism™ by the trapezoidal method.

To calculate the Selectivity Ratios, first, determine the AUC for the test compound for each receptor subtype as described above. Second, normalize the AUC's at each receptor subtype relative to the AUC determined for 5-HT at that receptor. The normalized AUC for a test compound at a given receptor is therefore expressed as a percentage of the AUC determined for 5-HT at that receptor. For example:

$5HT_{2A}$ Normalized $AUC =$ $$a = \frac{(AUC_{test\ compound}\ \text{at}\ 5HT_{2A}\ \text{receptor})}{(AUC_{5-HT}\ \text{at}\ 5HT_{2A}\ \text{receptor})} \times 100\%$$

$5HT_{2B}$ Normalized $AUC =$ $$b = \frac{(AUC_{test\ compound}\ \text{at}\ 5HT_{2B}\ \text{receptor})}{(AUC_{5-HT}\ \text{at}\ 5HT_{2B}\ \text{receptor})} \times 100\%$$

$5HT_{2C}$ Normalized $AUC =$ $$c = \frac{(AUC_{test\ compound}\ \text{at}\ 5HT_{2C}\ \text{receptor})}{(AUC_{5-HT}\ \text{at}\ 5HT_{2C}\ \text{receptor})} \times 100\%$$

Third, calculate the Selectivity Ratios for the test compound as follows:

Selectivity Ratio for 5-HT$_{2C}$ receptor/5-HT$_{2A}$ receptor (AUC 2C/2A)=c/a

Selectivity Ratio for 5-HT$_{2C}$ receptor/5-HT$_{2B}$ receptor (AUC 2C/2B)=c/b

For reference purposes, the AUC 2C/2A and AUC 2C/2B for 5-HT are each 1.0. Likewise, the ratios for mCPP (meta-chlorophenylpiperazine) are tested and are found to be 2.1 and 2.1 respectively.

Representative compounds of the present invention are tested in the G alpha q-GTPγ[$^{35}$S] assays for the 5-HT$_{2A}$, 5-HT$_{2B}$, and 5-HT$_{2C}$ receptors essentially as described above and are found to be a highly potent and selective agonists of the 5-HT$_{2C}$ receptor, with EC$_{50}$'s typically less than or equal to 250 nM, and AUC 2C/2A and AUC 2C/2B ratios greater than 1.5. Preferred compounds are those with EC50's less than or equal to 100 nM, and AUC 2C/2A and AUC 2C/2B ratios greater than or equal to 2.0. More preferred are those with EC50's less than or equal to 50 nM, and AUC 2C/2A and AUC 2C/2B ratios greater than or equal to 3.0.

Ligand Binding Assays

The ligand binding affinity of the compounds of the present invention to the 5-HT$_{2C}$ receptor subtype is measured essentially as described by Wainscott (Wainscott, et al., *Journal of Pharmacology and Experimental Therapeutics*, 276:720-727 (1996)). Data is analyzed by nonlinear regression analysis on the concentration response curves using the four parameter logistic equation described by DeLean (DeLean, et al., *Molecular Pharmacology*, 21, 5-16 (1982)). $IC_{50}$ values are converted to $K_i$ values using the Cheng-Prusoff equation (Cheng, et al., *Biochem. Pharmacol.*, 22, 3099-3108 (1973)).

Representative compounds of the present invention are tested essentially as described above and are found to have excellent affinity for the $5\text{-HT}_{2C}$ receptor, with $K_i$'s typically less than or equal to about 250 nM. Preferred compounds are those with $K_i$'s of less than or equal to about 100 nM. More preferred are those with $K_i$'s less than or equal to 50 nM.

Affinities for other receptor subtypes can readily be determined by slight modification of the above described radioligand receptor binding assay using cells transfected with the desired receptor in place of cells transfected with the $5\text{-HT}_{2C}$ receptor subtype and using an appropriate radioligand. The binding affinities for representative compounds of the present invention for a variety of receptors are determined in such assays and the compounds are found to have surprisingly higher affinity for the $5\text{-HT}_{2C}$ receptor. Affinity for the $5\text{-HT}_{2C}$ receptor is found to be significantly higher than for other 5-HT receptor subtypes, and notably higher than the $5\text{-HT}_{2A}$ and $5\text{-HT}_{2B}$ receptor subtypes. Preferred compounds are those with $IC_{50}$'s equal to or greater than 300 nM for the alpha 1 and alpha 2 adrenergic receptors and equal to or greater than 500 nM for $D_1$ and $D_2$ dopaminergic receptors. More preferred compounds are those with $IC_{50}$'s equal to or greater than 1000 nM for the alpha 1 and alpha 2 adrenergic receptors and the $D_1$ and $D_2$ dopaminergic receptors. Still more preferred are those compounds with $IC_{50}$'s equal to or greater than 3000 nM for the alpha 1 and alpha 2 adrenergic receptors and the $D_1$ and $D_2$ dopaminergic receptors.

For the above in vitro assays, exemplified compounds are assayed and found to have either an $EC_{50}$ or a $K_i$ value of equal to or less than 50 nM, and to have AUC 2C/2A and AUC 2C/2B ratios of greater than or equal to 2.0. Exemplified compounds are assayed and found to typically have alpha 1 and alpha 2 adrenergic receptor $IC_{50}$'s equal to or greater than 300 nM, and $D_1$ and $D_2$ dopaminergic receptor $IC_{50}$'s equal to or greater than 500 nM.

Rat Feeding Assays

The ability of the compounds of the present invention to treat obesity is demonstrated by testing in acute and chronic rat feeding assays.

Animals:

Obtain male Long-Evans rats (Harlan Sprague-Dawley, Indianapolis, Ind.) that are approximately one hundred-days old and have been maintained on a calorie rich diet since weaning (TD 95217, 40% calories from fat; Teklad, Madison, Wis.). House the rats individually with a 12 h:12 h light:dark cycle (lights on from about 22:00 h to about 10:00 h) and maintain rats on the same diet (TD 95217) with free access to water, for about 1-2 weeks to acclimate the rats to the environment. Dose rats orally with vehicle (10% acacia with 0.15% saccharin in water) once daily for at least 1 day (typically 1-2 days) to acclimate the rats to the procedures. Randomize the rats into groups so each group has similar mean body weights.

Calorimetric Acute Feeding Assay:

At approximately 8:00 h on the day of assay, weigh each rat and transfer to individual chambers of an open circuit calorimetry system (Oxymax, Columbus Instruments International Corporation; Columbus, Ohio), with free access to food (pre-weighed) and water, and begin measuring $VO_2$ and $VCO_2$. At approximately 10:00 h, dose rats orally with vehicle or test compound, return them to their calorimetry chambers, and continue measuring $VO_2$ and $VCO_2$ at regular time intervals (approximately hourly). At approximately 8:00 h the following day, measure rat body weight and the remaining food, assuming the difference in weight of food is equal to the mass of food consumed. Calculate the 24 h energy expenditure (EE) and respiratory quotient (RQ) essentially as described in Chen, Y. and Heiman, M. L., Regulatory Peptide, 92:113-119 (2000). EE during light photoperiod is indicative of the resting metabolic rate and RQ is indicative of the fuel source the animal utilizes (pure carbohydrate metabolism gives an RQ of about 1.0, pure fat metabolism gives an RQ of about 0.7, mixed carbohydrate and fat metabolism gives intermediate values for RQ). Calculate EE as the product of calorific value (CV) and $VO_2$ per body weight (kg); where $CV=3.815+1.232*RQ$, and RQ is the ratio of $CO_2$ produced ($VCO_2$) to $O_2$ consumed ($VO_2$). Caloric intake is calculated as (mass of 24 h food intake in grams)×(physiological fuel value of the diet in kilocalorie/g) per kg of body weight.

Acute Feeding Assay with a Selective $5\text{-HT}_{2C}$ Receptor Antagonist:

The above calorimetric acute feeding assay is conducted with the following modifications. Open circuit calorimetry systems are not used and only the 24 h periodic food intake and body weight are measured. Three groups of rats are used with the first group receiving a subcutaneous dose of saline (0.5 mL) about 15 minutes prior to the oral dose of vehicle, the second group receiving a subcutaneous dose of saline (0.5 mL) about 15 minutes prior to the oral dose of test compound in vehicle, and the third group receiving a subcutaneous injection of a selective $5\text{-HT}_{2C}$ receptor antagonist, 6-chloro-5-methyl-N-{2-[(2-methylpyridin-3-yl-oxy)pyridin-5-yl]aminocarbonyl}-2,3-dihydroindole (3 mg/Kg, in 35% cyclodextrin, 0.5 mL), about 15 min. prior to the oral dose of test compound in vehicle.

Chronic Feeding Assay:

At between approximately 8:00 h and 10:00 h on day one of the assay, weigh and orally dose each rat with vehicle or test compound and return the animal to its home cage, with free access to food (pre-weighed) and water. For each of days 2-15, at between approximately 8:00 h and 10:00 h, measure rat body weight and the weight of food consumed in the last 24 h period, and administer daily oral dose of test compound or vehicle. On days—2 and 15 measure total fat mass and lean mass by nuclear magnetic resonance (NMR) using an EchoMRI™ system (Echo Medical Systems, Houston Tex.). (See Frank C. Tinsley, Gersh Z. Taicher, and Mark L. Heiman, "Evaluation of a New Quantitative Magnetic Resonance (QMR) Method for Mouse Whole Body Composition Analysis", Obesity Research, submitted May 1, 2003.)

Representative compounds of the present invention are tested in acute and chronic feeding assays essentially as described above. In the acute assays, the compounds are found to significantly reduce 24 h food intake, which effect is blocked by pre-administration of the $5\text{-HT}_{2C}$ receptor antagonist. The compounds also are found to dose-dependently reduce RQ without significantly changing the energy expenditure during the light photo-period. Thus the compounds are found to reduce caloric intake and increase the proportion of fuel deriving from fat utilization, without significantly changing the resting metabolic rate. In the chronic assay, the compounds are found to significantly decrease cumulative food intake and cumulative body weight change in a dose-dependent manner compared to control animals. The decrease in body weight is found to be due to loss of adipose tissue while lean body mass is not changed.

The ability of the 5-HT$_{2C}$ receptor agonists of the present invention to treat obsessive/compulsive disorder is demonstrated by testing in a variety of in vivo assays as follows:

Marble Burying Assay

Marble burying in mice has been used to model anxiety disorders including obsessive-compulsive disorders (OCD) due to ethological study of the behavior (e.g. Gyertyan I. "Analysis of the marble burying response: Marbles serve to measure digging rather than evoke burying", *Behavioural Pharmacology* 6: 24-31, (1995)) and due to the pharmacological effects of clinical standards (c.f., Njung'E K. Handley S L. "Evaluation of marble-burying behavior as a model of anxiety", *Pharmacology, Biochemistry & Behavior.* 38: 63-67, (1991)); Borsini F., Podhorna J., and Marazziti, D. "Do animal models of anxiety predict anxiolytic effects of antidepressants?", *Psychopharmacology* 163: 121-141, (2002)). Thus, drugs used in the treatment of generalized anxiety in humans (e.g. benzodiazepines) as well as compounds used to treat OCD (e.g. SSRIs like fluoxetine) decrease burying.

House experimentally-naïve male, NIH Swiss mice (Harlan Sprague-Dawley, Indianapolis, Ind.) weighing between 28-35 g in groups of 12 for at least three days prior to testing in a vivarium with 12 h light and dark cycles. Conduct experiments during the light cycle in a dimly lit experimental testing room. Dose mice with vehicle or test compound and, after a specified pretreatment interval (generally 30 min.), place each mouse individually on a rotorod (Ugo Basile 7650) operating at a speed of 6 revolutions/min. and observe for falling. After 2 min. on the rotorod, place the mice individually in a 17×28×12 cm high plastic tub with 5 mm sawdust shavings on the floor that are covered with 20 blue marbles (1.5 cm diameter) placed in the center. After 30 min., count the number of marbles buried (⅔ covered with sawdust). Assess the test compound's effect on marble burying with Dunnett's test and the effect on rotorod performance by Fisher's exact test.

Clinically effective standard compounds suppress marble burying at doses that are devoid of motor-impairing effects as measured on the rotorod. The in vivo efficacy of 5HT$_{2C}$ compounds at the 5HT$_{2C}$ receptor is confirmed by the prevention of effects of the 5HT$_{2C}$ agonists on marble burying by co-administration of the 5HT$_{2C}$ receptor antagonist, 6-chloro-5-methyl-N-{2-[(2-methylpyridin-3-yl-oxy)pyridin-5-yl]aminocarbonyl}-2,3-dihydroindole.

Representative compounds of the present invention are assayed in the marble burying assay essentially as described and are surprisingly found to reduce burying behavior in the test mice. The reduction of burying behavior is found to be blocked by co-administration of the 5-HT$_{2C}$ antagonist. In contrast to the compounds of the present invention, the anxiolytic compound chlordiazepoxide and the antipsychotic compound chlorpromazine decrease marble burying only at doses that also disrupt rotorod performance.

Nestlet Shredding

Mice naturally will construct nests of material available in their living environment. Since this behavior is obsessive in nature, it has been used to model OCD (Xia Li, Denise Morrow and Jeffrey M. Witkin, "Decreases in nestlet shredding of mice by serotonin uptake inhibitors: comparison with marble burying", Psychopharmacology, submitted Jul. 14, 2003). House experimentally-naïve male, NIH Swiss mice (Harlan Sprague-Dawley, Indianapolis, Ind.) weighing between 28-35 g in groups of 12 for at least three days prior to testing in a vivarium with a 12 h light/dark cycle. Conduct experiments during the light cycle in an experimental room with normal overhead fluorescent lighting. Dose mice with vehicle or test compound and after a specified pretreatment interval (generally 30 min.), place the mice individually in a 17×28×12 cm high plastic tub with about 5 mm sawdust shavings on the floor along with a pre-weighed multi-ply gauze pad (51 mm square). After 30 min., weigh the remainder of the gauze pad not removed by the mouse. Determine the weight of the gauze used for nestlet construction by subtraction. Compare the results for test compound treated mice to the results for vehicle control treated mice with Dunnett's test.

Clinically effective OCD treatment standard compounds suppress nestlet shredding at doses that are devoid of motor-impairing effects as measured by the rotorod test. The in vivo efficacy of 5HT$_{2C}$ compounds at the 5HT$_{2C}$ receptor is confirmed by the prevention of effects of the 5HT$_{2C}$ agonists on nestlet shredding by co-administration of the 5HT$_{2C}$ receptor antagonist, 6-chloro-5-methyl-N-{2-[(2-methylpyridin-3-yl-oxy)pyridin-5-yl]aminocarbonyl}-2,3-dihydroindole.

Representative compounds of the present invention are assayed essentially as described above and are surprisingly found to suppress nestlet shredding at doses that are devoid of motor-impairing effects as measured by the rotorod test.

In contrast to the compounds of the present invention, the anxiolytic chlordiazepoxide and the psychomotor stimulant d-amphetamine decreases nestlet shredding only at doses that produce motoric side effects (depression or stimulation, respectively).

Schedule-Induced Polydipsia

Food-deprived rats exposed to intermittent presentations of food will drink amounts of water that are far in excess of their normal daily intake and in excess of their intake when given all of their food at one time (Falk J L. "Production of polydipsia in normal rats by an intermittent food schedule", *Science* 133: 195-196, (1961)). This excessive behavior is persistent and has been used to model OCD.

Maintain Wistar rats on a food restricted diet (to maintain 85% free feeding weight), but with free access to water. Train the rats in a behavioral testing chamber to press a lever to receive a food pellet under a fixed interval schedule, such that the rats are rewarded with a 45 mg food pellet the first time they press a lever after a 120 second interval has elapsed. The fixed interval is then reset to 120 seconds and the process repeated. Thus, during a 90 min. test session, the rats can earn a maximum of 45 pellets. The behavioral chamber is also equipped with a water bottle that is weighed before and after the session to determine the amount of water consumed.

Administer test compounds on Tuesdays and Fridays. Determine control day performances on Thursdays. Administer compounds either orally at 60 min. before the beginning of a test session, or subcutaneously at 20 min. before the beginning of a test session. Compare the rates of lever pressing and water consumption for each animal's performance during sessions after test compound treatment with that animal's performance during control sessions, expressed as a percent of the control rate. Average the individual percent of control rates for each dose and calculate the standard error of the mean.

Clinically effective OCD treatment standard compounds (e.g. chlomipramine, fluoxetine) suppress schedule-induced polydipsia without producing notable changes in motor patterns, food intake, or behavior the following day. The in vivo efficacy of 5HT$_{2C}$ compounds at the 5HT$_{2C}$ receptor is confirmed by the prevention of effects of the 5HT$_{2C}$ agonists on excessive drinking by co-administration of the 5HT$_{2C}$ receptor antagonist, 6-chloro-5-methyl-N-{2-[(2-methylpyridin-3-yl-oxy)pyridin-5-yl]aminocarbonyl}-2,3-dihydroindole.

Representative compounds of the present invention are assayed in the schedule-induced polydipsia assay essentially as described above and are surprisingly found to suppress schedule-induced polydipsia without producing notable changes in motor patterns, food intake, or behavior the following day. The behavior suppression is blocked by co-administration of the 5-HT$_{2C}$ antagonist.

In contrast to the compounds of the present invention, the psychomotor stimulant d-amphetamine decreases excessive drinking only at behaviorally stimulating doses and these effects are not prevented by the 5HT$_{2C}$ receptor antagonist.

While it is possible to administer compounds employed in the methods of this invention directly without any formulation, the compounds are usually administered in the form of pharmaceutical compositions comprising a pharmaceutically acceptable excipient and at least one compound of Formula I or a pharmaceutically acceptable salt thereof. These compositions can be administered by a variety of routes including oral, rectal, transdermal, subcutaneous, intravenous, intramuscular, and intranasal. The compounds employed in the methods of this invention are effective as both injectable and oral compositions. Such compositions are prepared in a manner well known in the pharmaceutical art. See, e.g. REMINGTON'S PHARMACEUTICAL SCIENCES, (16th ed. 1980).

In making the compositions employed in the present invention the active ingredient is usually mixed with at least one excipient, diluted by at least one excipient, or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 0.05 to about 100 mg, more usually about 1.0 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The compounds are generally effective over a wide dosage range. For examples, dosages per day normally fall within the range of about 0.01 to about 30 mg/kg. In the treatment of adult humans, the range of about 0.1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Under some circumstances, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, issued Apr. 30, 1991, which is herein incorporated by reference.

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

The type of formulation employed for the administration of the compounds employed in the methods of the present invention may be dictated by the particular compound employed, the type of pharmacokinetic profile desired from the route of administration, and the state of the patient.

We claim:
1. A compound of Formula I:

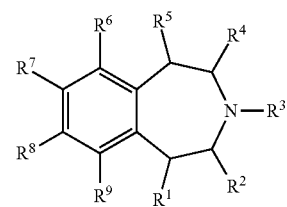

I where:
- $R^1$ is hydrogen;
- $R^2$, $R^3$, and $R^4$ are each hydrogen;
- $R^5$ is hydrogen;
- $R^6$ is —$NR^{10}R^{11}$;
- $R^7$ is chloro;
- $R^8$ is hydrogen;
- $R^9$ is hydrogen;
- $R^{10}$ is $Ph^2$-methyl or $Ar^1$-methyl;
- $R^{11}$ is hydrogen;
- $Ph^1$ is phenyl optionally substituted with 1 to 5 independently selected halo substituents, or with 1 to 3 substituents independently selected from the group consisting of halo, cyano, —$SCF_3$, ($C_1$-$C_6$)alkyl optionally further substituted with 1 to 6 fluoro substituents, and ($C_1$-$C_6$)alkoxy optionally further substituted with 1 to 6 fluoro substituents;
- $Ph^2$ is phenyl substituted with $R^{12}$ and optionally further substituted with 1 or 2 substituents independently selected from the group consisting of halo, cyano, —$SCF_3$, methyl, —$CF_3$, methoxy, —$OCF_3$, nitro, and hydroxy;
- $Ar^1$ is 5-$R^{13}$-pyridin-2-yl or 6-$R^{13}$-pyridin-3-yl optionally further substituted with one or two substituents independently selected from the group consisting of halo, cyano, methyl, —$CF_3$, hydroxy, and methoxy;
- $R^{12}$ is a substituent selected from the group consisting of:
  a) $Het^1$-($C_0$-$C_3$)alkyl optionally substituted on the alkyl moiety with 1 to 6 fluoro substituents;
  b) $Het^2$-($C_0$-$C_3$)alkyl optionally substituted on the alkyl moiety with 1 to 6 fluoro substituents;
  c) $Het^3$-($C_0$-$C_3$)alkyl optionally substituted on the alkyl moiety with 1 to 6 fluoro substituents;
  d) $Ar^2$—($C_0$-$C_3$)alkyl optionally substituted on the alkyl moiety with 1 to 6 fluoro substituents;
  e) ($C_1$-$C_6$)alkyl-C($R^{14}$)=C($R^{14}$)— optionally substituted on the alkyl moiety with 1 to 6 fluoro substituents;
  f) ($R^{14}$)$_2$C=C[($C_1$-$C_6$)alkyl]- optionally substituted on the alkyl moiety with 1 to 6 fluoro substituents;
  g) ($C_3$-$C_7$)cycloalkyl-($C_0$-$C_3$)alkyl-C($R^{14}$)=C($R^{15}$)— optionally substituted on the cycloalkyl moiety with 1 to 4 substituents selected from the group consisting of methyl and fluoro, and independently optionally substituted on the alkyl moiety with 1 to 4 fluoro substituents;
  h) ($R^{15}$)CH=C[($C_3$-$C_7$)cycloalkyl-($C_0$-$C_3$)alkyl]- optionally substituted on the cycloalkyl moiety with 1 to 4 substituents selected from the group consisting of methyl and fluoro, and independently optionally substituted on the alkyl moiety with 1 to 4 fluoro substituents;
  i) ($C_1$-$C_6$)alkyl-C≡C— optionally substituted on the alkyl moiety with 1 to 6 fluoro substituents;
  j) ($C_3$-$C_7$)cycloalkyl-($C_0$-$C_3$)alkyl-C≡C— optionally substituted on the cycloalkyl moiety with 1 to 4 substituents selected from the group consisting of methyl and fluoro, and independently optionally substituted on the alkyl moiety with 1 to 4 fluoro substituents;
  k) ($C_3$-$C_7$)cycloalkyl-($C_0$-$C_3$)alkyl-C(O)—($C_1$-$C_5$)alkyl optionally substituted on the cycloalkyl moiety with 1 to 4 substituents selected from the group consisting of methyl and fluoro, and independently optionally substituted on either or both alkyl moieties independently with 1 to 4 fluoro substituents;
  l) $Ph^1$-($C_0$-$C_3$)alkyl-C(O)—($C_1$-$C_5$)alkyl optionally substituted on either or both alkyl moieties independently with 1 to 4 fluoro substituents;
  m) pyridyl-($C_0$-$C_3$)alkyl-C(O)—($C_1$-$C_5$)alkyl, optionally substituted on the pyridyl moiety with 1 to 3 substituents independently selected from the group consisting of halo, ($C_1$-$C_3$)alkyl, ($C_1$-$C_3$)alkoxy, —$CF_3$, —O—$CF_3$, nitro, cyano, and trifluoromethylthio, and independently optionally substituted on either or both alkyl moieties independently with 1 to 4 fluoro substituents;
  n) ($C_1$-$C_6$)alkyl-O—($C_1$-$C_3$)alkyl-C(O)— optionally substituted on the ($C_1$-$C_6$)alkyl moiety with 1 to 6 fluoro substituents and independently optionally substituted on the ($C_1$-$C_3$)alkyl moiety with 1 to 4 fluoro substituents;
  o) ($C_3$-$C_7$)cycloalkyl-($C_0$-$C_3$)alkyl-O—($C_1$-$C_3$)alkyl-C(O)— optionally substituted on the cycloalkyl moiety with 1 to 4 substituents selected from the group consisting of methyl and fluoro, and independently optionally substituted on either or both alkyl moieties independently with 1 to 4 fluoro substituents;
  p) $Ph^1$-($C_0$-$C_3$)alkyl-O—($C_1$-$C_3$)alkyl-C(O)— optionally substituted on either or both alkyl moieties independently with 1 to 4 fluoro substituents;
  q) ($C_1$-$C_6$)alkyl-S—($C_1$-$C_3$)alkyl-C(O)— optionally substituted on the ($C_1$-$C_6$)alkyl moiety with 1 to 6 fluoro substituents and independently optionally substituted on the ($C_1$-$C_3$)alkyl moiety with 1 to 4 fluoro substituents;
  r) ($C_3$-$C_7$)cycloalkyl-($C_0$-$C_3$)alkyl-S—($C_1$-$C_3$)alkyl-C(O)— optionally substituted on the cycloalkyl moiety with 1 to 4 substituents selected from the group consisting of methyl and fluoro, and independently optionally substituted on either or both alkyl moieties independently with 1 to 4 fluoro substituents;
  s) $Ph^1$-($C_0$-$C_3$)alkyl-S—($C_1$-$C_3$)alkyl-C(O)— optionally substituted on either or both alkyl moieties independently with 1 to 4 fluoro substituents;
  t) ($C_1$-$C_6$)alkyl-$NR^{16}$—($C_1$-$C_3$)alkyl-C(O)— optionally substituted on the ($C_1$-$C_6$)alkyl moiety with 1 to 6 fluoro substituents and independently optionally substituted on the ($C_1$-$C_3$)alkyl moiety with 1 to 4 fluoro substituents;
  u) ($C_3$-$C_7$)cycloalkyl-($C_0$-$C_3$)alkyl-$NR^{16}$—($C_1$-$C_3$)alkyl-C(O)— optionally substituted on the cycloalkyl moiety with 1 to 4 substituents selected from the group consisting of methyl and fluoro, and independently optionally substituted on either or both alkyl moieties independently with 1 to 4 fluoro substituents;
  v) $Ph^1$-($C_0$-$C_3$)alkyl-$NR^{16}$—($C_1$-$C_3$)alkyl-C(O)— optionally substituted on either or both alkyl moieties independently with 1 to 4 fluoro substituents;
  w) ($C_1$-$C_6$)alkyl-O—($C_1$-$C_3$)alkyl-$SO_2$— optionally substituted on the ($C_1$-$C_6$)alkyl moiety with 1 to 6 fluoro substituents and independently optionally substituted on the ($C_1$-$C_3$)alkyl moiety with 1 to 4 fluoro substituents;
  x) ($C_3$-$C_7$)cycloalkyl-($C_0$-$C_3$)alkyl-O—($C_1$-$C_3$)alkyl-$SO_2$— optionally substituted on the cycloalkyl moiety with 1 to 4 substituents selected from the group consisting of methyl and fluoro, and independently optionally substituted on either or both alkyl moieties independently with 1 to 4 fluoro substituents;
  y) $Ph^1$-($C_0$-$C_3$)alkyl-O—($C_1$-$C_3$)alkyl-$SO_2$— optionally substituted on either or both alkyl moieties independently with 1 to 4 fluoro substituents;
  z) ($C_1$-$C_6$)alkyl-S—($C_1$-$C_3$)alkyl-$SO_2$— optionally substituted on the ($C_1$-$C_6$)alkyl moiety with 1 to 6 fluoro substituents and independently optionally substituted on the $(C_1-C_3)$alkyl moiety with 1 to 4 fluoro substituents;

aa) $(C_3-C_7)$cycloalkyl-$(C_0-C_3)$alkyl-S—$(C_1-C_3)$alkyl-SO$_2$— optionally substituted on the cycloalkyl moiety with 1 to 4 substituents selected from the group consisting of methyl and fluoro, and independently optionally substituted on either or both alkyl moieties independently with 1 to 4 fluoro substituents;

ab) Ph$^1$-$(C_0-C_3)$alkyl-S—$(C_1-C_3)$alkyl-SO$_2$— optionally substituted on either or both alkyl moieties independently with 1 to 4 fluoro substituents;

ac) $(C_1-C_6)$alkyl-NR$^{16}$—$(C_1-C_3)$alkyl-SO$_2$— optionally substituted on the $(C_1-C_6)$alkyl moiety with 1 to 6 fluoro substituents and independently optionally substituted on the $(C_1-C_3)$alkyl moiety with 1 to 4 fluoro substituents;

ad) $(C_3-C_7)$cycloalkyl-$(C_0-C_3)$alkyl-NR$^{16}$—$(C_1-C_3)$alkyl-SO$_2$— optionally substituted on the cycloalkyl moiety with 1 to 4 substituents selected from the group consisting of methyl and fluoro, and independently optionally substituted on either or both alkyl moieties independently with 1 to 4 fluoro substituents;

ae) Ph$^1$-$(C_0-C_3)$alkyl-NR$^{16}$—$(C_1-C_3)$alkyl-SO$_2$— optionally substituted on either or both alkyl moieties independently with 1 to 4 fluoro substituents;

af) R$^{17}$R$^{18}$—N—C(O)—$(C_1-C_5)$alkyl optionally substituted on the alkyl moiety with 1 to 6 fluoro substituents;

ag) R$^{17}$R$^{18}$—N—C(S)—$(C_1-C_5)$alkyl optionally substituted on the alkyl moiety with 1 to 6 fluoro substituents;

ai) $(C_3-C_7)$cycloalkyl-$(C_0-C_3)$alkyl-S—$(C_1-C_5)$alkyl optionally substituted on the cycloalkyl moiety with 1 to 4 substituents selected from the group consisting of methyl and fluoro, and independently optionally substituted on either or both alkyl moieties independently with 1 to 4 fluoro substituents;

aj) Ph$^1$-$(C_0-C_3)$alkyl-S—$(C_1-C_5)$alkyl optionally substituted on the $(C_1-C_5)$alkyl moiety with 1 to 6 fluoro substituents and independently optionally substituted on the —$(C_0-C_3)$alkyl moiety with 1 to 4 fluoro substituents;

ak) Ar$^3$—$(C_0-C_3)$alkyl-S—$(C_1-C_5)$alkyl optionally substituted on the $(C_1-C_5)$alkyl moiety with 1 to 6 fluoro substituents and independently optionally substituted on the —$(C_0-C_3)$alkyl moiety with 1 to 4 fluoro substituents;

al) Ar$^3$—$(C_0-C_3)$alkyl-O—$(C_1-C_5)$alkyl optionally substituted on the $(C_1-C_5)$alkyl moiety with 1 to 6 fluoro substituents and independently optionally substituted on the —$(C_0-C_3)$alkyl moiety with 1 to 4 fluoro substituents;

am) Het$^1$-$(C_0-C_3)$alkyl-S—$(C_0-C_5)$alkyl wherein Het$^1$ is linked through any carbon atom of Het$^1$ and wherein the $(C_0-C_5)$alkyl moiety is optionally substituted with 1 to 6 fluoro substituents and independently optionally substituted on the —$(C_0-C_3)$alkyl moiety with 1 to 4 fluoro substituents;

an) Het$^1$-$(C_0-C_3)$alkyl-O—$(C_0-C_5)$alkyl wherein Het$^1$ is linked through any carbon atom of Het$^1$ and wherein the $(C_0-C_5)$alkyl moiety is optionally substituted with 1 to 6 fluoro substituents and independently optionally substituted on the —$(C_0-C_3)$alkyl moiety with 1 to 4 fluoro substituents;

ao) Het$^2$-$(C_0-C_3)$alkyl-S—$(C_0-C_5)$alkyl optionally substituted on the $(C_0-C_5)$alkyl moiety with 1 to 6 fluoro substituents and independently optionally substituted on the —$(C_0-C_3)$alkyl moiety with 1 to 4 fluoro substituents;

ap) R$^{16}$R$^{19}$—N—C(O)—S—$(C_0-C_5)$alkyl optionally substituted on the alkyl moiety with 1 to 6 fluoro substituents;

aq) R$^{16}$R$^{19}$—N—C(O)—O—$(C_0-C_5)$alkyl optionally substituted on the alkyl moiety with 1 to 6 fluoro substituents;

ar) R$^{16}$R$^{19}$—N—C(O)—NR$^{16}$—$(C_0-C_5)$alkyl optionally substituted on the alkyl moiety with 1 to 6 fluoro substituents;

as) $(C_1-C_6)$alkyl-C(O)—$(C_1-C_3)$alkyl-S— optionally substituted on the $(C_1-C_6)$alkyl moiety with 1 to 6 fluoro substituents and independently optionally substituted on the $(C_1-C_3)$alkyl moiety with 1 to 4 fluoro substituents;

at) $(C_1-C_6)$alkyl-SO$_2$—$(C_1-C_3)$alkyl-S— optionally substituted on the $(C_1-C_6)$alkyl moiety with 1 to 6 fluoro substituents and independently optionally substituted on the $(C_1-C_3)$alkyl moiety with 1 to 4 fluoro substituents;

au) $(C_3-C_7)$cycloalkyl-$(C_0-C_3)$alkyl-C(O)—$(C_1-C_3)$alkyl-O— optionally substituted on the cycloalkyl moiety with 1 to 4 substituents selected from the group consisting of methyl and fluoro, and independently optionally substituted on either or both alkyl moieties independently with 1 to 4 fluoro substituents;

av) $(C_3-C_7)$cycloalkyl-$(C_0-C_3)$alkyl-SO$_2$—$(C_1-C_3)$alkyl-O— optionally substituted on the cycloalkyl moiety with 1 to 4 substituents selected from the group consisting of methyl and fluoro, and independently optionally substituted on either or both alkyl moieties independently with 1 to 4 fluoro substituents;

aw) $(C_3-C_7)$cycloalkyl-$(C_0-C_3)$alkyl-C(O)—$(C_1-C_3)$alkyl-S— optionally substituted on the cycloalkyl moiety with 1 to 4 substituents selected from the group consisting of methyl and fluoro, and independently optionally substituted on either or both alkyl moieties independently with 1 to 4 fluoro substituents;

ax) $(C_3-C_7)$cycloalkyl-$(C_0-C_3)$alkyl-SO$_2$—$(C_1-C_3)$alkyl-S— optionally substituted on the cycloalkyl moiety with 1 to 4 substituents selected from the group consisting of methyl and fluoro, and independently optionally substituted on either or both alkyl moieties independently with 1 to 4 fluoro substituents;

ay) Ph$^1$-$(C_0-C_3)$alkyl-SO$_2$—$(C_1-C_3)$alkyl-O— optionally substituted on either or both alkyl moieties independently with 1 to 4 fluoro substituents;

az) Ph$^1$-$(C_0-C_3)$alkyl-C(O)—$(C_1-C_3)$alkyl-S— optionally substituted on either or both alkyl moieties independently with 1 to 4 fluoro substituents;

ba) Ph$^1$-$(C_0-C_3)$alkyl-SO$_2$—$(C_1-C_3)$alkyl-S— optionally substituted on either or both alkyl moieties independently with 1 to 4 fluoro substituents;

bb) R$^{17}$R$^{18}$N—C(O)—$(C_1-C_3)$alkyl-S— optionally substituted on the alkyl moiety with 1 to 4 fluoro substituents;

bc) R$^{17}$R$^{18}$N—C(S)—$(C_1-C_3)$alkyl-S— optionally substituted on the alkyl moiety with 1 to 4 fluoro substituents;

bd) $R^{17}R^{18}N-C(S)-(C_1-C_3)$alkyl-O— optionally substituted on the alkyl moiety with 1 to 4 fluoro substituents;

be) $(C_3-C_7)$cycloalkyl-$(C_0-C_3)$alkyl-$SO_2$—$(C_1-C_5)$alkyl optionally substituted on the cycloalkyl moiety with 1 to 4 substituents selected from the group consisting of methyl and fluoro, and independently optionally substituted on the $(C_0-C_3)$alkyl moiety with 1 to 4 fluoro substituents and further optionally substituted on the $(C_1-C_5)$alkyl moiety with 1 to 6 fluoro substituents;

bf) $Ph^1$-$(C_0-C_3)$alkyl-$SO_2$—$(C_1-C_5)$alkyl optionally substituted on the $(C_0-C_3)$alkyl moiety with 1 to 4 fluoro substituents and independently optionally substituted on the $(C_1-C_5)$alkyl moiety with 1 to 6 fluoro substituents;

bg) $Ar^3$—$(C_0-C_3)$alkyl-$SO_2$—$(C_1-C_5)$alkyl optionally substituted on the $(C_0-C_3)$alkyl moiety with 1 to 4 fluoro substituents and independently optionally substituted on the $(C_1-C_5)$alkyl moiety with 1 to 6 fluoro substituents;

bh) $Het^2$-$(C_0-C_3)$alkyl-$SO_2$—$(C_0-C_5)$alkyl optionally substituted on the $(C_0-C_3)$alkyl moiety with 1 to 4 fluoro substituents and independently optionally substituted on the $(C_0-C_5)$alkyl moiety with 1 to 6 fluoro substituents;

bi) $R^{17}R^{18}N$—$(C_1-C_3)$alkyl optionally substituted on the alkyl moiety with 1 to 4 fluoro substituents;

bj) $(C_1-C_6)$alkyl-C(O)—$N(R^{16})$—$(C_0-C_5)$alkyl optionally substituted on either or both alkyl moieties independently with 1 to 6 fluoro substituents;

bk) $(C_3-C_7)$cycloalkyl-C(O)—$N(R^{16})$—$(C_0-C_5)$alkyl optionally substituted on the cycloalkyl moiety with 1 to 4 substituents selected from the group consisting of methyl and fluoro, and independently optionally substituted on the alkyl moiety with 1 to 6 fluoro substituents;

bl) $Ph^1$-$(C_0-C_3)$alkyl-C(O)—$N(R^{16})$—$(C_0-C_5)$alkyl optionally substituted on the $(C_0-C_3)$alkyl moiety with 1 to 4 fluoro substituents and independently optionally substituted on the $(C_0-C_5)$alkyl moiety with 1 to 6 fluoro substituents;

bm) $Ar^3$—$(C_0-C_3)$alkyl-C(O)—$N(R^{16})$—$(C_0-C_5)$alkyl optionally substituted on the $(C_0-C_3)$alkyl moiety with 1 to 4 fluoro substituents and independently optionally substituted on the $(C_0-C_5)$alkyl moiety with 1 to 6 fluoro substituents;

bn) $(C_1-C_6)$alkyl-C(S)—$N(R^{16})$—$(C_0-C_5)$alkyl optionally substituted on either or both alkyl moieties independently with 1 to 6 fluoro substituents;

bo) $(C_3-C_7)$cycloalkyl-C(S)—$N(R^{16})$—$(C_0-C_5)$alkyl optionally substituted on the cycloalkyl moiety with 1 to 4 substituents selected from the group consisting of methyl and fluoro, and independently optionally substituted on the alkyl moiety with 1 to 6 fluoro substituents;

bp) $Ph^1$-$(C_0-C_3)$alkyl-C(S)—$N(R^{16})$—$(C_0-C_5)$alkyl optionally substituted on the $(C_0-C_3)$alkyl moiety with 1 to 4 fluoro substituents and independently optionally substituted on the $(C_0-C_5)$alkyl moiety with 1 to 6 fluoro substituents;

bq) $Ar^3$—$(C_0-C_3)$alkyl-C(S)—$N(R^{16})$—$(C_0-C_5)$alkyl optionally substituted on the $(C_0-C_3)$alkyl moiety with 1 to 4 fluoro substituents and independently optionally substituted on the $(C_0-C_5)$alkyl moiety with 1 to 6 fluoro substituents;

br) $(C_1-C_6)$alkyl-O—N=$C(CH_3)$— optionally substituted on the $(C_1-C_6)$alkyl moiety with 1 to 6 fluoro substituents;

bs) $(C_0-C_3)$alkyl-O—N=$C[(C_1-C_6)$alkyl]- optionally substituted on the $(C_0-C_3)$alkyl moiety with 1 to 4 fluoro substituents and independently optionally substituted on the $(C_1-C_6)$alkyl moiety with 1 to 6 fluoro substituents;

bt) HO—N=$C[(C_0-C_1)$alkyl-$(C_3-C_7)$cycloalkyl]- optionally substituted on the cycloalkyl moiety with 1 to 4 substituents selected from the group consisting of methyl and fluoro, and independently optionally substituted on either or both of the $(C_0-C_1)$alkyl and $(C_3-C_7)$cycloalkyl moieties independently with 1 to 2 fluoro substituents; and bu) $CH_3$—O—N=$C[(C_0-C_1)$alkyl-$(C_3-C_7)$cycloalkyl]- optionally substituted on the cycloalkyl moiety with 1 to 4 substituents selected from the group consisting of methyl and fluoro, and independently optionally substituted on either or both-of the $(C_0-C_1)$alkyl and $(C_3-C_7)$cycloalkyl moieties independently with 1 to 2 fluoro substituents;

$R^{13}$ is a substituent selected from the group consisting of:

a) $Het^2$-$(C_0-C_3)$alkyl optionally substituted on the alkyl moiety with 1 to 6 fluoro substituents;

b) $Het^3$-$(C_0-C_3)$alkyl optionally substituted on the alkyl moiety with 1 to 6 fluoro substituents;

c) $Ar^2$—$(C_0-C_3)$alkyl optionally substituted on the alkyl moiety with 1 to 6 fluoro substituents;

d) $(C_1-C_6)$alkyl-$C(R^{14})$=$C(R^{14})$— optionally substituted on the alkyl moiety with 1 to 6 fluoro substituents;

e) $(R^{14})_2C$=$C[(C_1-C_6)$alkyl]- optionally substituted on the alkyl moiety with 1 to 6 fluoro substituents;

f) $(C_3-C_7)$cycloalkyl-$(C_0-C_3)$alkyl-$C(R^{14})$=$C(R^{15})$— optionally substituted on the cycloalkyl moiety with 1 to 4 substituents selected from the group consisting of methyl and fluoro, and independently optionally substituted on the alkyl moiety with 1 to 4 fluoro substituents;

g) $(R^{15})CH$=$C[(C_3-C_7)$cycloalkyl-$(C_0-C_3)$alkyl]- optionally substituted on the cycloalkyl moiety with 1 to 4 substituents selected from the group consisting of methyl and fluoro, and independently optionally substituted on the alkyl moiety with 1 to 4 fluoro substituents;

h) $(C_1-C_6)$alkyl-C≡C— optionally substituted on the alkyl moiety with 1 to 6 fluoro substituents;

i) $(C_3-C_7)$cycloalkyl-$(C_0-C_1)$alkyl-C≡C— optionally substituted on the cycloalkyl moiety with 1 to 4 substituents selected from the group consisting of methyl and fluoro, and independently optionally substituted on the alkyl moiety with 1 to 2 fluoro substituents;

j) $(C_1-C_6)$alkyl-O—$(C_1-C_5)$alkyl optionally substituted on either or both alkyl moieties independently with 1 to 6 fluoro substituents;

k) $(C_3-C_7)$cycloalkyl-$(C_0-C_3)$alkyl-O—$(C_0-C_5)$alkyl optionally substituted on the cycloalkyl moiety with 1 to 4 substituents selected from the group consisting of methyl and fluoro, and independently optionally substituted on the $(C_0-C_3)$alkyl moiety with 1 to 4 fluoro substituents and further optionally substituted on the $(C_0-C_5)$alkyl moiety with 1 to 6 fluoro substituents;

l) $Ph^1$-$(C_0-C_3)$alkyl-O—$(C_0-C_5)$alkyl optionally substituted on the $(C_0-C_3)$alkyl moiety with 1 to 4 fluoro substituents and independently optionally substituted on the $(C_0-C_5)$alkyl moiety with 1 to 6 fluoro substituents;

m) $Ar^3$—$(C_0-C_3)$alkyl-O—$(C_0-C_5)$alkyl optionally substituted on the $(C_0-C_3)$alkyl moiety with 1 to 4 fluoro substituents and independently optionally substituted on the $(C_0-C_5)$alkyl moiety with 1 to 6 fluoro substituents;

n) $Het^2$-$(C_0-C_3)$alkyl-O—$(C_0-C_5)$alkyl optionally substituted on the $(C_0-C_3)$alkyl moiety with 1 to 4 fluoro substituents and independently optionally substituted on the $(C_0-C_5)$alkyl moiety with 1 to 6 fluoro substituents;

o) $(C_3-C_7)$cycloalkyl-$(C_0-C_3)$alkyl-C(O)—$(C_1-C_5)$alkyl optionally substituted on the cycloalkyl moiety with 1 to 4 substituents selected from the group consisting of methyl and fluoro, and independently optionally substituted on the $(C_0-C_3)$alkyl moiety with 1 to 4 fluoro substituents and further optionally substituted on the $(C_1-C_5)$alkyl moiety with 1 to 6 fluoro substituents;

p) $Ph^1$-$(C_0-C_3)$alkyl-C(O)—$(C_1-C_5)$alkyl optionally substituted on the $(C_0-C_3)$alkyl moiety with 1 to 4 fluoro substituents and independently optionally substituted on the $(C_1-C_5)$alkyl moiety with 1 to 6 fluoro substituents;

q) pyridyl-$(C_0-C_3)$alkyl-C(O)—$(C_1-C_5)$alkyl optionally be substituted on the pyridyl moiety with 1 to 3 substituents independently selected from the group consisting of halo, $(C_1-C_3)$alkyl, $(C_1-C_3)$alkoxy, —$CF_3$, —O—$CF_3$, nitro, cyano, and trifluoromethylthio, and independently optionally substituted on the $(C_0-C_3)$alkyl moiety with 1 to 4 fluoro substituents, and independently optionally substituted on the $(C_1-C_5)$alkyl moiety with 1 to 6 fluoro substituents;

r) $(C_1-C_6)$alkyl-C(O)—$(C_1-C_3)$alkyl-O— optionally substituted on the $(C_1-C_6)$alkyl moiety with 1 to 6 fluoro substituents and independently optionally substituted on the $(C_1-C_3)$alkyl moiety with 1 to 4 fluoro substituents;

s) $(C_3-C_7)$cycloalkyl-$(C_0-C_3)$alkyl-C(O)—$(C_1-C_3)$alkyl-O— optionally substituted on the cycloalkyl moiety with 1 to 4 substituents selected from the group consisting of methyl and fluoro, and independently optionally substituted on either or both of the alkyl moieties independently with 1 to 4 fluoro substituents;

t) $Ph^1$-$(C_0-C_3)$alkyl-C(O)—$(C_1-C_3)$alkyl-O— optionally substituted on either or both of the alkyl moieties independently with 1 to 4 fluoro substituents;

u) pyridyl-$(C_0-C_3)$alkyl-C(O)—$(C_1-C_3)$alkyl-O— optionally be substituted on the pyridyl moiety with 1 to 3 substituents independently selected from the group consisting of halo, $(C_1-C_3)$alkyl, $(C_1-C_3)$alkoxy, —$CF_3$, —O—$CF_3$, nitro, cyano, and trifluoromethylthio, and independently optionally substituted on either or both of the alkyl moieties independently with 1 to 4 fluoro substituents;

v) $R^{17}R^{18}N$—C(O)—$(C_1-C_3)$alkyl-O— optionally substituted on the alkyl moiety with 1 to 4 fluoro substituents;

w) $R^{17}R^{18}N$—C(S)—$(C_1-C_3)$alkyl-O— optionally substituted on the alkyl moiety with 1 to 4 fluoro substituents;

y) $(C_1-C_6)$alkyl-S—$(C_1-C_5)$alkyl optionally substituted on either or both alkyl moieties independently with 1 to 6 fluoro substituents;

z) $(C_3-C_7)$cycloalkyl-$(C_0-C_3)$alkyl-S—$(C_1-C_5)$alkyl optionally substituted on the cycloalkyl moiety with 1 to 4 substituents selected from the group consisting of methyl and fluoro, and independently optionally substituted on the $(C_0-C_3)$alkyl moiety with 1 to 4 fluoro substituents, and independently optionally substituted on the $(C_1-C_5)$alkyl moiety with 1 to 6 fluoro substituents;

aa) $Ph^1$-$(C_0-C_3)$alkyl-S—$(C_1-C_5)$alkyl optionally substituted on the $(C_0-C_3)$alkyl moiety with 1 to 4 fluoro substituents and independently optionally substituted on the $(C_1-C_5)$alkyl moiety with 1 to 6 fluoro substituents;

ab) $Ar^3$—$(C_0-C_3)$alkyl-S—$(C_1-C_5)$alkyl optionally substituted on the $(C_0-C_3)$alkyl moiety with 1 to 4 fluoro substituents and independently optionally substituted on the $(C_1-C_5)$alkyl moiety with 1 to 6 fluoro substituents;

ac) $(C_1-C_6)$alkyl-C(O)—$(C_1-C_3)$alkyl-S— optionally substituted on the $(C_1-C_6)$alkyl moiety with 1 to 6 fluoro substituents and independently optionally substituted on the $(C_1-C_3)$alkyl moiety with 1 to 4 fluoro substituents;

ad) $(C_3-C_7)$cycloalkyl-$(C_0-C_3)$alkyl-C(O)—$(C_1-C_3)$alkyl-S— optionally substituted on the cycloalkyl moiety with 1 to 4 substituents selected from the group consisting of methyl and fluoro, and independently optionally substituted on either or both of the alkyl moieties independently with 1 to 4 fluoro substituents;

ae) $Ph^1$-$(C_0-C_3)$alkyl-C(O)—$(C_1-C_3)$alkyl-S— optionally substituted on either or both of the alkyl moieties independently with 1 to 4 fluoro substituents;

af) pyridyl-$(C_0-C_3)$alkyl-C(O)—$(C_1-C_3)$alkyl-S— optionally be substituted on the pyridyl moiety with 1 to 3 substituents independently selected from the group consisting of halo, $(C_1-C_3)$alkyl, $(C_1-C_3)$alkoxy, —$CF_3$, —O—$CF_3$, nitro, cyano, and trifluoromethylthio, and independently optionally substituted on either or both of the alkyl moieties independently with 1 to 4 fluoro substituents;

ag) $R^{17}R^{18}N$—C(O)—$(C_1-C_3)$alkyl-S— optionally substituted on the alkyl moiety with 1 to 4 fluoro substituents;

ah) $R^{17}R^{18}N$—C(S)—$(C_1-C_3)$alkyl-S— optionally substituted on the alkyl moiety with 1 to 4 fluoro substituents;

ai) $(C_1-C_6)$alkyl-$SO_2$—$(C_0-C_5)$alkyl optionally substituted on either or both of the alkyl moieties independently with 1 to 6 fluoro substituents;

aj) $(C_3-C_7)$cycloalkyl-$(C_0-C_3)$alkyl-$SO_2$—$(C_0-C_5)$alkyl optionally substituted on the cycloalkyl moiety with 1 to 4 substituents selected from the group consisting of methyl and fluoro, and independently optionally substituted on the $(C_0-C_3)$alkyl moiety with 1 to 4 fluoro substituents, and independently optionally substituted on the $(C_0-C_5)$alkyl moiety with 1 to 6 fluoro substituents;

ak) $Ph^1$-$(C_0-C_3)$alkyl-$SO_2$—$(C_0-C_5)$alkyl optionally substituted on the $(C_0-C_3)$alkyl moiety with 1 to 4 fluoro substituents and independently optionally substituted on the $(C_0-C_5)$alkyl moiety with 1 to 6 fluoro substituents;

al) $Ar^3$—$(C_0-C_3)$alkyl-$SO_2$—$(C_0-C_5)$alkyl optionally substituted on the $(C_0-C_3)$alkyl moiety with 1 to 4 fluoro substituents and independently optionally substituted on the $(C_0-C_5)$alkyl moiety with 1 to 6 fluoro substituents;
am) $Het^2-(C_0-C_3)$alkyl-$SO_2$—$(C_0-C_5)$alkyl optionally substituted on the $(C_0-C_3)$alkyl moiety with 1 to 4 fluoro substituents and independently optionally substituted on the $(C_0-C_5)$alkyl moiety with 1 to 6 fluoro substituents;
an) $R^{17}R^{18}$—N—C(O)—$(C_1-C_5)$alkyl optionally substituted on the $(C_1-C_5)$alkyl moiety with 1 to 6 fluoro substituents;
ao) $R^{17}R^{18}$—N—C(S)—$(C_1-C_5)$alkyl optionally substituted on the $(C_1-C_5)$alkyl moiety with 1 to 6 fluoro substituents;
ap) $R^{17}R^{18}$N—$(C_1-C_3)$alkyl optionally substituted on the $(C_1-C_3)$alkyl moiety with 1 to 4 fluoro substituents;
aq) $(C_1-C_6)$alkyl-C(O)—N($R^{16}$)—$(C_0-C_5)$alkyl optionally substituted on either or both of the alkyl moieties independently with 1 to 6 fluoro substituents;
ar) $(C_3-C_7)$cycloalkyl-C(O)—N($R^{16}$)—$(C_0-C_5)$alkyl optionally substituted on the cycloalkyl moiety with 1 to 4 substituents selected from the group consisting of methyl and fluoro, and independently optionally substituted on the $(C_0-C_5)$alkyl moiety with 1 to 6 fluoro substituents;
as) $Ph^1-(C_0-C_3)$alkyl-C(O)—N($R^{16}$)—$(C_0-C_5)$alkyl optionally substituted on the $(C_0-C_3)$alkyl moiety with 1 to 4 fluoro substituents and independently optionally substituted on the $(C_0-C_5)$alkyl moiety with 1 to 6 fluoro substituents;
at) $Ar^3$—$(C_0-C_3)$alkyl-C(O)—N($R^{16}$)—$(C_0-C_5)$alkyl optionally substituted on the $(C_0-C_3)$alkyl moiety with 1 to 4 fluoro substituents and independently optionally substituted on the $(C_0-C_5)$alkyl moiety with 1 to 6 fluoro substituents;
au) $(C_1-C_6)$alkyl-C(S)—N($R^{16}$)—$(C_0-C_5)$alkyl optionally substituted on either or both of the alkyl moieties independently with 1 to 6 fluoro substituents;
av) $(C_3-C_7)$cycloalkyl-C(S)—N($R^{16}$)—$(C_0-C_5)$alkyl optionally substituted on the cycloalkyl moiety with 1 to 4 substituents selected from the group consisting of methyl and fluoro, and independently optionally substituted on the $(C_0-C_5)$alkyl moiety with 1 to 6 fluoro substituents;
aw) $Ph^1-(C_0-C_3)$alkyl-C(S)—N($R^{16}$)—$(C_0-C_5)$alkyl optionally substituted on the $(C_0-C_3)$alkyl moiety with 1 to 4 fluoro substituents and independently optionally substituted on the $(C_0-C_5)$alkyl moiety with 1 to 6 fluoro substituents; and
ax) $Ar^3$—$(C_0-C_3)$alkyl-C(S)—N($R^{16}$)—$(C_0-C_5)$alkyl optionally substituted on the $(C_0-C_3)$alkyl moiety with 1 to 4 fluoro substituents and independently optionally substituted on the $(C_0-C_5)$alkyl moiety with 1 to 6 fluoro substituents;

$R^{14}$ is hydrogen or $(C_1-C_2)$alkyl optionally substituted with 1 to 5 fluoro substituents;
$R^{15}$ is hydrogen or methyl optionally substituted with 1 to 3 fluoro substituents;
$R^{16}$ is hydrogen or $(C_1-C_3)$alkyl optionally substituted with 1 to 5 fluoro substituents;
$R^{17}$ is $(C_1-C_6)$alkyl optionally substituted with 1 to 6 fluoro substituents, $Ph^1-(C_1-C_3)$alkyl optionally substituted on the alkyl moiety with 1 to 4 fluoro substituents, or $(C_3-C_7)$cycloalkyl-$(C_0-C_3)$alkyl optionally substituted on the cycloalkyl moiety with 1 to 4 substituents independently selected from methyl and fluoro and independently optionally substituted on the alkyl moiety with 1 to 4 fluoro substituents;
$R^{18}$ is hydrogen or $(C_1-C_3)$alkyl, or $R^{17}$ and $R^{18}$ taken together with the nitrogen atom to which they are attached, form $Het^1$, imidazolidin-2-onyl, imidazolidin-2,4-dionyl, or tetrahydropyrimidin-2-onyl optionally substituted with 1 or 2 methyl substituents;
$R^{19}$ is $(C_1-C_3)$alkyl optionally substituted with 1 to 5 fluoro substituents;
$Ar^2$ is an aromatic heterocycle substituent selected from the group consisting of pyrrolyl, pyrazolyl, imidazolyl, oxazolyl, isoxazolyl, 1,2,3-oxadiazolyl, 1,2,4-oxadiazolyl, 1,3,4-oxadiazolyl, 1,2,5-oxadiazolyl, thiophenyl, thiazolyl, isothiazolyl, 1,2,3-thiadiazolyl, 1,2,4-thiadiazolyl, 1,3,4-thiadiazolyl, 1,2,5-thiadiazolyl, 1,2,3-triazolyl, and 1,2,4-triazolyl, wherein the heterocycle is substituted with $R^{15}R^{17}N$—, wherein $R^{15}$ is hydrogen and $R^{17}$ is $(C_1-C_6)$alkyl or $(C_3-C_7)$cycloalkyl-$(C_0-C_3)$alkyl;
$Ar^3$ is an aromatic heterocycle substituent selected from the group consisting of pyrrolyl, furanyl, thiophenyl, thiazolyl, isothiazolyl, oxazolyl, isoxazolyl, and pyridyl, any of which may optionally be substituted with 1 to 3 substituents independently selected from the group consisting of halo, $(C_1-C_3)$alkyl, $(C_1-C_3)$alkoxy, —$CF_3$, —O—$CF_3$, nitro, cyano, and trifluoromethylthio;
$Het^1$ is a saturated, nitrogen-containing heterocycle substituent selected from the group consisting of pyrrolidinyl, piperidinyl, homopiperidinyl, morpholinyl, thiomorpholinyl, homomorpholinyl, and homothiomorpholinyl, any of which may optionally be substituted with $(C_1-C_6)$alkyl or with 2 methyl substituents;
$Het^2$ is a saturated, oxygen-containing heterocycle substituent selected from the group consisting of tetrahydrofuranyl and tetrahydropyranyl, any of which may optionally be substituted with $(C_1-C_6)$alkyl or with 2 methyl substituents;
$Het^3$ is a nitrogen containing heterocycle selected from the group consisting of pyrrolidin-2-onyl, piperidin-2-onyl, oxazolidin-2-onyl, pyrrolin-2-onyl, and dihydropyridin-2-onyl;
or a pharmaceutically acceptable salt thereof;
or a compound selected from 7-chloro-6-[4-(3,3-dimethyl-cyclohexylthio)-benzylamino]-2,3,4,5-tetrahydro-1H-benzo[d]azepine and 7-chloro-6-{6-[(3,3-dimethyl-cyclohexylthio)-pyridin-3-ylmethyl]-amino}-2,3,4,5-tetrahydro-1H-benzo[d]azepine;
or a pharmaceutically acceptable salt thereof;
with the proviso that $R^{12}$ is not HON=C($CH_3$)— or $Het^1$ ($C_0$) alkyl.

2. The compound according to claim 1 having the Formula (Ia):

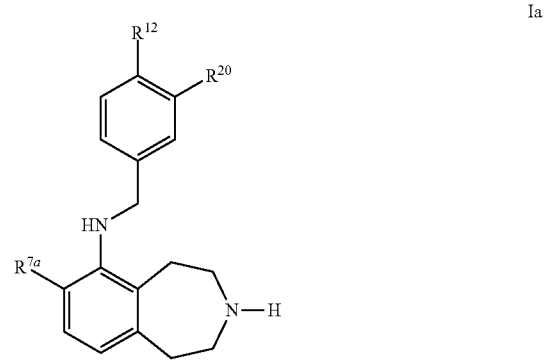

wherein
R$^{7a}$ is chloro;
R$^{12}$ is as defined in claim 1; and
R$^{20}$ is halo, hydroxy, or cyano;
or a pharmaceutically acceptable salt thereof.

3. The compound according to claim 1 having the Formula (Ib):

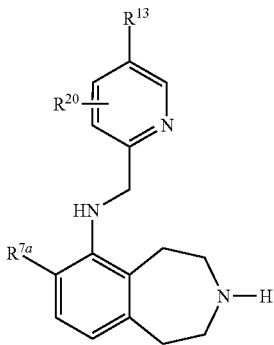

wherein
R$^{7a}$ is chloro;
R$^{13}$ is as defined in claim 1; and
R$^{20}$ is halo, hydroxy, or cyano;
or a pharmaceutically acceptable salt thereof.

4. The compound according to claim 1 having the Formula (Ic):

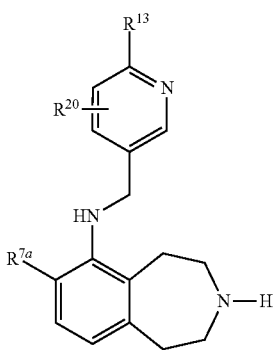

wherein
R$^{7a}$ is chloro;
R$^{13}$ is as defined in claim 1; and
R$^{20}$ is halo, hydroxy, or cyano;
or a pharmaceutically acceptable salt thereof.

5. A compound according to claim 2 wherein R$^{20}$ is fluoro or chloro.

6. A compound according to claim 3 wherein R$^{20}$ is fluoro or chloro.

7. A compound according to claim 4 wherein R$^{20}$ is fluoro or chloro.

8. A pharmaceutical composition comprising a compound according to claim 1 as an active ingredient in association with a pharmaceutically acceptable carrier, diluent or excipient.

9. A method for the treatment of obesity in mammals, comprising administering to a mammal in need of such treatment an effective amount of a compound according to claim 1.

10. The method of claim 9, where the mammal is human.

11. A method for the treatment of obsessive compulsive disorder in mammals, comprising administering to a mammal in need of such treatment an effective amount of a compound according to claim 1.

12. The method of claim 11, where the mammal is human.

13. A method for the treatment of depression in mammals, comprising administering to a mammal in need of such treatment an effective amount of a compound according to claim 1.

14. The method of claim 13, where the mammal is human.

15. A method for the treatment of anxiety in mammals, comprising administering to a mammal in need of such treatment an effective amount of a compound according to claim 1.

16. The method of claim 15, where the mammal is human.

17. A compound according to claim 1 which is 7-Chloro-6-[4-(2-cyclopropylmethylamino-thiazol-4-yl)-benzylamino]-2,3,4,5-tetrahydro-1H-benzo[d]azepine; or a pharmaceutically acceptable salt thereof.

18. A compound according to claim 1 which is 7-Chloro-6-[6-(3,3-dimethyl-cyclohexyloxy)-pyridin-3-ylmethylamino]-2,3,4,5-tetrahydro-1H-benzo[d]azepine (L)-Tartrate; or a pharmaceutically acceptable salt thereof.

19. A compound according to claim 1 which is 7-Chloro-6-[4-(piperidin-1-ylmethyl)-benzylamino]-2,3,4,5-tetrahydro-1H-benzo[d]azepine; or a pharmaceutically acceptable salt thereof.

20. A compound which is:
7-Chloro-6-[4-(1-methoxyimino-ethyl)-benzylamino]-2,3,4,5-tetrahydro-1H-benzo[d]azepine;
7-Chloro-6-[4-(1-ethoxyimino-ethyl)-benzylamino]-2,3,4,5-tetrahydro-1H-benzo[d]azepine;
7-Chloro-6-[4-(1-iso-butoxyimino-ethyl)-benzylamino]-2,3,4,5-tetrahydro-1H-benzo[d]azepine;
7-Chloro-6-[4-(1-hydroxyimino-3-methyl-butyl)-benzylamino]-2,3,4,5-tetrahydro-1H-benzo[d]azepine;
7-Chloro-6-[4-(1-methoxyimino-3-methyl-butyl)-benzylamino]-2,3,4,5-tetrahydro-1H-benzo[d]azepine;
7-Chloro-6-[4-(2-methylamino-thiazol-4-yl)-benzylamino]-2,3,4,5-tetrahydro-1H-benzo[d]azepine;
7-Chloro-6-[4-(2-ethylamino-thiazol-4-yl)-benzylamino]-2,3,4,5-tetrahydro-1H-benzo[d]azepine;
7-Chloro-6-[4-(2-iso-propylamino-thiazol-4-yl)-benzylamino]-2,3,4,5-tetrahydro-1H-benzo[d]azepine;
7-Chloro-6-[4-(2-n-propylamino-thiazol-4-yl)-benzylamino]-2,3,4,5-tetrahydro-1H-benzo[d]azepine;
7-Chloro-6-[4-(2-piperidin-1-yl-thiazol-4-yl)-benzylamino]-2,3,4,5-tetrahydro-1H-benzo[d]azepine;
7-Chloro-6-[4-(2-iso-butylamino-thiazol-4-yl)-benzylamino]-2,3,4,5-tetrahydro-1H-benzo[d]azepine;
7-Chloro-6-[4-(2-methylamino-oxazol-4-yl)-benzylamino]-2,3,4,5-tetrahydro-1H-benzo[d]azepine;
7-Chloro-6-[4-(cyclopentylthiomethyl)-benzylamino]-2,3,4,5-tetrahydro-1H-benzo[d]azepine;
7-Chloro-6-[4-(cyclohexylthiomethyl)-benzylamino]-2,3,4,5-tetrahydro-1H-benzo[d]azepine;
7-Chloro-6-[(5-cyclopentylthiomethyl-pyridin-2-ylmethyl)-amino]-2,3,4,5-tetrahydro-1H-benzo[d]azepine;
7-Chloro-6-[(5-cyclohexylthio-methyl-pyridin-2-ylmethyl)-amino]-2,3,4,5-tetrahydro-1H-benzo[d]azepine;
7-Chloro-6-[(5-iso-propylthio-methyl-pyridin-2-ylmethyl)-amino]-2,3,4,5-tetrahydro-1H-benzo[ld]azepine;
7-Chloro-6-[(5-iso-butylthio-methyl-pyridin-2-ylmethyl)-amino]-2,3,4,5-tetrahydro-1H-benzo[d]azepine;

7-Chloro-6-[6-(2,2-dimethyl-propylthiomethyl)-pyridin-3-ylmethyl-amino]-2,3,4,5-tetrahydro-1H-benzo[d]azepine;
7-Chloro-6-[4-(3,3-dimethyl-cyclohexylthiomethyl)-benzylamino]-2,3,4,5-tetrahydro-1H-benzo[d]azepine;
7-Chloro-6-[4-(3,3-dimethyl-cyclohexylthio)-benzylamino]-2,3,4,5-tetrahydro-1H-benzo[d]azepine;
7-Chloro-6-[6-(3,3-dimethyl-cyclohexylthio)-pyridin-3-ylmethyl-amino]-2,3,4,5-tetrahydro-1H-benzo[d]azepine;
6-[6-(tert-Butylthiomethyl)-pyridin-3-ylmethyl-amino]-7-chloro-2,3,4,5-tetrahydro-1H-benzo[d]azepine;
7-Chloro-6-[6-(cyclopentylthiomethyl)-pyridin-3-ylmethyl-amino]-2,3,4,5-tetrahydro-1H-benzo[d]azepine;
7-Chloro-6-[6-(cyclohexylthiomethyl)-pyridin-3-ylmethyl-amino]-2,3,4,5-tetrahydro-1H-benzo[d]azepine;
7-Chloro-6-[6-(cyclohexyloxy)-pyridin-3-ylmethyl-amino]-2,3,4,5-tetrahydro-1H-benzo[d]azepine;
7-Chloro-6-[6-(4,4-dimethyl-cyclohexyloxy)-pyridin-3-ylmethyl-amino]-2,3,4,5-tetrahydro-1H-benzo[d]azepine;
7-Chloro-6-[6-(2-methyl-2-propane-sulfonylmethyl)-pyridin-3-ylmethyl-amino]-2,3,4,5-tetrahydro-1H-benzo[d]azepine;
7-Chloro-6-[6-(iso-propoxymethyl)-pyridin-3-ylmethyl-amino]-2,3,4,5-tetrahydro-1H-benzo[d]azepine;
7-Chloro-6-[6-(iso-propoxymethyl)-pyridin-3-ylmethyl-amino]-2,3,4,5-tetrahydro-1H-benzo[d]azepine;
7-Chloro-6-[6-(cyclopentyloxymethyl)-pyridin-3-ylmethyl-amino]-2,3,4,5-tetrahydro-1H-benzo[d]azepine;
7-Chloro-6-[6-(cyclohexyloxymethyl)-pyridin-3-ylmethyl-amino]-2,3,4,5-tetrahydro-1H-benzo[d]azepine;
7-Chloro-6-[5-(cyclohexyloxy)-pyridin-2-ylmethyl-amino]-2,3,4,5-tetrahydro-1H-benzo[d]azepine;
7-Chloro-6-[5-(cycloheptyloxy)-pyridin-2-ylmethyl-amino]-2,3,4,5-tetrahydro-1H-benzo[d]azepine;
7-Chloro-6-[5-(3,3-dimethylcyclohexyloxy)-pyridin-2-ylmethyl-amino]-2,3,4,5-tetrahydro-1H-benzo[d]azepine;
-(E)-7-Chloro-6-[6-(2-cyclohexyl-vinyl)-pyridin-3-ylmethyl-amino]-2,3,4,5-tetrahydro-1H-benzo[d]azepine;
-(E)-7-Chloro-6-[5-(2-cyclohexyl-vinyl)-pyridin-2-ylmethyl-amino]-2,3,4,5-tetrahydro-1H-benzo[d]azepine;
-(Z)-7-Chloro-6-[6-(2-cyclohexyl-vinyl)-pyridin-3-ylmethyl-amino]-2,3,4,5-tetrahydro-1H-benzo[d]azepine;
(Z)-7-Chloro-6-[5-(2-cyclohexyl-vinyl)-pyridin-2-ylmethyl-amino]-2,3,4,5-tetrahydro-1H-benzo[d]azepine;
(Z)-7-Chloro-6-[4-(2-cyclohexyl-vinyl)-benzylamino]-2,3,4,5-tetrahydro-1H-benzo[d]azepine (L)-Tartrate;
7-Chloro-6-[4-(2-cyclohexyl-2-oxo-ethyl)-benzylamino]-2,3,4,5-tetrahydro-1H-benzo[d]azepine;
7-Chloro-6-[4-(morpholin-4-ylmethyl)-benzylamino]-2,3,4,5-tetrahydro-1H-benzo[d]azepine;
(R)-7-Chloro-6-[4-(1-methyl-2,2,2-trifluoro-ethylamino)-methyl-benzylamino]-7-chloro-2,3,4,5-tetrahydro-1H-benzo[d]azepine;
7-Chloro-6-[4-(2,2,2-trifluoroethylamino-methyl)-benzylamino]-7-chloro-2,3,4,5-tetrahydro-1H-benzo[d]azepine;
7-Chloro-6-[4-(pyrrolidin-1-ylmethyl)-benzylamino]-2,3,4,5-tetrahydro-1H-benzo[d]azepine;
7-Chloro-6-[4-(azepan-1-ylmethyl)-benzylamino]-2,3,4,5-tetrahydro-1H-benzo[d]azepine;
7-Chloro-6-[4-(1-methyl-2,2,2-trifluoro-ethylamino-methyl)-benzylamino]-7-chloro-2,3,4,5-tetrahydro-1H-benzo[d]azepine;
7-Chloro-6-[4-(N-cyclohexyl-aminomethyl)-benzylamino]-2,3,4,5-tetrahydro-1H-benzo[d]azepine;
6-[4-(N-iso-Butyl-aminomethyl)-benzylamino]-7-chloro-2,3,4,5-tetrahydro-1H-benzo[d]azepine;
7-Chloro-6-[4-(N-iso-propyl-aminomethyl)-benzylamino]-2,3,4,5-tetrahydro-1H-benzo[d]azepine;
7-Chloro-6-[4-(N-methyl-iso-propylamino-methyl)-benzylamino]-2,3,4,5-tetrahydro-1H-benzo[d]azepine;
7-Chloro-6-[5-(N-cyclohexyl-aminomethyl)-pyridin-2-yl-methyl-amino]-2,3,4,5-tetrahydro-1H-benzo[d]azepine;
7-Chloro-6-[6-(piperidin-1-ylmethyl)-pyridin-3-yl-methyl-amino]-2,3,4,5-tetrahydro-1H-benzo[d]azepine;
7-Chloro-6-[4-(2,2-dimethyl-propionylamino)-benzylamino]-2,3,4,5-tetrahydro-1H-benzo[d]-azepine;
7-Chloro-6-[4-(cyclopropanecarbonyl-amino)-benzylamino]-2,3,4,5-tetrahydro-1H-benzo[d]-azepine;
7-Chloro-6-[4-(1-methyl-cyclopropanecarbonyl-amino)-benzylamino]-2,3,4,5-tetrahydro-1H-benzo[d]-azepine;
7-Chloro-6-[4-(2,2,3,3-tetramethyl-cyclopropanecarbonyl-amino)-benzylamino]-2,3,4,5-tetrahydro-1H-benzo[d]-azepine;
(+)-7-Chloro-6-[4-(2-methyl-cyclopropanecarbonyl-amino)-benzylamino]-2,3,4,5-tetrahydro-1H-benzo[d]-azepine;
(−)-7-Chloro-6-[4-(2-methyl-cyclopropanecarbonyl-amino)-benzylamino]-2,3,4,5-tetrahydro-1H-benzo[d]-azepine;
7-Chloro-6-[4-(N-methyl-2,2-dimethyl-propionylamino)-benzylamino]-2,3,4,5-tetrahydro-1H-benzo[d]-azepine;
7-Chloro-6-[4-(cyclohexanecarbonyl-amino)-benzylamino]-2,3,4,5-tetrahydro-1H-benzo[d]-azepine;
7-Chloro-6-[4-(cyclopentanecarbonyl-amino)-benzylamino]-2,3,4,5-tetrahydro-1H-benzo[d]-azepine;
7-Chloro-6-[4-(cycloheptanecarbonyl-amino)-benzylamino]-2,3,4,5-tetrahydro-1H-benzo[d]-azepine;
7-Chloro-6-[4-(2,2-dimethyl-propionylamino-methyl)-benzylamino]-2,3,4,5-tetrahydro-1H-benzo[d]azepine;
7-Chloro-6-[4-(cyclopropanecarbonyl-amino-methyl)-benzylamino]-2,3,4,5-tetrahydro-1H-benzo[d]azepine;
7-Chloro-6-{4-[2-(2,2-dimethyl-propionylamino)-ethyl]-benzylamino}-2,3,4,5-tetrahydro-1H-benzo[d]azepine;
7-Chloro-6-[4-(iso-propylcarbamoyl-methyl)-benzylamino]-2,3,4,5-tetrahydro-1H-benzo[d]azepine;
7-Chloro-6-{4-[(2,2-dimethylpropyl-carbamoyl)-methyl]-benzylamino}-2,3,4,5-tetrahydro-1H-benzo[d]azepine;
7-Chloro-6-[4-(2-oxo-2-pyrrolidin-1-yl-ethyl)-benzylamino]-2,3,4,5-tetrahydro-1H-benzo[d]azepine;
(±)-7-Chloro-6-{4-[1-(2,2-dimethylpropyl-carbamoyl)-ethyl]-benzylamino}-2,3,4,5-tetrahydro-1H-benzo[d]azepine;
7-Chloro-6-{4-[(cyclohexylmethyl-carbamoyl)-methyl]-benzylamino}-2,3,4,5-tetrahydro-1H-benzo[d]azepine;
7-Chloro-6-{4-[(3,3-dimethylbutyl-carbamoyl)-methyl]-benzylamino}-2,3,4,5-tetrahydro-1H-benzo[d]azepine;
(R)-7-Chloro-6-{4-[(1-methyl-2,2,2-trifluoro-ethylcarbamoyl)-methyl]-benzylamino}-2,3,4,5-tetrahydro-1H-benzo[d]azepine;
6-{4-[2-(tert-Butylcarbamoyl)-ethyl]-benzylamino}-7-chloro-2,3,4,5-tetrahydro-1H-benzo[d]azepine;
7-Chloro-6-{4-[2-(2,2-dimethylpropyl-carbamoyl)-ethyl]-benzylamino}-2,3,4,5-tetrahydro-1H-benzo[d]azepine;

7-Chloro-6-{6-[(2,2-dimethyl-propanesulfonylmethyl)-pyridin-3-ylmethyl]-amino}-2,3,4,5-tetrahydro-1H-benzo[d]azepine;
7-Chloro-6-[(6-cyclohexanesulfonylmethyl-pyridin-3-yl-methyl)-amino]-2,3,4,5-tetrahydro-1H-benzo[d]azepine;
7-Chloro-6-[4-(2,2-dimethyl-propanesulfonylmethyl)-benzylamino]-2,3,4,5-tetrahydro-1H-benzo[d]azepine;
7-Chloro-6-(4-dimethylcarbamoylthio-benzylamino)-2,3,4,5-tetrahydro-1H-benzo[d]azepine;
7-Chloro-6-[4-(3,3-dimethyl-2-oxobutylthio)-benzylamino]-2,3,4,5-tetrahydro-1H-benzo[d]azepine;
7-Chloro-6-{4-[(2,2-dimethyl-propylcarbamoyl)-methylthio]-benzylamino}-2,3,4,5-tetrahydro-1H-benzo[d]azepine;
7-Chloro-6-[6-(3,3-dimethyl-2-oxo-butoxy)-pyridin-3-ylmethyl-amino]-2,3,4,5-tetrahydro-1H-benzo[d]azepine;
7-Chloro-6-({6-[(2,2-dimethyl-propylcarbamoyl)-methoxy]-pyridin-3-ylmethyl}-amino)-2,3,4,5-tetrahydro-1H-benzo[d]azepine;
7-Chloro-6-{4-[5-(cyclopropylmethyl-amino)-isothiazol-3-yl]-benzylamino}-2,3,4,5-tetrahydro-1H-benzo[d]azepine;
7-Chloro-6-{4-[2-(2,2,2-trifluoroethylamino)-thiazol-4-yl]-benzylamino}-2,3,4,5-tetrahydro-1H-benzo[d]azepine;
7-Chloro-6-{4-[2-(3-methyl-butylamino)-thiazol-4-yl]-benzylamino}-2,3,4,5-tetrahydro-1H-benzo[d]azepine;
7-Chloro-6-{4-[2-(2,2-dimethyl-propylamino)-thiazol-4-yl]-benzylamino}-2,3,4,5-tetrahydro-1H-benzo[d]azepine;
7-Chloro-6-[4-(2-cyclopentylmethylamino-thiazol-4-yl)-benzylamino]-2,3,4,5-tetrahydro-1H-benzo[d]azepine;
7-Chloro-6-[4-(2-cyclohexylmethylamino-thiazol-4-yl)-benzylamino]-2,3,4,5-tetrahydro-1H-benzo[d]azepine;
7-Chloro-6-[4-(2-cyclopropylmethylamino-5-methyl-thiazol-4-yl)-benzylamino]-2,3,4,5-tetrahydro-1H-benzo[d]azepine;
(R)-7-Chloro-6-{4-[2-(1-methyl-2,2,2-trifluoroethyl-amino)-thiazol-4-yl]-benzylamino}-2,3,4,5-tetrahydro-1H-benzo[d]azepine;
(S)-7-Chloro-6-{4-[2-(1-methyl-2,2,2-trifluoroethyl-amino)-thiazol-4-yl]-benzylamino}-2,3,4,5-tetrahydro-1H-benzo[d]azepine;
6-[4-(2-Benzylamino-thiazol-4-yl)-benzylamino]-7-chloro-2,3,4,5-tetrahydro-1H-benzo[d]azepine;
7-Chloro-6-{4-[2-(3,3,3-trifluoropropylamino)-thiazol-4-yl]-benzylamino}-2,3,4,5-tetrahydro-1H-benzo[d]azepine;
7-Chloro-6-[5-(2-cyclopropylmethylamino-thiazol-4-yl)-pyridin-2-ylmethyl-amino]-2,3,4,5-tetrahydro-1H-benzo[d]azepine;
7-Chloro-6-[6-(2-cyclopropylmethylamino-thiazol-4-yl)-pyridin-3-ylmethyl-amino]-2,3,4,5-tetrahydro-1H-benzo[d]azepine;
7-Chloro-6-{4-[2-(cyclopropanecarbonyl-amino)-thiazol-4-yl]-benzylamino}-2,3,4,5-tetrahydro-1H-benzo[d]azepine;
7-Chloro-6-[4-(1-cyclopropylmethyl-1H-pyrazol-3-yl)-benzylamino]-2,3,4,5-tetrahydro-1H-benzo[d]azepine;
7-Chloro-6-[4-(3-cyclopropylmethylamino)-pyrazol-1-yl-benzylamino]-2,3,4,5-tetrahydro-1H-benzo[d]azepine;
7-Chloro-6-{4-[6-(cyclopropylmethyl-amino)-pyrimidin-4-yl]-benzylamino}-2,3,4,5-tetrahydro-1H-benzo[d]azepine;
7-Chloro-6-{4-[4-(cyclopropylmethyl-amino)-pyrimidin-2-yl]-benzylamino}-2,3,4,5-tetrahydro-1H-benzo[d]azepine;
7-Chloro-6-{4-[2-(cyclopropylmethyl-amino)-pyrimidin-4-yl]-benzylamino}-2,3,4,5-tetrahydro-1H-benzo[d]azepine;
7-Chloro-6-{4-[5-(3,3-dimethylbutyryl)-thiophen-2-yl]-benzylamino}-2,3,4,5-tetrahydro-1H-benzo[d]azepine;
7-Chloro-6-[6-(2,2-dimethylpropane-sulfonyl)-pyridin-3-yl-methyl-amino]-2,3,4,5-tetrahydro-1H-benzo[d]azepine; or
7-Chloro-6-[4-(2,2,2-trifluoroethylthio-methylcarbonyl)-benzylamino]-2,3,4,5-tetrahydro-1H-benzo[d]azepine;
or a pharmaceutically acceptable salt thereof.

21. A pharmaceutical composition comprising a compound according to claim 17 as an active ingredient in association with a pharmaceutically acceptable carrier, diluent or excipient.

22. A pharmaceutical composition comprising a compound according to claim 18 as an active ingredient in association with a pharmaceutically acceptable carrier, diluent or excipient.

23. A pharmaceutical composition comprising a compound according to claim 19 as an active ingredient in association with a pharmaceutically acceptable carrier, diluent or excipient.

24. A pharmaceutical composition comprising a compound according to claim 20 as an active ingredient in association with a pharmaceutically acceptable carrier, diluent or excipient.

* * * * *

UNITED STATES PATENT AND TRADEMARK OFFICE
CERTIFICATE OF CORRECTION

PATENT NO. : 8,680,091 B2
APPLICATION NO. : 13/156575
DATED : March 25, 2014
INVENTOR(S) : Briner et al.

Page 1 of 1

It is certified that error appears in the above-identified patent and that said Letters Patent is hereby corrected as shown below:

Title Page, Column 2 item (56), (Other Publications), Line 1, delete "Psycholpharmacology," and insert -- Psychopharmacology --, therefor.

In the Claims:

Column 238, Line 21, In Claim 1, delete "both-of" and insert -- both of --, therefor.

Signed and Sealed this
First Day of July, 2014

Michelle K. Lee
*Deputy Director of the United States Patent and Trademark Office*